United States Patent
Seo et al.

(10) Patent No.: US 12,091,416 B2
(45) Date of Patent: Sep. 17, 2024

(54) ORGANIC COMPOUND

(71) Applicant: Semiconductor Energy Laboratory Co., Ltd., Kanagawa-ken (JP)

(72) Inventors: Satoshi Seo, Kanagawa (JP); Satomi Watabe, Kanagawa (JP); Hideko Yoshizumi, Kanagawa (JP); Hiromitsu Kido, Kanagawa (JP); Toshiki Sasaki, Kanagawa (JP); Akira Nagasaka, Kanagawa (JP); Yuta Kawano, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 861 days.

(21) Appl. No.: 17/058,435

(22) PCT Filed: May 21, 2019

(86) PCT No.: PCT/IB2019/054166
§ 371 (c)(1),
(2) Date: Nov. 24, 2020

(87) PCT Pub. No.: WO2019/229583
PCT Pub. Date: Dec. 5, 2019

(65) Prior Publication Data
US 2021/0363151 A1    Nov. 25, 2021

(30) Foreign Application Priority Data
May 31, 2018   (JP) .................................. 2018-105410

(51) Int. Cl.
C07D 491/048     (2006.01)
C07D 513/04      (2006.01)
(Continued)

(52) U.S. Cl.
CPC ....... C07D 491/048 (2013.01); C07D 513/04 (2013.01); C07D 519/00 (2013.01);
(Continued)

(58) Field of Classification Search
CPC .............. C07D 491/048; C07D 513/04; C07D 519/00; H10K 85/626; H10K 85/6574;
(Continued)

(56) References Cited

U.S. PATENT DOCUMENTS 7,906,226 B2   3/2011   Matsuura et al.
8,105,701 B2   1/2012   Matsuura et al.
(Continued)

FOREIGN PATENT DOCUMENTS

CN   105103327 A   11/2015
CN   106573938 A   4/2017
(Continued)

OTHER PUBLICATIONS

Chinese Office Action (Application No. 201980036626.9) Dated Feb. 15, 2023.
(Continued)

*Primary Examiner* — Caleb E Henry
(74) *Attorney, Agent, or Firm* — Husch Blackwell LLP

(57) ABSTRACT

A benzofuropyrimidine derivative or benzothienopyrimidine derivative that is a novel organic compound is pro-
(Continued)

vided. An organic compound represented by General Formula (G1) below.

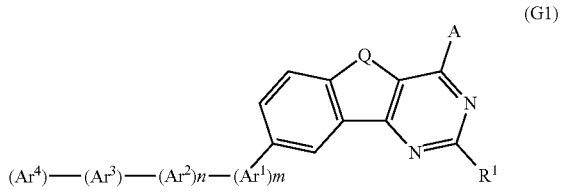

Q represents oxygen or sulfur. Ar1, Ar2, Ar3, and Ar4 each independently represent an aromatic hydrocarbon ring, and the number of carbon atoms included in the aromatic hydrocarbon ring is 6 to 25. m and n are each 0 or 1. A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure.

21 Claims, 44 Drawing Sheets

(51) Int. Cl.
  *C07D 519/00* (2006.01)
  *H10K 50/11* (2023.01)
  *H10K 85/60* (2023.01)
  *H10K 101/10* (2023.01)
(52) U.S. Cl.
  CPC ....... *H10K 85/626* (2023.02); *H10K 85/6574* (2023.02); *H10K 85/6576* (2023.02); *H10K 50/11* (2023.02); *H10K 2101/10* (2023.02)
(58) Field of Classification Search
  CPC ............. H10K 85/6576; H10K 50/11; H10K 2101/10; H10K 50/131; H10K 50/852; H10K 85/657; H10K 59/351; H10K 85/342; H10K 2101/20; H10K 2101/90; H10K 85/6572; C09K 11/06
  See application file for complete search history.

(56) References Cited

U.S. PATENT DOCUMENTS

| | | |
|---|---|---|
| 8,470,455 B2 | 6/2013 | Matsuura et al. |
| 9,905,782 B2 | 2/2018 | Inoue et al. |
| 10,193,086 B2 | 1/2019 | Inoue et al. |
| 10,361,388 B2 | 7/2019 | Mitsumori et al. |
| 10,586,931 B2 | 3/2020 | Kanamoto et al. |
| 10,658,604 B2 | 5/2020 | Mitsumori et al. |
| 10,700,291 B2 | 6/2020 | Inoue et al. |
| 10,717,744 B2 | 7/2020 | Park et al. |
| 10,734,588 B2 | 8/2020 | Park et al. |
| 10,868,258 B2 | 12/2020 | Kurihara et al. |
| 10,910,576 B2 | 2/2021 | Mitsumori et al. |
| 11,088,332 B2 | 8/2021 | Kanamoto et al. |
| 11,462,702 B2 | 10/2022 | Mitsumori et al. |
| 11,469,380 B2* | 10/2022 | Kurihara ................... G09F 9/30 |
| 2015/0207082 A1 | 7/2015 | Dyatkin et al. |
| 2016/0351826 A1* | 12/2016 | Kim ..................... H10K 85/615 |
| 2017/0186971 A1 | 6/2017 | Kanamoto et al. |
| 2017/0200903 A1* | 7/2017 | Park ..................... H10K 85/622 |
| 2017/0352447 A1* | 12/2017 | Lee ........................ H01B 1/127 |
| 2018/0006221 A1* | 1/2018 | Seo ........................ C09K 11/025 |
| 2018/0062084 A1* | 3/2018 | Watabe ................ H10K 85/342 |
| 2018/0247981 A1* | 8/2018 | Yamaoka ................ H10K 50/16 |
| 2019/0031673 A1* | 1/2019 | Yamaguchi ............ H10K 50/82 |
| 2020/0024282 A1 | 1/2020 | Parham et al. |
| 2020/0055865 A1 | 2/2020 | Kim et al. |
| 2020/0161564 A1 | 5/2020 | Kim et al. |
| 2020/0259099 A1* | 8/2020 | Kurihara .............. H10K 85/657 |
| 2020/0295267 A1 | 9/2020 | Kanamoto et al. |
| 2021/0013428 A1 | 1/2021 | Inoue et al. |
| 2023/0109651 A1 | 4/2023 | Mitsumori et al. |

FOREIGN PATENT DOCUMENTS

| | | |
|---|---|---|
| CN | 108431010 A | 8/2018 |
| CN | 109689658 A | 4/2019 |
| JP | 2010-182699 A | 8/2010 |
| JP | 2016-169210 A | 9/2016 |
| JP | 2017-119682 A | 7/2017 |
| JP | 2017-212443 A | 11/2017 |
| JP | 2018-127402 A | 8/2018 |
| KR | 2018-0022608 A | 3/2018 |
| KR | 2018-0095919 A | 8/2018 |
| KR | 2019-0035308 A | 4/2019 |
| KR | 2019-0059949 A | 5/2019 |
| TW | 201736378 | 10/2017 |
| WO | WO 2014/157599 A1 | 10/2014 |
| WO | WO 2017/109637 A1 | 6/2017 |
| WO | WO-2017/199163 | 11/2017 |
| WO | WO 2018/060307 A1 | 4/2018 |
| WO | WO 2019/058200 A1 | 3/2019 |
| WO | WO 2019/066282 A1 | 4/2019 |

OTHER PUBLICATIONS

Taiwanese Office Action (Application No. 108118549) Dated Mar. 8, 2023.
International Search Report (Application No. PCT/IB2019/054166) Dated Aug. 13, 2019.
Written Opinion (Application No. PCT/IB2019/054166) Dated Aug. 13, 2019.

* cited by examiner

4000

4200

ORGANIC COMPOUND

This application is a 371 of international application PCT/IB2019/054166 filed on May 21, 2019 which is incorporated herein by reference.

TECHNICAL FIELD

One embodiment of the present invention relates to an organic compound, a light-emitting element, a light-emitting device, an electronic device, and a lighting device. However, one embodiment of the present invention is not limited to the above technical field. That is, one embodiment of the present invention relates to an object, a method, a manufacturing method, or a driving method. Alternatively, one embodiment of the present invention relates to a process, a machine, manufacture, or a composition of matter. Specific examples include a semiconductor device, a display device, a liquid crystal display device, and the like.

BACKGROUND ART

A light-emitting element including an EL layer between a pair of electrodes (also referred to as an organic EL element) has characteristics such as thinness, light weight, high-speed response to input signals, and low power consumption; thus, a display including such a light-emitting element has attracted attention as a next-generation flat panel display.

In a light-emitting element, voltage application between a pair of electrodes causes, in an EL layer, recombination of electrons and holes injected from the electrodes, which brings a light-emitting substance (organic compound) contained in the EL layer into an excited state. Light is emitted when the light-emitting substance returns to the ground state from the excited state. The excited state can be a singlet excited state (S*) and a triplet excited state (T*). Light emission from a singlet excited state is referred to as fluorescence, and light emission from a triplet excited state is referred to as phosphorescence. The statistical generation ratio thereof in the light-emitting element is considered to be S*:T*=1:3. Since the emission spectrum obtained from a light-emitting substance depends on the light-emitting substance, the use of different types of organic compounds as light-emitting substances makes it possible to obtain light-emitting elements which exhibit various emission colors.

In order to improve element characteristics of such a light-emitting element, improvement of an element structure, development of a material, and the like have been actively carried out (see Patent Document 1, for example).

REFERENCE

Patent Document

[Patent Document 1] Japanese Published Patent Application No. 2010-182699

SUMMARY OF THE INVENTION

Problems to be Solved by the Invention

Thus, in one embodiment of the present invention, a novel organic compound is provided. In another embodiment of the present invention, a benzofuropyrimidine derivative or a benzothienopyrimidine derivative that is a novel organic compound is provided. In one embodiment of the present invention, a novel organic compound that can be used in a light-emitting element is provided. In one embodiment of the present invention, a novel organic compound that can be used in an EL layer of a light-emitting element is provided. In addition, a highly reliable and novel light-emitting element using a novel organic compound of one embodiment of the present invention is provided. In addition, a novel light-emitting device, a novel electronic device, or a novel lighting device is provided. Note that the description of these objects does not preclude the existence of other objects. In one embodiment of the present invention, there is no need to achieve all of these objects. Objects other than these are apparent from the description of the specification, the drawings, the claims, and the like, and objects other than these can be derived from the description of the specification, the drawings, the claims, and the like.

Means for Solving the Problems

One embodiment of the present invention is an organic compound, which is a benzofuropyrimidine derivative or a benzothienopyrimidine derivative and represented by General Formula (G1) below. As represented by General Formula (G1) below, the organic compound has a structure in which a plurality of aromatic hydrocarbon rings are bonded (specifically, two to four aromatic hydrocarbon rings are bonded) to the 8-position of a benzofuropyrimidine skeleton or a benzothienopyrimidine skeleton.

[Chemical Formula 1]

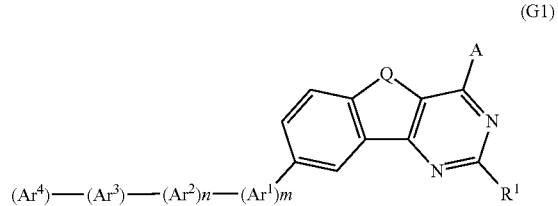

(G1)

In General Formula (G1) above, Q represents oxygen or sulfur. $Ar^1$, $Ar^2$, $Ar^3$, and $Ar^4$ each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is an organic compound which is a benzofuropyrimidine derivative or a benzothienopyrimidine derivative and represented by General Formula (G2) below. As represented by General Formula (G2) below, the organic compound has a structure in which a plurality of aromatic hydrocarbon rings are bonded (specifically, two to four aromatic hydrocarbon rings are bonded) to the 8-position of a benzofuropyrimidine skeleton or a benzothienopyrimidine skeleton and at least a hole-transport skeleton is included at the 4-position.

[Chemical Formula 2]

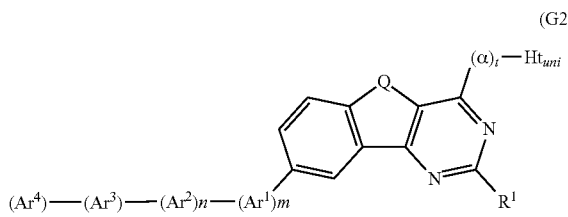

(G2)

In General Formula (G2) above, Q represents oxygen or sulfur. $Ar^1$, $Ar^2$, $Ar^3$, and $Ar^4$ represent the same group and each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, α represents a substituted or unsubstituted phenylene group, and t represents an integer of 0 to 4. In addition, $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is an organic compound which is a benzofuropyrimidine derivative or a benzothienopyrimidine derivative and represented by General Formula (G3) below. As represented by General Formula (G3) below, the organic compound has a structure in which a plurality of aromatic hydrocarbon rings are bonded (specifically, two to four aromatic hydrocarbon rings are bonded) to the 8-position of a benzofuropyrimidine skeleton or a benzothienopyrimidine skeleton and a hole-transport skeleton is included at the 4-position through a phenylene group.

[Chemical Formula 3]

(G3)

In General Formula (G3) above, Q represents oxygen or sulfur. $Ar^1$, $Ar^2$, $Ar^3$, and $Ar^4$ each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is an organic compound which is a benzofuropyrimidine derivative or a benzothienopyrimidine derivative and represented by General Formula (G4) below. As represented by General Formula (G4) below, the organic compound has a structure in which a plurality of aromatic hydrocarbon rings are bonded (specifically, two to four aromatic hydrocarbon rings are bonded) to the 8-position of a benzofuropyrimidine skeleton or a benzothienopyrimidine skeleton and a hole-transport skeleton is included at the 4-position through a biphenyldiyl group.

[Chemical Formula 4]

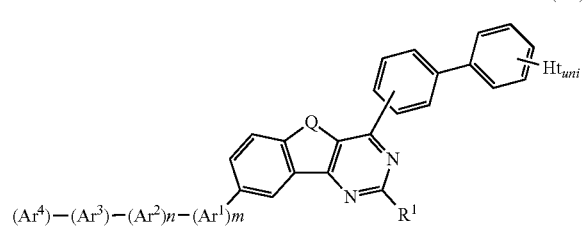

(G4)

In General Formula (G4) above, Q represents oxygen or sulfur. $Ar^1$, $Ar^2$, $Ar^3$, and $Ar^4$ each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

In each of the above structures, $Ht_{uni}$ in General Formulae (G2), (G3), and (G4) above each independently have any one of a pyrrole ring structure, a furan ring structure, and a thiophene ring structure.

In each of the above structures, $Ht_{uni}$ in General Formulae (G2), (G3), and (G4) above are each independently represented by any one of General Formulae (Ht-1) to (Ht-26) below.

[Chemical Formulae 5]

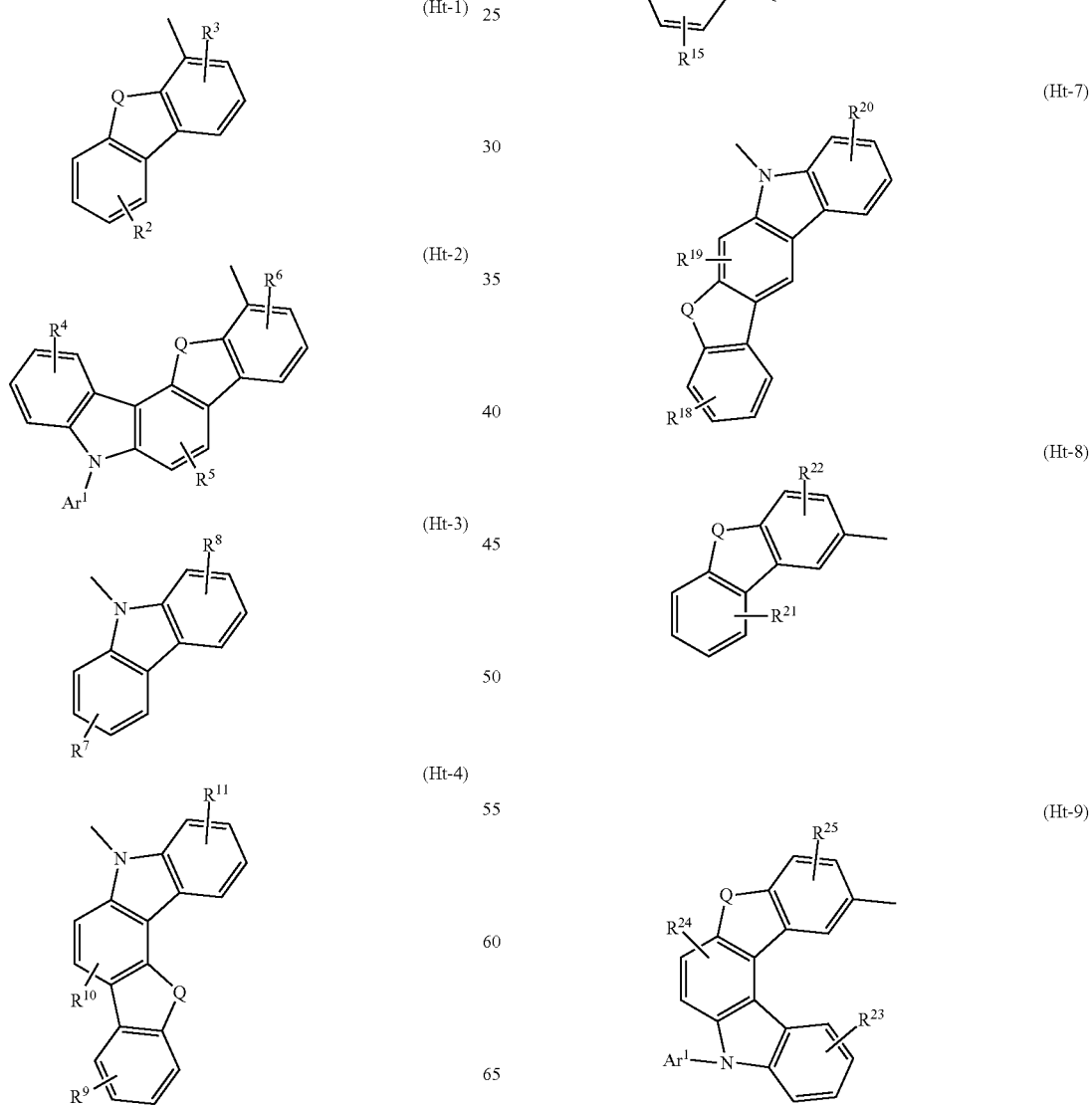

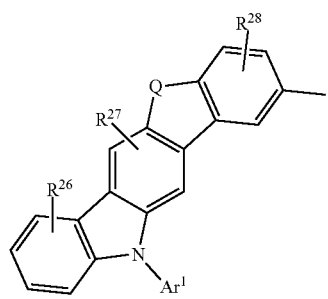
(Ht-10)
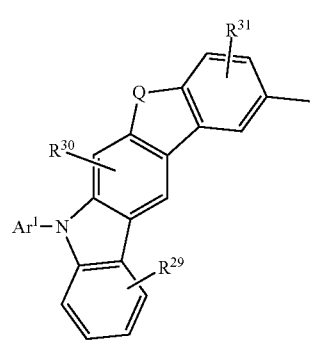
(Ht-11)
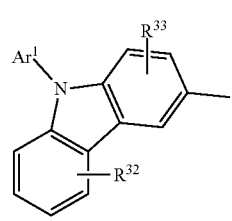
(Ht-12)
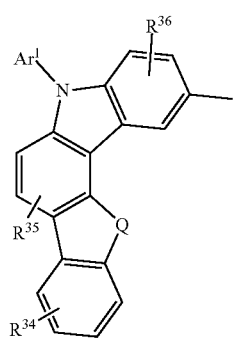
(Ht-13)
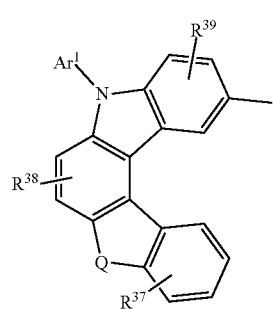
(Ht-14)
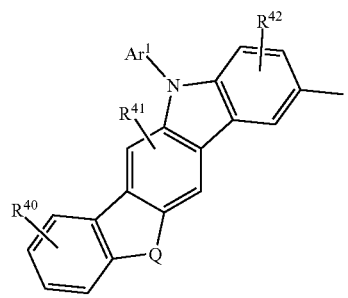
(Ht-15)
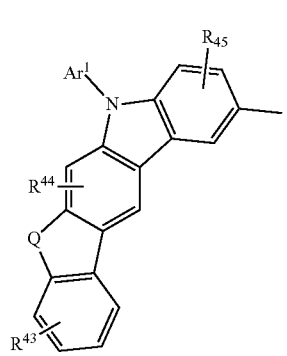
(Ht-16)
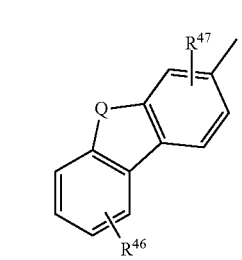
(Ht-17)
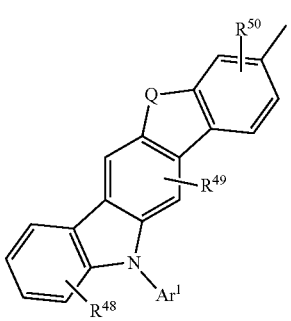
(Ht-18)
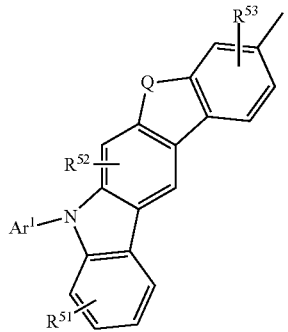
(Ht-19)

(Ht-20) 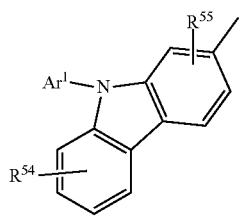

(Ht-21) 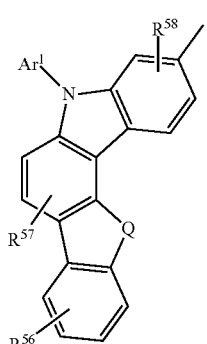

(Ht-22) 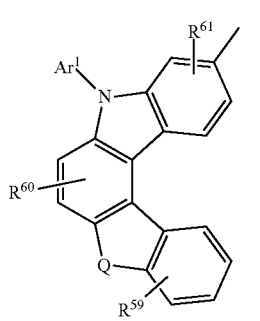

(Ht-23) 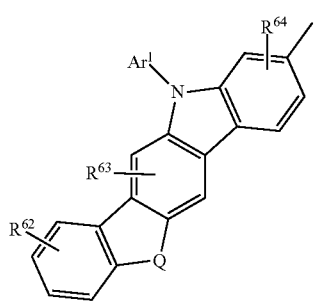

(Ht-24) 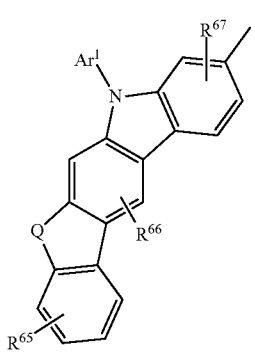

(Ht-25) 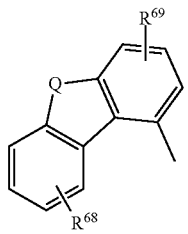

(Ht-26) 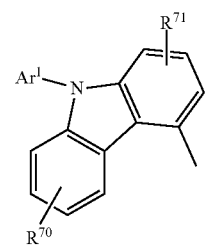

In General Formulae (Ht-1) to (Ht-26) above, Q represents oxygen or sulfur. Furthermore, $R^2$ to $R^{71}$ each represent 1 to 4 substituents and each independently represent any one of hydrogen, an alkyl group having 1 to 6 carbon atoms, and a substituted or unsubstituted phenyl group. Furthermore, $Ar^1$ represents a substituted or unsubstituted aryl group having 6 to 13 carbon atoms.

In each of the above structures, $Ar^1$, $Ar^2$, $Ar^3$, and $Ar^4$ in General Formulae (G1), (G2), (G3), and (G4) above each independently represent a substituted or unsubstituted benzene ring or naphthalene ring.

In each of the above structures, $Ar^1$, $Ar^2$, $Ar^3$, and $Ar^4$ in General Formulae (G1), (G2), (G3), and (G4) above are the same.

In each of the above structures, $Ar^1$, $Ar^2$, $Ar^3$, and $Ar^4$ in General Formulae (G1), (G2), (G3), and (G4) above are not substituted.

In each of the above structures, General Formula (G-X) below, which is a substructure in General Formulae (G1), (G2), (G3), and (G4) above, is represented by any one of Structural Formulae (G-X-p1) to (G-X-p12) and (G-X-n1) to (G-X-n6) below.

[Chemical Formula 6]

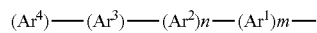

(G-X)

[Chemical Formulae 7]

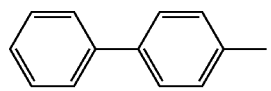

(G-X-p1)

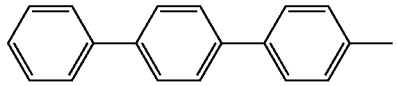

(G-X-p2)

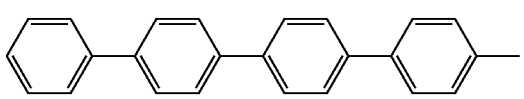

(G-X-p3)

(G-X-p4)
(G-X-p5)
(G-X-p6)
(G-X-p7)
(G-X-p8)
(G-X-p9)
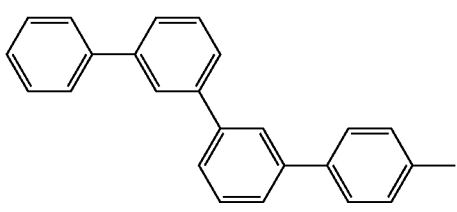
(G-X-p10)
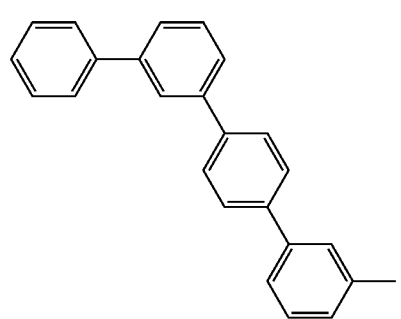
(G-X-p11)
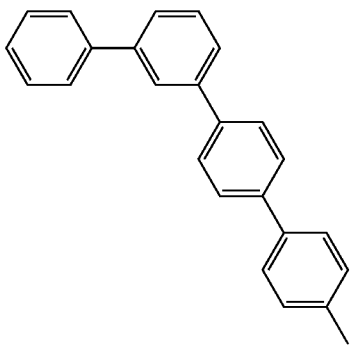
(G-X-p12)
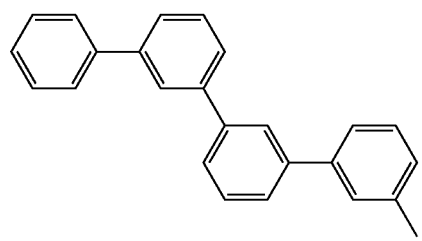
(G-X-n1)
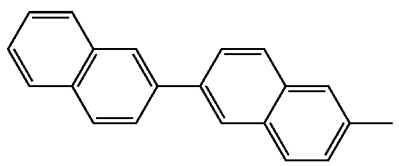
(G-X-n2)
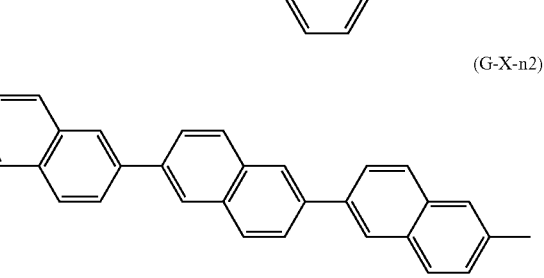
(G-X-n3)
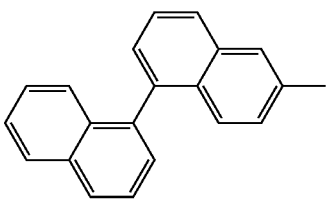
(G-X-n4)
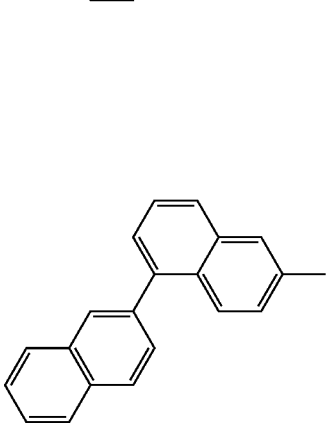

-continued (G-X-n5)

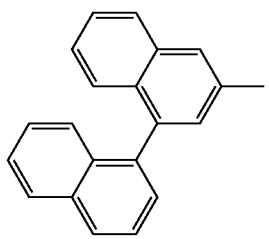

(G-X-n6)

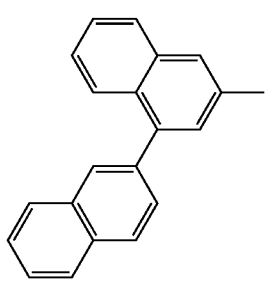

Another embodiment of the present invention is an organic compound represented by any one of Structural Formulae (100), (101), and (102).

[Chemical Formulae 8]

(100)

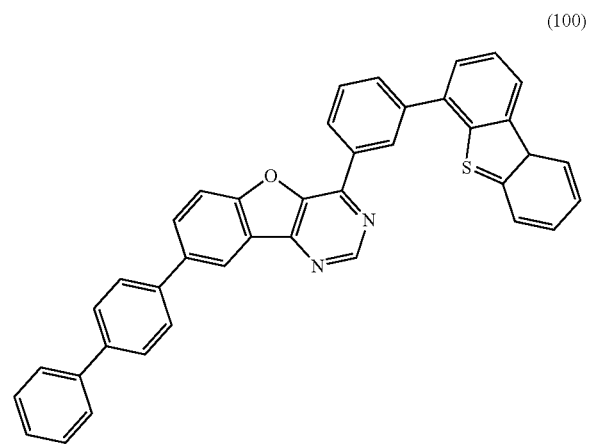

(101)

(102)

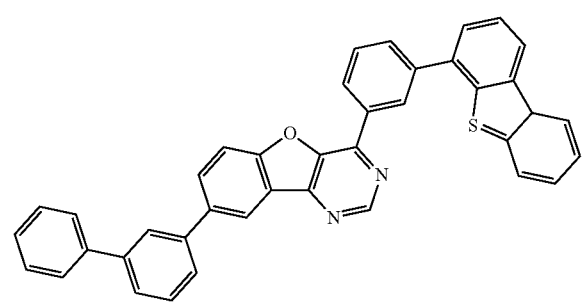

Another embodiment of the present invention is a light-emitting element using the above-described organic compound of one embodiment of the present invention. The present invention also includes a light-emitting element including a guest material in addition to the above-described organic compound. The present invention also includes a light-emitting element including a phosphorescent material in addition to the above-described organic compound. The present invention also includes a light-emitting element including a phosphorescent material and a carbazole derivative in addition to the above-described organic compound. Note that examples of the carbazole derivative include an aromatic amine including a bicarbazole derivative or a carbazolyl group.

Another embodiment of the present invention is a light-emitting element using the above-described organic compound of one embodiment of the present invention is used. Note that the present invention also includes a light-emitting element that is formed using the organic compound of one embodiment of the present invention for an EL layer between a pair of electrodes and a light-emitting layer in the EL layer. In addition to the above-described light-emitting elements, the present invention also includes a light-emitting element including a layer (e.g., a cap layer) that is in contact with an electrode and includes an organic compound. In addition to the light-emitting elements, a light-emitting device including a transistor, a substrate, and the like is also included in the scope of the invention. Furthermore, in addition to the light-emitting device, an electronic device and a lighting device that include a microphone, a camera, an operation button, an external connection portion, a housing, a cover, a support base, a speaker, or the like are also included in the scope of the invention.

In addition, the scope of one embodiment of the present invention includes a light-emitting device including a light-emitting element, and a lighting device including the light-emitting device. Accordingly, the light-emitting device in this specification refers to an image display device or a light source (including a lighting device). In addition, a light-emitting device includes a module in which a light-emitting device is connected to a connector such as an FPC (Flexible printed circuit) or a TCP (Tape Carrier Package), a module in which a printed wiring board is provided on the tip of a TCP, or a module in which an IC (integrated circuit) is directly mounted on a light-emitting element by a COG (Chip On Glass) method.

Effect of the Invention

In one embodiment of the present invention, a novel organic compound can be provided. In another embodiment of the present invention, a benzofuropyrimidine derivative or a benzothienopyrimidine derivative that is a novel organic compound can be provided. In one embodiment of the present invention, a novel organic compound that can be used in a light-emitting element can be provided. In one embodiment of the present invention, a novel organic compound that can be used in an EL layer of a light-emitting element can be provided. In addition, a highly reliable and novel light-emitting element can be provided by using a novel organic compound of one embodiment of the present invention. In addition, a novel light-emitting device, a novel electronic device, or a novel lighting device can be provided.

MODE FOR CARRYING OUT THE INVENTION

Figure 1A:
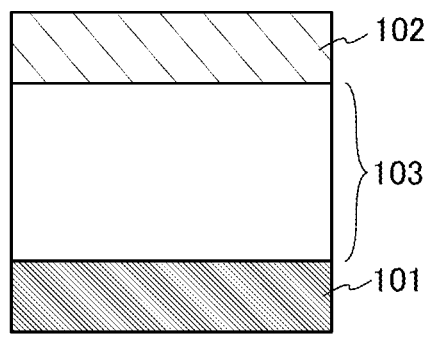
FIGS. 1A-1E are drawings illustrating structures of light-emitting elements.

Embodiments of the present invention are described in detail below with reference to drawings. Note that the present invention is not limited to the following description, and the modes and details of the present invention can be modified in various ways without departing from the spirit and scope of the present invention. Thus, the present invention should not be construed as being limited to the descriptions in the following embodiments.

Note that the position, size, range, or the like of each component illustrated in drawings and the like is not accurately represented in some cases for easy understanding. Therefore, the disclosed invention is not necessarily limited to the position, size, range, or the like disclosed in drawings and the like.

Furthermore, when describing the structures of the invention with reference to the drawings in this specification and the like, the reference numerals denoting the same components are commonly used in different drawings.

Embodiment 1

In this embodiment, organic compounds of embodiments of the present invention will be described. Note that an organic compound of one embodiment of the present invention is a benzofuropyrimidine derivative or a benzothienopyrimidine derivative represented by General Formula (G1) below. As represented by General Formula (G1) below, the organic compound of one embodiment of the present invention has a structure in which a plurality of aromatic hydrocarbon rings are bonded (specifically, two to four aromatic hydrocarbon rings are bonded) to the 8-position of a benzofuropyrimidine skeleton or a benzothienopyrimidine skeleton.

[Chemical Formula 9]

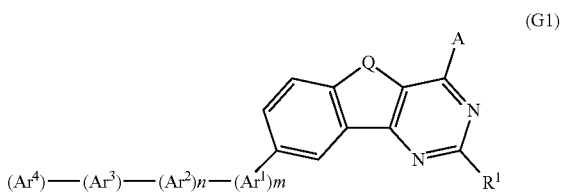

(G1)

In General Formula (G1), Q represents oxygen or sulfur. $Ar^1$, $Ar^2$, $Ar^3$, and $Ar^4$ each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is an organic compound represented by General Formula (G2) below. The organic compound represented by General Formula (G2) below has a structure in which a plurality of aromatic hydrocarbon rings are bonded (specifically, two to four aromatic hydrocarbon rings are bonded) to the 8-position of a benzofuropyrimidine skeleton or a benzothienopyrimidine skeleton and at least a hole-transport skeleton is included at the 4-position.

[Chemical Formula 10]

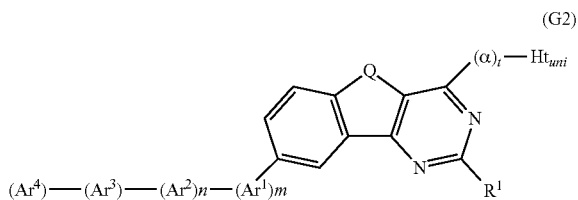

(G2)

In General Formula (G2) above, Q represents oxygen or sulfur. $Ar^1$, $Ar^2$, $Ar^3$, and $Ar^4$ represent the same group and each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, a represents a substituted or unsubstituted phenylene group, and t represents an integer of 0 to 4. In addition, $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is an organic compound represented by General Formula (G3) below. The organic compound represented by General Formula (G3) below has a structure in which a plurality of aromatic hydrocarbon rings are bonded (specifically, two to four aromatic hydrocarbon rings are bonded) to the 8-position of a benzofuropyrimidine skeleton or a benzothienopyrimidine skeleton and a hole-transport skeleton is included at the 4-position through a phenylene group.

[Chemical Formula 11]

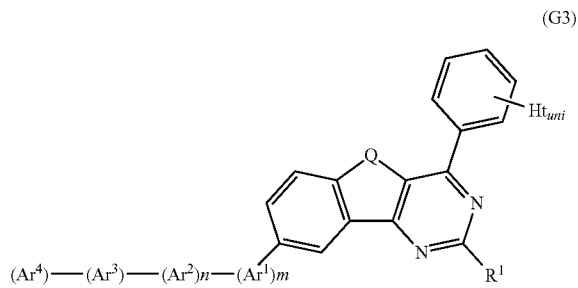

(G3)

In General Formula (G3) above, Q represents oxygen or sulfur. $Ar^1$, $Ar^2$, $Ar^3$, and $Ar^4$ each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is an organic compound represented by General Formula (G4) below. The organic compound represented by General Formula (G4) below has a structure in which a plurality of aromatic hydrocarbon rings are bonded (specifically, two to four aromatic hydrocarbon rings are bonded) to the 8-position of a benzofuropyrimidine skeleton or a benzothienopyrimidine skeleton and a hole-transport skeleton is included at the 4-position through a biphenyldiyl group.

[Chemical Formula 12]

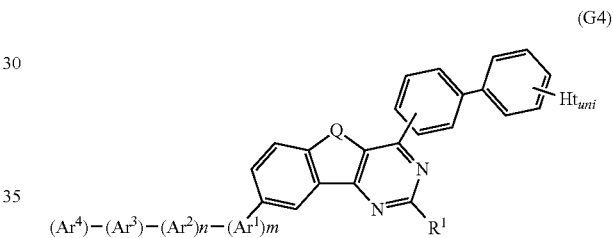

(G4)

In General Formula (G4) above, Q represents oxygen or sulfur. $Ar^1$, $Ar^2$, $Ar^3$, and $Ar^4$ each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, $Ht_{uni}$ represents a hole-transport skeleton. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

Note that $Ht_{uni}$ in General Formulae (G2), (G3), and (G4) above represent hole-transport skeletons each independently having any one of a pyrrole ring structure, a furan ring structure, and a thiophene ring structure.

In addition, $Ht_{uni}$ in General Formulae (G2), (G3), and (G4) above represent hole-transport skeletons that are each independently represented by any one of General Formulae (Ht-1) to (Ht-26) below.

[Chemical Formulae 13]
(Ht-1)
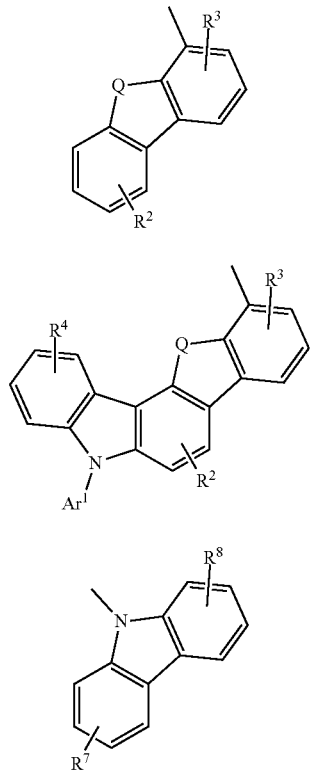
(Ht-2)
(Ht-3)
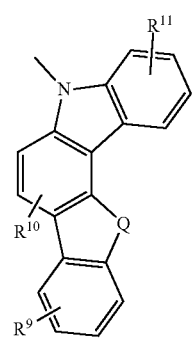
(Ht-4)
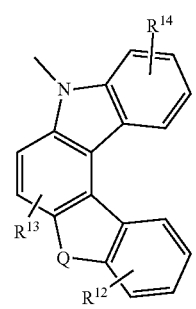
(Ht-5)
(Ht-6)
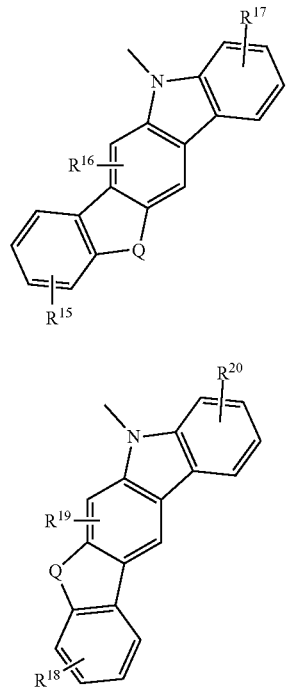
(Ht-7)
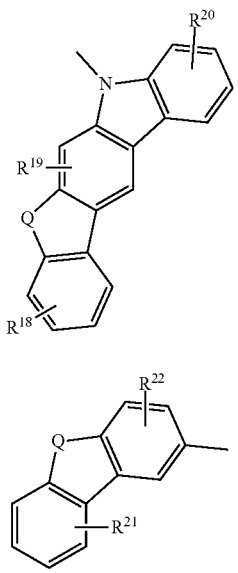
(Ht-8)
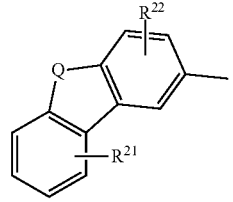
(Ht-9)
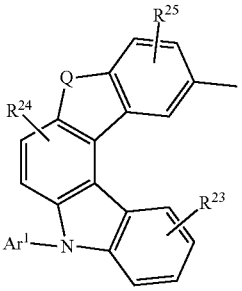
(Ht-10)
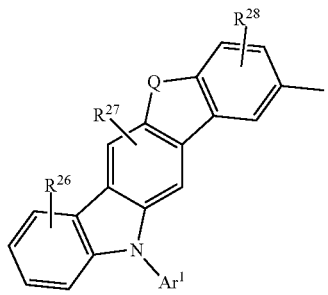

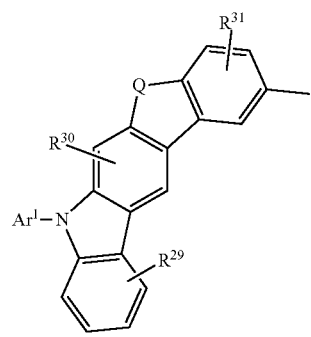
(Ht-11)
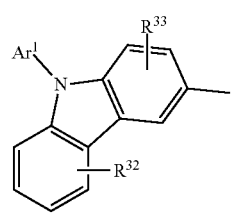
(Ht-12)
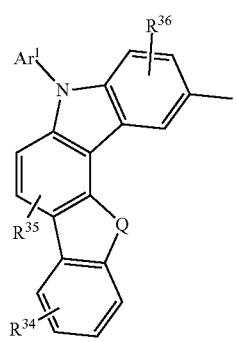
(Ht-13)
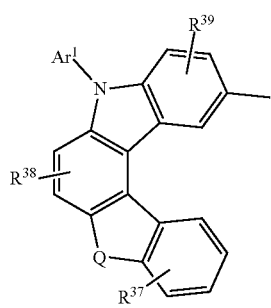
(Ht-14)
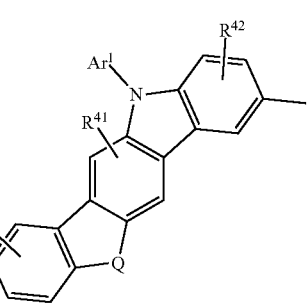
(Ht-15)
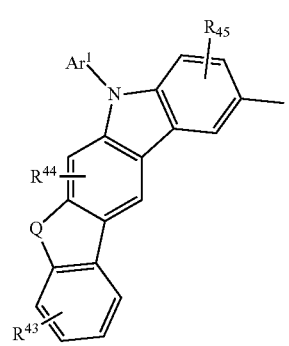
(Ht-16)
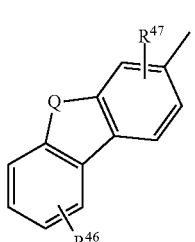
(Ht-17)
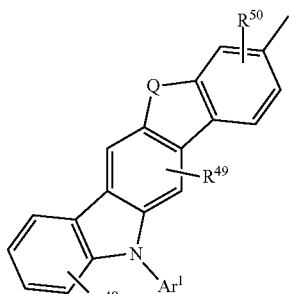
(Ht-18)
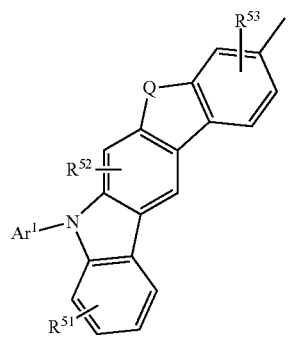
(Ht-19)
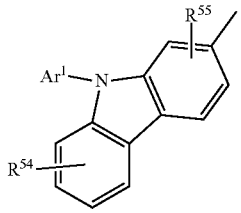
(Ht-20)

(Ht-21)

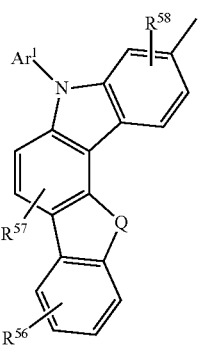

(Ht-22)

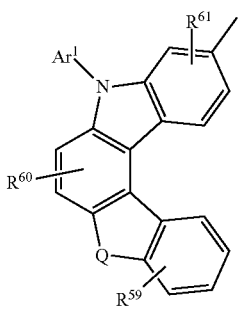

(Ht-23)

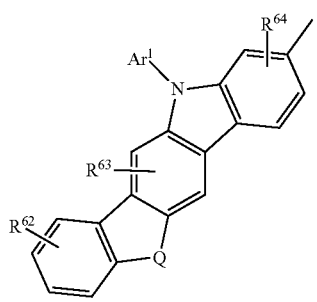

(Ht-24)

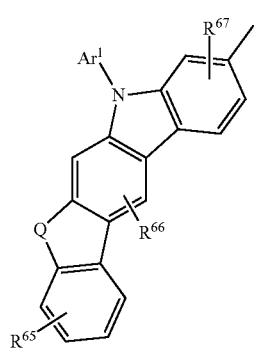

(Ht-25)

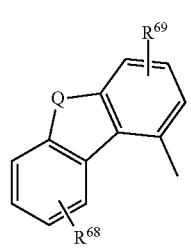

(Ht-26)

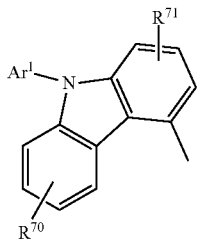

In General Formulae (Ht-1) to (Ht-26) above, Q represents oxygen or sulfur. Furthermore, $R^2$ to $R^{71}$ each represent 1 to 4 substituents and each independently represent any one of hydrogen, an alkyl group having 1 to 6 carbon atoms, and a substituted or unsubstituted phenyl group. Furthermore, $Ar^1$ represents a substituted or unsubstituted aryl group having 6 to 13 carbon atoms.

Note that $Ht_{uni}$ in General Formulae (G2), (G3), and (G4) above represent hole-transport skeletons; the use of the organic compound with this skeleton in combination with another substance (e.g., a light-emitting substance) in a light-emitting element can improve the element characteristics.

Note that in the case where the substituted or unsubstituted aromatic hydrocarbon ring in General Formulae (G1), (G2), (G3), and (G4) has a substituent, the substituent is any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group; for example, a methyl group, an ethyl group, a propyl group, an isopropyl group, a butyl group, an isobutyl group, a sec-butyl group, a tert-butyl group, and a pentyl group are given.

Note that in the case where the substituted or unsubstituted monocyclic saturated hydrocarbon group having 5 to 7 carbon atoms, the substituted or unsubstituted polycyclic saturated hydrocarbon group having 7 to 10 carbon atoms, the substituted or unsubstituted aryl group having 6 to 13 carbon atoms, the substituted or unsubstituted heteroaryl group having 3 to 12 carbon atoms, or the substituted or unsubstituted phenylene group in General Formulae (G1), (G2), (G3), and (G4) above has a substituent, examples of the substituent include an alkyl group having 1 to 7 carbon atoms such as a methyl group, an ethyl group, a propyl group, an isopropyl group, a butyl group, an isobutyl group, a sec-butyl group, a tert-butyl group, a pentyl group, or a hexyl group, a cycloalkyl group having 5 to 7 carbon atoms such as a cyclopentyl group, a cyclohexyl group, a cycloheptyl group, or a 8,9,10-trinorbornanyl group, and an aryl group having 6 to 12 carbon atoms such as a phenyl group, a naphthyl group, or a biphenyl group.

Moreover, $Ar^1$, $Ar^2$, $Ar^3$, and $Ar^4$ in General Formulae (G1), (G2), (G3), and (G4) above each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. Note that the aromatic hydrocarbon ring represents a monovalent or divalent aromatic hydrocarbon group, and specific examples of the aromatic hydrocarbon group having 6 to 25 carbon atoms are a phenyl group, a phenylene group, a naphthyl group, a naphthylene group, a fluorenyl group, a fluorenediyl group, a spirofluorenyl group, a spirofluorenediyl group, a triphenylene group, and a triphenylenediyl group. Note that it is preferable that polyacene, which is an aromatic hydrocarbon ring having three or more rings, be not used in order not to decrease the T1 level more than necessary. Note that the above-described fluorenyl group and fluorenediyl group each preferably have a substituent such as an alkyl group or a phenyl group at the 9-position.

Note that $Ar^1$, $Ar^2$, $Ar^3$, and $Ar^4$ in General Formulae (G1), (G2), (G3), and (G4) above each represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25, whereby the T1 level of the organic compound can be a desired value. Moreover, adequate sublimability can be maintained, and accordingly, decomposition in sublimation purification or vacuum evaporation can be suppressed. Furthermore, as described in one embodiment of the present invention, a plurality of aromatic hydrocarbon rings are bonded, whereby the organic compound used in a light-emitting element can have improved reliability compared to the case where the number of the aromatic hydrocarbon rings is one. In particular, the initial degradation of a light-emitting element can be suppressed compared to the case where a substituent including a heteroaromatic ring is introduced at the 8-position of a benzofuropyrimidine skeleton or a benzothienopyrimidine skeleton.

Furthermore, $Ar^1$, $Ar^2$, $Ar^3$, and $Ar^4$ in General Formulae (G1), (G2), (G3), and (G4) above may each independently represent a substituted or unsubstituted benzene ring or naphthalene ring.

Alternatively, $Ar^1$, $Ar^2$, $Ar^3$, and $Ar^4$ in General Formulae (G1), (G2), (G3), and (G4) above may be the same.

In addition, General Formula (G-X) below, which is a substructure in General Formulae (G1), (G2), (G3), and (G4) above, may be any one of Structural Formulae (G-X-p1) to (G-X-p12) and (G-X-n1) to (G-X-n6) below.

[Chemical Formula 14]

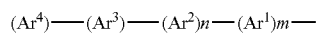
(G-X)

[Chemical Formulae 15]

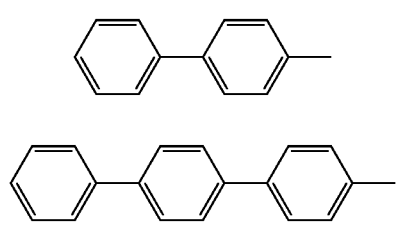

(G-X-p1)

(G-X-p2)

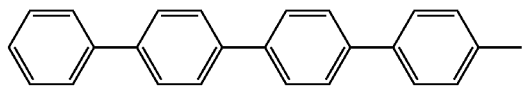
(G-X-p3)

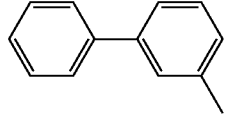
(G-X-p4)

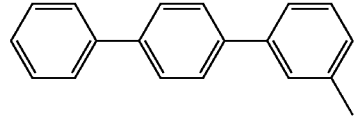
(G-X-p5)

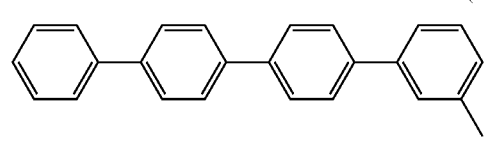
(G-X-p6)

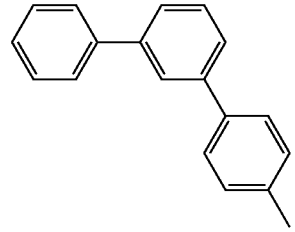
(G-X-p7)

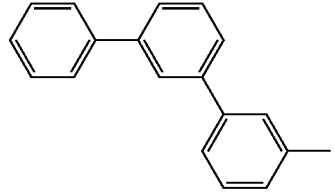
(G-X-p8)

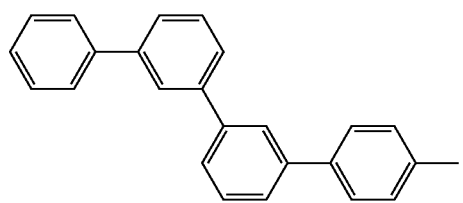
(G-X-p9)

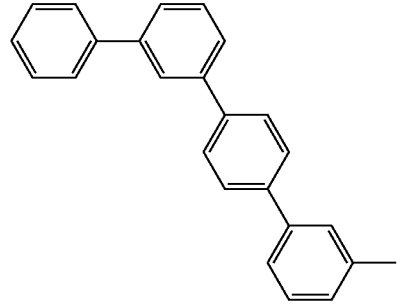
(G-X-p10)

(G-X-p11)
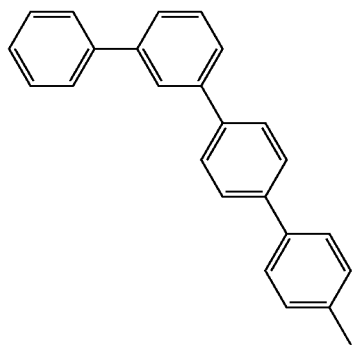

(G-X-p12)
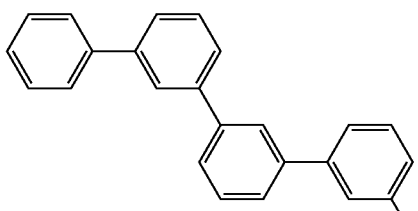

(G-X-n1)
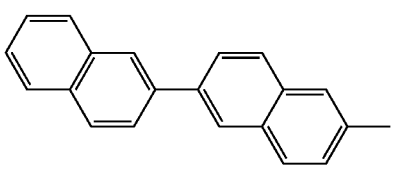

(G-X-n2)
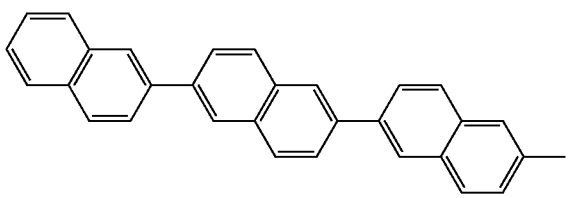

(G-X-n3)
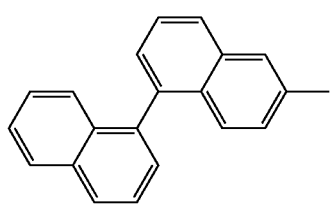

(G-X-n4)
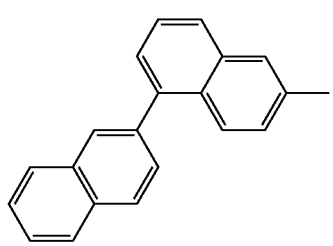

(G-X-n5)
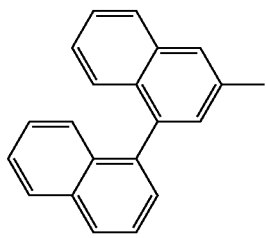

(G-X-n6)
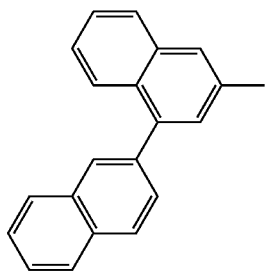

In the case where $R^1$ in General Formulae (G1), (G2), (G3), and (G4) above represents a monocyclic saturated hydrocarbon group having 5 to 7 carbon atoms, specific examples thereof include a cyclopropyl group, a cyclobutyl group, a cyclopentyl group, a cyclohexyl group, a 1-methylcyclohexyl group, and a cycloheptyl group.

In the case where $R^1$ in General Formulae (G1), (G2), (G3), and (G4) above represents a polycyclic saturated hydrocarbon group having 7 to 10 carbon atoms, specific examples thereof include a norbornyl group, an adamantyl group, a decalin group, and a tricyclodecyl group.

In the case where $R^1$ in General Formulae (G1), (G2), (G3), and (G4) above represents an aryl group having 6 to 13 carbon atoms, specific examples thereof include a phenyl group, an o-tolyl group, a m-tolyl group, a p-tolyl group, a mesityl group, an o-biphenyl group, a m-biphenyl group, a p-biphenyl group, a 1-naphthyl group, a 2-naphthyl group, and a fluorenyl group.

In the case where $R^1$ in General Formulae (G1), (G2), (G3), and (G4) above represents an alkyl group having 1 to 6 carbon atoms, specific examples thereof include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, and a 2,3-dimethylbutyl group.

In the case where $R^1$ in General Formulae (G1), (G2), (G3), and (G4) above represents a heteroaryl group having 3 to 12 carbon atoms, specific examples thereof include a triadinyl group, a pyrazinyl group, a pyrimidinyl group, a pyridinyl group, a quinolinyl group, an isoquinolinyl group, a benzothienyl group, a benzofuranyl group, an indolyl group, a dibenzothienyl group, a dibenzofuranyl group, and a carbazolyl group.

Note that when $R^1$ in General Formulae (G1), (G2), (G3), and (G4) above is any one of the above-described specific examples, the organic compound of one embodiment of the present invention has a high T1 level.

Next, specific structural formulae of the above-described organic compounds of embodiments of the present invention are shown below. Note that the present invention is not limited to these formulae.

[Chemical Formulae 16]
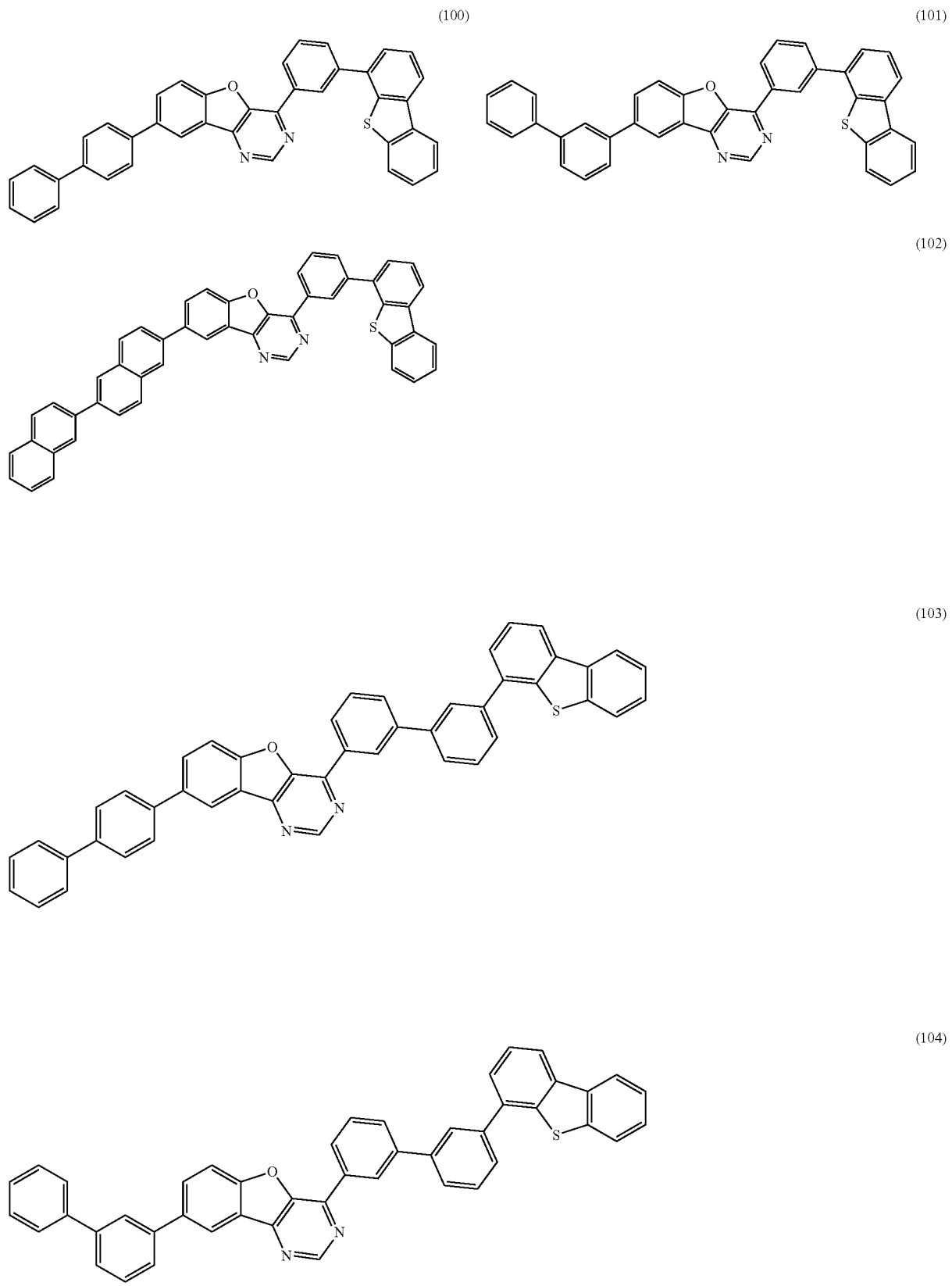

-continued
(105)
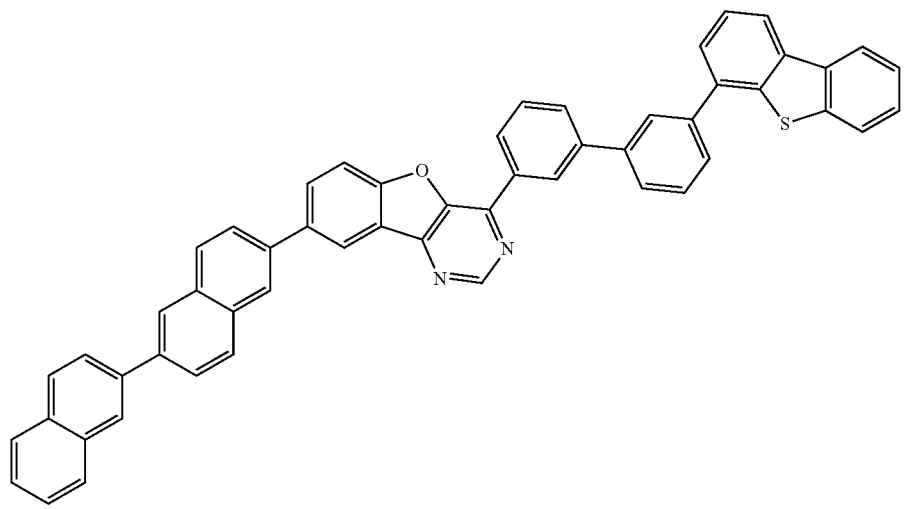
(106)
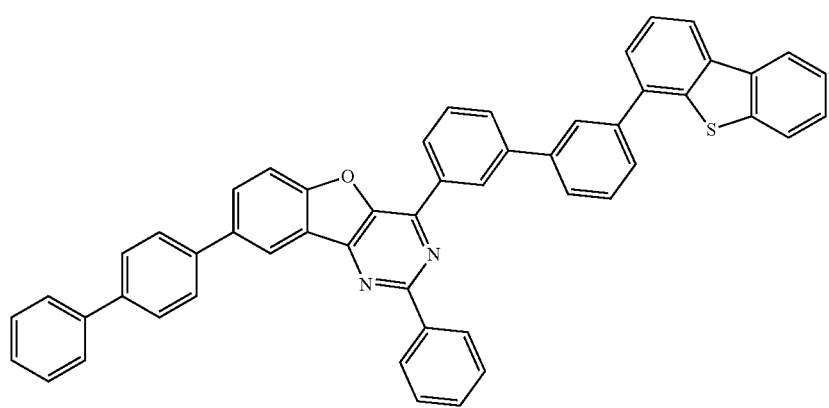
(107)
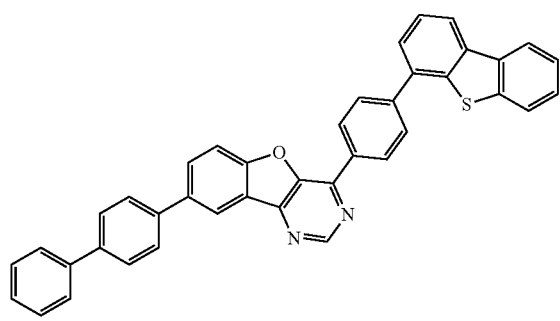

-continued
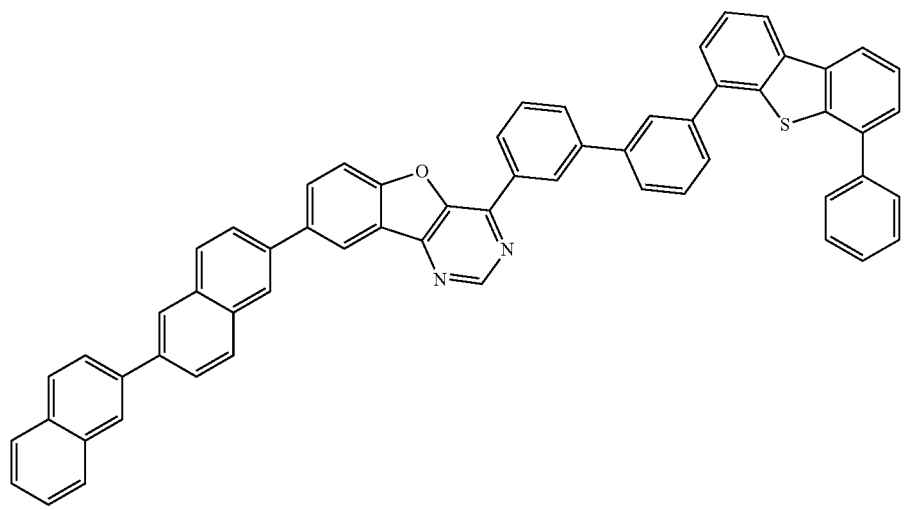
(108)
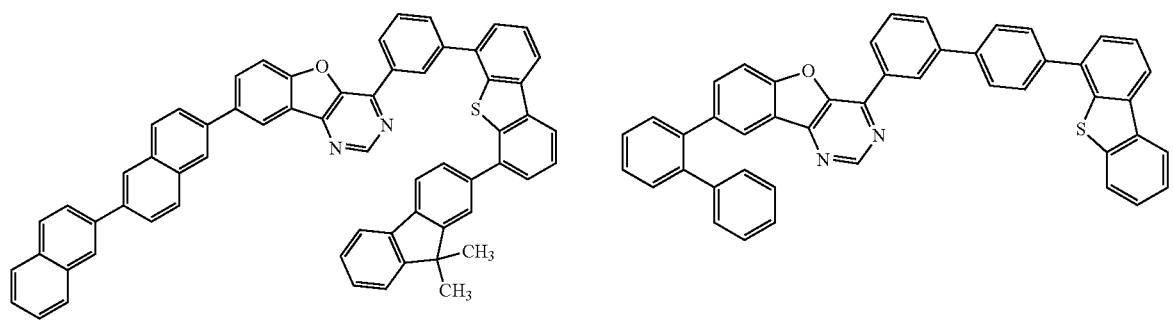
(109) (110)
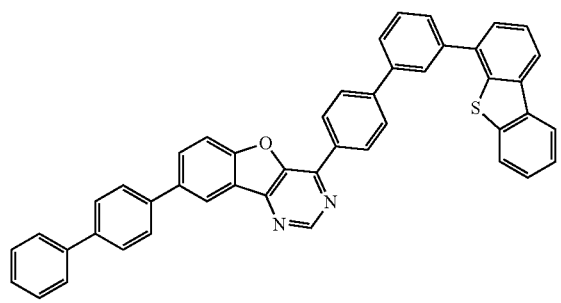
(111)

[Chemical Formulae 17]
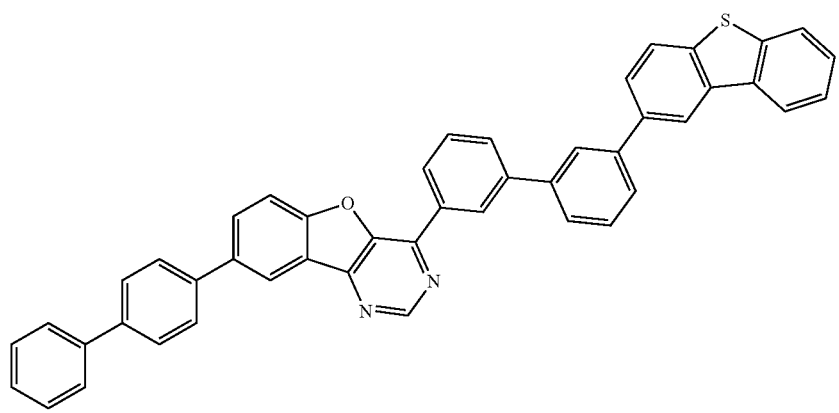
(112)
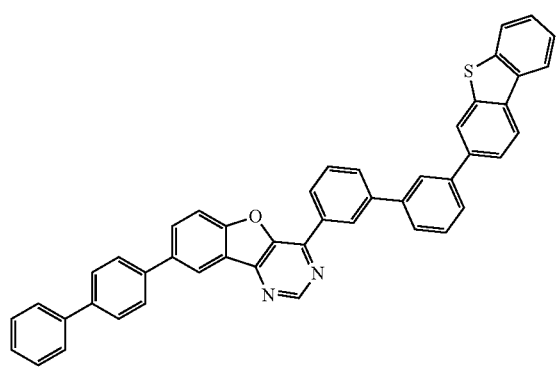
(113)
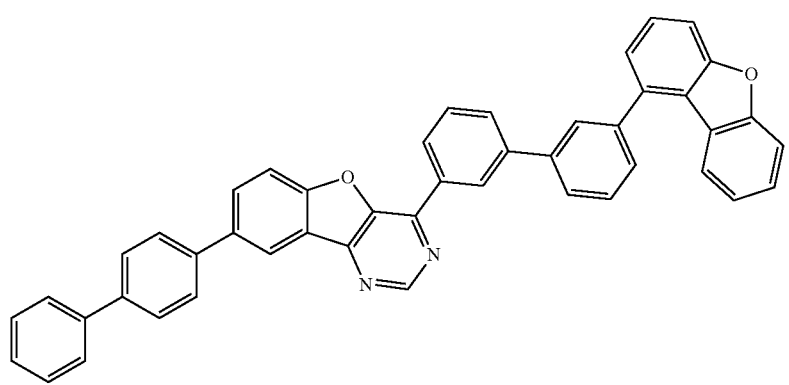
(114)
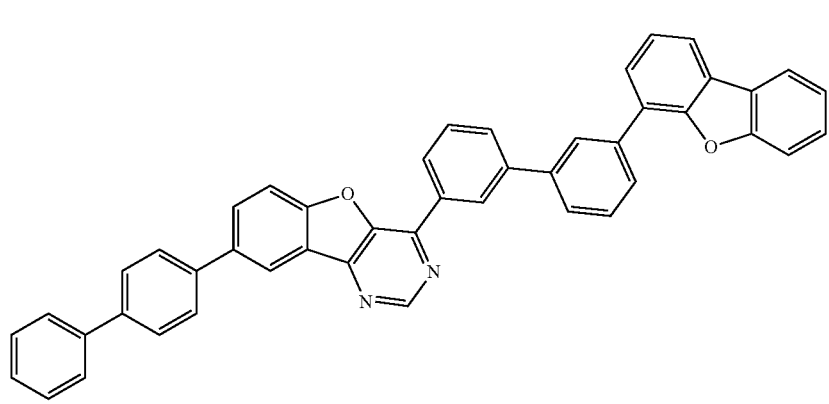
(115)

(116)
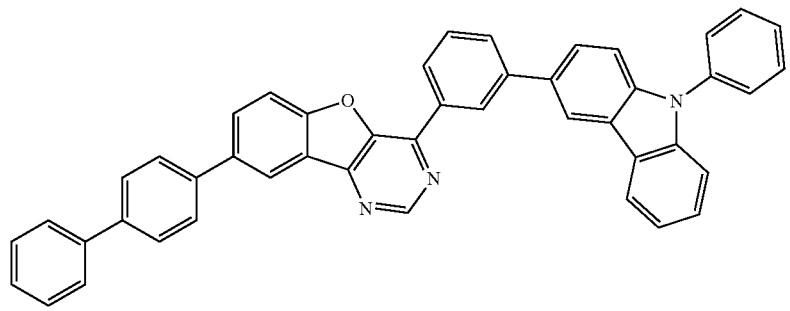
(117)
(118)
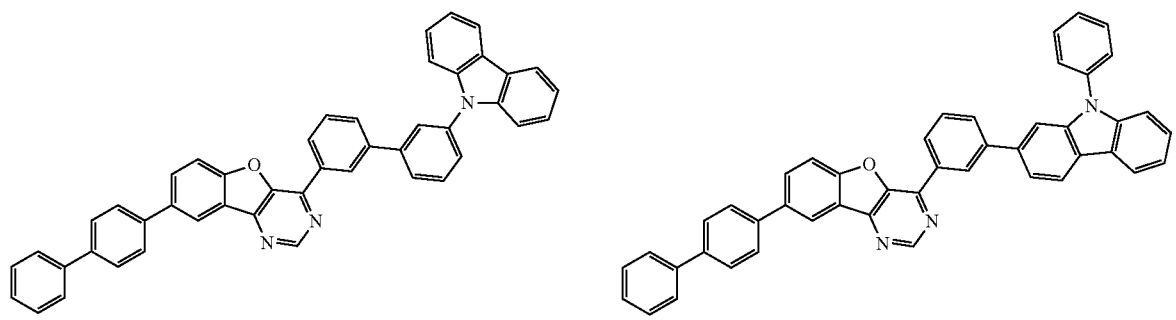
(119)
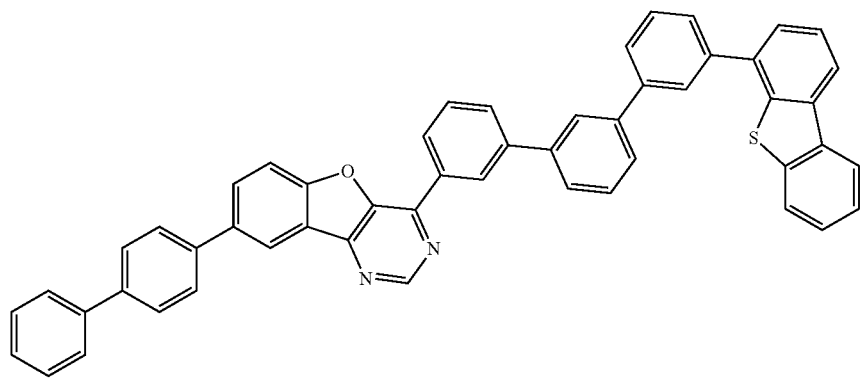
(120)
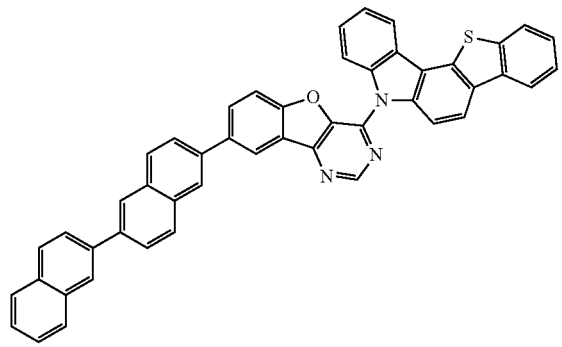

(121)
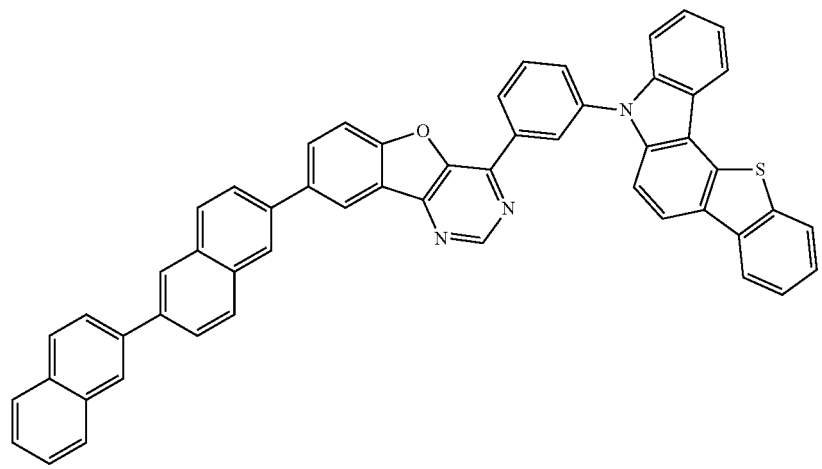
(122)
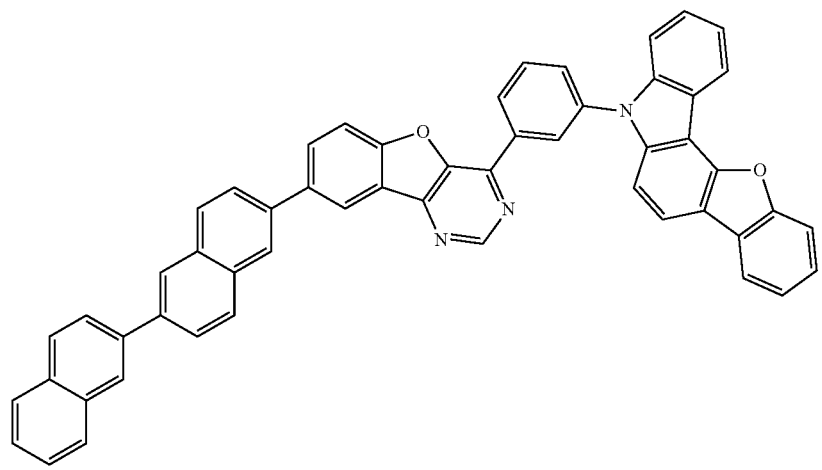
(123)
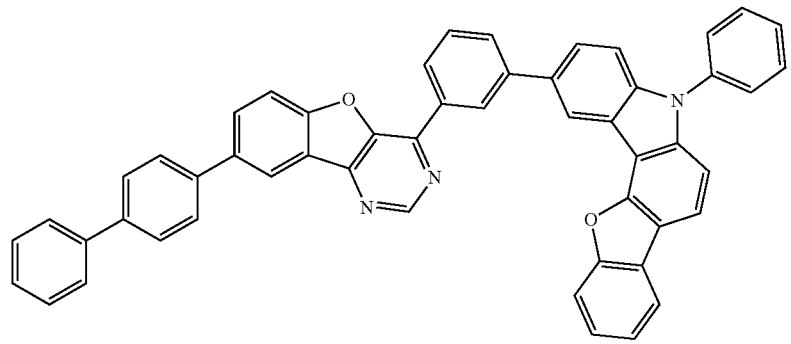

-continued
(124)
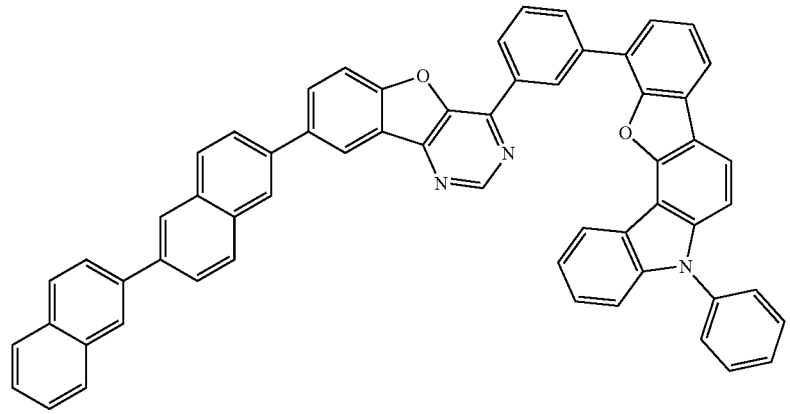
[Chemical Formulae 18]
(125)
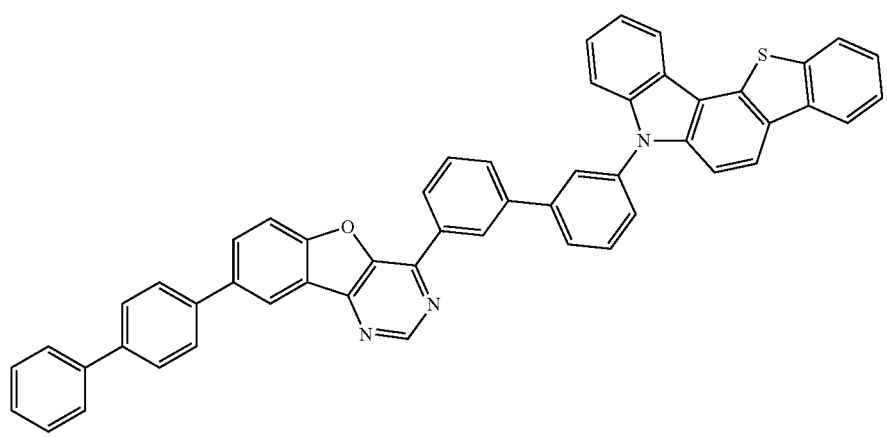
(126)
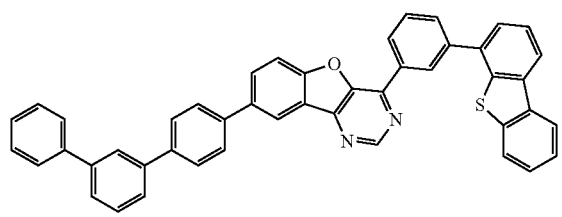
(127)
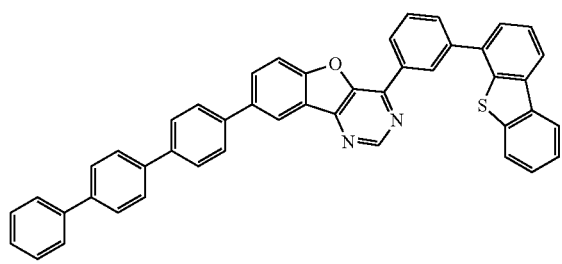

-continued
(128)
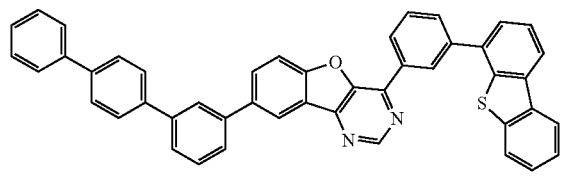
(129)
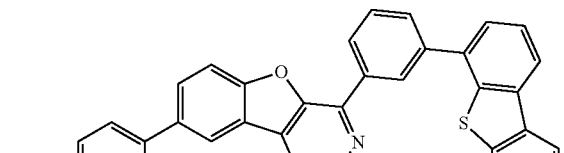
(130)
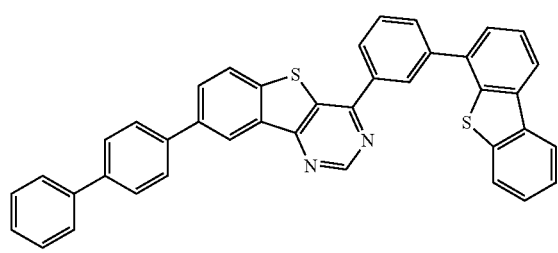
(131)
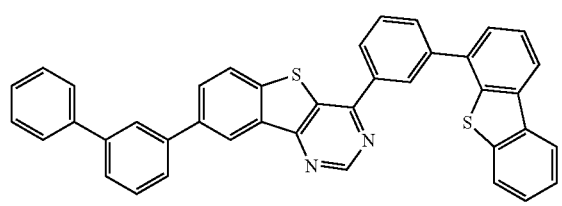
(132)
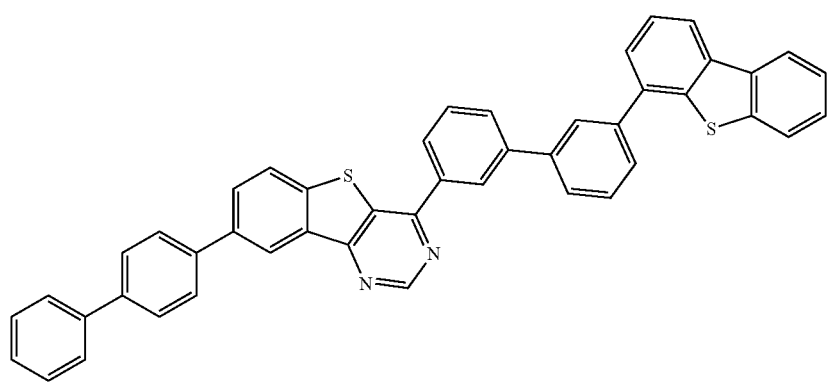
(133)
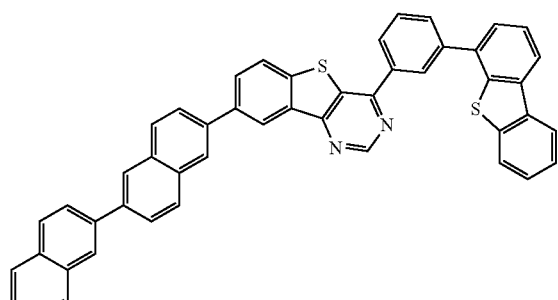
(134)
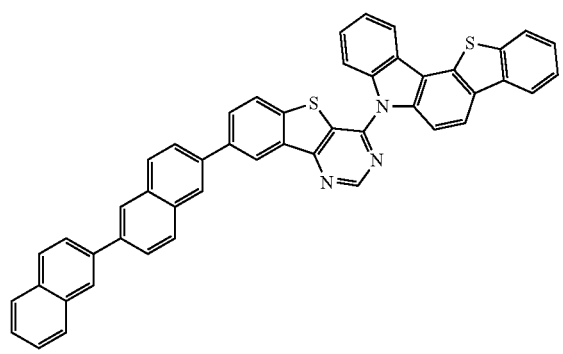

(135)
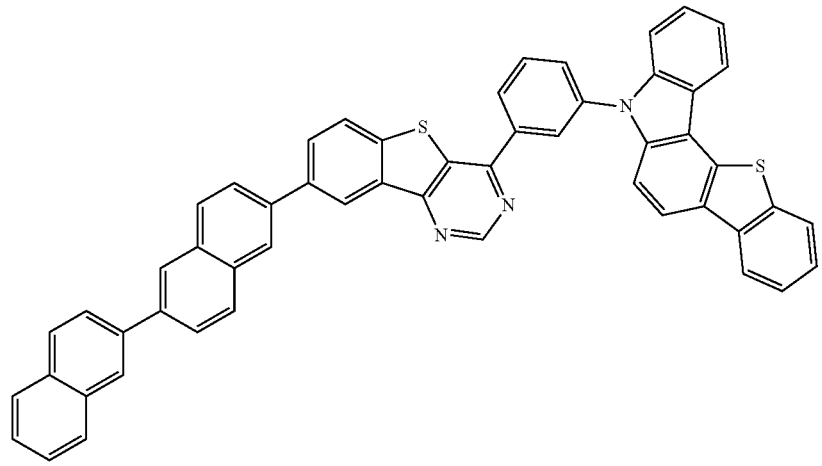
(136)
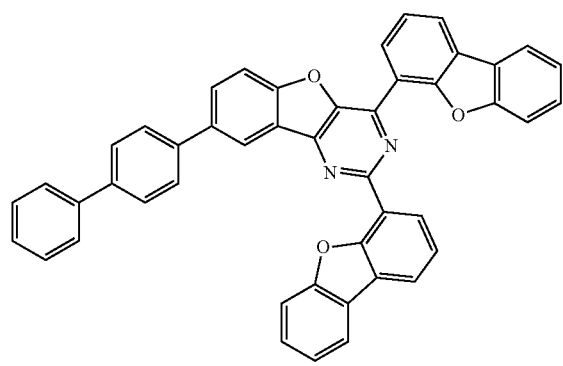
[Chemical Formulae 19]
(137)
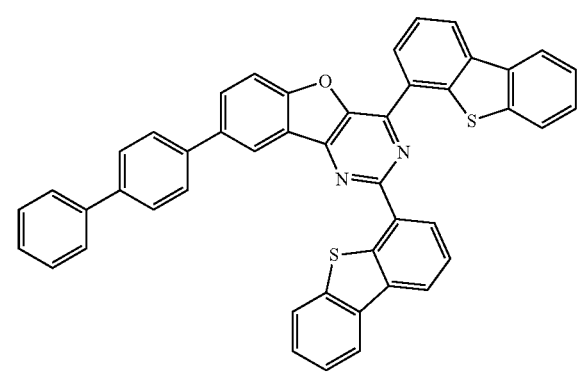
(138)
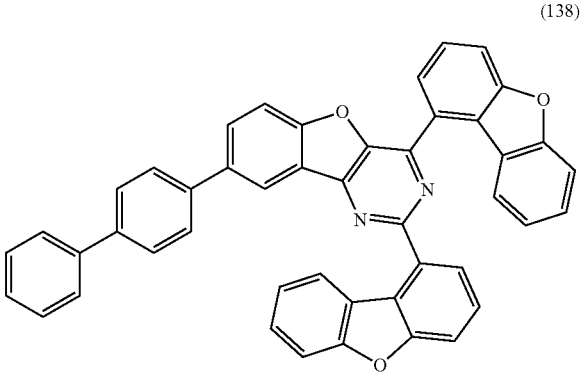

-continued (139)
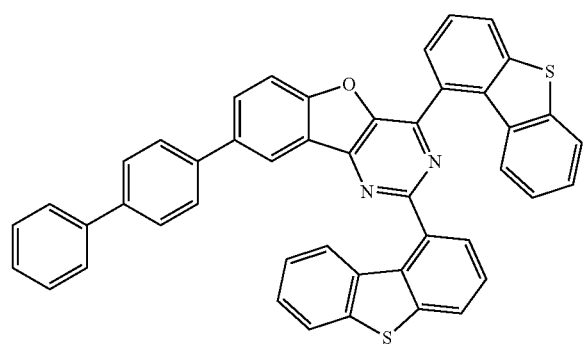

(140)
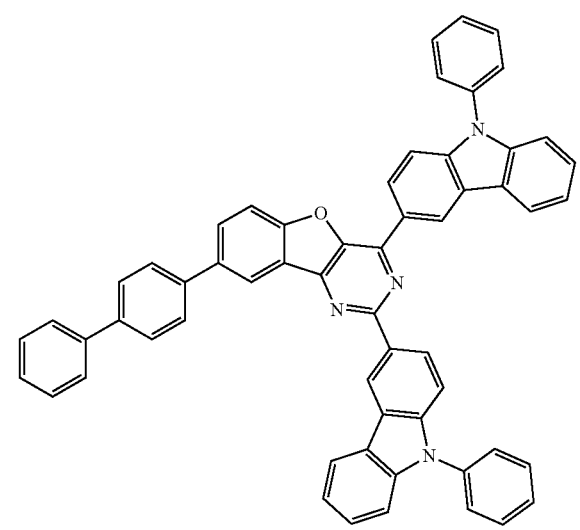

(141)
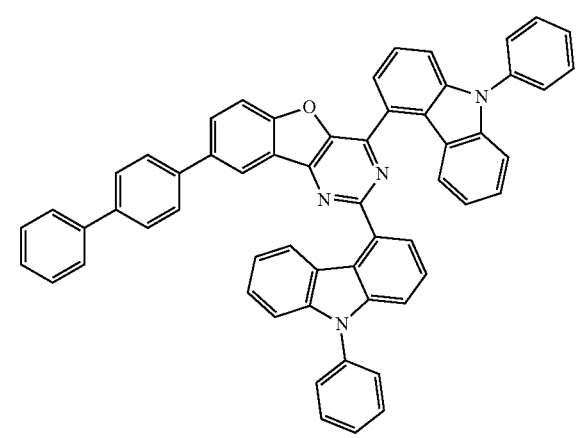

-continued (142)
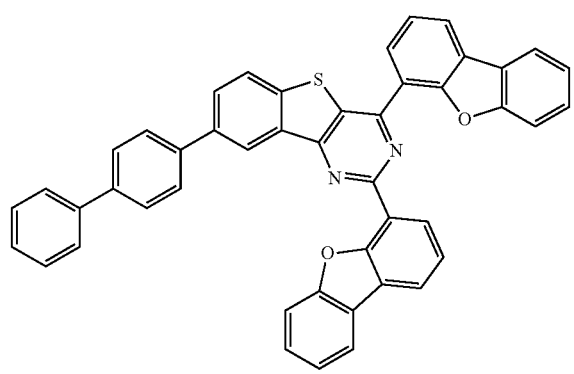

(143)

(144)
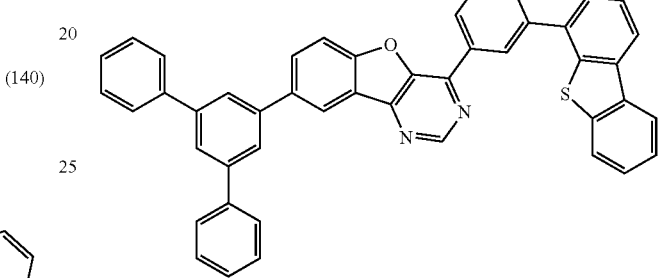

Note that although the organic compounds represented by Structural Formulae (100) to (144) are examples of the organic compound represented by General Formal (G1) above, the organic compound of one embodiment of the present invention is not limited thereto.

Next, a synthesis method of a benzofuropyrimidine derivative or a benzothienopyrimidine derivative, which is one embodiment of the present invention and represented by General Formula (G1) below, will be described.

[Chemical Formula 20]

(G1)
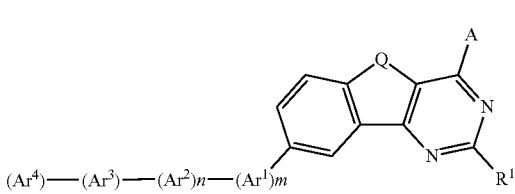

In General Formula (G1), Q represents oxygen or sulfur. $Ar^1$, $Ar^2$, $Ar^3$, and $Ar^4$ each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

<<Method for Synthesizing Organic Compound Represented by General Formula (G1)>>

A variety of reactions can be used for the synthesis of the organic compound represented by General Formula (G1) above; for example, the organic compound represented by General Formula (G1) can be synthesized by a simple method shown by synthesis schemes below.

The organic compound represented by General Formula (G1) can be obtained, as shown in Scheme (A-1) below, by reaction of a halogen compound (A1) including a benzofuropyrimidine skeleton or a benzothienopyrimidine skeleton including a substituent at the 8-position with a boronic acid compound of A (A2).

[Chemical Formulae 21]

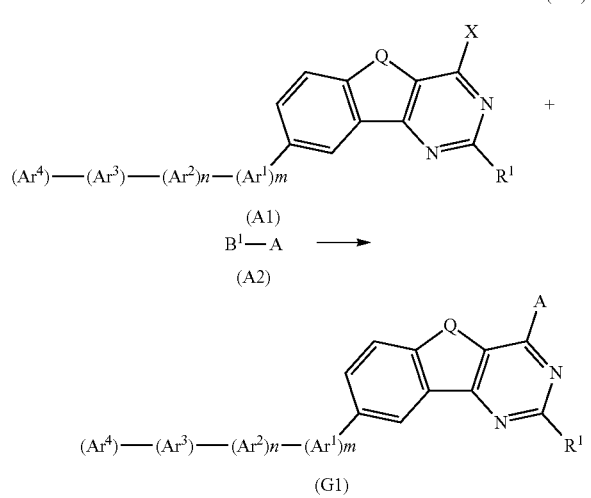

In Synthesis Scheme (A-1) above, X represents halogen and Q represents oxygen or sulfur. $Ar^1$, $Ar^2$, $Ar^3$, and $Ar^4$ each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

Alternatively, the organic compound represented by General Formula (G1) can be obtained, as shown in Synthesis Scheme (A-2) below, by reaction of a dihalogen compound (B1) including a benzofuropyrimidine skeleton or a benzothienopyrimidine skeleton with the boronic acid compound of A (A2) for obtaining an intermediate (B2), and subsequent reaction of the intermediate (B2) with a boronic acid compound (B3).

[Chemical Formulae 22]

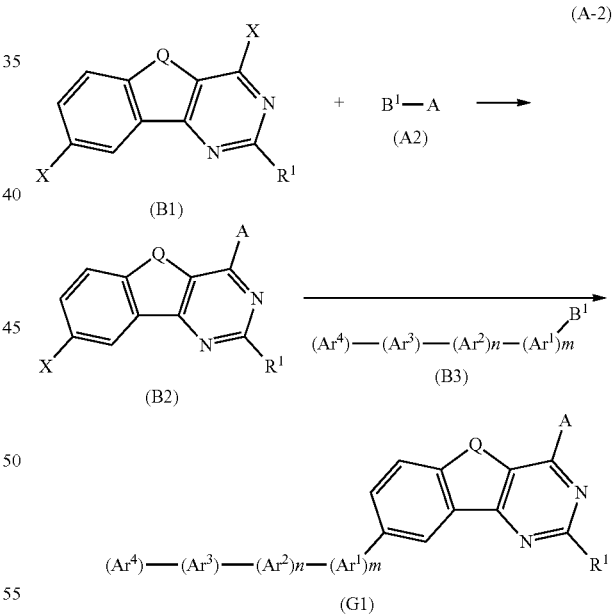

In Synthesis Scheme (A-2) above, Q represents oxygen or sulfur. $Ar^1$, $Ar^2$, $Ar^3$, and $Ar^4$ each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

Alternatively, the organic compound represented by General Formula (G1) can be obtained, as shown in Synthesis Scheme (A-3) below, by reaction of a trihalogen compound (C1) including a benzofuropyrimidine skeleton or a benzothienopyrimidine skeleton with the boronic acid compound of A (A2) for obtaining an intermediate (C2), subsequent reaction of the intermediate (C2) with a boronic acid compound of $R^1$ (C3) for obtaining an intermediate (C4), and subsequent reaction of the intermediate (C4) with the boronic acid compound (B3).

[Chemical Formulae 23]

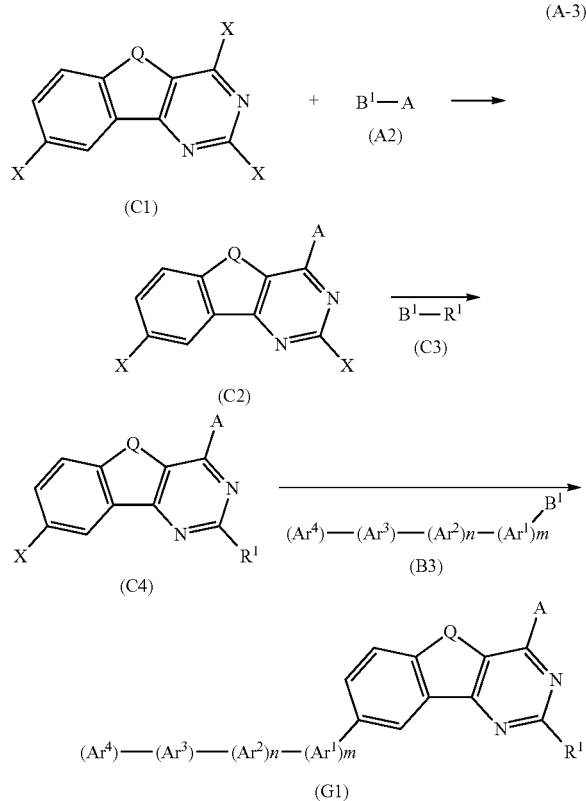

(A-3)

In Synthesis Scheme (A-3) above, Q represents oxygen or sulfur. $Ar^1$, $Ar^2$, $Ar^3$, and $Ar^4$ each independently represent a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is 6 to 25. In addition, m and n are each 0 or 1. Moreover, A is a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms. In addition, $B^1$ represents a boronic acid, a boronic ester, a cyclic-triolborate salt, or the like. As the cyclic-triolborate salt, a lithium salt, a potassium salt, or a sodium salt may be used.

Note that various kinds of the halogen compound (A1) including a benzofuropyrimidine skeleton or a benzothienopyrimidine skeleton including a skeleton at the 8-position, the boronic acid compound of A (A2), the dihalogen compound (B1) including a benzofuropyrimidine skeleton or a benzothienopyrimidine skeleton, the intermediate (B2), the boronic acid compound (B3), the trihalogen compound (C1) including a benzofuropyrimidine skeleton or a benzothienopyrimidine skeleton, the intermediate (C2), the boronic acid compound of $R^1$ (C3), and the intermediate (C4) used in Synthesis Schemes (A-1), (A-2), and (A-3) above are commercially available or can be synthesized; accordingly, many kinds of the benzofuropyrimidine derivatives or benzothienopyrimidine derivatives represented by General Formula (G1) can be synthesized. Thus, the organic compound of one embodiment of the present invention is characterized by having numerous variations.

Described above are the organic compounds of embodiments of the present invention and examples of their synthesis method; however, the present invention is not limited thereto and the organic compounds may be synthesized by another synthesis method.

The structures described in this embodiment can be used in an appropriate combination with the structures described in the other embodiments.

Embodiment 2

In this embodiment, a light-emitting element in which the organic compound described in Embodiment 1 is used will be described with reference to FIG. 1.

<<Basic Structure of Light-Emitting Element>>

First, a basic structure of a light-emitting element will be described. FIG. 1(A) illustrates an example of a light-emitting element including, between a pair of electrodes, an EL layer having a light-emitting layer. Specifically, the light-emitting element has a structure in which an EL layer 103 is sandwiched between a first electrode 101 and a second electrode 102.

Figure 1B:
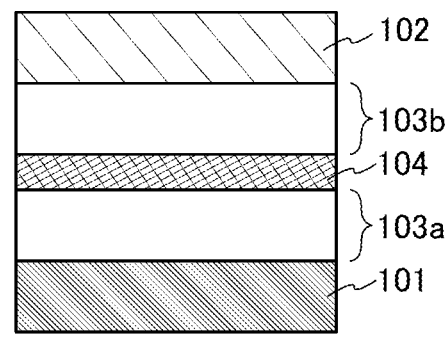

FIG. 1(B) illustrates an example of a light-emitting element with a stacked-layer structure (tandem structure) in which a plurality of (two layers, in FIG. 1(B)) EL layers (103a and 103b) are provided between a pair of electrodes and a charge-generation layer 104 is provided between the EL layers. With a tandem light-emitting element, a light-emitting device that can be driven at low voltage with low power consumption can be obtained.

The charge-generation layer 104 has a function of injecting electrons into one of the EL layers (103a or 103b) and injecting holes into the other of the EL layers (103b or 103a) when voltage is applied to the first electrode 101 and the second electrode 102. Thus, when voltage is applied in FIG. 1(B) such that the potential of the first electrode 101 is higher than that of the second electrode 102, the charge-generation layer 104 injects electrons into the EL layer 103a and injects holes into the EL layer 103b.

Note that in terms of light extraction efficiency, the charge-generation layer 104 preferably has a light-transmitting property with respect to visible light (specifically, the visible light transmittance with respect to the charge-generation layer 104 is 40% or higher). Furthermore, the charge-generation layer 104 functions even when having lower conductivity than the first electrode 101 or the second electrode 102.

Figure 1C:
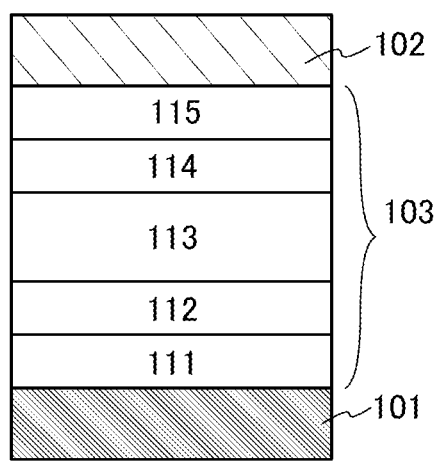

FIG. 1(C) illustrates an example of the case where the EL layer 103 illustrated in FIG. 1(A) has a stacked-layer structure (which also applies to the case where the EL layers (103a and 103b) in FIG. 1(B) have stacked-layer structures). Note that in this case, the first electrode 101 is regarded as functioning as an anode. The EL layer 103 has a structure in which a hole-injection layer 111, a hole-transport layer 112, a light-emitting layer 113, an electron-transport layer 114, and an electron-injection layer 115 are stacked sequentially over the first electrode 101. Even in the case where a plurality of EL layers are provided as in the tandem structure illustrated in FIG. 1(B), each EL layer has a stacked-layer structure, sequentially stacked from the anode side as described above. When the first electrode 101 is a cathode and the second electrode 102 is an anode, the stacking order in the EL layer is reversed.

The light-emitting layers 113 included in the EL layers (103, 103a, and 103b) each contain an appropriate combination of a light-emitting substance and a plurality of substances, so that fluorescence or phosphorescence with a desired emission color can be obtained. Furthermore, the light-emitting layer 113 may have a stacked-layer structure having different emission colors. In that case, different materials may be used for the light-emitting substance and other substances used in each of the light-emitting layers that are stacked. Furthermore, a structure in which different emission colors can be obtained from the plurality of EL layers (103a and 103b) illustrated in FIG. 1(B) may be employed. Also in that case, different materials may be used for the light-emitting substance and other substances used in each of the light-emitting layers.

In addition, in the light-emitting element of one embodiment of the present invention, a structure may be employed in which light emission obtained from the EL layers (103, 103a, and 103b) is resonated between both of the electrodes so that the obtained light emission is intensified. For example, in FIG. 1(C), the light-emitting element can have a micro optical resonator (microcavity) structure when the first electrode 101 is a reflective electrode and the second electrode 102 is a semi-transmissive and semi-reflective electrode, and light emission obtained from the EL layer 103 can be intensified.

Note that when the first electrode 101 of the light-emitting element is a reflective electrode having a stacked-layer structure of a reflective conductive material and a light-transmitting conductive material (transparent conductive film), optical adjustment can be performed by adjusting the thickness of the transparent conductive film. Specifically, when the wavelength of light obtained from the light-emitting layer 113 is λ, the distance between the first electrode 101 and the second electrode 102 is preferably adjusted to around mλ/2 (m is a natural number).

To amplify desired light (wavelength: k) obtained from the light-emitting layer 113, the optical path length from the first electrode 101 to a region where the desired light is obtained in the light-emitting layer 113 (light-emitting region) and the optical path length from the second electrode 102 to the region where the desired light is obtained in the light-emitting layer 113 (light-emitting region) are preferably adjusted to around (2m'+1)λ/4 (m' is a natural number). Here, the light-emitting region refers to a region where holes and electrons are recombined in the light-emitting layer 113.

By performing such optical adjustment, the spectrum of specific monochromatic light obtained from the light-emitting layer 113 can be narrowed and light emission with high color purity can be obtained.

However, in the above case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained with given positions in the first electrode 101 and the second electrode 102 being supposed to be reflective regions. Furthermore, the optical path length between the first electrode 101 and the light-emitting layer from which the desired light is obtained is, to be exact, the optical path length between the reflective region in the first electrode 101 and the light-emitting region in the light-emitting layer from which the desired light is obtained. However, it is difficult to precisely determine the reflective region in the first electrode 101 and the light-emitting region in the light-emitting layer from which the desired light is obtained; thus, it is assumed that the above effect can be sufficiently obtained with a given position in the first electrode 101 being supposed to be the reflective region and a given position in the light-emitting layer from which the desired light is obtained being supposed to be the light-emitting region.

In the case where the light-emitting element illustrated in FIG. 1(C) has a microcavity structure, light (monochromatic light) with different wavelengths can be extracted even when the same EL layer is used. Thus, separate coloring for obtaining different emission colors (e.g., R, G, and B) is not necessary, and high definition can be achieved. In addition, a combination with coloring layers (color filters) is also possible. Furthermore, emission intensity of light with a specific wavelength in the front direction can be increased, so that power consumption can be reduced.

Figure 1D:
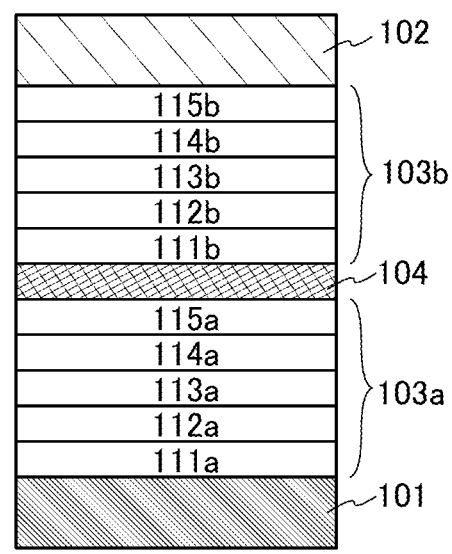
Figure 1E:
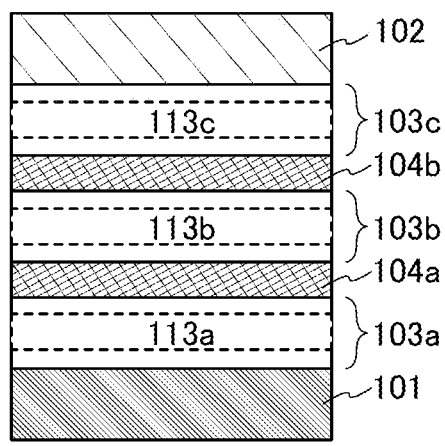

A light-emitting element illustrated in FIG. 1(E) is an example of the light-emitting element with the tandem structure illustrated in FIG. 1(B), and includes three EL layers (103a, 103b, and 103c) stacked with charge-generation layers (104a and 104b) sandwiched therebetween, as illustrated in the drawing. Note that the three EL layers (103a, 103b, and 103c) include respective light-emitting layers (113a, 113b, and 113c) and the emission colors of the respective light-emitting layers can be combined freely. For example, the light-emitting layer 113a can be blue, the light-emitting layer 113b can be red, green, or yellow, and the light-emitting layer 113c can be blue; for another example, the light-emitting layer 113a can be red, the light-emitting layer 113b can be blue, green, or yellow, and the light-emitting layer 113c can be red.

In the above light-emitting element of one embodiment of the present invention, at least one of the first electrode 101 and the second electrode 102 is a light-transmitting electrode (transparent electrode, semi-transmissive and semi-reflective electrode, or the like). In the case where the light-transmitting electrode is a transparent electrode, the visible light transmittance of the transparent electrode is 40% or higher. In the case where the light-transmitting electrode is a semi-transmissive and semi-reflective electrode, the visible light reflectance of the semi-transmissive and semi-reflective electrode is higher than or equal to 20% and lower than or equal to 80%, preferably higher than or equal to 40% and lower than or equal to 70%. The resistivity of these electrodes is preferably $1 \times 10^{-2}$ Ωcm or lower.

Furthermore, when one of the first electrode 101 and the second electrode 102 is a reflective electrode in the above light-emitting element of one embodiment of the present invention, the visible light reflectance of the reflective electrode is higher than or equal to 40% and lower than or equal to 100%, preferably higher than or equal to 70% and lower than or equal to 100%. The resistivity of this electrode is preferably $1 \times 10^{-2}$ Ωcm or lower.

<<Specific Structure and Fabrication Method of Light-Emitting Element>>

Next, specific structures and fabrication methods of the light-emitting elements of embodiments of the present invention illustrated in FIG. 1 will be described. Note that here, collective description is made on a light-emitting element with a tandem structure illustrated in FIG. 1(B), FIG. 1(D), and FIG. 1(E) in addition to the light-emitting element whose EL layer 103 has a single-layer structure as illustrated in FIG. 1(A) and FIG. 1(C). In the case where the light-emitting element illustrated in FIG. 1 has a microcavity structure, the first electrode 101 is formed as a reflective electrode and the second electrode 102 is formed as a semi-transmissive and semi-reflective electrode, for example. The electrode can be formed, using one or more kinds of desired electrode materials, as a single layer or a stacked layer. The second electrode 102 is formed after formation of the EL layer (103 or 103b), with the use of a material selected as described above. For fabrication of these electrodes, a sputtering method or a vacuum evaporation method can be used.

<First Electrode and Second Electrode>

As materials for forming the first electrode 101 and the second electrode 102, any of the following materials can be used in an appropriate combination as long as the functions of the electrodes described above can be fulfilled. For example, a metal, an alloy, an electrically conductive compound, a mixture of these, and the like can be used as appropriate. Specifically, an In—Sn oxide (also referred to as ITO), an In—Si—Sn oxide (also referred to as ITSO), an In—Zn oxide, and an In—W—Zn oxide can be given. In addition, it is also possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use an element belonging to Group 1 or Group 2 in the periodic table, which is not listed above as an example (for example, lithium (Li), cesium (Cs), calcium (Ca), or strontium (Sr)), a rare earth metal such as europium (Eu) or ytterbium (Yb), an alloy containing an appropriate combination of any of these elements, graphene, or the like.

When the light-emitting element illustrated in FIG. 1 includes the EL layer 103 having a stacked-layer structure as in FIG. 1(C) and the first electrode 101 is an anode, the hole-injection layer 111 and the hole-transport layer 112 of the EL layer 103 are sequentially stacked over the first electrode 101 by a vacuum evaporation method. Alternatively, when the plurality of EL layers (103a and 103b) each having a stacked-layer structure are stacked with the charge-generation layer 104 therebetween as in FIG. 1(D) and the first electrode 101 is an anode, a hole-injection layer 111a and a hole-transport layer 112a of the EL layer 103a are sequentially stacked over the first electrode 101 by a vacuum evaporation method. Furthermore, after the EL layer 103a and the charge-generation layer 104 are sequentially stacked, a hole-injection layer 111b and a hole-transport layer 112b of the EL layer 103b are sequentially stacked over the charge-generation layer 104 in a similar manner.

<Hole-Injection Layer and Hole-Transport Layer>

The hole-injection layers (111, 111a, and 111b) are each a layer that injects holes from the first electrode 101 which is an anode and the charge-generation layer (104) to the EL layers (103, 103a, and 103b) and contains a material with a high hole-injection property.

As examples of the material with a high hole-injection property, transition metal oxides such as a molybdenum oxide, a vanadium oxide, a ruthenium oxide, a tungsten oxide, and a manganese oxide can be given. Alternatively, it is possible to use a phthalocyanine-based compound such as phthalocyanine (abbreviation: H$_2$Pc) or copper phthalocyanine (abbreviation: CuPC), or the like.

It is also possible to use an aromatic amine compound, which is a low molecular compound, such as 4,4',4"-tris(N, N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N-(3-methylphenyl)-N-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), or 3-[N-(1-naphthyl)-N-(9-phenylcarbazol-3-yl)amino]-9-phenylcarbazole (abbreviation: PCzPCN1).

It is also possible to use a high molecular compound (an oligomer, a dendrimer, a polymer, or the like) such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl) methacrylamide] (abbreviation: PTPDMA), or poly[N,N-bis (4-butylphenyl)-N,N'-bis(phenyl)benzidine] (abbreviation: Poly-TPD). Alternatively, it is also possible to use a high molecular compound to which acid is added, such as poly (3,4-ethylenedioxythiophene)/poly(styrenesulfonic acid) (abbreviation: PEDOT/PSS) or polyaniline/poly(styrenesulfonic acid) (abbreviation: PAni/PSS).

Alternatively, as the material with a high hole-injection property, a composite material containing a hole-transport material and an acceptor material (electron-accepting material) can be used. In that case, the acceptor material extracts electrons from the hole-transport material, so that holes are generated in the hole-injection layers (111, 111a, and 111b) and the holes are injected into the light-emitting layers (113, 113a, and 113b) through the hole-transport layers (112, 112a, and 112b). Note that each of the hole-injection layers (111, 111a, and 111b) may be formed as a single layer formed of a composite material containing a hole-transport material and an acceptor material (electron-accepting material), or may be formed by stacking a layer including a hole-transport material and a layer including an acceptor material (electron-accepting material).

The hole-transport layers (112, 112a, and 112b) are each a layer that transports the holes, which are injected from the first electrode 101 by the hole-injection layers (111, 111a, and 111b), to the light-emitting layers (113, 113a, and 113b). Note that the hole-transport layers (112, 112a, and 112b) are each a layer containing a hole-transport material. It is particularly preferable that the HOMO level of the hole-transport material used in the hole-transport layers (112, 112a, and 112b) be the same as or close to the HOMO level of the hole-injection layers (111, 111a, and 111b).

As the acceptor material used in the hole-injection layers (111, 111a, and 111b), an oxide of a metal belonging to any of Group 4 to Group 8 of the periodic table can be used. Specific examples include molybdenum oxide, vanadium oxide, niobium oxide, tantalum oxide, chromium oxide, tungsten oxide, manganese oxide, and rhenium oxide. Among these, molybdenum oxide is especially preferable since it is stable in the air, has a low hygroscopic property, and is easy to handle. Alternatively, organic acceptors such as a quinodimethane derivative, a chloranil derivative, and a hexaazatriphenylene derivative can be used. As examples of ones having an electron-withdrawing group (halogen group or cyano group), 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyanonaphthoquinodimethane (abbreviation: F6-TCNNQ), and the like can be given. A compound in which electron-withdrawing groups are bonded to a condensed aromatic ring having a plurality of hetero atoms, such as HAT-CN, is particularly preferable because it is thermally stable. A [3]radialene derivative including an electron-withdrawing group (in particular, a cyano group or a halogen group such as a fluoro group) has a very high electron-accepting property and thus is preferred; specific examples include α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile].

The hole-transport materials used in the hole-injection layers (111, 111a, and 111b) and the hole-transport layers (112, 112a, and 112b) are preferably substances with a hole mobility of higher than or equal to $10^{-6}$ cm$^2$/Vs. Note that other substances can be used as long as the substances have a hole-transport property higher than an electron-transport property.

As the hole-transport material, materials having a high hole-transport property, such as a π-electron rich heteroaromatic compound (e.g., a carbazole derivative, a furan derivative, and a thiophene derivative) and an aromatic amine (compound having an aromatic amine skeleton), are preferred.

Examples of the above carbazole derivative (a compound having a carbazole skeleton) include a bicarbazole derivative (e.g., a 3,3'-bicarbazole derivative) and an aromatic amine having a carbazolyl group.

Note that specific examples of the bicarbazole derivative (e.g., a 3,3'-bicarbazole derivative) include 3,3'-bis(9-phenyl-9H-carbazole) (abbreviation: PCCP), 9,9'-bis(1,1'-biphenyl-4-yl)-3,3'-bi-9H-carbazole, 9,9'-bis(1,1'-biphenyl-3-yl)-3,3'-bi-9H-carbazole, 9-(1,1'-biphenyl-3-yl)-9'-(1,1'-biphenyl-4-yl)-9H,9'H-3,3'-bicarbazole (abbreviation: mBPCCBP), 9-(2-naphthyl)-9'-phenyl-9H,9'H-3,3'-bicarbazole (abbreviation: βNCCP).

Specific examples of the aromatic amine having a carbazolyl group include 4-phenyl-4'-(9-phenyl-9H-carbazol-3-yl)triphenylamine (abbreviation: PCBA1BP), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N-bis(9-phenylcarbazol-3-yl)-N,N-diphenylbenzene-1,3-diamine (abbreviation: PCA2B), N,N,N'-triphenyl-N,N,N'-tris(9-phenylcarbazol-3-yl)benzene-1,3,5-triamine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 3-[N-(9-phenylcarbazol-3-yl)-N-phenylamino]-9-phenyl-carbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 2-[N-(9-phenylcarbazol-3-yl)-N-phenylamino]spiro-9,9'-bifluorene (abbreviation: PCASF), N-[4-(9H-carbazol-9-yl)phenyl]-N-(4-phenyl)phenylaniline (abbreviation: YGA1BP), N,N-bis[4-(carbazol-9-yl)phenyl]-N,N-diphenyl-9,9-dimethylfluorene-2,7-diamine (abbreviation: YGA2F), and 4,4',4"-tris(carbazol-9-yl)triphenylamine (abbreviation: TCTA).

In addition to the above, other examples of the carbazole derivative include 3-[4-(9-phenanthryl)-phenyl]-9-phenyl-9H-carbazole (abbreviation: PCPPn), 3-[4-(1-naphthyl)-phenyl]-9-phenyl-9H-carbazole (abbreviation: PCPN), 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA).

Specific examples of the above thiophene derivative and the furan derivative include compounds having a thiophene skeleton, such as 1,3,5-tri(dibenzothiophen-4-yl)benzene (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV), and compounds having a furan skeleton, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II).

Specific examples of the above aromatic amine include 4,4'-bis[N-(1-naphthyl)-N-phenylamino]biphenyl (abbreviation: NPB or α-NPD), N,N-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 2,7-bis[N-(4-diphenylaminophenyl)-N-phenylamino]-spiro-9,9'-bifluorene (abbreviation: DPA2SF), 4,4',4''-tris[N-(1-naphthyl)-N-phenylamino]triphenylamine (abbreviation: 1-TNATA), 4,4',4''-tris(N,N-diphenylamino)triphenylamine (abbreviation: TDATA), 4,4', 4''-tris[N-(3-methylphenyl)-N-phenylamino]triphenylamine (abbreviation: m-MTDATA), N,N-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N-bis{4-[bis(3-methylphenyl)amino]phenyl}-N,N-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B).

Furthermore, as the hole-transport material, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), or poly[N,N-bis(4-butylphenyl)-N,N-bis(phenyl)benzidine](abbreviation: Poly-TPD) can also be used.

Note that the hole-transport material is not limited to the above examples and one of or a combination of various known materials can be used as the hole-transport material for the hole-injection layers (111, 111a, and 1/1b) and the hole-transport layers (112, 112a, and 112b). Note that the hole-transport layers (112, 112a, and 112b) may each be formed of a plurality of layers. That is, a first hole-transport layer and a second hole-transport layer may be stacked, for example.

In the light-emitting element illustrated in FIG. 1, the light-emitting layer (113 or 113a) is formed over the hole-transport layer (112 or 112a) of the EL layer (103 or 103a) by a vacuum evaporation method. Note that in the case of the light-emitting element with the tandem structure illustrated in FIG. 1(D), after the EL layer 103a and the charge-generation layer 104 are formed, the light-emitting layer 113b is also formed over the hole-transport layer 112b of the EL layer 103b by a vacuum evaporation method.

<Light-Emitting Layer>

The light-emitting layers (113, 113a, 113b, and 113c) each contain a light-emitting substance. Note that as the light-emitting substance, a substance that exhibits emission color of blue, purple, bluish purple, green, yellowish green, yellow, orange, red, or the like is appropriately used. When the light-emitting layers (113a, 113b, and 113c) are formed using different light-emitting substances, different emission colors can be exhibited (for example, complementary emission colors are combined to obtain white light emission). Furthermore, a stacked-layer structure in which one light-emitting layer contains different light-emitting substances may be employed.

The light-emitting layers (113, 113a, 113b, and 113c) may each contain one or more kinds of organic compounds (a host material and the like) in addition to a light-emitting substance (guest material). As the one or more kinds of organic compounds, the organic compound of one embodiment of the present invention or one or both of the hole-transport material and the electron-transport material described in this embodiment can be used.

The light-emitting substance that can be used in the light-emitting layers (113, 113a, 113b, and 113c) is not particularly limited, and a light-emitting substance that converts singlet excitation energy into light emission in the visible light range or a light-emitting substance that converts triplet excitation energy into light emission in the visible light range can be used.

Examples of other light-emitting substances are given below.

As an example of the light-emitting substance that converts singlet excitation energy into light emission, a substance that emits fluorescence (fluorescent material) can be given; examples include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N-bis(3-methylphenyl)-N,N-bis[3-(9-phenyl-9H-fluoren-9-yl)phenyl]pyrene-1,6-diamine (abbreviation: 1,6mMemFLPAPrn), N,N-diphenyl-N,N-bis[4-(9-phenyl-9H-fluoren-9-yl)phenyl]pyrene-1,6-diamine (abbreviation: 1,6FLPAPrn), N,N-bis(dibenzofuran-2-yl)-N,N-diphenylpyrene-1,6-diamine (abbreviation: 1,6FrAPrn), N,N-bis(dibenzothiophen-2-yl)-N,N-diphenylpyrene-1,6-diamine (abbreviation: 1,6ThAPrn), N,N-(pyrene-1,6-diyl)bis[(N-phenylbenzo[b]naphtho[1,2-d]furan)-6-amine] (abbreviation: 1,6BnfAPrn), N,N-(pyrene-1,6-diyl)bis[(N-phenylbenzo[b]naphtho[1,2-d]furan)-8-amine](abbreviation: 1,6BnfAPrn-02), and N,N-(pyrene-1,6-diyl)bis[(6,N-diphenylbenzo[b]naphtho[1,2-d]furan)-8-amine] (abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra-tert-butylperylene (abbreviation: TBP), N,N'''-(2-tert-butylanthracene-9,10-diyldi-4,1-phenylene)bis[N,N,N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), or the like.

As examples of the light-emitting substance that converts triplet excitation energy into light emission, a substance that emits phosphorescence (phosphorescent material) and a thermally activated delayed fluorescence (TADF) material that exhibits thermally activated delayed fluorescence can be given.

Examples of a phosphorescent material include an organometallic complex, a metal complex (platinum complex), and a rare earth metal complex. These substances exhibit different emission colors (emission peaks) and thus, any of them is selected and used appropriately according to need.

As a phosphorescent material that exhibits blue or green and whose emission spectrum has a peak wavelength at greater than or equal to 450 nm and less than or equal to 570 nm, the following substances can be given.

For example, organometallic complexes having a 4H-triazole skeleton, such as tris{2-[5-(2-methylphenyl)-4-(2,6-dimethylphenyl)-4H-1,2,4-triazol-3-yl-$N^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: [Ir(iPr5btz)$_3$]); organometallic complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); organometallic complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: [Ir(CF$_3$ppy)$_2$(pic)]), and bis[2-(4',6'-difluorophenyl)pyridinato-N,$C^{2'}$]iridium(III) acetylacetonate (abbreviation: FIr(acac)); and the like can be given.

As a phosphorescent material that exhibits green or yellow and whose emission spectrum has a peak wavelength at greater than or equal to 495 nm and less than or equal to 590 nm, the following substances can be given.

For example, organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(t-Buppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-$κN^3$]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,$C^{2'}$)iridium(III) (abbreviation: [Ir(ppy)$_3$]), bis(2-phenylpyridinato-N,$C^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,$C^{2'}$)iridium(III) (abbreviation: [Ir(pq)$_3$]), bis(2-phenylquinolinato-N,$C^{2'}$)iridium(III) acetylacetonate (abbreviation: [Ir(pq)$_2$(acac)]), bis[2-(2-pyridinyl-κN)phenyl-κC][2-(4-phenyl-2-pyridinyl-κN)phenyl-κC]iridium(III) (abbreviation: [Ir(ppy)$_2$(4dppy)]), and bis[2-(2-pyridinyl-κN)phenyl-κC][2-(4-methyl-5-phenyl-2-pyridinyl-κN)phenyl-cC]; organometallic complexes such as bis(2,4-diphenyl-1,3-oxazolato-N,$C^{2'}$)iridium(III) acetylacetonate (abbreviation: [Ir(dpo)$_2$(acac)]), bis{2-[4'-(perfluorophenyl)phenyl]pyridinato-N,$C^{2'}$}iridium(III) acetylacetonate (abbreviation: [Ir(p-PF-ph)$_2$(acac)]), and bis(2-phenylbenzothiazolato-N,$C^{2'}$)iridium(III) acetylacetonate (abbreviation: [Ir(bt)$_2$(acac)]); and rare earth metal complexes such as tris(acetylacetonato)(monophenanthroline)terbium(III) (abbreviation: [Tb(acac)$_3$(Phen)]) can be given.

As a phosphorescent material that exhibits yellow or red and whose emission spectrum has a peak wavelength at greater than or equal to 570 nm and less than or equal to 750 nm, the following substances can be given.

For example, organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and (dipivaloylmethanato)bis[4,6-di(naphthalen-1-yl)pyrimidinato]iridium(III) (abbreviation: [Ir(d1npm)$_2$(dpm)]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-$κ^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-N]phenyl-κC}(2,2,6,6-tetramethyl-3,5-heptanedionato-$κ^2$O,O')iridium(III) (abbreviation: [Ir(dmdppr-dmCP)$_2$(dpm)]), (acetylacetonato)bis[2-methyl-3-phenylquinoxalinato-N,$C^{2'}$]iridium(III) (abbreviation: [Ir(mpq)$_2$(acac)]), (acetylacetonato)bis(2,3-diphenylquinoxalinato-N,$C^{2'}$)iridium(III) (abbreviation: [Ir(dpq)$_2$(acac)]), and (acetylacetonato)bis[2,3-bis(4-fluorophenyl)quinoxalinato]iridium(III) (abbreviation: [Ir(Fdpq)$_2$(acac)]); organometallic complexes having a pyridine skeleton, such as tris(1-phenylisoquinolinato-N,$C^{2'}$)iridium(III) (abbreviation: [Ir(piq)$_3$]), bis(1-phenylisoquinolinato-N,$C^{2'}$)iridium(III) acetylacetonate (abbreviation: [Ir(piq)$_2$(acac)]), and bis[4,6-dimethyl-2-(2-quinolinyl-κN)phenyl-κC](2,4-pentanedionato-$κ^2$O,O')iridium(III); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]) can be given.

As the organic compounds (the host material and the like) used in the light-emitting layers (113, 113a, 113b, and 113c), one or more kinds of substances having a larger energy gap than the light-emitting substance (the guest material) are selected to be used.

Therefore, in the case where the light-emitting substance used in the light-emitting layers (113, 113a, 113b, and 113c) is a fluorescent material, an organic compound (a host material) used in combination with the light-emitting substance is preferably an organic compound that has a high energy level in a singlet excited state and has a low energy level in a triplet excited state. Note that as the organic compound (the host material) used in combination with the light-emitting substance, not only the hole-transport material (described above) or the electron-transport material (described below), which are described in this embodiment, but also a bipolar material or the like can be used.

In terms of a preferable combination with a light-emitting substance (a fluorescent material or a phosphorescent material), specific examples of the organic compounds are shown below though some of them overlap the specific examples shown above.

In the case where the light-emitting substance is a fluorescent material, examples of the organic compound (the host material) that can be used in combination with the light-emitting substance include condensed polycyclic aromatic compounds, such as an anthracene derivative, a tetracene derivative, a phenanthrene derivative, a pyrene derivative, a chrysene derivative, and a dibenzo[g,p]chrysene derivative.

Specific examples of the organic compound (the host material) used in combination with the fluorescent substance include 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 3-[4-(1-naphthyl)-phenyl]-9-phenyl-9H-carbazole (abbreviation: PCPN), 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N,N',N',N',N'',N''-octaphenyldibenzo[g,p]chrysene-2,7,10,15-tetraamine (abbreviation: DBC1), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)-biphenyl-4'-yl}-anthracene (abbreviation: FLPPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), 5,12-diphenyltetracene, and 5,12-bis(biphenyl-2-yl)tetracene.

In the case where the light-emitting substance is a phosphorescent material, an organic compound having triplet excitation energy (energy difference between a ground state and a triplet excited state) which is higher than that of the light-emitting substance is preferably selected as the organic compound (the host material) used in combination with the light-emitting substance. Note that in the case where a plurality of organic compounds (e.g., a first host material and a second host material (or an assist material)) are used in combination with a light-emitting substance in order to form an exciplex, the plurality of organic compounds are preferably mixed with a phosphorescent material.

Such a structure makes it possible to efficiently obtain light emission utilizing ExTET (Exciplex-Triplet Energy Transfer), which is energy transfer from an exciplex to a light-emitting substance. Note that a combination of the plurality of organic compounds that easily forms an exciplex is preferably employed, and it is particularly preferable to combine a compound that easily accepts holes (hole-transport material) and a compound that easily accepts electrons (electron-transport material). The organic compound of one embodiment of the present invention described in Embodiment 1 has a stable triplet excited state and thus is suitable for a host material in the case where the light-emitting substance is a phosphorescent material. Owing to its triplet excitation energy level, the organic compound is particularly suitable when used in combination with a phosphorescent material that emits green light.

In the case where the light-emitting substance is a phosphorescent material, examples of the organic compounds (the host material and the assist material) that can be used in combination with the light-emitting substance include an aromatic amine, a carbazole derivative, a dibenzothiophene derivative, a dibenzofuran derivative, a zinc- or aluminum-based metal complex, an oxadiazole derivative, a triazole derivative, a benzimidazole derivative, a quinoxaline derivative, a dibenzoquinoxaline derivative, a pyrimidine derivative, a triazine derivative, a pyridine derivative, a bipyridine derivative, and a phenanthroline derivative.

Among the above-described compounds, the same compounds as those given above as specific examples of the hole-transport material are given as specific examples of the aromatic amine (a compound having an aromatic amine skeleton), which is an organic compound having a high hole-transport property.

Moreover, the same compounds as those given above as specific examples of the hole-transport material are given as specific examples of the carbazole derivative, which is an organic compound having a high hole-transport property.

Specific examples of the dibenzothiophene derivative and the dibenzofuran derivative, which are organic compounds having a high hole-transport property, include 4-{3-[3-(9-phenyl-9H-fluoren-9-yl)phenyl]phenyl}dibenzofuran (abbreviation: mmDBFFLBi-II), 4,4',4''-(benzene-1,3,5-triyl)tri(dibenzofuran) (abbreviation: DBF3P-II), 1,3,5-tri(dibenzothiophen-4-yl)benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II).

Specific examples of zinc- and aluminum-based metal complexes, which are organic compounds having a high electron-transport property, include metal complexes having a quinoline skeleton or a benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), and bis(8-quinolinolato)zinc(II) (abbreviation: Znq).

Alternatively, a metal complex having an oxazole-based or thiazole-based ligand, such as bis[2-(2-benzoxazolyl)

phenolato]zinc(II) (abbreviation: ZnPBO) or bis[2-(2-benzothiazolyl)phenolato]zinc(II) (abbreviation: ZnBTZ), or the like can also be used.

Specific examples of the oxadiazole derivative, the triazole derivative, the benzimidazole derivative, the quinoxaline derivative, the dibenzoquinoxaline derivative, and the phenanthroline derivative, which are organic compounds having a high electron-transport property, include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-5-(4-tert-butylphenyl)-4-phenyl-1,2,4-triazole (abbreviation: TAZ), 2,2',2''-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), 4,4'-bis(5-methylbenzoxazol-2-yl)stilbene (abbreviation: BzOS), bathophenanthroline (abbreviation: Bphen), bathocuproine (abbreviation: BCP), 2,9-bis(naphthalen-2-yl)-4,7-diphenyl-1,10-phenanthroline (abbreviation: NBphen), 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Specific examples of a heterocyclic compound having a diazine skeleton, a heterocyclic compound having a triazine skeleton, and a heterocyclic compound having a pyridine skeleton, which are organic compounds having a high electron-transport property, include 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm), 2-{4-[3-(N-phenyl-9H-carbazol-3-yl)-9H-carbazol-9-yl]phenyl}-4,6-diphenyl-1,3,5-triazine (abbreviation: PCCzPTzn), 9-[3-(4,6-diphenyl-1,3,5-triazin-2-yl)phenyl]-9'-phenyl-2,3'-bi-9H-carbazole (abbreviation: mPCCzPTzn-02), 3,5-bis[3-(9H-carbazol-9-yl)phenyl]pyridine (abbreviation: 35DCzPPy), and 1,3,5-tri[3-(3-pyridyl)phenyl]benzene (abbreviation: TmPyPB).

Furthermore, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used as an organic compound having a high electron-transport property.

In the case where a plurality of organic compounds are used in the light-emitting layers (113, 113a, 113b, and 113c), two kinds of compounds that form an exciplex (a first compound and a second compound) and an organometallic complex may be mixed and used. In that case, various organic compounds can be combined appropriately to be used; to form an exciplex efficiently, it is particularly preferable to combine a compound that easily accepts holes (hole-transport material) and a compound that easily accepts electrons (electron-transport material). Note that, as specific examples of the hole-transport material and the electron-transport material, the materials described in this embodiment can be used. With the structure, high efficiency, low voltage, and a long lifetime can be achieved at the same time.

The TADF material refers to a material that can up-convert a triplet excited state into a singlet excited state (i.e., reverse intersystem crossing) using a little thermal energy and efficiently exhibits light emission (fluorescence) from the singlet excited state. As the condition under which the thermally activated delayed fluorescence is efficiently obtained, energy difference between the triplet excited level and the singlet excited level being greater than or equal to 0 eV and less than or equal to 0.2 eV, preferably greater than or equal to 0 eV and less than or equal to 0.1 eV can be given. Note that delayed fluorescence exhibited by the TADF material refers to light emission having a spectrum similar to that of normal fluorescence and an extremely long lifetime. The lifetime is $10^{-6}$ seconds or longer, preferably $10^3$ seconds or longer.

Examples of the TADF material include fullerene, a derivative thereof, an acridine derivative such as proflavine, and eosin. In addition, a metal-containing porphyrin containing magnesium (Mg), zinc (Zn), cadmium (Cd), tin (Sn), platinum (Pt), indium (In), palladium (Pd), or the like can be given. Examples of the metal-containing porphyrin include a protoporphyrin-tin fluoride complex (abbreviation: $SnF_2$(Proto IX)), a mesoporphyrin-tin fluoride complex (abbreviation: $SnF_2$(Meso IX)), a hematoporphyrin-tin fluoride complex (abbreviation: $SnF_2$(Hemato IX)), a coproporphyrin tetramethyl ester-tin fluoride complex (abbreviation: $SnF_2$(Copro III-4Me)), an octaethylporphyrin-tin fluoride complex (abbreviation: $SnF_2$(OEP)), an etioporphyrin-tin fluoride complex (abbreviation: $SnF_2$(Etio I)), and an octaethylporphyrin-platinum chloride complex (abbreviation: $PtCl_2OEP$).

Other than these, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. Note that a substance in which the π-electron rich heteroaromatic ring is directly bonded to the π-electron deficient heteroaromatic ring is particularly preferable because both the donor property of the π-electron rich heteroaromatic ring and the acceptor property of the π-electron deficient heteroaromatic ring are increased and the energy difference between the singlet excited state and the triplet excited state becomes small.

Note that when a TADF material is used, the TADF material can also be used in combination with another organic compound. In particular, the TADF material can be combined with the host materials, the hole-transport materials, and the electron-transport materials described above, and the organic compound of one embodiment of the present invention described in Embodiment 1 is preferably used as a host material for the TADF material.

Furthermore, when the above materials are used in combination with a low molecular material or a high molecular material, the above materials can be used to form the light-emitting layers (113, 113*a*, 113*b*, and 113*c*). For the deposition, a known method (an evaporation method, a coating method, a printing method, or the like) can be used as appropriate.

In the light-emitting element illustrated in FIG. 1, an electron-transport layer (114 or 114*a*) is formed over the light-emitting layer (113 or 113*a*) of the EL layer (103 or 103*a*). Note that in the case of the light-emitting element with the tandem structure illustrated in FIG. 1(D), after the EL layer 103*a* and the charge-generation layer 104 are formed, an electron-transport layer 114*b* is also formed over the light-emitting layer 113*b* of the EL layer 103*b*.

<Electron-Transport Layer>

The electron-transport layers (114, 114*a*, and 114*b*) are each a layer that transports the electrons, which are injected from the second electrode 102 by the electron-injection layers (115, 115*a*, and 115*b*), to the light-emitting layers (113, 113*a*, and 113*b*). Note that the electron-transport layers (114, 114*a*, and 114*b*) are each a layer containing an electron-transport material. It is preferable that the electron-transport materials used in the electron-transport layers (114, 114*a*, and 114*b*) be substances with an electron mobility of higher than or equal to $1 \times 10^{-6}$ cm$^2$/Vs. Note that other substances can be used as long as the substances have an electron-transport property higher than a hole-transport property. The organic compound of one embodiment of the present invention described in Embodiment 1 has an excellent electron-transport property and thus can also be used for an electron-transport layer.

As the electron-transport material, it is possible to use a material having a high electron-transport property, such as a metal complex having a quinoline skeleton, a metal complex having a benzoquinoline skeleton, a metal complex having an oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative having a quinoline ligand, a benzoquinoline derivative, a quinoxaline derivative, a dibenzoquinoxaline derivative, a pyridine derivative, a bipyridine derivative, a pyrimidine derivative, or a π-electron deficient heteroaromatic compound such as a nitrogen-containing heteroaromatic compound.

Specific examples of the electron-transport material include metal complexes having a quinoline skeleton or a benzoquinoline skeleton, such as tris(8-quinolinolato)aluminum(III) (abbreviation: Alq$_3$), tris(4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq), and metal complexes having an oxazole skeleton or a thiazole skeleton, such as bis[2-(2-benzoxazolyl)phenolato]zinc(II) (abbreviation: ZnPBO), bis[2-(2-benzothiazolyl)phenolato]zinc(II) (abbreviation: ZnBTZ), and bis[2-(2-hydroxyphenyl)benzothiazolato]zinc(II) (abbreviation: Zn(BTZ)$_2$).

Other than metal complexes, any of the following can also be used: an oxadiazole derivative such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), and 9-[4-(5-phenyl-1,3,4-oxadiazol-2-yl)phenyl]-9H-carbazole (abbreviation: CO11); a triazole derivative such as 3-(4-biphenylyl)-5-(4-tert-butylphenyl)-4-phenyl-1,2,4-triazole (abbreviation: TAZ) and 3-(4-tert-butylphenyl)-4-(4-ethylphenyl)-5-(4-biphenylyl)-1,2,4-triazole (abbreviation: p-EtTAZ); an imidazole derivative (including a benzimidazole derivative) such as 2,2',2"-(1,3,5-benzenetriyl)tris(1-phenyl-1H-benzimidazole) (abbreviation: TPBI) and 2-[3-(dibenzothiophen-4-yl)phenyl]-1-phenyl-1H-benzimidazole (abbreviation: mDBT-BIm-II); an oxazole derivative such as 4,4'-bis(5-methylbenzoxazol-2-yl)stilbene (abbreviation: BzOS); a phenanthroline derivative such as bathophenanthroline (abbreviation: Bphen), bathocuproine (abbreviation: BCP), and 2,9-bis(naphthalen-2-yl)-4,7-diphenyl-1,10-phenanthroline (abbreviation: NBphen); a quinoxaline derivative or a dibenzoquinoxaline derivative such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II); a pyridine derivative such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB); a pyrimidine derivative such as 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), and 4,6-bis[3-(9H-carbazol-9-yl)phenyl]pyrimidine (abbreviation: 4,6mCzP2Pm); and a triazine derivative such as 2-{4-[3-(N-phenyl-9H-carbazol-3-yl)-9H-carbazol-9-yl]phenyl}-4,6-diphenyl-1,3,5-triazine (abbreviation: PCCzPTzn).

Furthermore, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can also be used.

Each of the electron-transport layers (114, 114*a*, and 114*b*) is not limited to a single layer, and may be a stack of two or more layers each made of any of the above substances.

In the light-emitting element illustrated in FIG. 1(D), the electron-injection layer 115*a* is formed over the electron-transport layer 114*a* of the EL layer 103*a* by a vacuum evaporation method. Subsequently, the EL layer 103*a* and the charge-generation layer 104 are formed, the components up to the electron-transport layer 114*b* of the EL layer 103*b* are formed, and then the electron-injection layer 115*b* is formed thereover by a vacuum evaporation method.

<Electron-Injection Layer>

The electron-injection layers (115, 115*a*, and 115*b*) are each a layer containing a substance having a high electron-injection property. The electron-injection layers (115, 115*a*, and 115*b*) can each be formed using an alkali metal, an alkaline earth metal, or a compound thereof, such as lithium fluoride (LiF), cesium fluoride (CsF), calcium fluoride (CaF$_2$), or lithium oxide (LiO$_x$). A rare earth metal compound such as erbium fluoride (ErF$_3$) can be used. Electride may also be used for the electron-injection layers (115, 115*a*, and 115*b*). Examples of the electride include a substance in which electrons are added at high concentration to a mixed oxide of calcium and aluminum. Note that any of the substances used in the electron-transport layers (114, 114*a*, and 114*b*), which are given above, can also be used.

A composite material in which an organic compound and an electron donor (donor) are mixed may also be used in the electron-injection layers (115, 115*a*, and 115*b*). Such a composite material is excellent in an electron-injection property and an electron-transport property because electrons are generated in the organic compound by the electron donor. In this case, the organic compound is preferably a material excellent in transporting the generated electrons; specifically, for example, the above-mentioned electron-transport materials (metal complexes, heteroaromatic compounds, and the like) used in the electron-transport layers (114, 114a, and 114b) can be used. Any substance showing an electron-donating property with respect to the organic compound can serve as an electron donor. Specifically, an alkali metal, an alkaline earth metal, and a rare earth metal are preferable, and lithium, cesium, magnesium, calcium, erbium, ytterbium, and the like are given. In addition, an alkali metal oxide and an alkaline earth metal oxide are preferable, and lithium oxide, calcium oxide, barium oxide, and the like are given. A Lewis base such as magnesium oxide can also be used. An organic compound such as tetrathiafulvalene (abbreviation: TTF) can also be used.

Note that in the case where light obtained from the light-emitting layer 113b is amplified in the light-emitting element illustrated in FIG. 1(D), the optical path length between the second electrode 102 and the light-emitting layer 113b is preferably less than one fourth of the wavelength k of light emitted from the light-emitting layer 113b. In that case, the optical path length can be adjusted by changing the thickness of the electron-transport layer 114b or the electron-injection layer 115b.

<Charge-Generation Layer>

In the light-emitting element illustrated in FIG. 1(D), the charge-generation layer 104 has a function of injecting electrons into the EL layer 103a and injecting holes into the EL layer 103b when voltage is applied between the first electrode (anode) 101 and the second electrode (cathode) 102. Note that the charge-generation layer 104 may have either a structure in which an electron acceptor (acceptor) is added to a hole-transport material or a structure in which an electron donor (donor) is added to an electron-transport material. Alternatively, both of these structures may be stacked. Note that forming the charge-generation layer 104 with the use of any of the above materials can suppress an increase in drive voltage in the case where the EL layers are stacked.

In the case where the charge-generation layer 104 has a structure in which an electron acceptor is added to a hole-transport material, any of the materials described in this embodiment can be used as the hole-transport material. As the electron acceptor, 7,7,8,8-tetracyano-2,3,5,6-tetrafluoro-quinodimethane (abbreviation: $F_4$-TCNQ), chloranil, and the like can be given. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, rhenium oxide, and the like can be given.

In the case where the charge-generation layer 104 has a structure in which an electron donor is added to an electron-transport material, any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the electron donor.

Note that the EL layer 103c in FIG. 1(E) has a structure similar to those of the above-described EL layers (103, 103a, and 103b). In addition, the charge-generation layers 104a and 104b each have a structure similar to that of the above-described charge-generation layer 104.

<Substrate>

The light-emitting element described in this embodiment can be formed over any of a variety of substrates. Note that the type of the substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, a laminate film, paper including a fibrous material, and a base material film.

Note that examples of the glass substrate include barium borosilicate glass, aluminoborosilicate glass, and soda lime glass. Examples of the flexible substrate, the laminate film, and the base material film include plastics typified by polyethylene terephthalate (PET), polyethylene naphthalate (PEN), and polyether sulfone (PES); a synthetic resin such as an acrylic resin; polypropylene; polyester; polyvinyl fluoride; polyvinyl chloride; polyamide; polyimide; an aramid resin; an epoxy resin; an inorganic vapor deposition film; and paper.

Note that for fabrication of the light-emitting element described in this embodiment, a vacuum process such as an evaporation method or a solution process such as a spin coating method or an ink-jet method can be used. In the case where an evaporation method is used, a physical vapor deposition method (PVD method) such as a sputtering method, an ion plating method, an ion beam evaporation method, a molecular beam evaporation method, or a vacuum evaporation method; a chemical vapor deposition method (CVD method); or the like can be used. Specifically, the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), and the electron-injection layers (115, 115a, and 115b)) included in the EL layers and the charge-generation layers (104, 104a, and 104b) of the light-emitting element can be formed by an evaporation method (e.g., a vacuum evaporation method), a coating method (e.g., a dip coating method, a die coating method, a bar coating method, a spin coating method, or a spray coating method), a printing method (e.g., an ink-jet method, a screen printing (stencil) method, an offset printing (planography) method, a flexography (relief printing) method, a gravure printing method, a micro-contact printing method, or a nanoinprinting method), or the like.

Note that materials that can be used for the functional layers (the hole-injection layers (111, 111a, and 1l1b), the hole-transport layers (112, 112a, and 112b), the light-emitting layers (113, 113a, 113b, and 113c), the electron-transport layers (114, 114a, and 114b), and the electron-injection layers (115, 115a, and 115b)) included in the EL layers (103, 103a, and 103b) and the charge-generation layers (104, 104a, and 104b) of the light-emitting element described in this embodiment are not limited to the above materials, and other materials can also be used in combination as long as the functions of the layers are fulfilled. For example, a high molecular compound (e.g., an oligomer, a dendrimer, and a polymer), a middle molecular compound (a compound between a low molecular compound and a high molecular compound with a molecular weight of 400 to 4000), or an inorganic compound (e.g., a quantum dot material) can be used. Note that as the quantum dot material, a colloidal quantum dot material, an alloyed quantum dot material, a core-shell quantum dot material, a core quantum dot material, or the like can be used.

The structure described in this embodiment can be used in an appropriate combination with any of the structures described in the other embodiments.

Embodiment 3

Figure 2A:
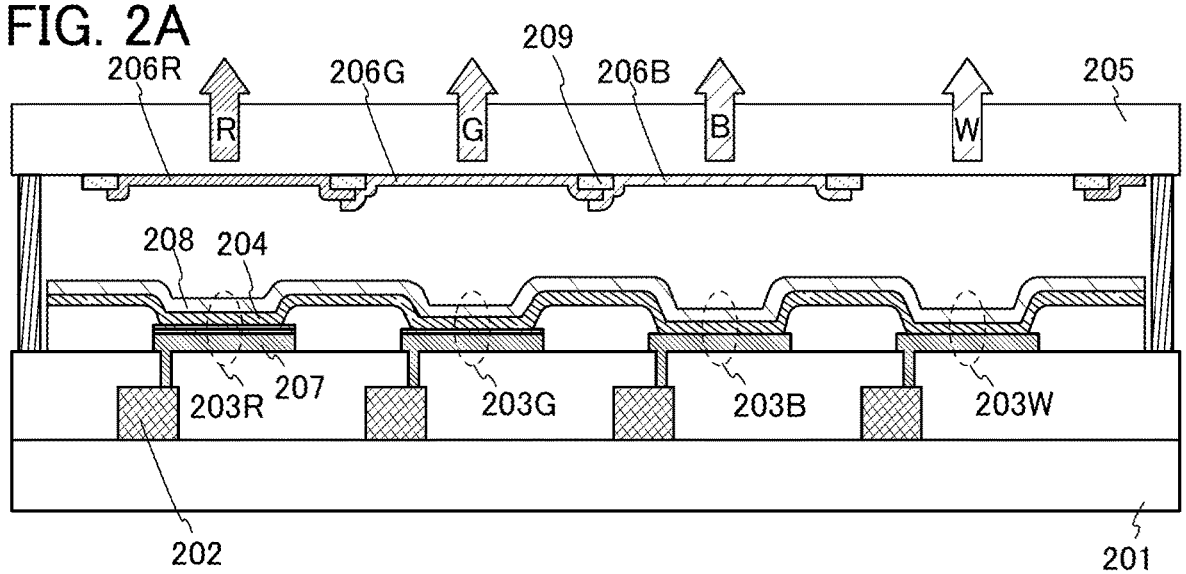
FIGS. 2A-2C are drawings illustrating light-emitting devices.

In this embodiment, a light-emitting device of one embodiment of the present invention will be described. Note that a light-emitting device illustrated in FIG. 2(A) is an active-matrix light-emitting device in which transistors (FETs) 202 over a first substrate 201 are electrically connected to light-emitting elements (203R, 203G, 203B, and 203W); the light-emitting elements (203R, 203G, 203B, and 203W) include a common EL layer 204 and each have a microcavity structure in which the optical path length between electrodes of each light-emitting element is adjusted according to the emission color of the light-emitting element. In addition, the light-emitting device is a top-emission light-emitting device in which light is emitted from the EL layer 204 through color filters (206R, 206G, and 206B) formed on a second substrate 205.

In the light-emitting device illustrated in FIG. 2(A), the first electrode 207 is formed so as to function as a reflective electrode. The second electrode 208 is formed so as to function as a semi-transmissive and semi-reflective electrode. Note that description in any of the other embodiments can be referred to for electrode materials forming the first electrode 207 and the second electrode 208 and appropriate materials can be used.

Figure 2B:
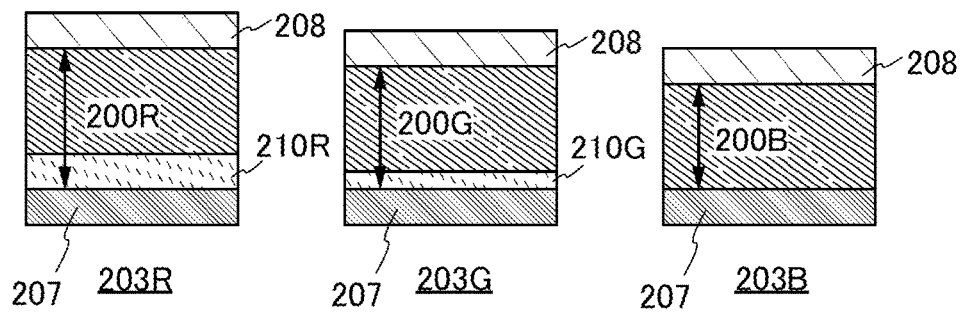

In the case where the light-emitting element 203R is a red-light-emitting element, the light-emitting element 203G is a green-light-emitting element, the light-emitting element 203B is a blue-light-emitting element, and the light-emitting element 203W is a white-light-emitting element in FIG. 2(A), for example, a gap between the first electrode 207 and the second electrode 208 in the light-emitting element 203R is adjusted to have an optical path length 200R, a gap between the first electrode 207 and the second electrode 208 in the light-emitting element 203G is adjusted to have an optical path length 200G, and a gap between the first electrode 207 and the second electrode 208 in the light-emitting element 203B is adjusted to have an optical path length 200B as illustrated in FIG. 2(B). Note that optical adjustment can be performed in such a manner that a conductive layer 210R is stacked over the first electrode 207 in the light-emitting element 203R and a conductive layer 210G is stacked over the first electrode 207 in the light-emitting element 203G as illustrated in FIG. 2(B).

The color filters (206R, 206G, and 206B) are formed on the second substrate 205. Note that the color filters each transmit visible light in a specific wavelength range and blocks visible light in a specific wavelength range. Thus, as illustrated in FIG. 2(A), the color filter 206R that transmits only light in the red wavelength range is provided in a position overlapping with the light-emitting element 203R, whereby red light emission can be obtained from the light-emitting element 203R. The color filter 206G that transmits only light in the green wavelength range is provided in a position overlapping with the light-emitting element 203G, whereby green light emission can be obtained from the light-emitting element 203G. The color filter 206B that transmits only light in the blue wavelength range is provided in a position overlapping with the light-emitting element 203B, whereby blue light emission can be obtained from the light-emitting element 203B. Note that the light-emitting element 203W can emit white light without a color filter. Note that a black layer (black matrix) 209 may be provided at an end portion of one type of color filter. The color filters (206R, 206G, and 206B) and the black layer 209 may be covered with an overcoat layer using a transparent material.

Figure 2C:
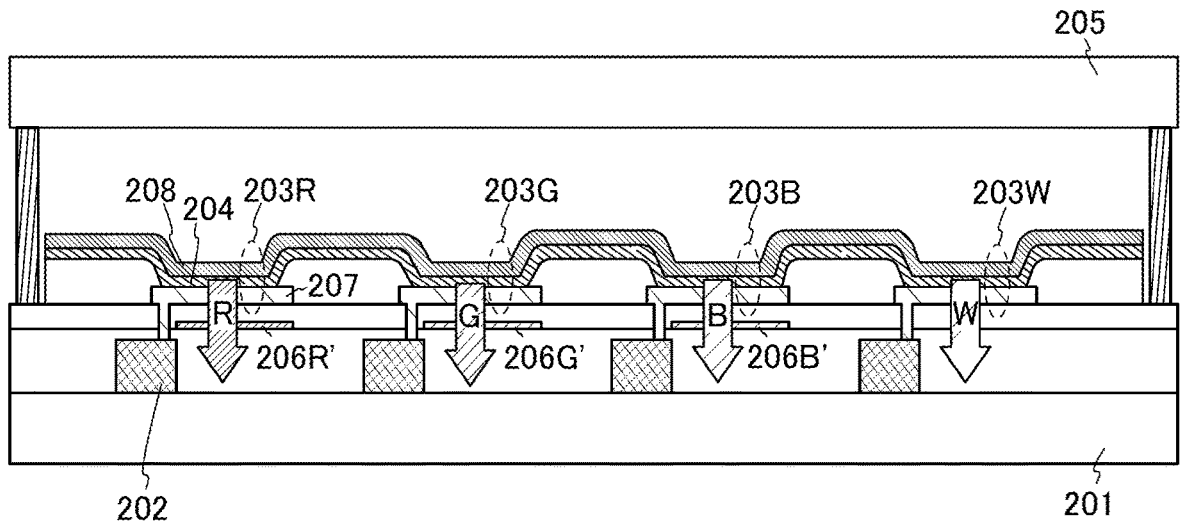

Although the light-emitting device illustrated in FIG. 2(A) has a structure in which light is extracted from the second substrate 205 side (top emission structure), the light-emitting device may have a structure in which light is extracted from the first substrate 201 side where the FETs 202 are formed (bottom emission structure) as illustrated in FIG. 2(C). For a bottom-emission light-emitting device, the first electrode 207 is formed so as to function as a semi-transmissive and semi-reflective electrode and the second electrode 208 is formed so as to function as a reflective electrode. As the first substrate 201, a substrate having at least a light-transmitting property is used. As illustrated in FIG. 2(C), color filters (206R', 206G', and 206B') are provided closer to the first substrate 201 than the light-emitting elements (203R, 203G, and 203B) are.

FIG. 2(A) illustrates the case where the light-emitting elements are the red-light-emitting element, the green-light-emitting element, the blue-light-emitting element, and the white-light-emitting element; however, the light-emitting elements of embodiments of the present invention are not limited to the above structures, and a yellow-light-emitting element or an orange-light-emitting element may be included. Note that description in any of the other embodiments can be referred to for materials that are used for the EL layers (a light-emitting layer, a hole-injection layer, a hole-transport layer, an electron-transport layer, an electron-injection layer, a charge-generation layer, and the like) to fabricate each of the light-emitting elements and appropriate materials can be used. In that case, a color filter needs to be appropriately selected according to the emission color of the light-emitting element.

With the above structure, a light-emitting device including light-emitting elements that exhibit a plurality of emission colors can be obtained.

Note that the structures described in this embodiment can be used in an appropriate combination with any of the structures described in the other embodiments.

Embodiment 4

In this embodiment, a light-emitting device of one embodiment of the present invention will be described.

The use of the element structure of the light-emitting element of one embodiment of the present invention allows fabrication of an active-matrix light-emitting device or a passive-matrix light-emitting device. Note that an active-matrix light-emitting device has a structure including a combination of a light-emitting element and a transistor (FET). Thus, each of a passive-matrix light-emitting device and an active-matrix light-emitting device is included in one embodiment of the present invention. Note that any of the light-emitting elements described in the other embodiments can be used in the light-emitting device described in this embodiment.

In this embodiment, an active-matrix light-emitting device will be described with reference to FIG. 3.

Figure 3A:
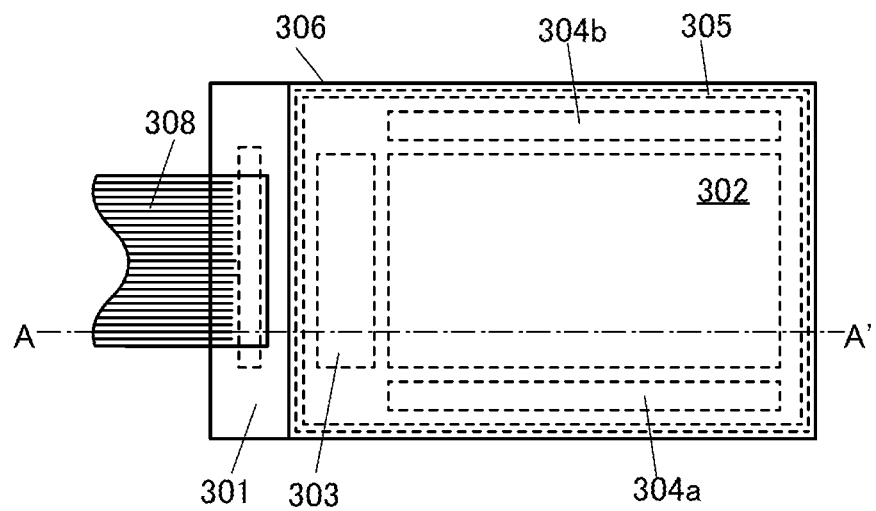
FIGS. 3A and 3B are drawings illustrating a light-emitting device.
Figure 3B:
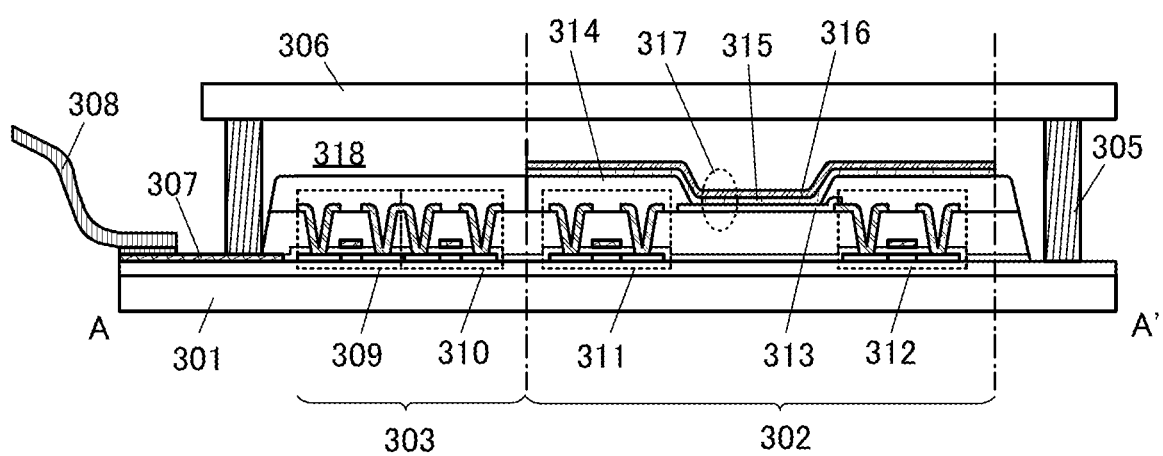

FIG. 3(A) is a top view illustrating a light-emitting device, and FIG. 3(B) is a cross-sectional view taken along a chain line A-A' in FIG. 3(A). The active-matrix light-emitting device includes a pixel portion 302, a driver circuit portion (source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is electrically connected to an FPC 308 which is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting device provided with an FPC or a PWB is included in the category of a light-emitting device.

Next, FIG. 3(B) illustrates the cross-sectional structure.

The pixel portion 302 is made up of a plurality of pixels each of which includes an FET (switching FET) 311, an FET (current control FET) 312, and a first electrode 313 electrically connected to the FET 312. Note that the number of FETs included in each pixel is not particularly limited and can be set appropriately as needed.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. The use of a semiconductor having crystallinity can suppress deterioration of the transistor characteristics, which is preferable.

For these semiconductors, a Group 14 element, a compound semiconductor, an oxide semiconductor, an organic semiconductor, or the like can be used, for example. Typically, a semiconductor containing silicon, a semiconductor containing gallium arsenide, an oxide semiconductor containing indium, or the like can be used.

The driver circuit portion 303 includes the FET 309 and the FET 310. The FET 309 and the FET 310 may be formed with a circuit including transistors having the same conductivity type (either n-channel transistors or p-channel transistors) or a CMOS circuit including an n-channel transistor and a p-channel transistor. Furthermore, a structure including a driver circuit outside may be employed.

An end portion of the first electrode 313 is covered with an insulator 314. For the insulator 314, an organic compound such as a negative photosensitive resin or a positive photosensitive resin (acrylic resin), or an inorganic compound such as silicon oxide, silicon oxynitride, or silicon nitride can be used. An upper end portion or a lower end portion of the insulator 314 preferably has a curved surface with curvature. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the structure of a light-emitting element 317 described in this embodiment.

Although not illustrated here, the second electrode 316 is electrically connected to the FPC 308 which is an external input terminal.

Although the cross-sectional view illustrated in FIG. 3(B) illustrates only one light-emitting element 317, a plurality of light-emitting elements are arranged in a matrix in the pixel portion 302. Light-emitting elements from which light of three kinds of colors (R, G, and B) are obtained are selectively formed in the pixel portion 302, whereby a light-emitting device capable of full-color display can be formed. In addition to the light-emitting elements from which light of three kinds of colors (R, G, and B) are obtained, for example, light-emitting elements from which light of white (W), yellow (Y), magenta (M), cyan (C), and the like are obtained may be formed. For example, the light-emitting elements from which light of some of the above colors are obtained are added to the light-emitting elements from which light of three kinds of colors (R, G, and B) are obtained, whereby effects such as an improvement in color purity and a reduction in power consumption can be obtained. Alternatively, a light-emitting device that is capable of full-color display may be fabricated by a combination with color filters. As the kinds of color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting element 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy-based resin or glass frit can be used for the sealant 305. It is preferable to use a material that is permeable to as little moisture and oxygen as possible for the sealant 305. As the second substrate 306, a material that can be used as the first substrate 301 can be similarly used. Thus, any of the various substrates described in the other embodiments can be appropriately used. As the substrate, a glass substrate, a quartz substrate, or a plastic substrate made of FRP (Fiber-Reinforced Plastics), PVF (polyvinyl fluoride), polyester, an acrylic resin, or the like can be used. In the case where glass frit is used for the sealant, the first substrate 301 and the second substrate 306 are preferably glass substrates in terms of adhesion.

In the above manner, the active-matrix light-emitting device can be obtained.

In the case where the active-matrix light-emitting device is formed over a flexible substrate, the FETs and the light-emitting element may be directly formed over the flexible substrate; alternatively, the FETs and the light-emitting element may be formed over a substrate provided with a separation layer and then separated at the separation layer by application of heat, force, laser irradiation, or the like to be transferred to a flexible substrate. For the separation layer, a stack including inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupro, rayon, or regenerated polyester), or the like), a leather substrate, and a rubber substrate. With the use of any of these substrates, high durability, high heat resistance, a reduction in weight, and a reduction in thickness can be achieved.

Note that the structures described in this embodiment can be used in an appropriate combination with the structures described in the other embodiments.

Embodiment 5

In this embodiment, examples of a variety of electronic devices and an automobile completed using the light-emitting element of one embodiment of the present invention or a light-emitting device including the light-emitting element of one embodiment of the present invention are described. Note that the light-emitting device can be used mainly in a display portion of the electronic device described in this embodiment.

Figure 4A:
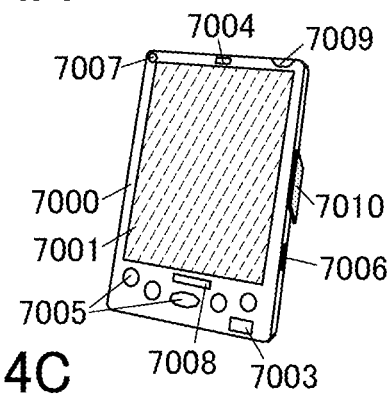
FIGS. 4A-4G are drawings illustrating electronic devices.
Figure 4B:
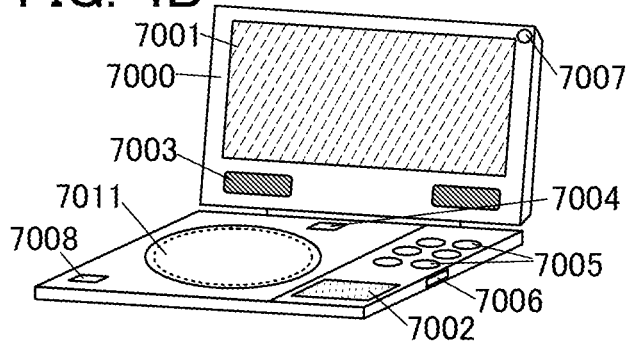
Figure 4C:
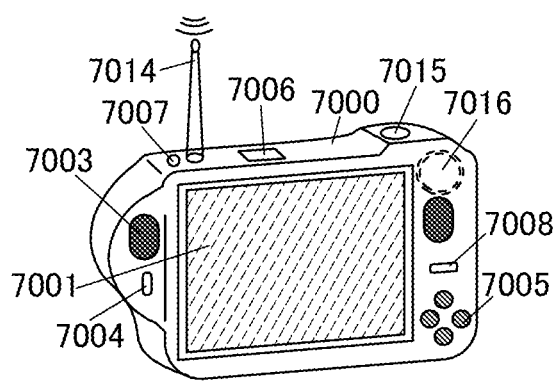

Electronic devices illustrated in FIG. 4(A) to FIG. 4(C) can include a housing 7000, a display portion 7001, a speaker 7003, an LED lamp 7004, operation keys 7005 (including a power switch or an operation switch), a connection terminal 7006, a sensor 7007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 7008, and the like.

FIG. 4(A) is a mobile computer which can include a switch 7009, an infrared port 7010, and the like in addition to the above components.

FIG. 4(B) is a portable image reproducing device (e.g., a DVD player) which is provided with a recording medium and can include a second display portion 7002, a recording medium reading portion 7011, and the like in addition to the above components.

FIG. 4(C) is a digital camera with a television reception function, which can include an antenna 7014, a shutter button 7015, an image receiving portion 7016, and the like in addition to the above components.

Figure 4D:
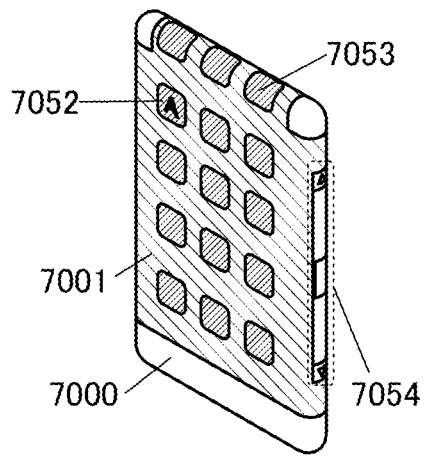

FIG. 4(D) is a portable information terminal. The portable information terminal has a function of displaying information on three or more surfaces of the display portion 7001. Here, an example in which information 7052, information 7053, and information 7054 are displayed on different surfaces is shown. For example, the user can check the information 7053 displayed in a position that can be observed from above the portable information terminal, with the portable information terminal put in a breast pocket of his/her clothes. The user can see the display without taking out the portable information terminal from the pocket and decide whether to answer the call, for example.

Figure 4E:
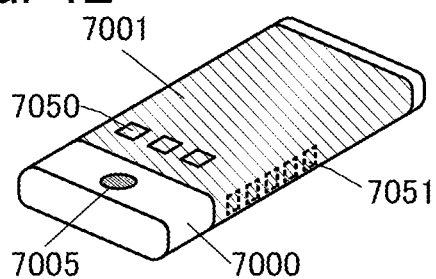

FIG. 4(E) is a portable information terminal (e.g., a smartphone) and can include the display portion 7001, the operation key 7005, and the like in the housing 7000. Note that a speaker, a connection terminal, a sensor, or the like may be provided in the portable information terminal. The portable information terminal can display characters and image information on its plurality of surfaces. Here, an example is shown in which three icons 7050 are displayed. Information 7051 indicated by dashed rectangles can be displayed on another surface of the display portion 7001. Examples of the information 7051 include notification of reception of an e-mail, SNS, or an incoming call, the title and sender of an e-mail, SNS, or the like, the date, the time, remaining battery, and the reception strength of an antenna. Alternatively, the icon 7050 or the like may be displayed in the position where the information 7051 is displayed.

Figure 4F:
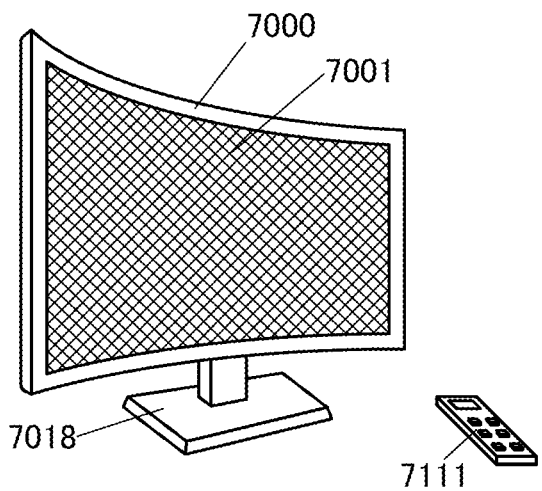

FIG. 4(F) is a large-size television set (also referred to as TV or a television receiver), which can include the housing 7000, the display portion 7001, and the like. In addition, shown here is a structure where the housing 7000 is supported by a stand 7018. The television set can be operated with a separate remote controller 7111 or the like. Note that the display portion 7001 may include a touch sensor, in which case the television set may be operated by touch on the display portion 7001 with a finger or the like. The remote controller 7111 may be provided with a display portion for displaying data output from the remote controller 7111. With operation keys or a touch panel provided in the remote controller 7111, channels and volume can be operated and images displayed on the display portion 7001 can be operated.

The electronic devices illustrated in FIG. 4(A) to FIG. 4(F) can have a variety of functions. For example, they can have a function of displaying a variety of data (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion. Furthermore, the electronic device including a plurality of display portions can have a function of displaying image data mainly on one display portion while displaying text data mainly on the other display portion, a function of displaying a three-dimensional image by displaying images on a plurality of display portions with a parallax taken into account, or the like. Furthermore, the electronic device including an image receiving portion can have a function of taking a still image, a function of taking a moving image, a function of automatically or manually correcting a taken image, a function of storing a taken image in a recording medium (an external recording medium or a recording medium incorporated in the camera), a function of displaying a taken image on the display portion, or the like. Note that functions that the electronic devices illustrated in FIG. 4(A) to FIG. 4(F) can have are not limited to those, and the electronic devices can have a variety of functions.

Figure 4G:
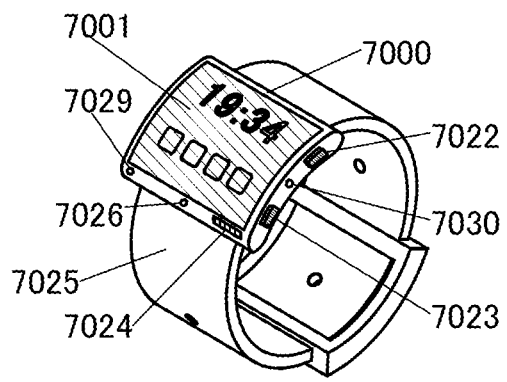

FIG. 4(G) is a watch-type portable information terminal, which can be used as a smart watch, for example. The watch-type portable information terminal includes the housing 7000, the display portion 7001, operation buttons 7022 and 7023, a connection terminal 7024, a band 7025, a microphone 7026, a sensor 7029, a speaker 7030, and the like. The display surface of the display portion 7001 is bent, and display can be performed on the bent display surface. Furthermore, mutual communication between the portable information terminal and, for example, a headset capable of wireless communication can be performed, and thus hands-free calling is possible with the portable information terminal. With the connection terminal 7024, the portable information terminal can perform mutual data transmission with another information terminal and charging. Wireless power feeding can also be employed for the charging operation.

The display portion 7001 mounted in the housing 7000 also serving as a bezel includes a non-rectangular display region. The display portion 7001 can display an icon indicating time, another icon, and the like. The display portion

7001 may be a touch panel (input/output device) including a touch sensor (input device).

Note that the smart watch illustrated in FIG. 4(G) can have a variety of functions. For example, they can have a function of displaying a variety of data (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion.

Moreover, a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like can be included inside the housing 7000.

Note that the light-emitting device of one embodiment of the present invention and the display device including the light-emitting element of one embodiment of the present invention can be used in the display portions of the electronic devices described in this embodiment, enabling the electronic devices to have a long lifetime.

Figure 5A:
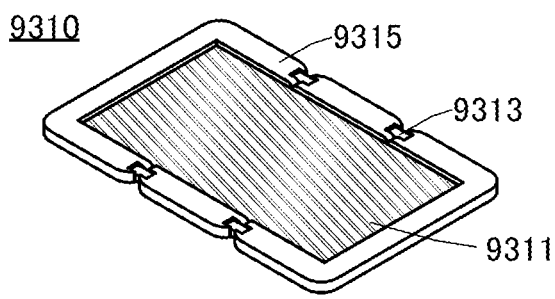
FIGS. 5A-5C are drawings illustrating an electronic device.
Figure 5B:
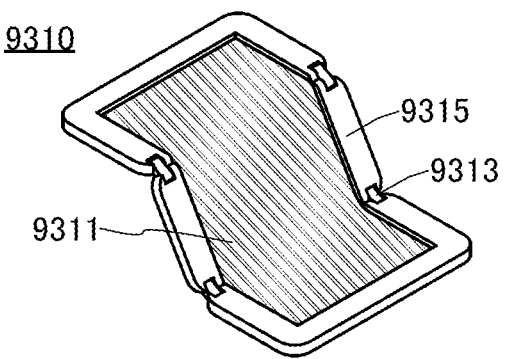
Figure 5C:
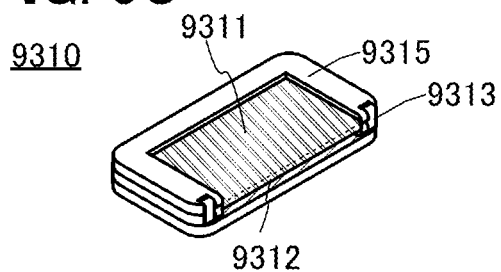

Another electronic device including the light-emitting device is a foldable portable information terminal illustrated in FIGS. 5(A) to 5(C). FIG. 5(A) illustrates a portable information terminal 9310 which is opened. FIG. 5(B) illustrates the portable information terminal 9310 in a state in the middle of change from one of an opened state and a folded state to the other. FIG. 5(C) illustrates the portable information terminal 9310 which is folded. The portable information terminal 9310 is excellent in portability when folded, and is excellent in display browsability when opened because of a seamless large display region.

A display portion 9311 is supported by three housings 9315 joined together by hinges 9313. Note that the display portion 9311 may be a touch panel (input/output device) including a touch sensor (input device). By bending the display portion 9311 at a portion between two housings 9315 with the use of the hinges 9313, the portable information terminal 9310 can be reversibly changed in shape from an opened state to a folded state. The light-emitting device of one embodiment of the present invention can be used for the display portion 9311. In addition, an electronic device having a long lifetime can be provided. A display region 9312 in the display portion 9311 is a display region that is positioned at a side surface of the portable information terminal 9310 which is folded. On the display region 9312, information icons, file shortcuts of frequently used applications or programs, and the like can be displayed, and confirmation of information and start of an application can be smoothly performed.

Figure 6A:
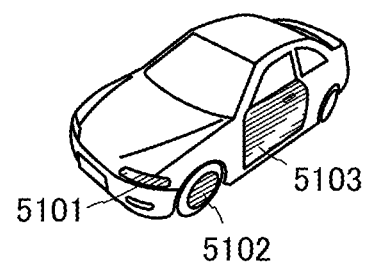
FIGS. 6A and 6B are drawings illustrating an automobile.
Figure 6B:
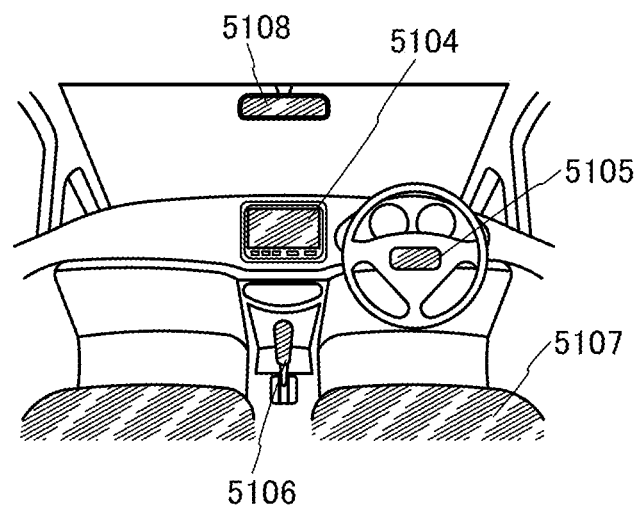

FIGS. 6(A) and 6(B) illustrate an automobile including the light-emitting device. In other words, the light-emitting device can be integrated into an automobile. Specifically, the light-emitting device can be applied to lights 5101 (including lights of the rear part of the car), a wheel 5102, a part or the whole of a door 5103, or the like on the outer side of the automobile which is illustrated in FIG. 6(A). The light-emitting device can also be applied to a display portion 5104, a steering wheel 5105, a shifter 5106, a seat 5107, an inner rearview mirror 5108, or the like on the inner side of the automobile which is illustrated in FIG. 6(B). Apart from that, the light-emitting device may be used for a part of the glass window.

In the above manner, the electronic devices and automobiles in which the light-emitting device or the display device of one embodiment of the present invention is used can be obtained. In that case, a long-lifetime electronic device can be obtained. Note that the light-emitting device or the display device can be used for electronic devices and automobiles in a variety of fields without being limited to those described in this embodiment.

Note that the structures described in this embodiment can be used in an appropriate combination with any of the structures described in the other embodiments.

Embodiment 6

In this embodiment, the structure of a lighting device fabricated using the light-emitting device of one embodiment of the present invention or the light-emitting element which is part of the light-emitting device will be described with reference to FIG. 7.

Figure 7A:
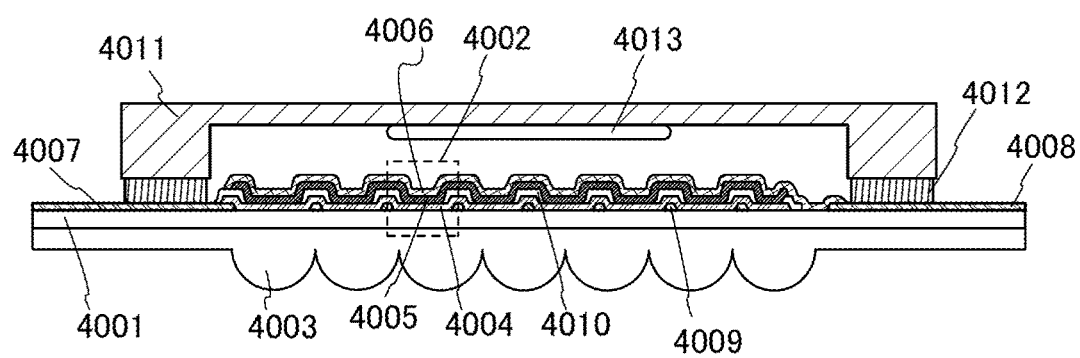
FIGS. 7A and 7B are drawings illustrating lighting devices.
Figure 7B:
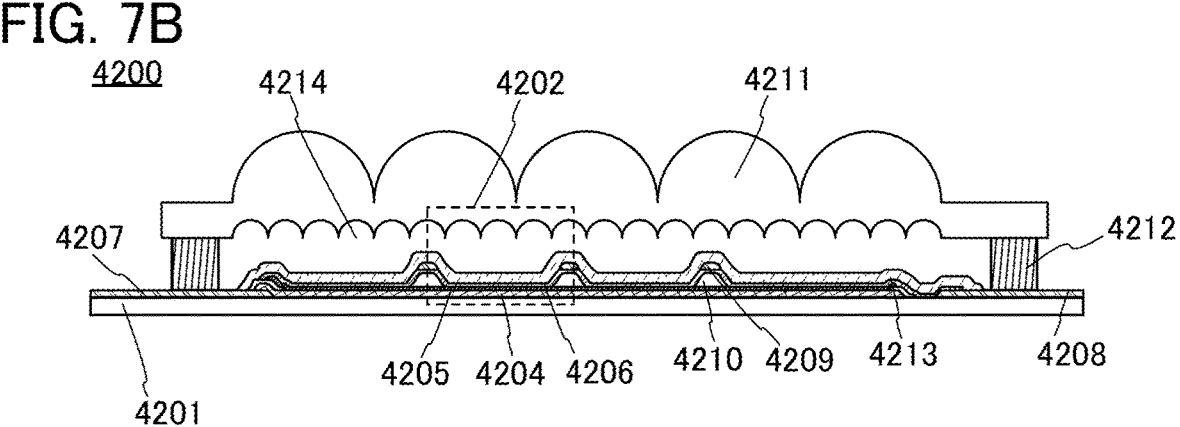

FIGS. 7(A) and 7(B) show examples of cross-sectional views of lighting devices. FIG. 7(A) is a bottom-emission lighting device in which light is extracted from the substrate side, and FIG. 7(B) is a top-emission lighting device in which light is extracted from the sealing substrate side.

A lighting device 4000 illustrated in FIG. 7(A) includes a light-emitting element 4002 over a substrate 4001. In addition, the lighting device 4000 includes a substrate 4003 with unevenness on the outside of the substrate 4001. The light-emitting element 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting element 4002. The substrate 4003 has the unevenness illustrated in FIG. 7(A), whereby the extraction efficiency of light generated in the light-emitting element 4002 can be increased.

A lighting device 4200 illustrated in FIG. 7(B) includes a light-emitting element 4202 over a substrate 4201. The light-emitting element 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may also be provided. In addition, an insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting element 4202. The sealing substrate 4211 has the unevenness illustrated in FIG. 7(B), whereby the extraction efficiency of light generated in the light-emitting element 4202 can be increased.

Application examples of such lighting devices include a ceiling light for indoor lighting. Examples of the ceiling light include a ceiling direct mount light and a ceiling embedded light. Such a lighting device is fabricated using the light-emitting device and a housing or a cover in combination.

For another example, such lighting devices can be used for a foot light that illuminates a floor so that safety on the floor can be improved. For example, the foot light can be effectively used in a bedroom, on a staircase, or on a passage. In that case, the size or shape of the foot light can be changed depending on the area or structure of a room. The foot light can be a stationary lighting device fabricated using the light-emitting device and a support base in combination.

Such lighting devices can also be used for a sheet-like lighting device (sheet-like lighting). The sheet-like lighting, which is attached to a wall when used, is space-saving and thus can be used for a wide variety of uses. Furthermore, the area of the sheet-like lighting can be easily increased. The sheet-like lighting can also be used on a wall or housing having a curved surface.

Besides the above examples, the light-emitting device which is one embodiment of the present invention or the light-emitting element which is a part of the light-emitting device can be used as part of furniture in a room, so that a lighting device which has a function of the furniture can be obtained.

As described above, a variety of lighting devices that include the light-emitting device can be obtained. Note that these lighting devices are also embodiments of the present invention.

The structure described in this embodiment can be used in an appropriate combination with the structures described in the other embodiments.

Example 1

Synthesis Example 1

Described in this example is a method for synthesizing 8-(1,1'-biphenyl-4-yl)-4-[3-(dibenzothiophen-4-yl)phenyl]-[1]benzofuro[3,2-d]pyrimidine (abbreviation: 8BP-4mDBtPBfpm), which is an organic compound of one embodiment of the present invention represented by Structural Formula (100) in Embodiment 1. Note that the structure of 8BP-4mDBtPBfpm is shown below.

[Chemical Formula 24]

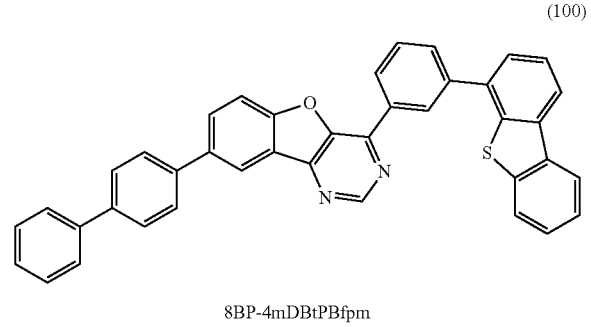

8BP-4mDBtPBfpm (100)

Synthesis of 8-(1,1'-biphenyl-4-yl)-4-[3-(dibenzothiophen-4-yl)phenyl]-[1]benzofuro[3,2-d]pyrimidine Into a three-neck flask, 1.37 g of 8-chloro-4-[3-(dibenzothiophen-4-yl)phenyl]-[1]benzofuro[3,2-d]pyrimidine, 0.657 g of 4-biphenylboronic acid, 1.91 g of tripotassium phosphate, 30 mL of diethylene glycol dimethyl ether (diglyme), and 0.662 g of t-butanol were put, they were degassed by being stirred under reduced pressure, and the air in the flask was replaced with nitrogen.

This mixture was heated to 60° C. and 23.3 mg of palladium(II) acetate and 66.4 mg of di(1-adamantyl)-n-butylphosphine were added, followed by stirring at 120° C. for 27 hours. Water was added to this reaction liquid, suction filtration was performed, and the obtained residue was washed with water, ethanol, and toluene. This residue was dissolved in heated toluene, followed by filtration through a filter aid filled with Celite, alumina, and Celite in this order. The obtained solution was concentrated and dried, and then recrystallized with toluene to give 1.28 g of a target white solid in a yield of 74%.

By a train sublimation method, 1.26 g of the white solid was sublimated and purified. The conditions of the sublimation purification were such that the solid was heated under a pressure of 2.56 Pa at 310° C. while the argon gas flowed at a flow rate of 10 mL/min. After the sublimation purification, 1.01 g of a target pale yellow solid was obtained at a collection rate of 80%. The synthesis scheme is shown in Formula (a-1) below.

[Chemical Formulae 25]

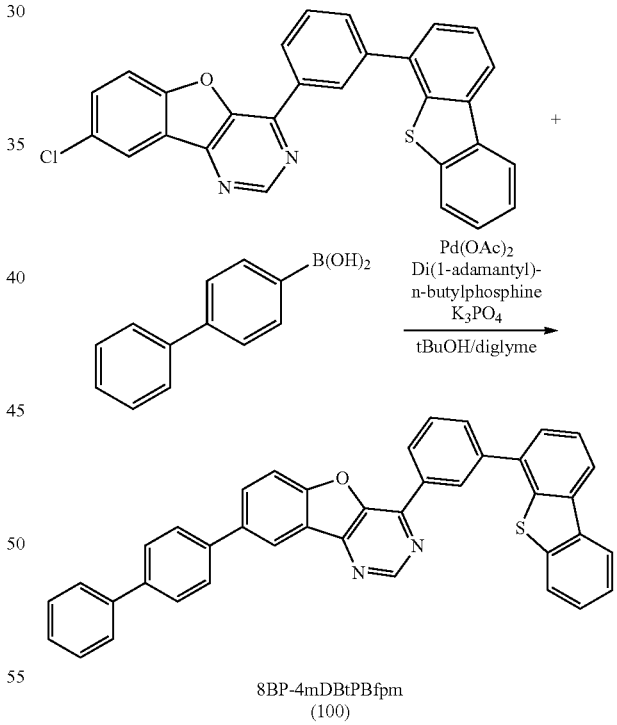

8BP-4mDBtPBfpm (100)

Figure 8:
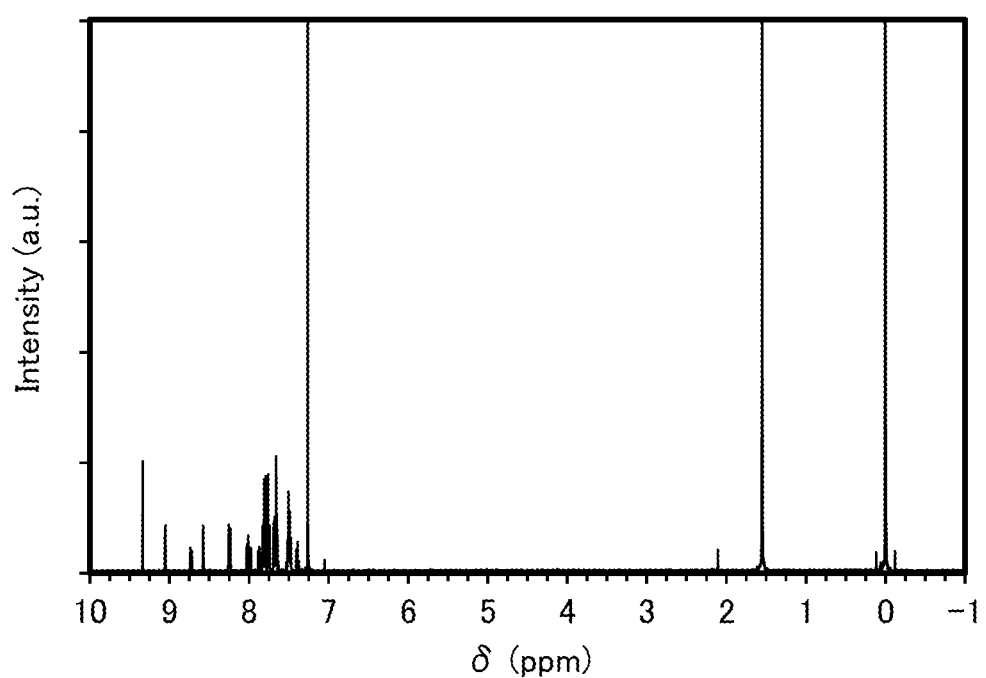
FIG. 8 is a 1H-NMR chart of an organic compound represented by Structural Formula (100).

Note that analysis results by nuclear magnetic resonance ($^1$H-NMR) spectroscopy of the pale yellow solid obtained by the above-described reaction are shown below. FIG. 8 shows a $^1$H-NMR chart. The results reveal that 8BP-4mDBtPBfpm, the organic compound of one embodiment of the present invention represented by Structural Formula (100) above, was obtained in this example.

$^1$H-NMR. δ (CDCl$_3$): 7.39 (t, 1H), 7.47-7.53 (m, 4H), 7.63-7.67 (m, 2H), 7.68 (d, 2H), 7.75 (d, 2H), 7.79-7.83 (m,

4H), 7.87 (d, 1H), 7.98 (d, 1H), 8.02 (d, 1H), 8.23-8.26 (m, 2H), 8.57 (s, 1H), 8.73 (d, 1H), 9.05 (s, 1H), 9.34 (s, 1H).

<<Physical Properties of 8BP-4mDBtPBfpm>>

Next, the ultraviolet-visible absorption spectra (hereinafter, simply referred to as "absorption spectra") and emission spectra of a toluene solution and a solid thin film of 8BP-4mDBtPBfpm were measured.

Figure 9A:
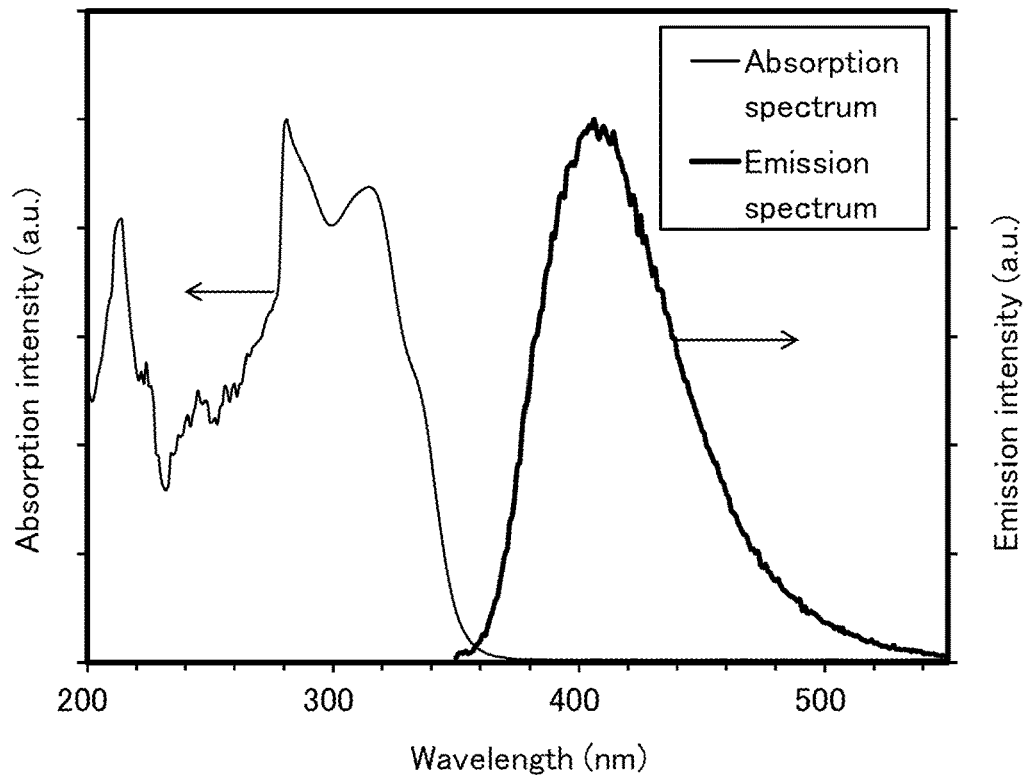
FIG. 9A is an ultraviolet-visible absorption spectrum and an emission spectrum of an organic compound represented by Structural Formula (100) in a toluene solution.

The absorption spectrum in the toluene solution was measured with an ultraviolet-visible spectrophotometer (V550, manufactured by JASCO Corporation). The emission spectrum in the toluene solution was measured with a fluorescence spectrophotometer (FS920, manufactured by Hamamatsu Photonics K.K.). FIG. 9(A) shows the measurement results on the obtained absorption spectrum and emission spectrum in the toluene solution. The horizontal axis represents the wavelength and the vertical axes represent the absorption intensity and the emission intensity.

As shown in FIG. 9(A), 8BP-4mDBtPBfpm in the toluene solution had absorption peaks at approximately 332 nm, 316 nm, and 281 nm, and an emission wavelength peak at 406 nm (at an excitation wavelength of 318 nm).

Figure 9B:
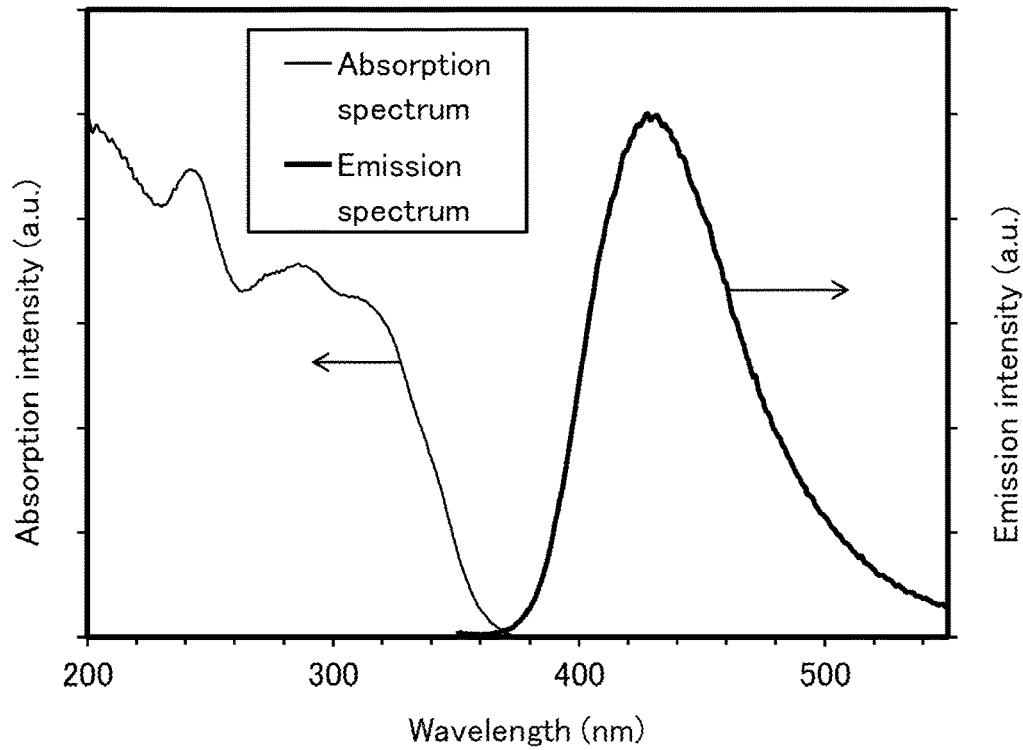
FIG. 9B is an ultraviolet-visible absorption spectrum and an emission spectrum of a solid thin film of the organic compound represented by Structural Formula (100).

For the measurement of the absorption spectrum of the solid thin film, a solid thin film formed on a quartz substrate by a vacuum evaporation method was used, and the measurement was performed with a UV-visible spectrophotometer (U-4100, manufactured by Hitachi High-Technologies Corporation). A solid thin film similar to the above was used for the measurement of the emission spectrum of the solid thin film, and the measurement was performed with a fluorescence spectrophotometer (FS920, manufactured by Hamamatsu Photonics K.K.). FIG. 9(B) shows the measurement results on the obtained absorption spectrum and emission spectrum of the solid thin film. The horizontal axis represents the wavelength and the vertical axes represent the absorption intensity and the emission intensity. In addition, a solid thin film similar to the above was used for the measurement of the emission spectrum at a low temperature (10 K); for the measurement, a PL microscope, LabRAM HR-PL (HORIBA, Ltd.) was used, the measurement temperature was 10 K, He—Cd laser having a wavelength of 325 nm was used as excitation light, and a CCD detector was used as a detector.

As shown in FIG. 9(B), the solid thin film of 8BP-4mDBtPBfpm had absorption peaks at approximately 341 nm, 308 nm, 286 nm, 273 nm, and 243 nm, and an emission wavelength peak at 428 nm (at an excitation wavelength of 340 nm). From the results on the emission spectrum at a low temperature (10 K), the wavelength of a peak (including a shoulder) on the shortest wavelength side of the phosphorescent component of the emission spectrum of 8BP-4mDBtPBfpm was 482 nm. Thus, from the peak wavelength, the T1 level of 8BP-4mDBtPBfpm was calculated to be 2.57 eV.

It can be said that 8BP-4mDBtPBfpm, which is the organic compound of one embodiment of the present invention, has a high T1 level and is a host material suitable for a phosphorescent material (guest material) that emits light in the vicinity of green to red regions. Note that 8BP-4mDBtPBfpm, which is the organic compound of one embodiment of the present invention, can also be used as a host material for a substance that emits phosphorescence in the visible region or a light-emitting substance.

Example 2

Synthesis Example 2

Described in this example is a method for synthesizing 8-(1,1'-biphenyl-3-yl)-4-[3-(dibenzothiophen-4-yl)phenyl]-[1]benzofuro[3,2-d]pyrimidine (abbreviation: 8mBP-4mDBtPBfpm), which is an organic compound of one embodiment of the present invention represented by Structural Formula (101) in Embodiment 1. Note that the structure of 8mBP-4mDBtPBfpm is shown below.

[Chemical Formula 26]

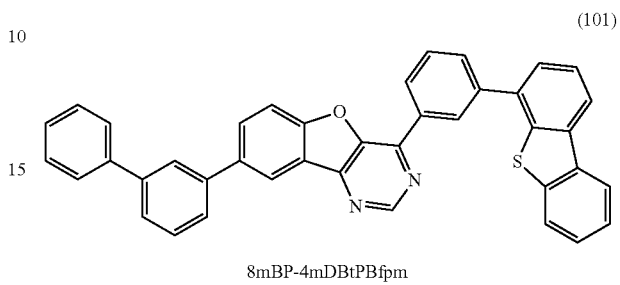

(101)

8mBP-4mDBtPBfpm

Synthesis of 8-(1,1'-biphenyl-3-yl)-4-[3-(dibenzothiophen-4-yl)phenyl]-[1]benzofuro[3,2-d]pyrimidine Into a three-neck flask, 1.37 g of 8-chloro-4-[3-(dibenzothiophen-4-yl)phenyl]-[1]benzofuro[3,2-d]pyrimidine, 0.664 g of 3-biphenylboronic acid, 1.90 g of tripotassium phosphate, 0.663 g of t-butanol, and 30 mL of diglyme were put, they were degassed by being stirred under reduced pressure, and the air was replaced with nitrogen. This mixture was heated to 60° C. and 21.4 mg of palladium(II) acetate and 65.6 mg of di(1-adamantyl)-n-butylphosphine were added, followed by stirring at 120° C. for 21 hours.

Then, 23.5 mg of palladium(II) acetate and 66.4 mg of di(1-adamantyl)-n-butylphosphine were added to this reaction product, followed by stirring at 120° C. for 8 hours. Water was added to this reaction product, suction filtration was performed, and the obtained residue was washed with water, ethanol, and toluene. This residue was dissolved in heated toluene, followed by filtration through a filter aid filled with Celite, alumina, and Celite in this order. The obtained solution was concentrated and dried, and then recrystallized with toluene to give 1.10 g of a target white solid in a yield of 64%.

By a train sublimation method, 1.10 g of the white solid was sublimated and purified. The conditions of the sublimation purification were such that the solid was heated under a pressure of 2.57 Pa at 300° C. while the argon gas flowed at a flow rate of 10 mL/min. After the sublimation purification, 0.895 g of a target pale yellow solid was obtained at a collection rate of 81%. The synthesis scheme is shown in Formula (b-1) below.

[Chemical Formulae 27]

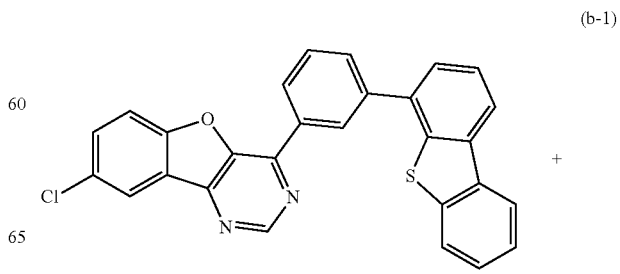

(b-1)

-continued

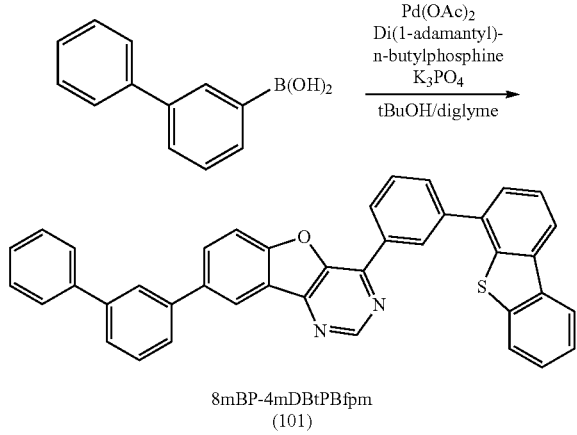

8mBP-4mDBtPBfpm
(101)

Figure 10:
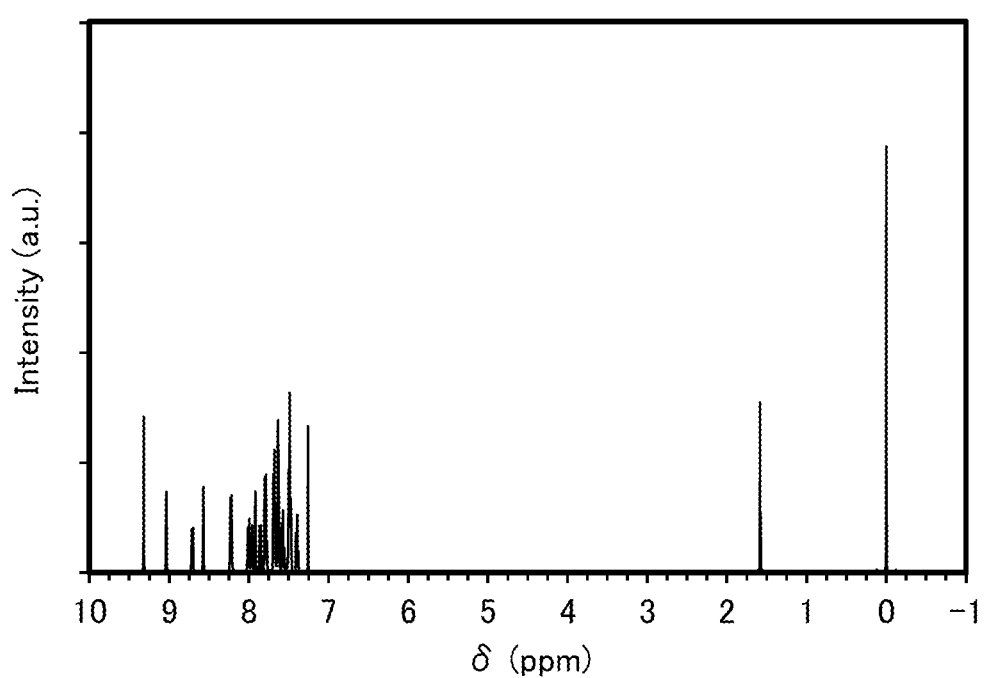
FIG. 10 is a 1H-NMR chart of an organic compound represented by Structural Formula (101).

Note that analysis results by nuclear magnetic resonance (¹H-NMR) spectroscopy of the pale yellow solid obtained by the above-described reaction are shown below. FIG. 10 shows a ¹H-NMR chart. The results reveal that 8mBP-4mDBtPBfpm, the organic compound of one embodiment of the present invention represented by Structural Formula (101) above, was obtained in this example.

¹H-NMR. δ (CDCl$_3$): 7.39 (t, 1H), 7.47-7.50 (m, 4H), 7.57 (t, 1H), 7.62-7.64 (m, 3H), 7.67-7.69 (m, 3H), 7.77-7.80 (m, 2H), 7.86 (d, 1H), 7.92 (s, 1H), 7.79 (d, 1H), 8.00 (d, 1H), 8.21-8.23 (m, 2H), 8.57 (s, 1H), 8.71 (d, 1H), 9.03 (s, 1H), 9.32 (s, 1H).

<<Physical Properties of 8mBP-4mDBtPBfpm>>

Next, the ultraviolet-visible absorption spectra (hereinafter, simply referred to as "absorption spectra") and emission spectra of a toluene solution and a solid thin film of 8mBP-4mDBtPBfpm were measured.

Figure 11A:
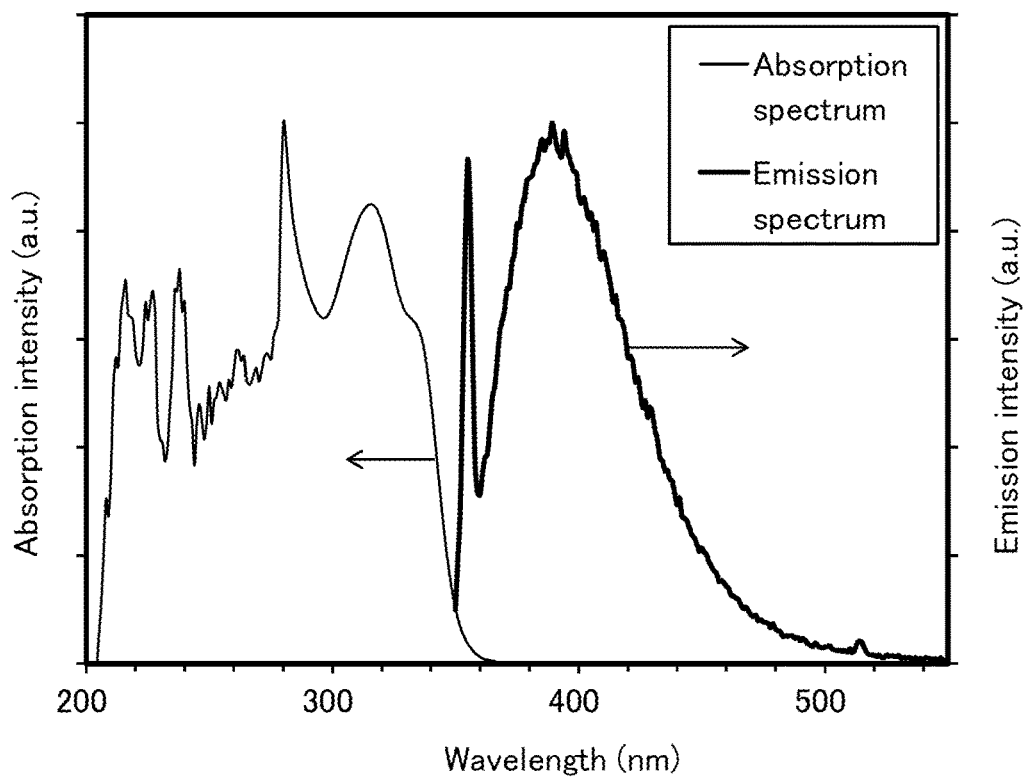
FIG. 11A is an ultraviolet-visible absorption spectrum and an emission spectrum of the organic compound represented by Structural Formula (101) in a toluene solution.

The absorption spectrum in the toluene solution was measured with an ultraviolet-visible spectrophotometer (V550, manufactured by JASCO Corporation). The emission spectrum in the toluene solution was measured with a fluorescence spectrophotometer (FS920, manufactured by Hamamatsu Photonics K.K.). FIG. 11(A) shows the measurement results on the obtained absorption spectrum and emission spectrum in the toluene solution. The horizontal axis represents the wavelength and the vertical axes represent the absorption intensity and the emission intensity.

As shown in FIG. 11(A), 8mBP-4mDBtPBfpm in the toluene solution had absorption peaks at approximately 331 nm, 315 nm, and 280 nm, and an emission wavelength peak at 389 nm (at an excitation wavelength of 320 nm).

Figure 11B:
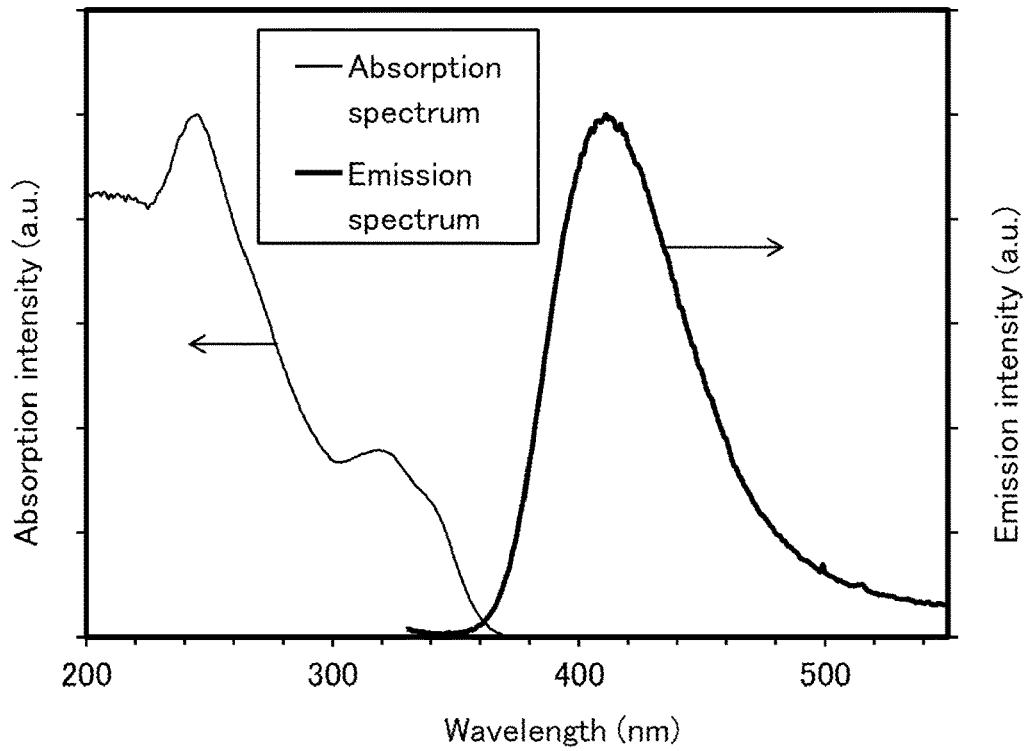
FIG. 11B is an ultraviolet-visible absorption spectrum and an emission spectrum of a solid thin film of the organic compound represented by Structural Formula (101).

For the measurement of the absorption spectrum of the solid thin film, a solid thin film formed on a quartz substrate by a vacuum evaporation method was used, and the measurement was performed with a UV-visible spectrophotometer (U-4100, manufactured by Hitachi High-Technologies Corporation). A solid thin film similar to the above was used for the measurement of the emission spectrum of the solid thin film, and the measurement was performed with a fluorescence spectrophotometer (FS920, manufactured by Hamamatsu Photonics K.K.). FIG. 11(B) shows the measurement results on the obtained absorption spectrum and emission spectrum of the solid thin film. The horizontal axis represents the wavelength and the vertical axes represent the absorption intensity and the emission intensity. In addition, a solid thin film similar to the above was used for the measurement of the emission spectrum at a low temperature (10 K); for the measurement, a PL microscope, LabRAM HR-PL (HORIBA, Ltd.) was used, the measurement temperature was 10 K, He—Cd laser having a wavelength of 325 nm was used as excitation light, and a CCD detector was used as a detector.

As shown in FIG. 11(B), the solid thin film of 8mBP-4mDBtPBfpm had absorption peaks at approximately 343 nm, 319 nm, and 245 nm, and an emission wavelength peak at 411 nm (at an excitation wavelength of 320 nm). From the results on the emission spectrum at a low temperature (10 K), the wavelength of a peak (including a shoulder) on the shortest wavelength side of the phosphorescent component of the emission spectrum of 8mBP-4mDBtPBfpm was 456 nm. Thus, from the peak wavelength, the T1 level of 8mBP-4mDBtPBfpm was calculated to be 2.72 eV.

It can be said that 8mBP-4mDBtPBfpm, which is the organic compound of one embodiment of the present invention, has a high T1 level and is a host material suitable for a phosphorescent material (guest material) that emits light in the vicinity of green to red regions. Note that 8mBP-4mDBtPBfpm, which is the organic compound of one embodiment of the present invention, can also be used as a host material for a substance that emits phosphorescence in the visible region or a light-emitting substance.

Example 3

Synthesis Example 3

Described in this example is a method for synthesizing 8-[(2,2'-binaphthalen)-6-yl]-4-[3-(dibenzothiophen-4-yl) phenyl]-[1]benzofuro[3,2-d]pyrimidine (abbreviation: 8(βN2)-4mDBtPBfpm), which is an organic compound of one embodiment of the present invention represented by Structural Formula (102) in Embodiment 1. Note that the structure of 8(βN2)-4mDBtPBfpm is shown below.

[Chemical Formula 28]

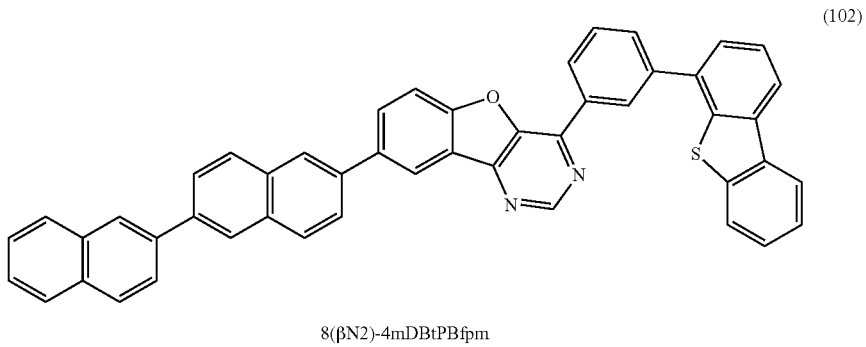

8(βN2)-4mDBtPBfpm

Synthesis of 8-[(2,2'-binaphthalen)-6-yl]-4-[3-(dibenzothiophen-4-yl)phenyl]-[1]benzofuro[3,2-d]pyrimidine Into a three-neck flask, 1.21 g of 8-chloro-4-[3-(dibenzothiophen-4-yl)phenyl]-[1]benzofuro[3,2-d]pyrimidine, 0.857 g of [2,2'-binaphthalen]-6-ylboronic acid, 1.67 g of tripotassium phosphate, 26 mL of diglyme, and 0.583 g of t-butanol were put, they were degassed by being stirred under reduced pressure, and the air in the flask was replaced with nitrogen.

This mixture was heated to 60° C. and 18.9 mg of palladium(II) acetate and 61.1 mg of di(1-adamantyl)-n-butylphosphine were added, followed by stirring at 120° C. for 10 hours. Water was added to this reaction liquid, suction filtration was performed, and the obtained residue was washed with water, ethanol, and toluene. This residue was dissolved in heated toluene, followed by filtration through a filter aid filled with Celite, alumina, and Celite in this order. The obtained solution was concentrated and dried to give a white solid.

were put, they were degassed by being stirred under reduced pressure, and the air in the flask was replaced with nitrogen. This mixture was heated to 60° C. and 8.7 mg of palladium (II) acetate and 25.1 mg of di(1-adamantyl)-n-butylphosphine were added, followed by stirring at 120° C. for 18.5 hours. Water was added to this reaction liquid, suction filtration was performed, and the obtained residue was washed with water, ethanol, and toluene.

This residue was dissolved in heated toluene, followed by filtration through a filter aid filled with Celite, alumina, and Celite in this order. The obtained solution was concentrated and dried, and then recrystallized with toluene to give 1.16 g of a target white solid in a yield of 65%. By a train sublimation method, 1.15 g of the obtained white solid was sublimated and purified. The conditions of the sublimation purification were such that the solid was heated under a pressure of 2.64 Pa at 365° C. while the argon gas flowed at a flow rate of 10 mL/min. After the sublimation purification, 0.958 g of 8(βN2)-4mDBtPBfpm was obtained (a collection rate was 83%, a white solid). The synthesis scheme is shown in Formula (c-1) below.

[Chemical Formulae 29]

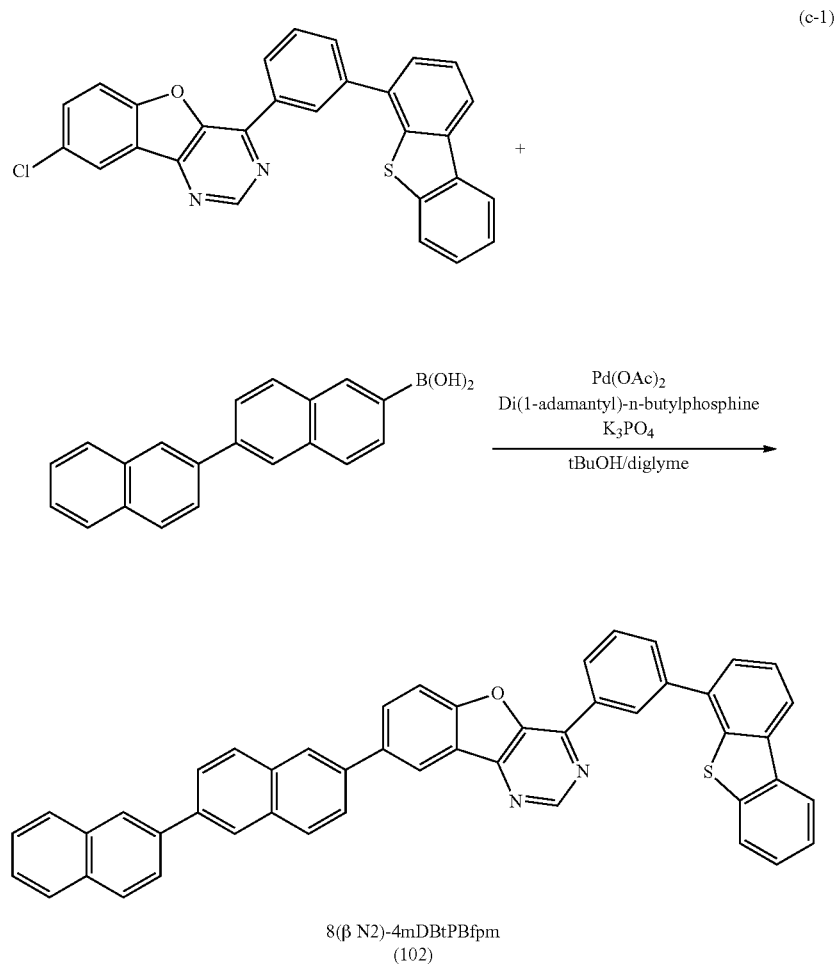

Figure 12:
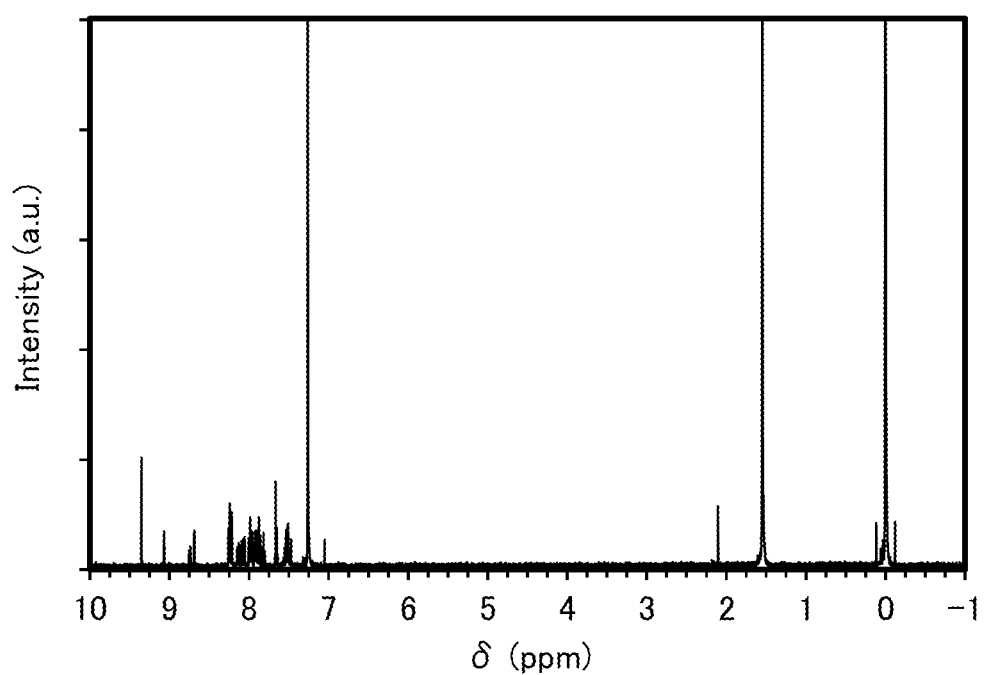
FIG. 12 is a 1H-NMR chart of an organic compound represented by Structural Formula (102).

Into a three-neck flask, all of the obtained solid, 0.348 g of [2,2'-binaphthalen]-6-ylboronic acid, 0.621 g of tripotassium phosphate, 13 mL of diglyme, and 0.239 g of t-butanol Note that analysis results by nuclear magnetic resonance ($^1$H-NMR) spectroscopy of the white solid obtained by the above-described reaction are shown below. FIG. 12 shows a ¹H-NMR chart. The results reveal that 8(βN2)-4mDBtPBfpm, the organic compound of one embodiment of the present invention represented by Structural Formula (102) above, was obtained in this example.

¹H-NMR. δ (CDCl₃): 7.50-7.7.57 (m, 4H), 7.64-7.67 (m, 2H), 7.82 (t, 1H), 7.86-8.00 (m, 9H), 8.05-8.09 (m, 2H), 8.14 (d, 1H), 8.22-8.26 (m, 5H), 8.69 (s, 1H), 8.74 (d, 1H), 9.07 (s, 1H), 9.35 (s, 1H).

<<Physical Properties of 8(βN2)-4mDBtPBfpm>>

Next, the ultraviolet-visible absorption spectra (hereinafter, simply referred to as "absorption spectra") and emission spectra of a toluene solution and a solid thin film of 8(βN2)-4mDBtPBfpm were measured.

Figure 13A:
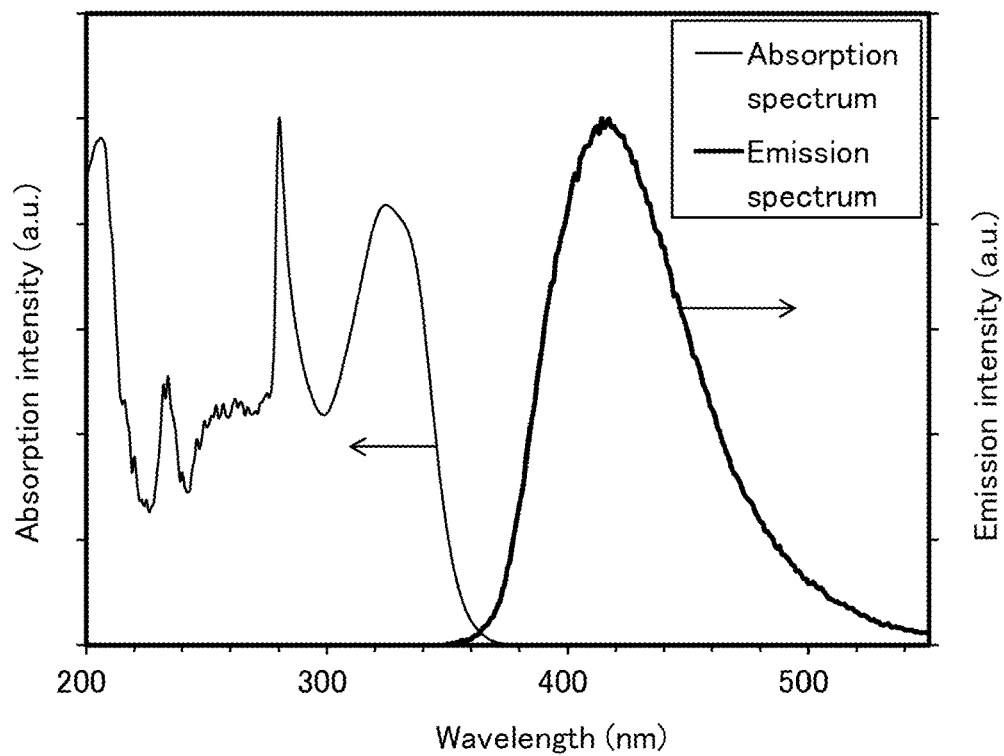
FIG. 13A is an ultraviolet-visible absorption spectrum and an emission spectrum of the organic compound represented by Structural Formula (102) in a toluene solution.

The absorption spectrum in the toluene solution was measured with an ultraviolet-visible spectrophotometer (V550, manufactured by JASCO Corporation). The emission spectrum in the toluene solution was measured with a fluorescence spectrophotometer (FS920, manufactured by Hamamatsu Photonics K.K.). FIG. 13(A) shows the measurement results on the obtained absorption spectrum and emission spectrum in the toluene solution. The horizontal axis represents the wavelength and the vertical axes represent the absorption intensity and the emission intensity.

As shown in FIG. 13(A), 8(βN2)-4mDBtPBfpm in the toluene solution had absorption peaks at approximately 333 nm, 325 nm, and 280 nm, and an emission wavelength peak at 414 nm (at an excitation wavelength of 329 nm).

Figure 13B:
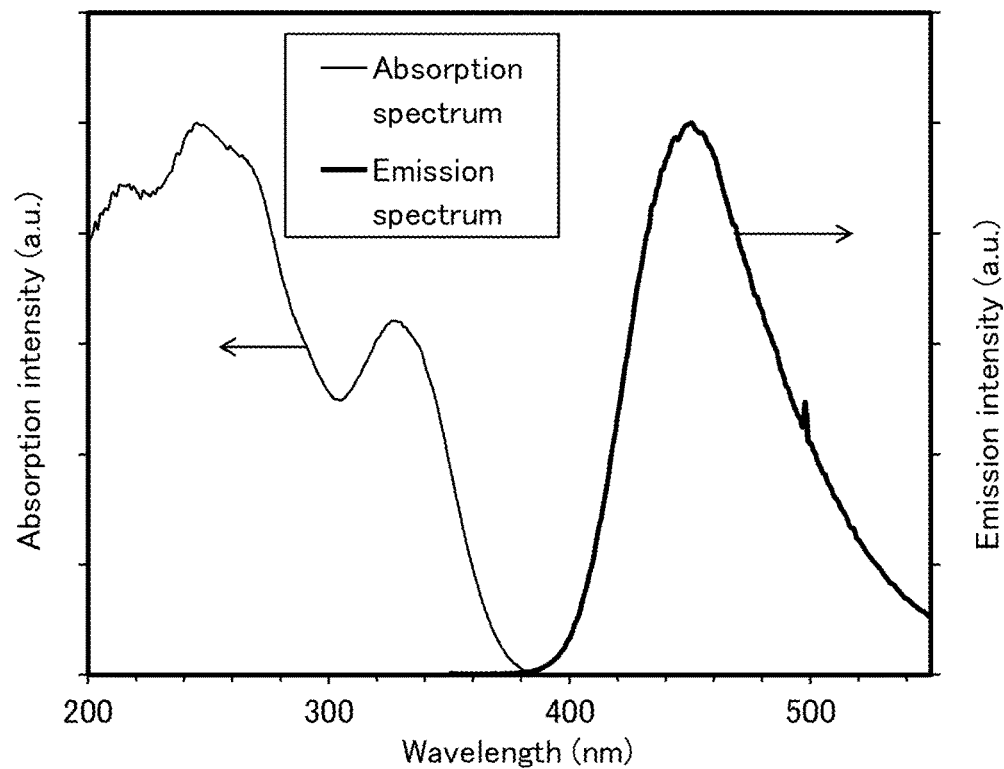
FIG. 13B is an ultraviolet-visible absorption spectrum and an emission spectrum of a solid thin film of the organic compound represented by Structural Formula (102).

For the measurement of the absorption spectrum of the solid thin film, a solid thin film formed on a quartz substrate by a vacuum evaporation method was used, and the measurement was performed with a UV-visible spectrophotometer (U-4100, manufactured by Hitachi High-Technologies Corporation). A solid thin film similar to the above was used for the measurement of the emission spectrum of the solid thin film, and the measurement was performed with a fluorescence spectrophotometer (FS920, manufactured by Hamamatsu Photonics K.K.). FIG. 13(B) shows the measurement results on the obtained absorption spectrum and emission spectrum of the solid thin film. The horizontal axis represents the wavelength and the vertical axes represent the absorption intensity and the emission intensity. In addition, a solid thin film similar to the above was used for the measurement of the emission spectrum at a low temperature (10 K); for the measurement, a PL microscope, LabRAM HR-PL (HORIBA, Ltd.) was used, the measurement temperature was 10 K, He—Cd laser having a wavelength of 325 nm was used as excitation light, and a CCD detector was used as a detector.

As shown in FIG. 13(B), the solid thin film of 8(βN2)-4mDBtPBfpm had absorption peaks at approximately 328 nm, 266 nm, and 245 nm, and an emission wavelength peak at 451 nm (at an excitation wavelength of 340 nm). From the results on the emission spectrum at a low temperature (10 K), the wavelength of a peak (including a shoulder) on the shortest wavelength side of the phosphorescent component of the emission spectrum of 8(βN2)-4mDBtPBfpm was 543 nm. Thus, from the peak wavelength, the T1 level of 8(βN2)-4mDBtPBfpm was calculated to be 2.28 eV.

It can be said that 8(βN2)-4mDBtPBfpm, which is the organic compound of one embodiment of the present invention, has a high T1 level and is a host material suitable for a phosphorescent material (guest material) that emits light in the vicinity of yellow to red regions. Note that 8(βN2)-4mDBtPBfpm, which is the organic compound of one embodiment of the present invention, can also be used as a host material for a substance that emits phosphorescence in the visible region or a light-emitting substance.

Example 4

Figure 14:
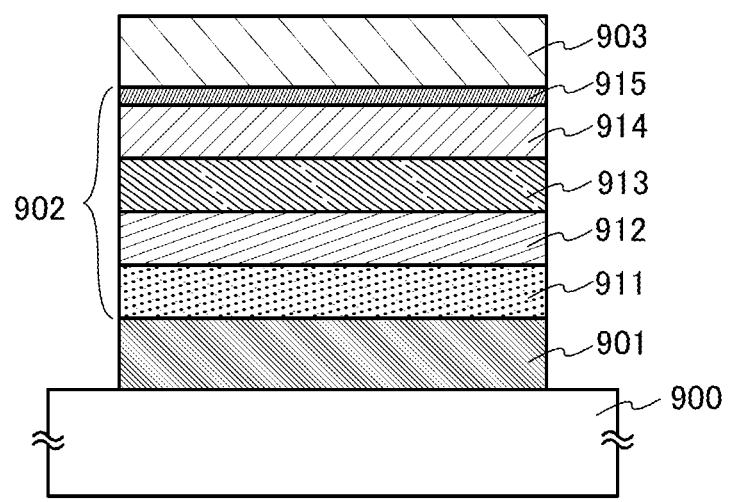
FIG. 14 is a drawing illustrating a light-emitting element.
Figure 15:
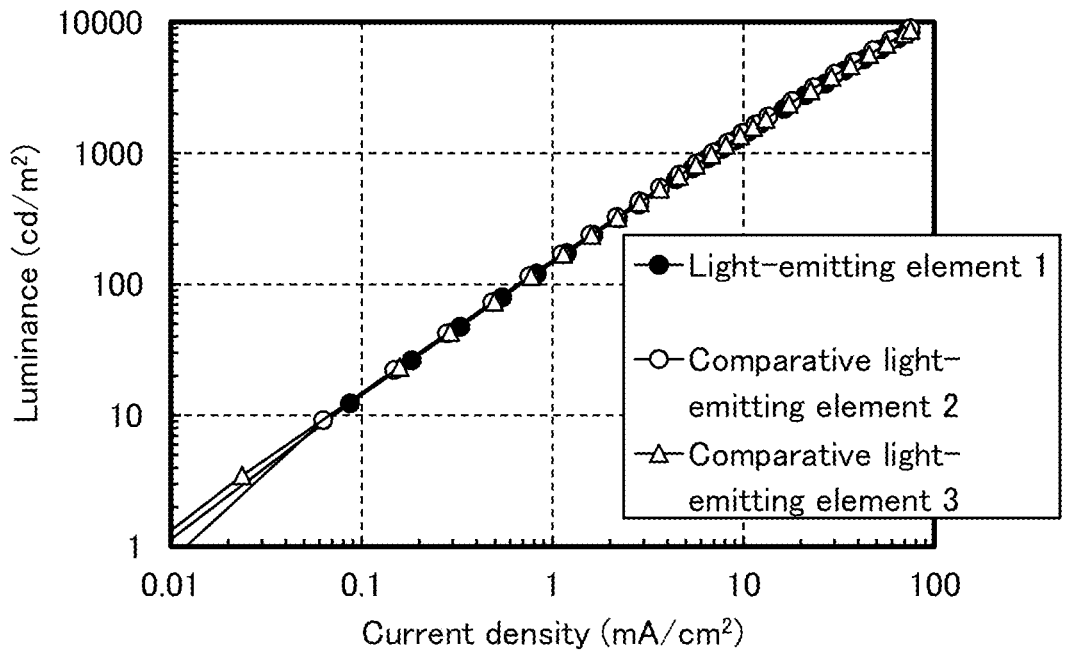
FIG. 15 is a drawing showing current density-luminance characteristics of a light-emitting element 1, a comparative light-emitting element 2, and a comparative light-emitting element 3.
Figure 16:
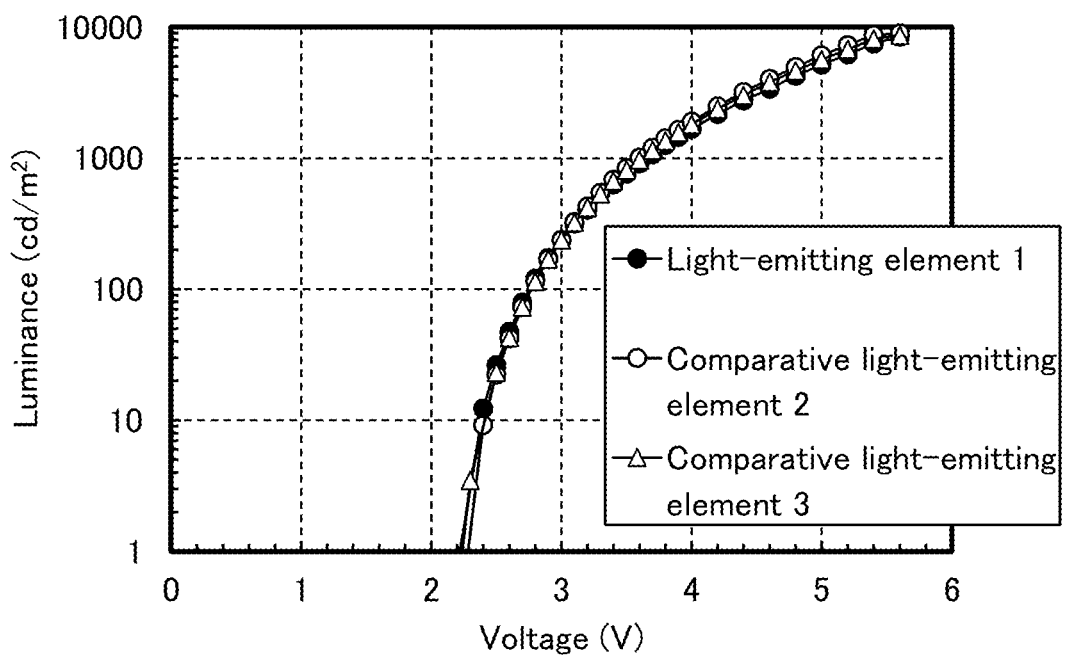
FIG. 16 is a drawing showing voltage-luminance characteristics of the light-emitting element 1, the comparative light-emitting element 2, and the comparative light-emitting element 3.
Figure 17:
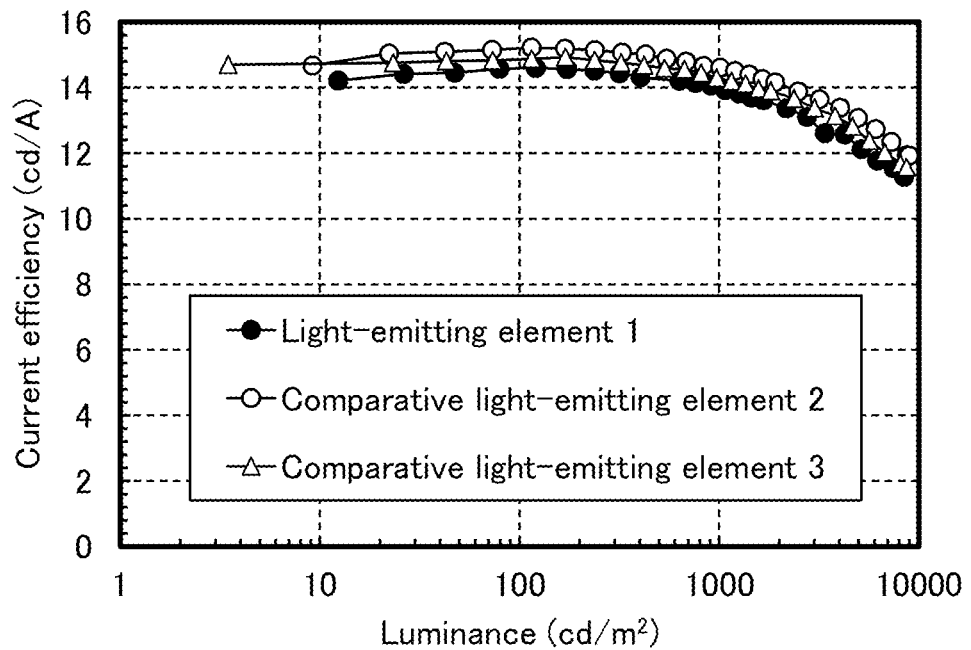
FIG. 17 is a drawing showing luminance-current efficiency characteristics of the light-emitting element 1, the comparative light-emitting element 2, and the comparative light-emitting element 3.
Figure 18:
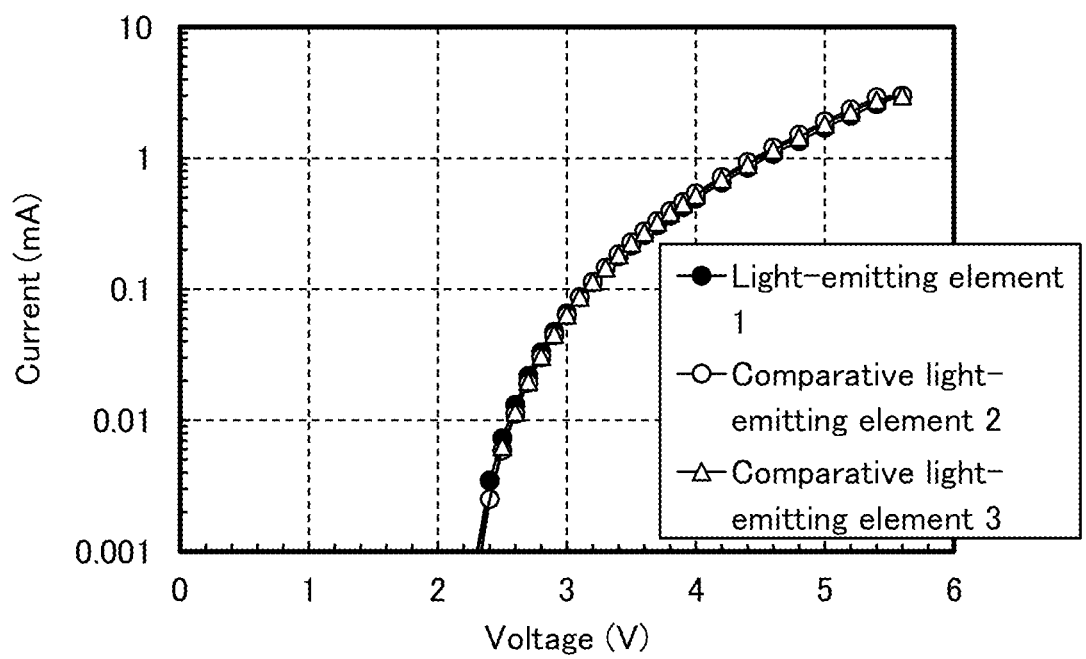
FIG. 18 is a drawing showing voltage-current characteristics of the light-emitting element 1, the comparative light-emitting element 2, and the comparative light-emitting element 3.

Described in this example are element structures, fabrication methods, and characteristics of a light-emitting element 1, which uses 8-[(2,2'-binaphthalen)-6-yl]-4-[3-(dibenzothiophen-4-yl)phenyl]-[1]benzofuro[3,2-d]pyrimidine (abbreviation: 8(βN2)-4mDBtPBfpm) (Structural Formula (102)) described in Example 3 for a light-emitting layer as a light-emitting element of one embodiment of the present invention; a comparative light-emitting element 2 for comparison, which uses 4-[3-(dibenzothiophen-4-yl)phenyl]-8-(naphthalen-2-yl)-[1]benzofuro[3,2-d]pyrimidine (abbreviation: 8βN-4mDBtPBfpm) (Structural Formula (301)) for a light-emitting layer; and a comparative light-emitting element 3, for comparison which uses 4,8-bis[3-(dibenzothiophen-4-yl)phenyl]benzofuro[3,2-d]pyrimidine (abbreviation: 4,8mDBtP2Bfpm) (Structural Formula (302)) for a light-emitting layer. Note that FIG. 14 illustrates the element structure of the light-emitting elements used in this example, and Table 1 shows specific structures. Chemical formulae of materials used in this example are shown below.

TABLE 1

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 1 | ITSO (70 nm) | DBT3P-II:MoOx (2:1 60 nm) | PCBBiIBP (20 nm) | * | 8(βN2)-4mDBtPBfpm (25 nm) | NBphen (15 nm) | LiF (1 nm) | Al (200 nm) |
| Comparative light-emitting element 2 | ITSO (70 nm) | DBT3P-II:MoOx (2:1 60 nm) | PCBBiIBP (20 nm) | ** | 8βN-4mDBtPBfpm (25 nm) | NBphen (15 nm) | LiF (1 nm) | Al (200 nm) |
| Comparative light-emitting element 3 | ITSO (70 nm) | DBT3P-II:MoOx (2:1 60 nm) | PCBBiIBP (20 nm) | *** | 4,8mDBtP2Bfpm (25 nm) | NBphen (15 nm) | LiF (1 nm) | Al (200 nm) |

* 8(βN2)-4mDBtPBfpm:PCBBiF:Ir(dmpqn)₂(acac) (0.75:0.25:0.1 40 nm)

** 8βN-4mDBtPBfpm:PCBBiF:Ir(dmpqn)₂(acac) (0.75:0.25:0.1 40 nm)

*** 4,8mDBtP2Bfpm:PCBBiF:Ir(dmpqn)₂(acac) (0.75:0.25:0.1 40 nm)

[Chemical Formulae 30]
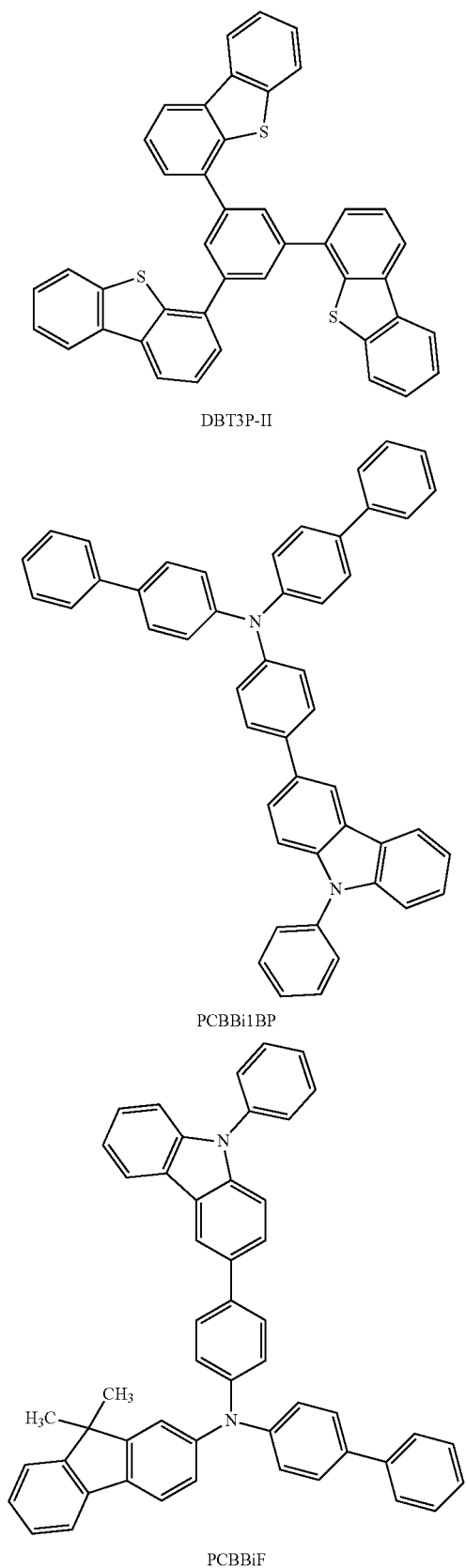
DBT3P-II
PCBBi1BP
PCBBiF
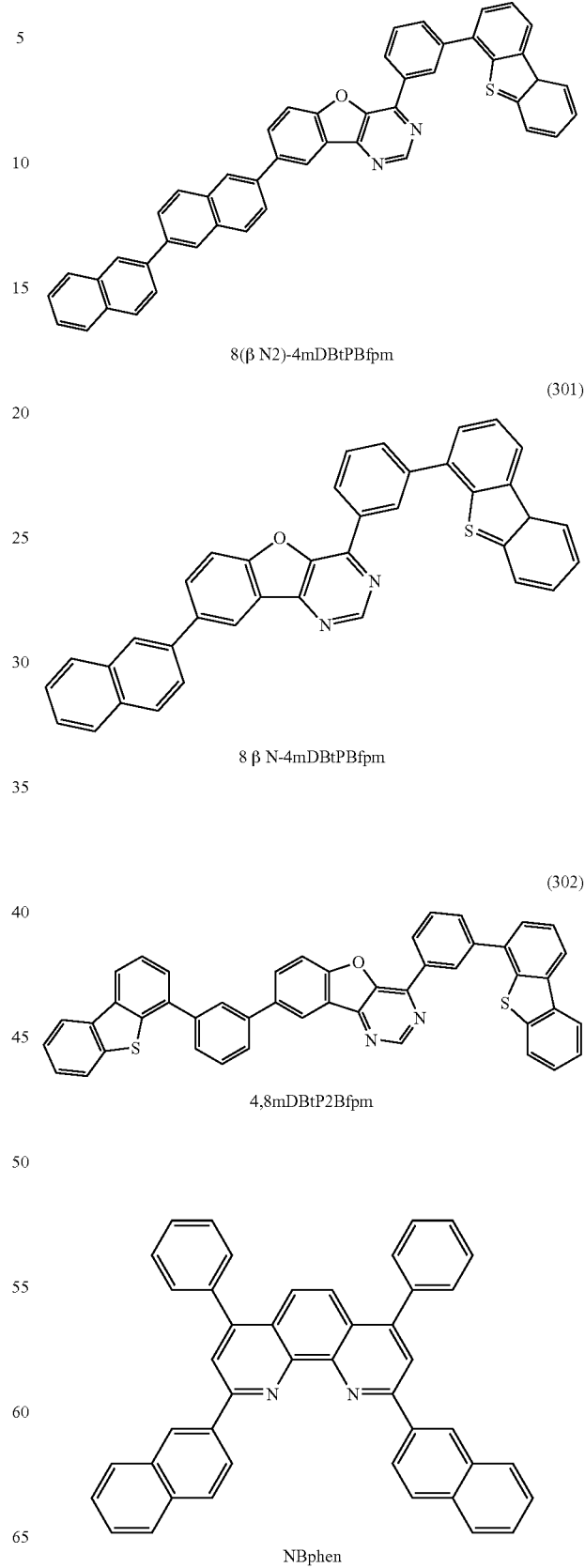
(102)
8(β N2)-4mDBtPBfpm
(301)
8 β N-4mDBtPBfpm
(302)
4,8mDBtP2Bfpm
NBphen

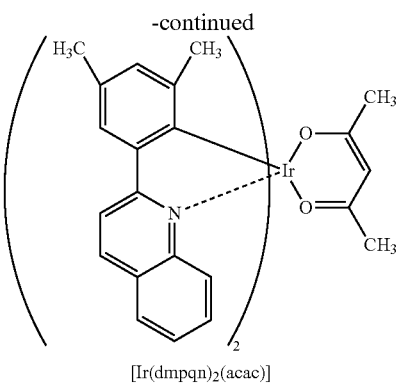

[Ir(dmpqn)₂(acac)]

<<Fabrication of Light-Emitting Elements>>

The light-emitting elements described in this example have a structure as illustrated in FIG. 14, in which a hole-injection layer 911, a hole-transport layer 912, a light-emitting layer 913, an electron-transport layer 914, and an electron-injection layer 915 are stacked in this order over a first electrode 901 formed over a substrate 900, and a second electrode 903 is stacked over the electron-injection layer 915.

First, the first electrode 901 was formed over the substrate 900. The electrode area was set to 4 mm² (2 mm×2 mm). A glass substrate was used as the substrate 900. The first electrode 901 was deposited to a thickness of 70 nm using indium tin oxide containing silicon oxide (ITSO) by a sputtering method.

As pretreatment, a surface of the substrate was washed with water, baking was performed at 200° C. for one hour, and then UV ozone treatment was performed for 370 seconds. After that, the substrate was transferred into a vacuum evaporation apparatus in which the pressure was reduced to approximately 10⁻⁴ Pa, vacuum baking at 170° C. for 30 minutes was performed in a heating chamber in the vacuum evaporation apparatus, and then the substrate was cooled down for approximately 30 minutes.

Next, the hole-injection layer 911 was formed over the first electrode 901. For the formation of the hole-injection layer 911, the pressure in the vacuum evaporation apparatus was reduced to 10⁻⁴ Pa, and then 1,3,5-tri(dibenzothiophen-4-yl)benzene (abbreviation: DBT3P-II) and molybdenum oxide were co-evaporated such that DBT3P-II: molybdenum oxide=2:1 (mass ratio) and the thickness was 60 nm.

Then, the hole-transport layer 912 was formed over the hole-injection layer 911. The hole-transport layer 912 was formed to a thickness of 20 nm by evaporation using 4,4'-diphenyl-4''-(9-phenyl-9H-carbazol-3-yl)triphenylamine (abbreviation: PCBBi1BP).

Next, the light-emitting layer 913 was formed over the hole-transport layer 912.

The light-emitting layer 913 in the light-emitting element 1 was deposited by co-evaporation using bis[4,6-dimethyl-2-(2-quinolinyl-κN)phenyl-κC](2,4-pentanedionato-κ²O,O')iridium(III) (abbreviation: [Ir(dmpqn)₂(acac)]) as a guest material (phosphorescent light-emitting material) in addition to 8(βN2)-4mDBtPBfpm and N-(1,1'-biphenyl-4-yl)-N-[4-(9-phenyl-9H-carbazol-3-yl)phenyl]-9,9-dimethyl-9H-fluoren-2-amine (abbreviation: PCBBiF) to have a weight ratio of 8(βN2)-4mDBtPBfpm to PCBBiF and [Ir(dmpqn)₂(acac)] of 0.75:0.25:0.1. The thickness was set to 40 nm. The light-emitting layer 913 in the comparative light-emitting element 2 was deposited by co-evaporation using [Ir(dmpqn)₂(acac)] as a guest material (phosphorescent light-emitting material) in addition to 8βN-4mDBtPBfpm and PCBBiF to have a weight ratio of 8βN-4mDBtPBfpm to PCBBiF and [Ir(dmpqn)₂(acac)] of 0.75:0.25:0.1. The thickness was set to 40 nm. The light-emitting layer 913 in the comparative light-emitting element 3 was deposited by co-evaporation using [Ir(dmpqn)₂(acac)] as a guest material (phosphorescent light-emitting material) in addition to 4.8mDBtP2Bfpm and PCBBiF to have a weight ratio of 4.8mDBtP2Bfpm to PCBBiF and [Ir(dmpqn)₂(acac)] of 0.75:0.25:0.1. The thickness was set to 40 nm.

Next, the electron-transport layer 914 was formed over the light-emitting layer 913.

The electron-transport layer 914 in the light-emitting element 1 was formed by sequential deposition by evaporation so that the thickness of 8(βN2)-4mDBtPBfpm was 25 nm and the thickness of 2,9-bis(naphthalen-2-yl)-4,7-diphenyl-1,10-phenanthroline (abbreviation: NBphen) was 15 nm. The electron-transport layer 914 in the comparative light-emitting element 2 was formed by sequential deposition by evaporation so that the thickness of 8βN-4mDBtPBfpm was 25 nm and the thickness of NBphen was 15 nm. The electron-transport layer 914 in the comparative light-emitting element 3 was formed by sequential deposition by evaporation so that the thickness of 4.8mDBtP2Bfpmm was 25 nm and the thickness of NBphen was 15 nm.

Then, the electron-injection layer 915 was formed over the electron-transport layer 914. The electron-injection layer 915 was formed to a thickness of 1 nm by evaporation using lithium fluoride (LiF).

After that, the second electrode 903 was formed over the electron-injection layer 915. The second electrode 903 was formed using aluminum to a thickness of 200 nm by an evaporation method. In this example, the second electrode 903 functions as a cathode.

Through the above steps, the light-emitting elements in each of which an EL layer 902 was provided between a pair of electrodes over the substrate 900 were fabricated. The hole-injection layer 911, the hole-transport layer 912, the light-emitting layer 913, the electron-transport layer 914, and the electron-injection layer 915 described in the above steps were functional layers forming the EL layer in one embodiment of the present invention. Furthermore, in all the evaporation steps in the above fabrication method, an evaporation method by a resistance-heating method was used.

The light-emitting elements fabricated as described above were sealed using another substrate (not illustrated). At the time of the sealing using the another substrate (not illustrated), the another substrate (not illustrated) on which a sealant that solidifies by ultraviolet light was applied was fixed onto the substrate 900 in a glove box containing a nitrogen atmosphere, and the substrates were bonded to each other such that the sealant attached to the periphery of the light-emitting element formed over the substrate 900. At the time of the sealing, the sealant was irradiated with 365-nm ultraviolet light at 6 J/cm² to be solidified, and the sealant was subjected to heat treatment at 80° C. for one hour to be stabilized.

<<Operation Characteristics of Light-Emitting Elements>>

Operation characteristics of each of the fabricated light-emitting elements were measured. Note that the measurement was carried out at room temperature (an atmosphere maintained at 25° C.). As the results on the operation characteristics of the light-emitting elements, the current density-luminance characteristics, the voltage-luminance characteristics, the luminance-current efficiency characteristics, and the voltage-current characteristics are shown in FIG. 15, FIG. 16, FIG. 17, and FIG. 18, respectively.

Table 2 below shows initial values of main characteristics of each of the light-emitting elements at around 1000 cd/m².

TABLE 2

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 1 | 3.7 | 0.31 | 7.7 | (0.68, 0.32) | 1100 | 14 | 12 | 16 |
| Comparative light-emitting element 2 | 3.6 | 0.28 | 6.9 | (0.68, 0.32) | 1000 | 15 | 13 | 16 |
| Comparative light-emitting element 3 | 3.6 | 0.270 | 6.8 | (0.68, 0.32) | 970 | 14 | 12 | 16 |

Figure 19:
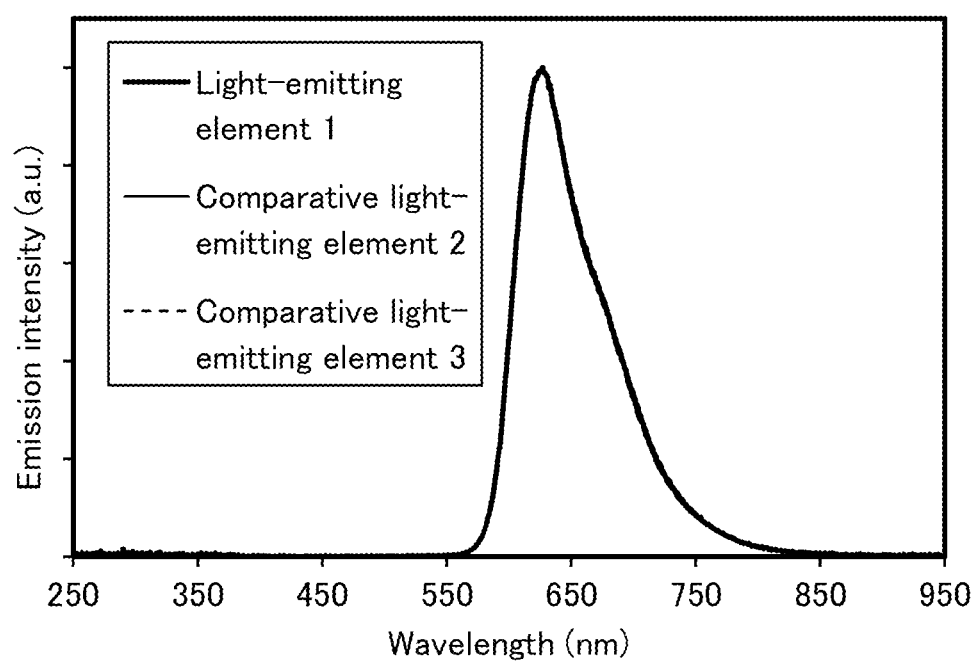
FIG. 19 is a drawing showing emission spectra of the light-emitting element 1, the comparative light-emitting element 2, and the comparative light-emitting element 3.

FIG. 19 shows emission spectra when current at a current density of 2.5 mA/cm$^2$ was applied to the light-emitting element 1, the comparative light-emitting element 2, and the comparative light-emitting element 3. As shown in FIG. 19, the emission spectrum of each of the light-emitting element 1, the comparative light-emitting element 2, and the comparative light-emitting element 3 has a peak at around 626 nm, which is suggested to be derived from light emission of [Ir(dmpqn)$_2$(acac)] contained in the light-emitting layer 913.

Figure 20:
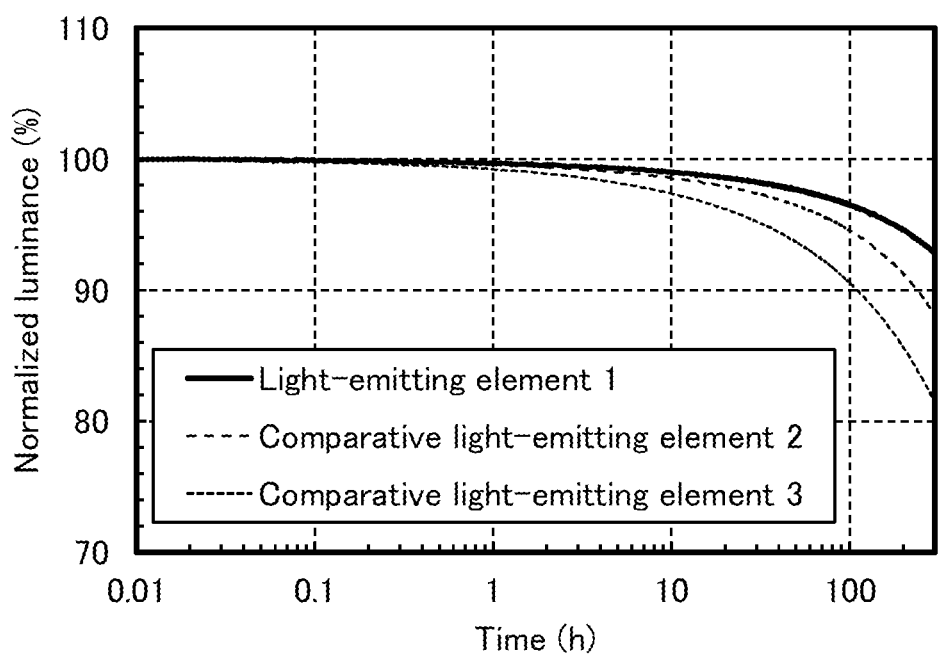
FIG. 20 is a drawing showing reliability of the light-emitting element 1, the comparative light-emitting element 2, and the comparative light-emitting element 3.
Figure 21:
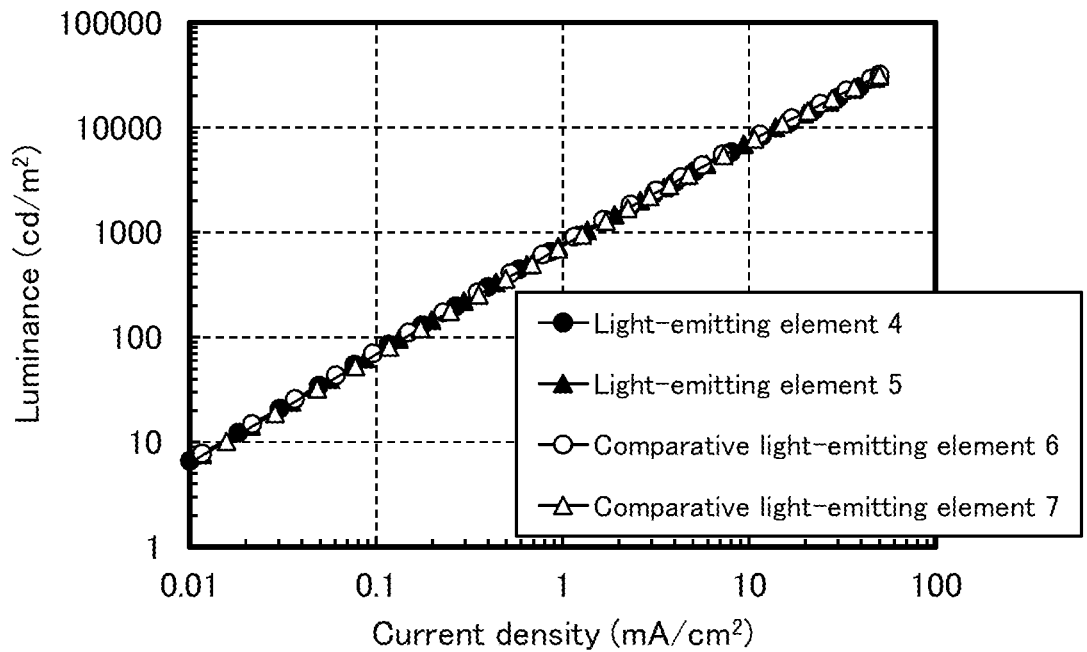
FIG. 21 is a drawing showing current density-luminance characteristics of a light-emitting element 4, a light-emitting element 5, a comparative light-emitting element 6, and a comparative light-emitting element 7.
Figure 22:
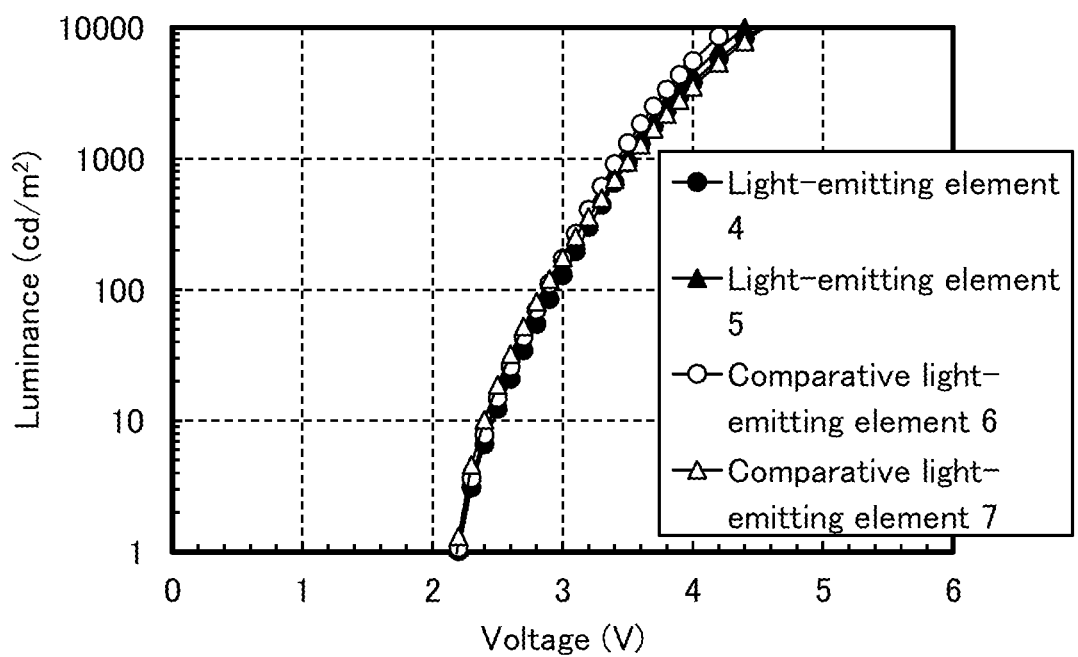
FIG. 22 is a drawing showing voltage-luminance characteristics of the light-emitting element 4, the light-emitting element 5, the comparative light-emitting element 6, and the comparative light-emitting element 7.
Figure 23:
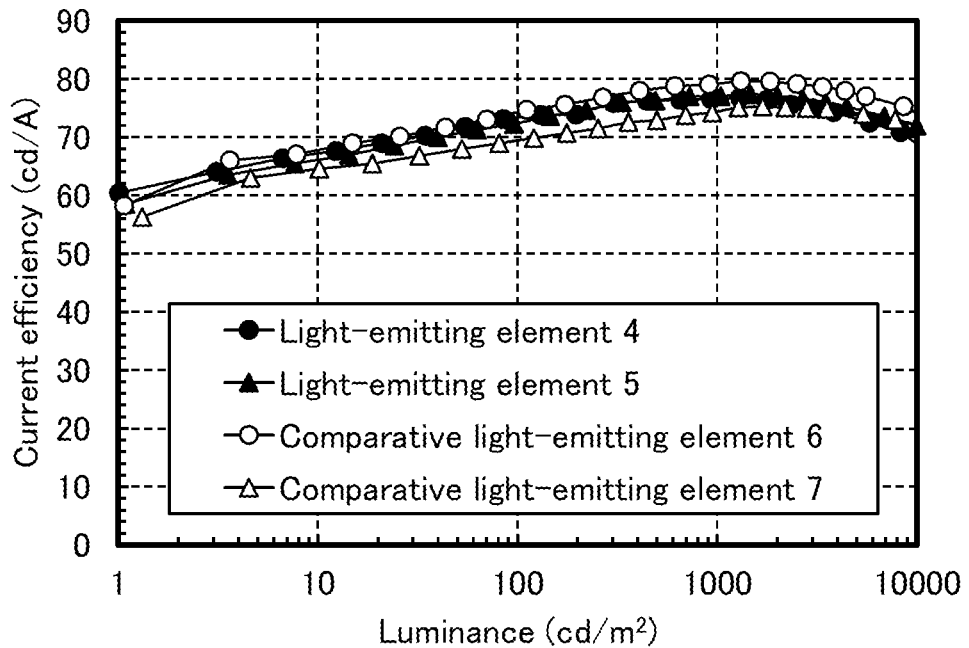
FIG. 23 is a drawing showing luminance-current efficiency characteristics of the light-emitting element 4, the comparative light-emitting element 5, the comparative light-emitting element 6, and the comparative light-emitting element 7.
Figure 24:
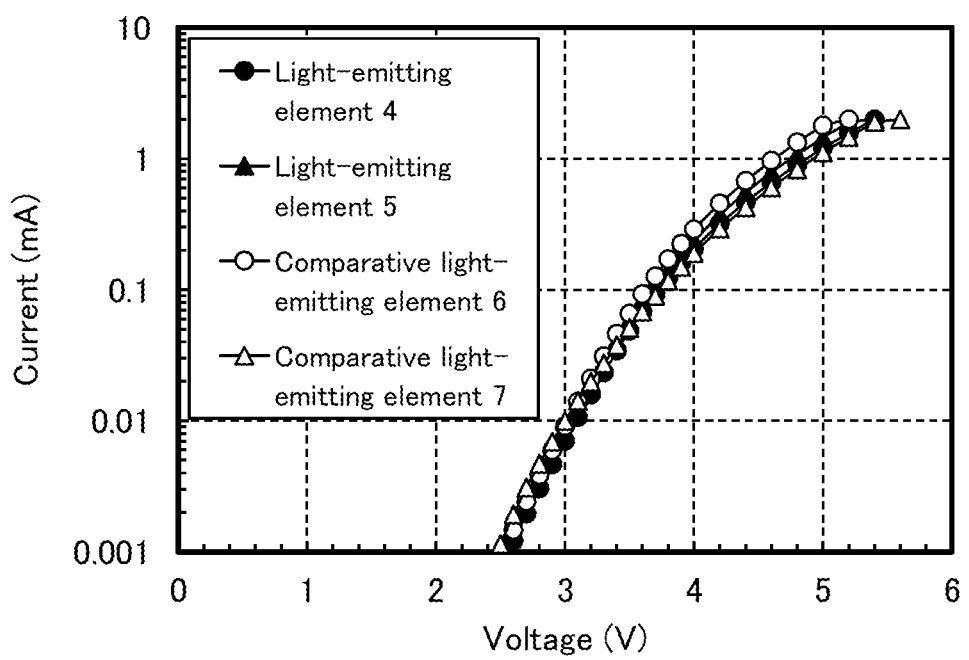
FIG. 24 is a drawing showing voltage current characteristics of the light-emitting element 4, the light-emitting element 5, the comparative light-emitting element 6, and the comparative light-emitting element 7.

Next, reliability tests were performed on the light-emitting element 1, the comparative light-emitting element 2, and the comparative light-emitting element 3. FIG. 20 shows the results of the reliability tests. In FIG. 20, the vertical axis represents normalized luminance (%) with an initial luminance of 100%, and the horizontal axis represents driving time (h) of the element. As the reliability tests, constant current driving tests where a constant current was supplied at a current density of 75 mA/cm$^2$ were performed.

The results of the reliability tests revealed that degradation at the initial driving stage of the light-emitting element 1 is smaller than those of the comparative light-emitting element 2 and the comparative light-emitting element 3. The use of 8(βN2)-4mDBtPBfpm (Structural Formula (102)), which is the organic compound of one embodiment of the present invention, is considered effective in improving the element characteristics of the light-emitting element. Note that 8βN-4mDBtPBfpm (Structural Formula (301)) used in the comparative light-emitting element 2 has a structure in which a naphthyl group is bonded to the 8-position of a benzofuropyrimidine skeleton, and 4,8mDBtP2Bfpm (Structural Formula (302)) used in the comparative light-emitting element 3 has a structure in which dibenzothiophen is bonded to the 8-position of a benzofuropyrimidine skeleton through a phenyl group; meanwhile, 8(PN2)-4mDBtPBfpm used in the light-emitting element 1 has a structure in which a plurality of arylene groups are bonded to the 8-position of a benzofuropyrimidine skeleton, specifically, a molecular structure including a binaphthyl group in which the same two naphthyl groups are bonded to each other.

Thus, when the organic compound having the structure in which a biarylene group is included at the 8-position of a benzofuropyrimidine skeleton or a benzothienopyrimidine skeleton like the organic compound of one embodiment of the present invention is used in a light-emitting element, time taken until the luminance decreases from the initial luminance by 5% (LT95) of the light-emitting element 1 is 173 hours while LT95 of the comparative light-emitting element 2 is 86 hours and LT95 of the comparative light-emitting element 3 is 32 hours, that is, the use of the above-described organic compound is effective in suppressing initial degradation of the light-emitting element; thus, a highly-reliable light-emitting element can be provided.

Example 5

In this example, a light-emitting element 4 which uses 8BP-4mDBtPBfpm (Structural Formula (100)) described in Example 1 for a light-emitting layer and a light-emitting element 5 which uses 8mBP-4mDBtPBfpm (Structural Formula (101)) described in Example 2 for a light-emitting layer as light-emitting elements of embodiments of the present invention; a comparative light-emitting element 6 for comparison which uses 8Ph-4mDBtPBfpm (Structural Formula (300)) for a light-emitting layer; and a comparative light-emitting element 7 for comparison which uses 8DBt-4mDBtPBfpm (Structural Formula (303)) for a light-emitting layer were fabricated. The measurement results on their characteristics are described.

The element structures of the light-emitting element 4, the light-emitting element 5, the comparative light-emitting element 6, and the comparative light-emitting element 7 which were fabricated in this example are similar to that in FIG. 14 mentioned in Example 4, and specific compositions of layers that constitute the element structure are as shown in Table 3. Chemical formulae of materials used in this example are shown below.

TABLE 3

|  | First electrode | Hole-injection layer | Hole-transport layer | Light-emitting layer | Electron-transport layer | | Electron-injection layer | Second electrode |
|---|---|---|---|---|---|---|---|---|
| Light-emitting element 4 | ITSO (70 nm) | DBT3P-II:MoO$x$ (2:1 50 nm) | PCBBiLBP (20 nm) | * | 8BP-4mDBtPBfpm (20 nm) | NBphen (15 nm) | LiF (1 nm) | Al (200 nm) |
| Light-emitting element 5 | ITSO (70 nm) | DBT3P-II:MoO$x$ (2:1 50 nm) | PCBBiLBP (20 nm) | ** | 8mBP-4mDBtPBfpm (20 nm) | NBphen (15 nm) | LiF (1 nm) | Al (200 nm) |
| Comparative light-emitting element 6 | ITSO (70 nm) | DBT3P-II:MoO$x$ (2:1 50 nm) | PCBBiLBP (20 nm) | *** | 8Ph-4mDBtPfpm (20 nm) | NBphen (15 nm) | LiF (1 nm) | Al (200 nm) |

TABLE 3-continued

| | First electrode | Hole-injection layer | Hole-transport layer | Light-emitting layer | Electron-transport layer | Electron-injection layer | Second electrode |
|---|---|---|---|---|---|---|---|
| Comparative light-emitting element 7 | ITSO (70 nm) | DBT3P-II:MoOx (2:1 50 nm) | PCBBi1BP (20 nm) | **** | 8DBt-4mDBtPBfpm (20 nm) | NBphen (15 nm) | LiF (1 nm) | Al (200 nm) |

\* 8BP-4mDBtPBfpm:PCCP:[Ir(ppy)$_2$(4dppy)] (0.6:0.4:0.1 40 nm)

\*\* 8mBP-4mDBtPBfpm:PCCP:[Ir(ppy)$_2$(4dppy)] (0.6:0.4:0.1 40 nm)

\*\*\* 8Ph-4mDBtPBfpm:PCCP:[Ir(ppy)$_2$(4dppy)] (0.6:0.4:0.1 40 nm)

\*\*\*\* 8DBt-4mDBtPBfpm:PCCP:[Ir(ppy)$_2$(4dppy)] (0.6:0.4:0.1 40 nm)

[Chemical Formulae 31]

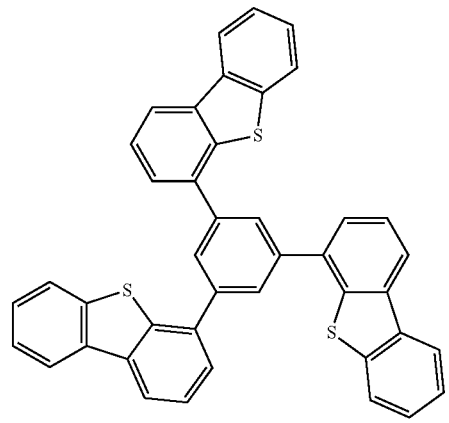

DBT3P-II

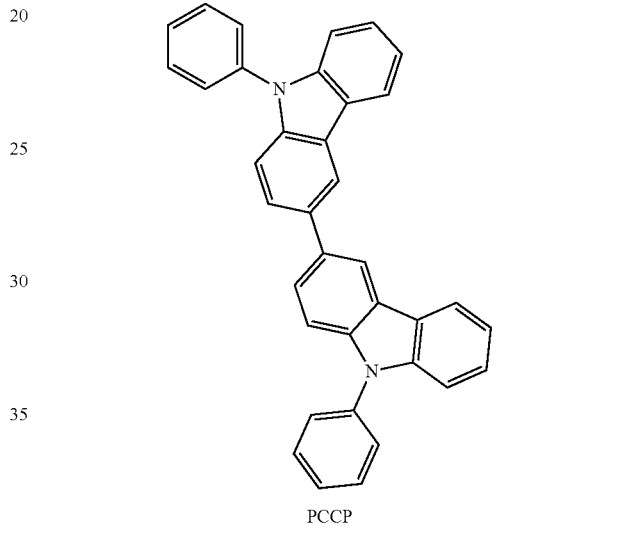

PCCP

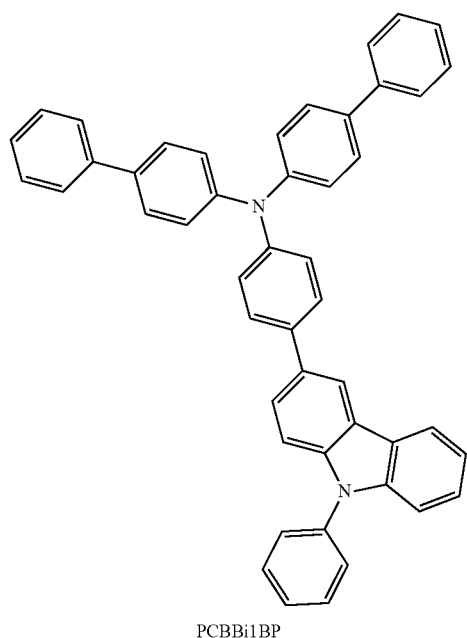

PCBBi1BP

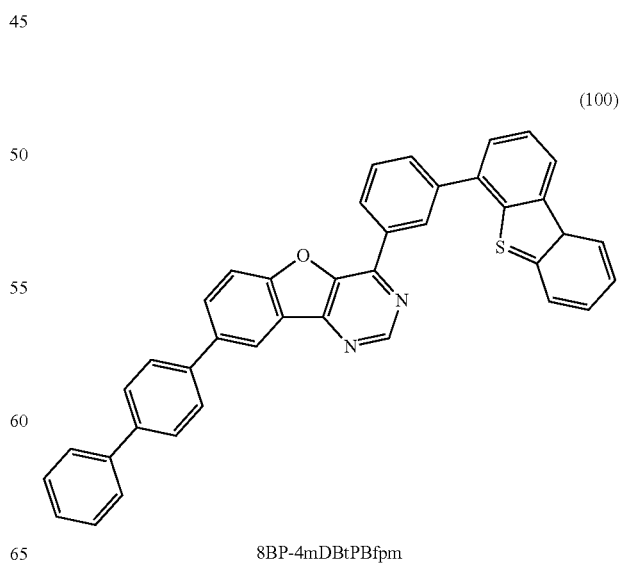

(100)

8BP-4mDBtPBfpm

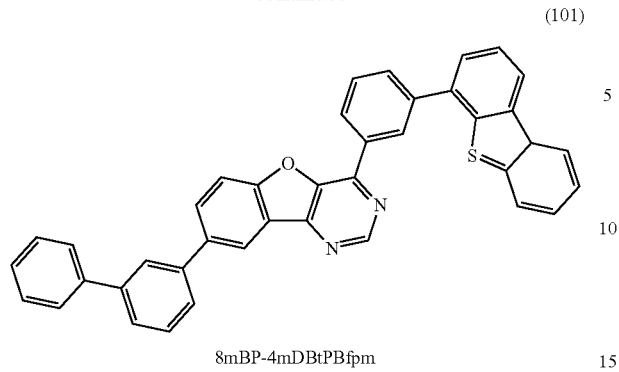

8mBP-4mDBtPBfpm (101)

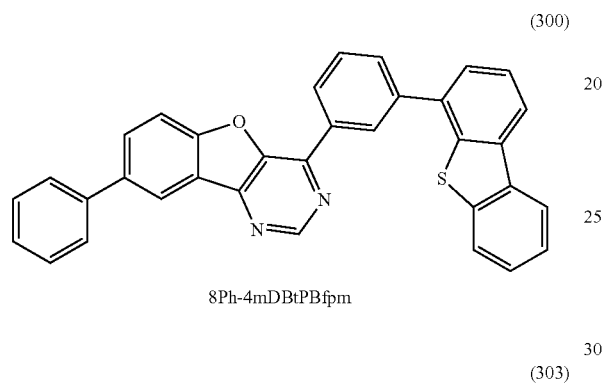

8Ph-4mDBtPBfpm (300)

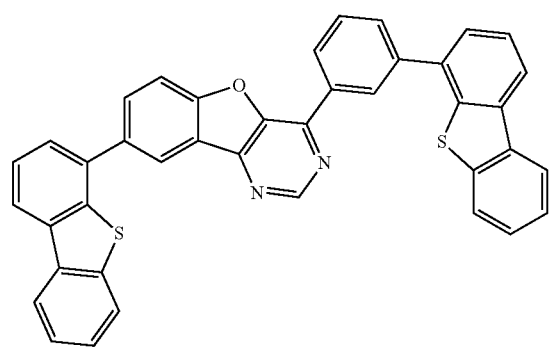

8DBt-4mDBtPBfpm (303)

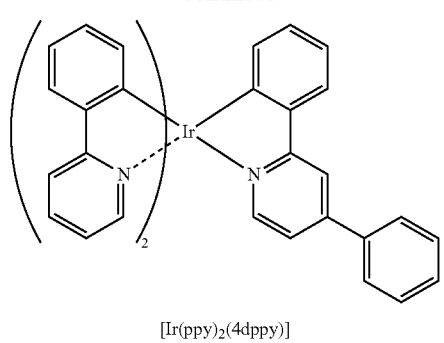

[Ir(ppy)₂(4dppy)]

NBphen

<<Operation Characteristics of Light-Emitting Elements>>

Operation characteristics of the fabricated light-emitting element 4, light-emitting element 5, comparative light-emitting element 6, and comparative light-emitting element 7 were measured. Note that the measurement was carried out at room temperature (an atmosphere maintained at 25° C.).

The current density-luminance characteristics, voltage-luminance characteristics, luminance-current efficiency characteristics, and voltage-current characteristics of the light-emitting elements are shown in FIG. 21, FIG. 22, FIG. 23, and FIG. 24, respectively.

Table 4 below shows initial values of main characteristics of each of the light-emitting elements at around 1000 cd/m².

TABLE 4

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 4 | 3.5 | 0.049 | 1.2 | (0.45, 0.54) | 930 | 77 | 69 | 23 |
| Light-emitting element 5 | 3.5 | 0.054 | 1.4 | (0.45, 0.54) | 1000 | 77 | 69 | 23 |
| Comparative light-emitting element 6 | 3.4 | 0.046 | 1.2 | (0.45, 0.54) | 910 | 79 | 73 | 24 |
| Comparative light-emitting element 7 | 3.5 | 0.051 | 1.3 | (0.44, 0.55) | 950 | 74 | 67 | 22 |

Figure 25:
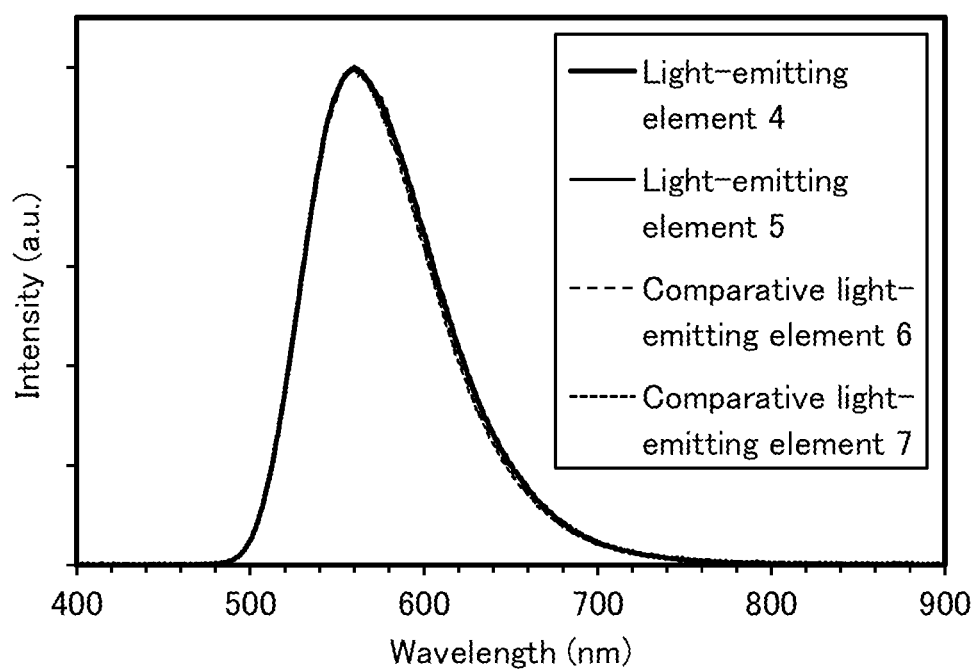
FIG. 25 is a drawing showing emission spectra of the light-emitting element 4, the light-emitting element 5, the comparative light-emitting element 6, and the comparative light-emitting element 7.

FIG. 25 shows emission spectra when current at a current density of 2.5 mA/cm² was applied to each of the light-emitting elements. As shown in FIG. 25, the emission spectrum of each of the light-emitting elements has a peak at around 560 nm, which is suggested to be derived from light emission of [Ir(ppy)₂(4dppy)] contained in the light-emitting layer 913.

Figure 26:
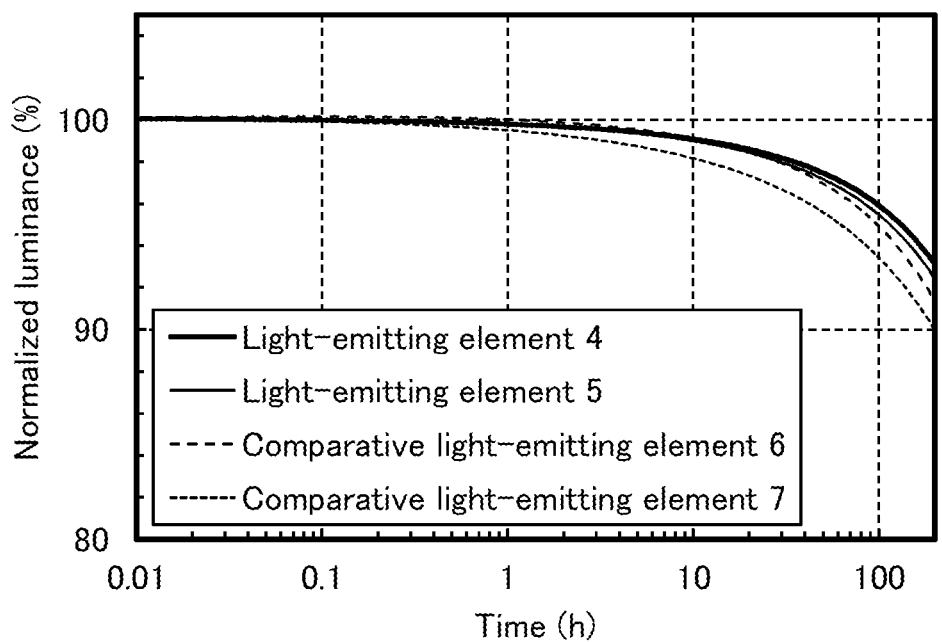
FIG. 26 is a drawing showing reliability of the light-emitting element 4, the light-emitting element 5, the comparative light-emitting element 6, and the comparative light-emitting element 7.
Figure 27:
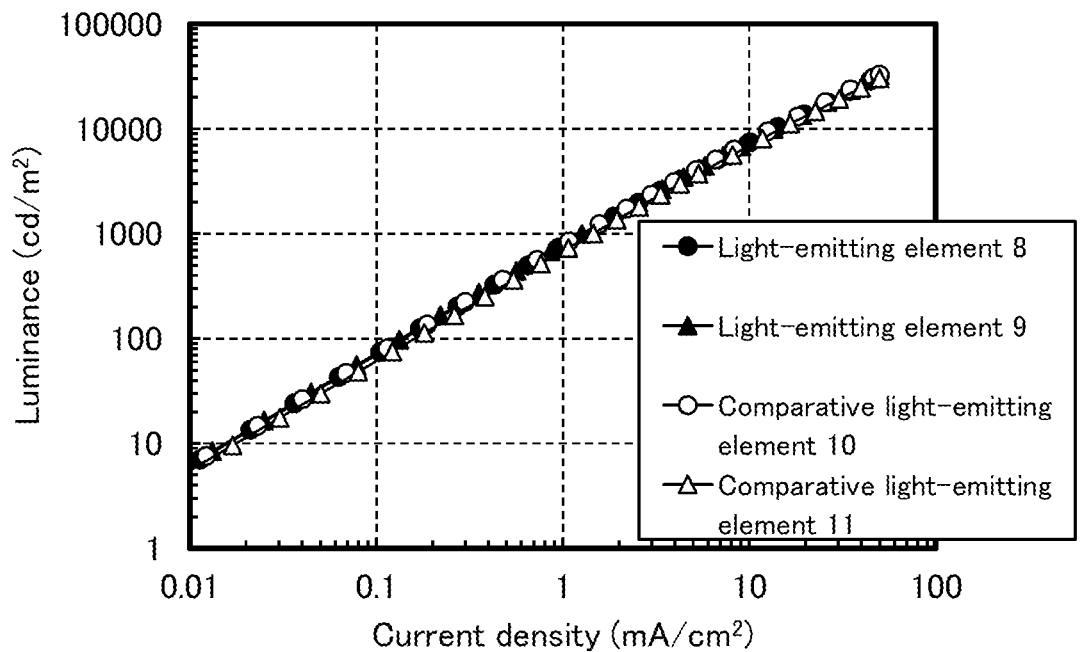
FIG. 27 is a drawing showing current density-luminance characteristics of a light-emitting element 8, a light-emitting element 9, a comparative light-emitting element 10, and a comparative light-emitting element 11.
Figure 28:
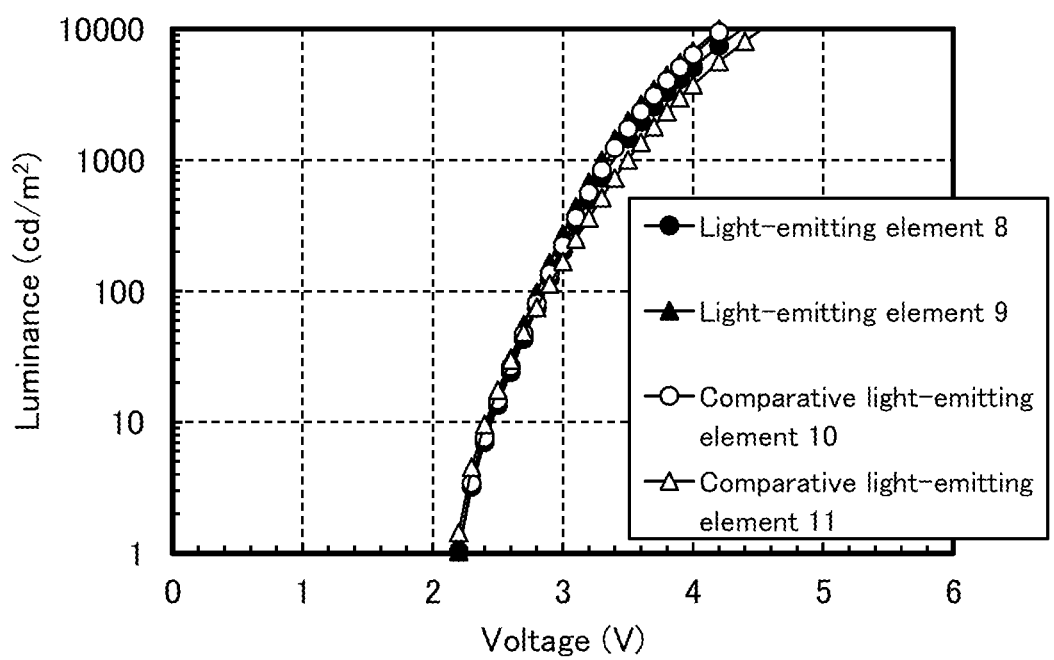
FIG. 28 is a drawing showing voltage-luminance characteristics of the light-emitting element 8, the light-emitting element 9, the comparative light-emitting element 10, and the comparative light-emitting element 11.
Figure 29:
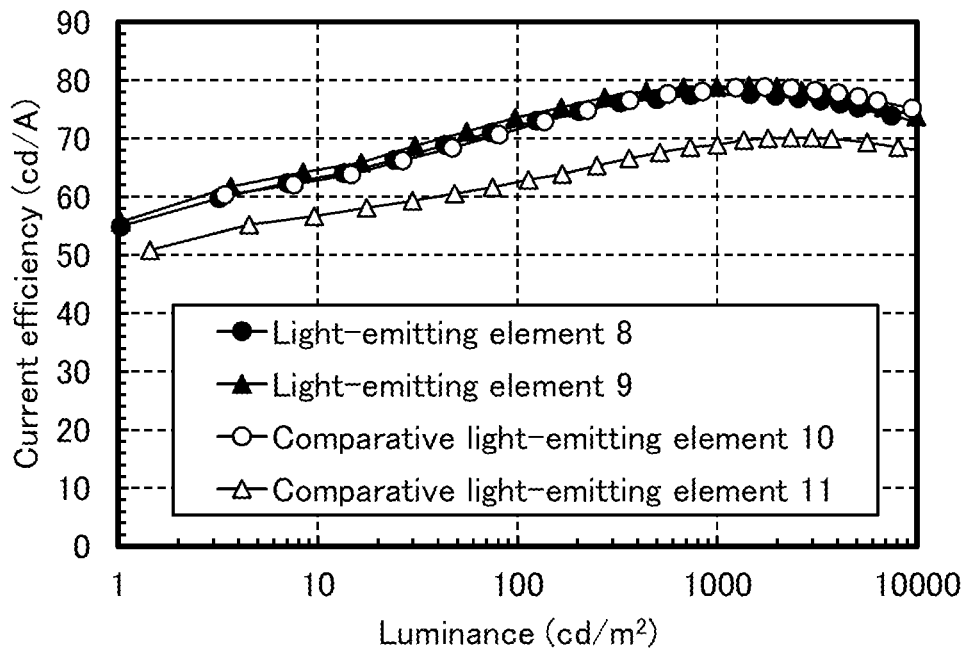
FIG. 29 is a drawing showing luminance-current efficiency characteristics of the light-emitting element 8, the light-emitting element 9, the comparative light-emitting element 10, and the comparative light-emitting element 11.
Figure 30:
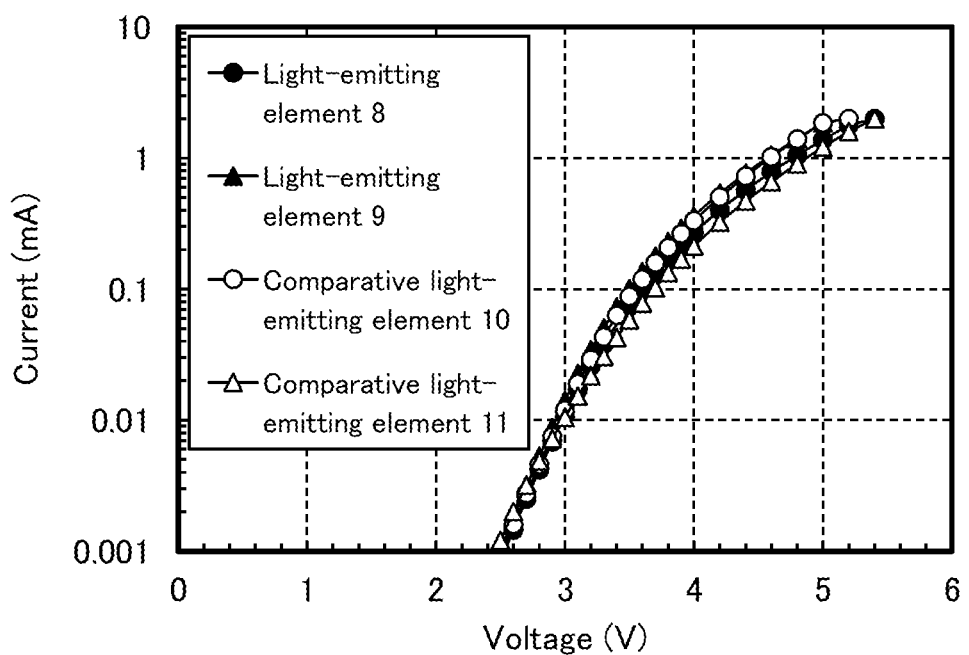
FIG. 30 is a drawing showing voltage-current characteristics of the light-emitting element 8, the light-emitting element 9, the comparative light-emitting element 10, and the comparative light-emitting element 11.

Next, reliability tests were performed on the light-emitting elements. FIG. 26 shows the results of the reliability tests. In FIG. 26, the vertical axis represents normalized luminance (%) with an initial luminance of 100%, and the horizontal axis represents driving time (h) of the element. As the reliability tests, constant current driving tests where a constant current was supplied at a current density of 50 mA/cm² were performed.

According to the results of the reliability tests, time taken until the luminance decreases from the initial luminance by 5% (LT95) of the light-emitting element 4 using 8BP-4mDBtPBfpm (Structural Formula (100)), which is the organic compound of one embodiment of the present invention, for the light-emitting layer was 131 hours, LT95 of the light-emitting element 5 using 8mBP-4mDBtPBfpm (Structural Formula (101)) for the light-emitting layer was 112 hours, LT95 of the comparative light-emitting element 6

Example 6

In this example, a light-emitting element 8 which uses 8BP-4mDBtPBfpm (Structural Formula (100)) described in Example 1 for a light-emitting layer and a light-emitting element 9 which uses 8mBP-4mDBtPBfpm (Structural Formula (101)) described in Example 2 for a light-emitting layer as light-emitting elements of embodiments of the present invention; a comparative light-emitting element 10 for comparison which uses 8Ph-4mDBtPBfpm (Structural Formula (300)) for a light-emitting layer; and a comparative light-emitting element 11 for comparison which uses 8DBt-4mDBtPBfpm (Structural Formula (303)) for a light-emitting layer were fabricated. The measurement results on their characteristics are described.

The element structures of the light-emitting element 8, the light-emitting element 9, the comparative light-emitting element 10, and the comparative light-emitting element 11 which were fabricated in this example are similar to that in FIG. 14 mentioned in Example 4, and specific compositions of layers that constitute the element structure are as shown in Table 5. Chemical formulae of materials used in this example are shown below.

TABLE 5

|  | First electrode | Hole-injection layer | Hole-transport layer | Light-emitting layer |  | Electron-transport layer | | Electron-injection layer | Second electrode |
| --- | --- | --- | --- | --- | --- | --- | --- | --- | --- |
| Light-emitting element 8 | ITSO (70 nm) | DBT3P-II:MoOx (2:1 50 nm) | PCBBiIBP (20 nm) | * | | 8BP-4mDBtPBfpm (20 nm) | NBphen (10 nm) | LiF (1 nm) | Al (200 nm) |
| Light-emitting element 9 | ITSO (70 nm) | DBT3P-II:MoOx (2:1 50 nm) | PCBBiIBP (20 nm) | ** | | 8mBP-4mDBtPBfpm (20 nm) | NBphen (10 nm) | LiF (1 nm) | Al (200 nm) |
| Comparative light-emitting element 10 | ITSO (70 nm) | DBT3P-II:MoOx (2:1 50 nm) | PCBBiIBP (20 nm) | *** | | 8Ph-4mDBtPBfpm (20 nm) | NBphen (10 nm) | LiF (1 nm) | Al (200 nm) |
| Comparative light-emitting element 11 | ITSO (70 nm) | DBT3P-II:MoOx (2:1 50 nm) | PCBBiIBP (20 nm) | **** | | 8DBt-4mDBtPBfpm (20 nm) | NBphen (10 nm) | LiF (1 nm) | Al (200 nm) |

* 8BP-4mDBtPBfpm:PCCP:[Ir(ppy)₂(mdppy)] (0.5:0.5:0.1 40 nm)
** 8mBP-4mDBtPBfpm:PCCP:[Ir(ppy)₂(mdppy)] (0.5:0.5:0.1 40 nm)
*** 8Ph-4mDBtPBfpm:PCCP:[Ir(ppy)₂(mdppy)] (0.5:0.5:0.1 40 nm)
**** 8DBt-4mDBtPBfpm:PCCP:[Ir(ppy)₂(mdppy)] (0.5:0.5:0.1 40 nm)

using 8Ph-4mDBtPBfpm (Structural Formula (300)), which is a comparative organic compound, for the light-emitting layer was 98 hours, and LT95 of the comparative light-emitting element 7 using 8DBt-4mDBtPBfpm (Structural Formula (303)) for the light-emitting layer was 62 hours; thus, initial degradation of the light-emitting elements using the organic compounds of embodiments of the present invention for the light-emitting layers was suppressed. This effect is owing to 8BP-4mDBtPBfpm and 8mBP-4mDBtPBfpm, which are the organic compounds of embodiments of the present invention, each having a structure in which a plurality of arylene groups are bonded to the 8-position of a benzofuropyrimidine skeleton, preferably a biphenyl group in which the same two phenyl groups are bonded to each other. Thus, the use of the organic compound of one embodiment of the present invention is considered effective in improving the reliability of the light-emitting element.

[Chemical Formulae 32]

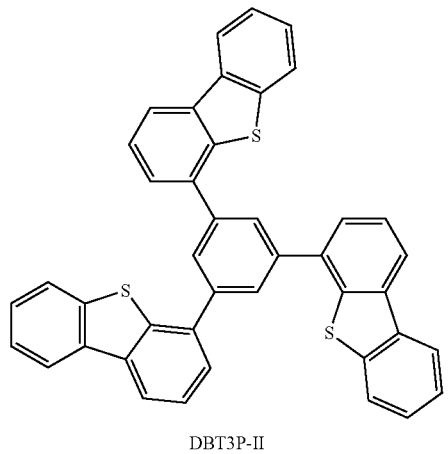

DBT3P-II

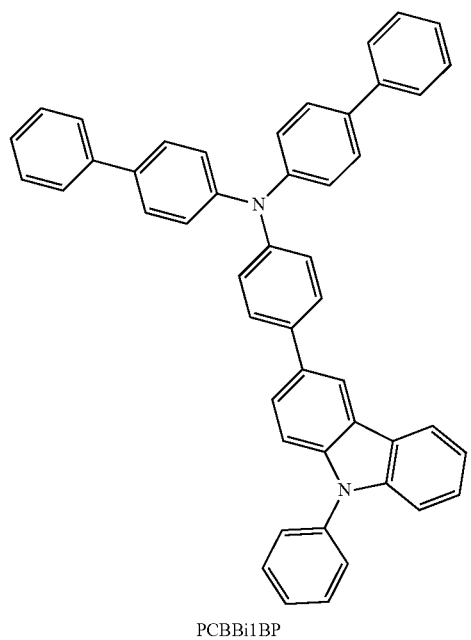
PCBBi1BP
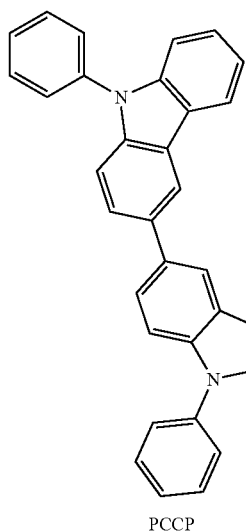
PCCP
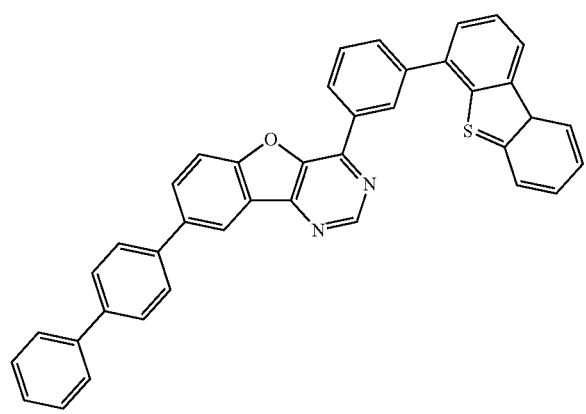
(100)
8BP-4mDBtPBfpm
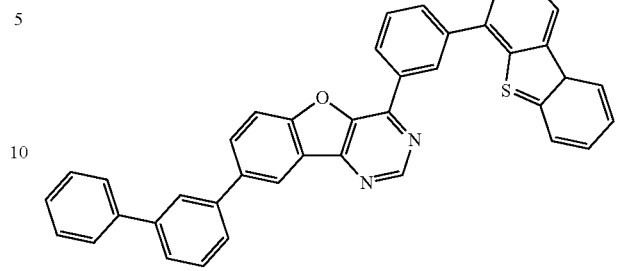
(101)
8mBP-4mDBtPBfpm
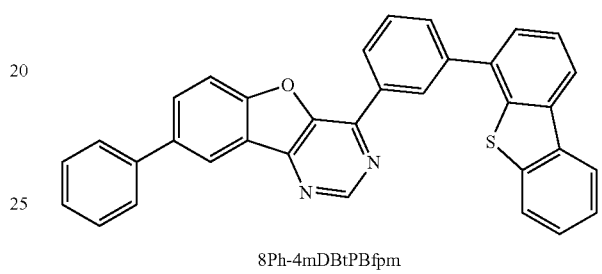
(300)
8Ph-4mDBtPBfpm
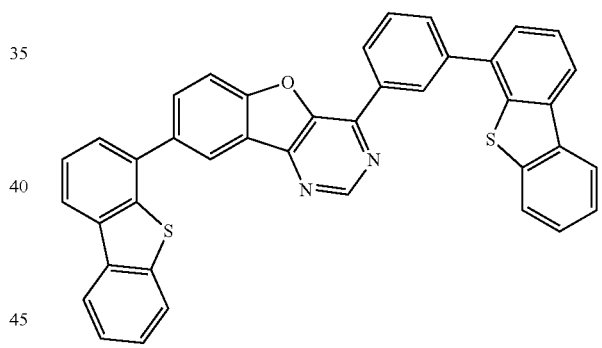
(303)
8DBt-4mDBtPBfpm
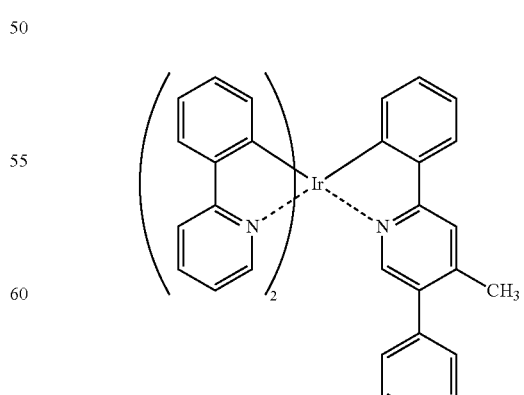
[Ir(ppy)₂(mdppy)]

-continued

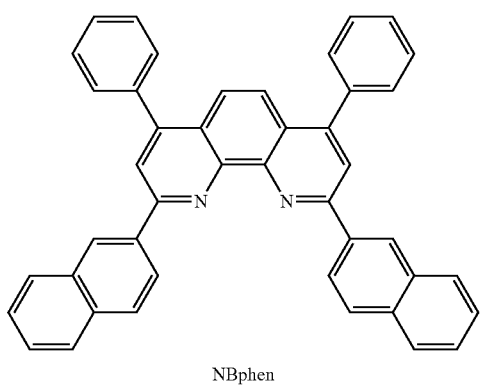

NBphen

<<Operation Characteristics of Light-Emitting Elements>>

Operation characteristics of the fabricated light-emitting element 8, light-emitting element 9, comparative light-emitting element 10, and comparative light-emitting element 11 were measured. Note that the measurement was carried out at room temperature (an atmosphere maintained at 25° C.).

The current density-luminance characteristics, voltage-luminance characteristics, luminance-current efficiency characteristics, and voltage-current characteristics of the light-emitting elements are shown in FIG. 27, FIG. 28, FIG. 29, and FIG. 30, respectively.

Table 6 below shows initial values of main characteristics of each of the light-emitting elements at around 1000 cd/m$^2$.

TABLE 6

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting element 8 | 3.3 | 0.038 | 0.95 | (0.35, 0.62) | 740 | 77 | 74 | 21 |
| Light-emitting element 9 | 3.3 | 0.051 | 1.3 | (0.35, 0.62) | 1000 | 79 | 75 | 22 |
| Comparative light-emitting element 10 | 3.3 | 0.043 | 1.1 | (0.35, 0.62) | 840 | 78 | 74 | 21 |
| Comparative light-emitting element 11 | 3.5 | 0.058 | 1.5 | (0.35, 0.62) | 1000 | 69 | 62 | 19 |

Figure 31:
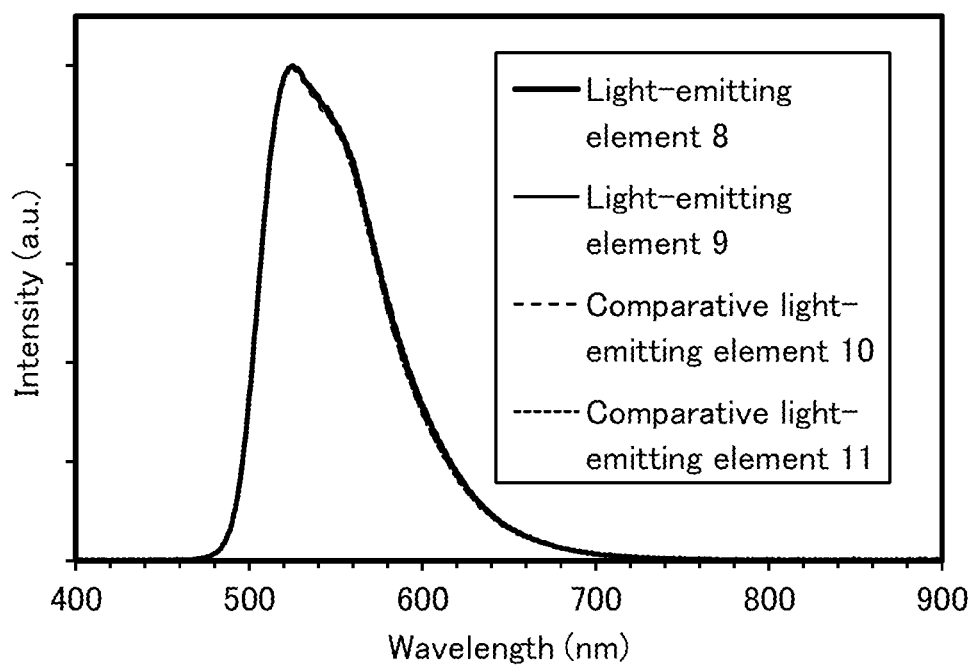
FIG. 31 is a drawing showing emission spectra of the light-emitting element 8, the light-emitting element 9, the comparative light-emitting element 10, and the comparative light-emitting element 11.

FIG. 31 shows emission spectra when current at a current density of 2.5 mA/cm$^2$ was applied to each of the light-emitting elements. As shown in FIG. 31, the emission spectrum of each of the light-emitting elements has a peak at around 524 nm, which is suggested to be derived from light emission of [2-(4-methyl-5-phenyl-2-pyridinyl-κN)phenyl-κC]bis[2-(2-pyridinyl-KN)phenyl-κC] iridium (abbreviation: [Ir(ppy)$_2$(mdppy)]) contained in the light-emitting layer 913.

Figure 32:
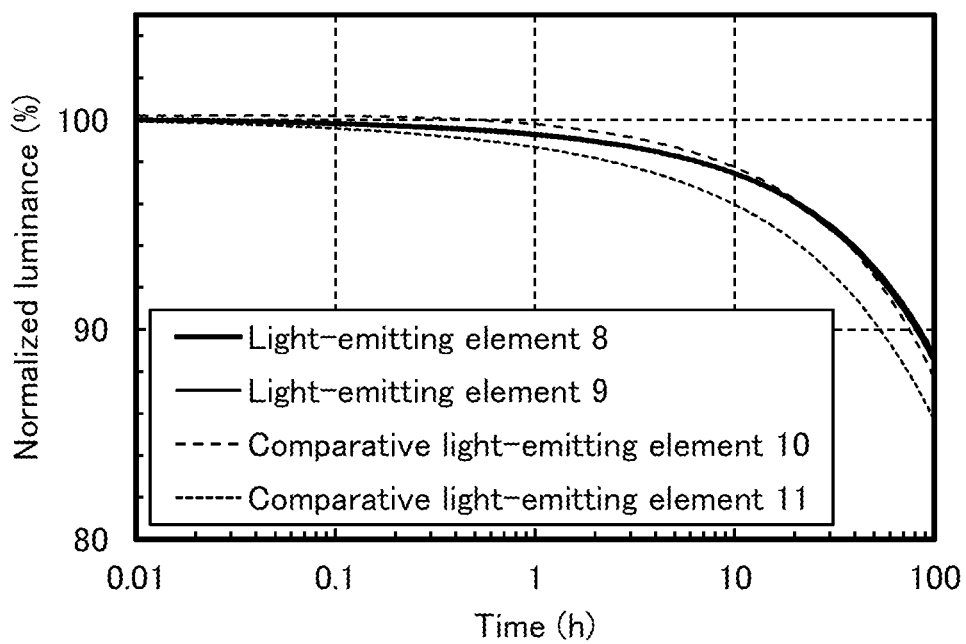
FIG. 32 is a drawing showing reliability of the light-emitting element 8, the light-emitting element 9, the comparative light-emitting element 10, and the comparative light-emitting element 11.

Next, reliability tests were performed on the light-emitting elements. FIG. 32 shows the results of the reliability tests. In FIG. 32, the vertical axis represents normalized luminance (%) with an initial luminance of 100%, and the horizontal axis represents driving time (h) of the element. As the reliability tests, constant current driving tests where a constant current was supplied at a current density of 50 mA/cm$^2$ were performed.

According to the results of the reliability tests, time taken until the luminance decreases from the initial luminance by 5% (LT95) of the light-emitting element 8 using 8BP-4mDBtPBfpm (Structural Formula (100)), which is the organic compound of one embodiment of the present invention, for the light-emitting layer was 30 hours, LT95 of the light-emitting element 9 using 8mBP-4mDBtPBfpm (Structural Formula (101)) for the light-emitting layer was 28 hours, and LT95 of the comparative light-emitting element 11 using 8DBt-4mDBtPBfpm (Structural Formula (303)), which is a comparative organic compound, for the light-emitting layer was 15 hours; thus, initial degradation of the organic compounds of embodiments of the present invention was suppressed. In addition, LT95 of the comparative light-emitting element 10 using 8Ph-4mDBtPBfpm (Structural Formula (300)), which is a comparative organic compound, for the light-emitting layer was 29 hours, which is favorable, but the slope of long-term degradation thereof was steeper than those of the organic compounds of embodiments of the present invention. These effects are owing to 8BP-4mDBtPBfpm and 8mBP-4mDBtPBfpm, which are the organic compounds of embodiments of the present invention, each having a structure in which a plurality of arylene groups are bonded to the 8-position of a benzofuropyrimidine skeleton, preferably a biphenyl group in which the same two phenyl groups are bonded to each other. Thus, the use of the organic compound of one embodiment of the present invention is considered effective in improving the reliability of the light-emitting element.

Reference Synthesis Example 1

Specifically exemplified in this reference synthesis example is a method for synthesizing 4-[3-(dibenzothiophen-4-yl)phenyl]-8-phenyl-[1]benzofuro[3,2-d]pyrimidine (abbreviation: 8Ph-4mDBtPBfpm) (Structural Formula (300)), which is the organic compound used in the comparative light-emitting element 6 in Example 5 and the comparative light-emitting element 10 in Example 6 and represented by a structural formula below.

[Chemical Formula 33]

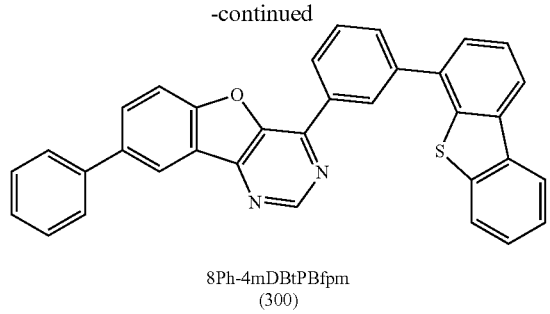

8Ph-4mDBtPBfpm
(300)

Note that analysis results by nuclear magnetic resonance ($^1$H-NMR) spectroscopy of the white solid obtained above are shown below. The results reveal that 8Ph-4mDBtPBfpm was obtained.

$^1$H-NMR. δ (CDCl$_3$): 7.42 (t, 1H), 7.49-7.53 (m, 4H), 7.64-7.66 (m, 2H), 7.71 (d, 2H), 7.79-7.82 (m, 2H), 7.87 (d, 1H), 7.97 (t, 2H), 8.23-8.25 (m, 2H), 8.52 (s, 1H), 8.72 (d, 1H), 9.05 (s, 1H), 9.33 (s, 1H).

Reference Synthesis Example 2

Specifically exemplified in this reference synthesis example is a method for synthesizing 4-[3-(dibenzothiophen-4-yl)phenyl]-8-(naphtarene-2-yl)-[1]benzofuro[3,2-d]pyrimidine (abbreviation: 8βN-4mDBtPBfpm) (Structural Formula (301)), which is the organic compound used in the comparative light-emitting element 2 in Example 4 and represented by a structural formula below.

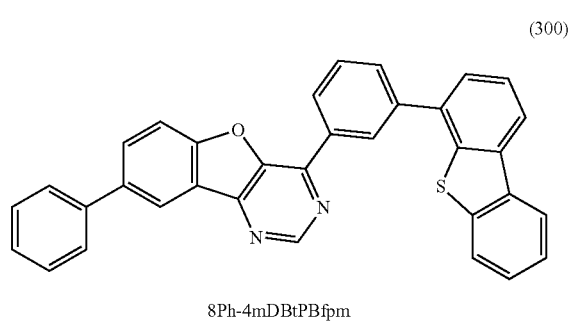

8Ph-4mDBtPBfpm

<Synthesis of 8Ph-4mDBtPBfpm>

Into a three-neck flask, 3.00 g of 8-chloro-4-[3-(dibenzothiophen-4-yl)phenyl]-[1]benzofuro[3,2-d]pyrimidine, 0.95 g of phenylboronic acid, 4.12 g of tripotassium phosphate, 65 mL of diglyme, and 1.44 g of t-butanol were put, they were degassed by being stirred under reduced pressure, and the air in the flask was replaced with nitrogen. To this mixture, 42.7 mg of palladium(II) acetate and 140 mg of di(1-adamantyl)-n-butylphosphine were added, followed by stirring at 120° C. for 15.5 hours.

To this reaction liquid, 45.2 mg of palladium(II) acetate and 140 mg of di(1-adamantyl)-n-butylphosphine were added, followed by stirring at 120° C. for 6 hours and at 140° C. for 3 hours. Water was added to this reaction liquid, suction filtration was performed, and the obtained residue was washed with ethyl acetate and hexane. This residue was dissolved in heated toluene, followed by filtration through a filter aid filled with Celite, alumina, and Celite in this order. The obtained solution was concentrated and dried, and then recrystallized with toluene to give 1.50 g of a white solid containing a target substance.

By a train sublimation method, 1.50 g of the obtained white solid was sublimated and purified. The conditions of the sublimation purification were such that the solid was heated under a pressure of 3.48 Pa at 280° C. while the argon gas flowed at a flow rate of 15 mL/min. After the sublimation purification, a target substance was obtained (1.02 g of a white solid, a collection rate was 68%). The synthesis scheme is shown in Formula (d-1) below.

[Chemical Formula 35]

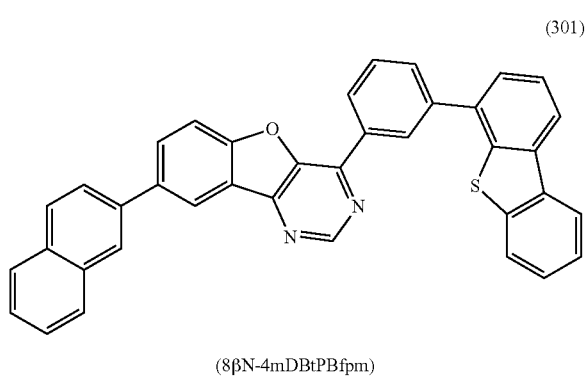

(8βN-4mDBtPBfpm)

<Synthesis of 8βN-4mDBtPBfpm>

First, 1.5 g of 8-chloro-4-[3-(dibenzothiophen-4-yl)phenyl]-[1]benzofuro[3,2-d]pyrimidine, 0.73 g of 2-naphthaleneboronic acid, 1.5 g of cesium fluoride, and 32 mL of mesitylene were added, the air in a 100 mL three-neck flask was replaced with nitrogen, and 70 mg of 2'-(dicyclohexylphosphino)acetophenone ethylene ketal and 89 mg of tris(dibenzylideneacetone)dipalladium(0) (abbreviation: Pd$_2$(dba)$_3$) were added, followed by heating at 120° C. for 5 hours under a nitrogen stream. Water was added to the obtained reaction product, filtration was performed, and the residue was washed with water and ethanol in this order.

This residue was dissolved in toluene, followed by filtration using a filter aid filled with Celite, alumina, and Celite in this order. The solvent of the obtained solution was

[Chemical Formulae 34]

(d-1)

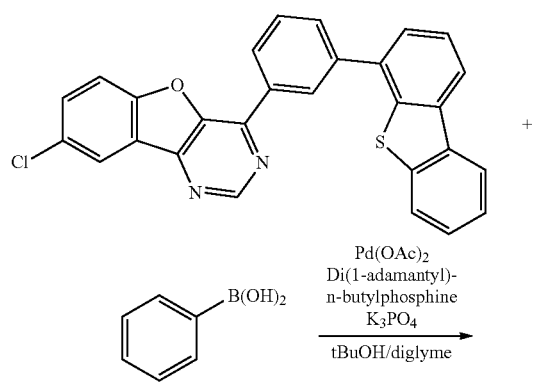

concentrated and recrystallized to give 1.5 g of a target pale yellow solid in a yield of 64%. The synthesis scheme is shown in Formula (e-1) below.

[Chemical Formulae 36]

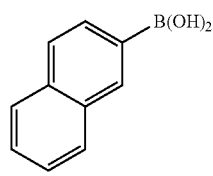

+

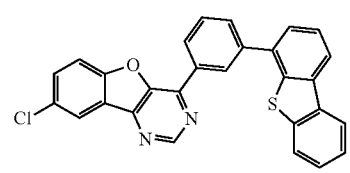

(e-1)

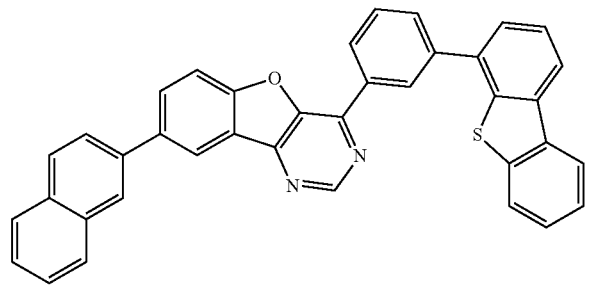

(8βN-4mDBtPBfpm)
(301)

By a train sublimation method, 1.5 g of the obtained pale yellow solid was sublimated and purified. The conditions of the sublimation purification were such that the solid was heated under a pressure of 2.0 Pa at 290° C. while the argon gas flowed at a flow rate of 10 mL/min. After the sublimation purification, 0.60 g of a target yellow solid was obtained at a collection rate of 39%.

Note that analysis results by nuclear magnetic resonance ($^1$H-NMR) spectroscopy of the obtained yellow solid are shown below. The results reveal that 8βN-4mDBtPBfpm was obtained.

$^1$H-NMR. δ (TCE-$d_2$): 7.45-7.50 (m, 4H), 7.57-7.62 (m, 2H), 7.72-7.93 (m, 8H), 8.03 (d, 1H), 8.10 (s, 1H), 8.17 (d, 2H), 8.60 (s, 1H), 8.66 (d, 1H), 8.98 (s, 1H), 9.28 (s, 1H).

Example 7

Synthesis Example 4

Described in this example is a method for synthesizing 8-(1,1'-biphenyl-4-yl)-4-[3'-(dibenzothiophen-4-yl)biphenyl-3-yl]-[1]benzofuro[3,2-d]pyrimidine (abbreviation: 8BP-4mDBtBPBfpm), which is an organic compound of one embodiment of the present invention represented by Structural Formula (103) in Embodiment 1. Note that the structure of 8BP-4mDBtBPBfpm is shown below.

[Chemical Formula 37]

(103)

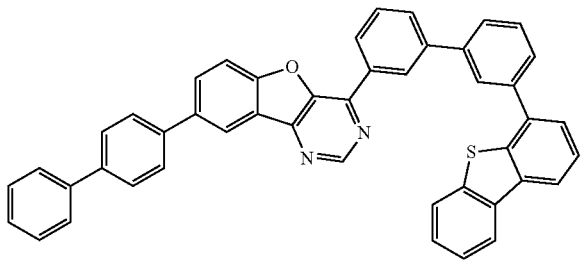

8BP-4mDBtPBfpm

<Synthesis of 8BP-4mDBtBPBfpm>

Into a three-neck flask, 2.26 g of 8-chloro-4-[3'-(dibenzothiophen-4-yl)biphenyl-3-yl]-[1]benzofuro[3,2-d]pyrimidine, 0.915 g of 4-biphenylboronic acid, 1.27 g of cesium fluoride, and 42 mL of mesitylene were put, they were degassed by being stirred under reduced pressure, and the air was replaced with nitrogen. This mixture was heated to 60° C. and 0.116 g of tris(dibenzylideneacetone)dipalladium(0) and 90.2 mg of 2'-(dicyclohexylphosphino)acetophenone ethylene ketal were added, followed by heating at 100° C. for 13.5 hours and at 120° C. for 7.5 hours. To this mixture, 0.115 g of tris(dibenzylideneacetone)dipalladium(0) and 90.3 mg of 2'-(dicyclohexylphosphino)acetophenone ethylene ketal were added, followed by stirring at 120° C. for 28 hours. Water was added to this reaction liquid, suction filtration was performed, and the obtained residue was washed with water, ethanol, and toluene. This residue was dissolved in heated toluene, followed by filtration through a filter aid filled with Celite, alumina, and Celite in this order. The obtained solution was concentrated and dried, and then recrystallized with toluene to give 1.93 g of a target pale yellow solid in a yield of 70%. By a train sublimation method, 1.93 g of the obtained pale yellow solid was sublimated and purified. The conditions of the sublimation purification were such that the solid was heated under a pressure of 2.35 Pa at 355° C. while the argon gas flowed at a flow rate of 10 mL/min. After the sublimation purification, 1.66 g of a target pale yellow solid was obtained at a collection rate of 86%. The synthesis scheme is shown in Formula (f-1) below.

[Chemical Formulae 38]

(f-1)

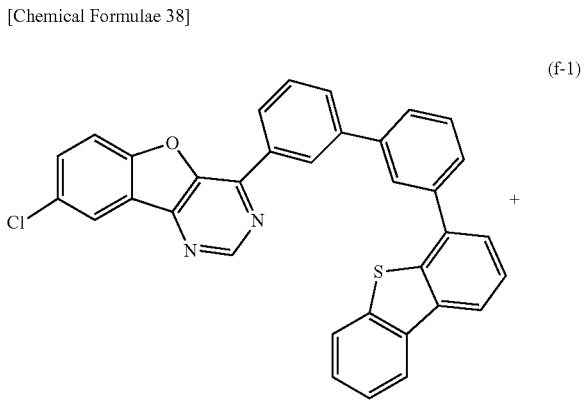

+

-continued

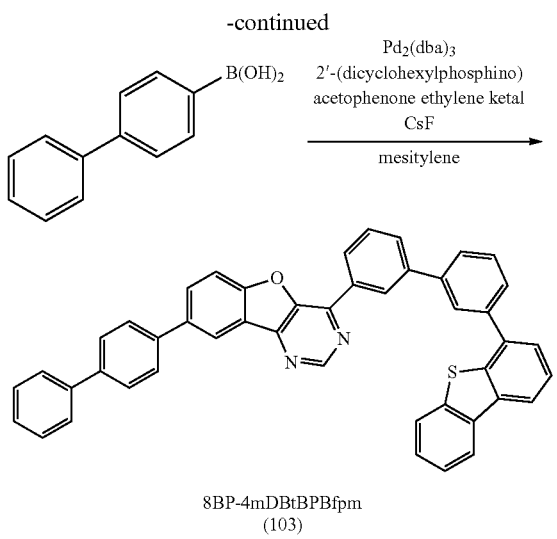

8BP-4mDBtBPBfpm
(103)

Figure 33:
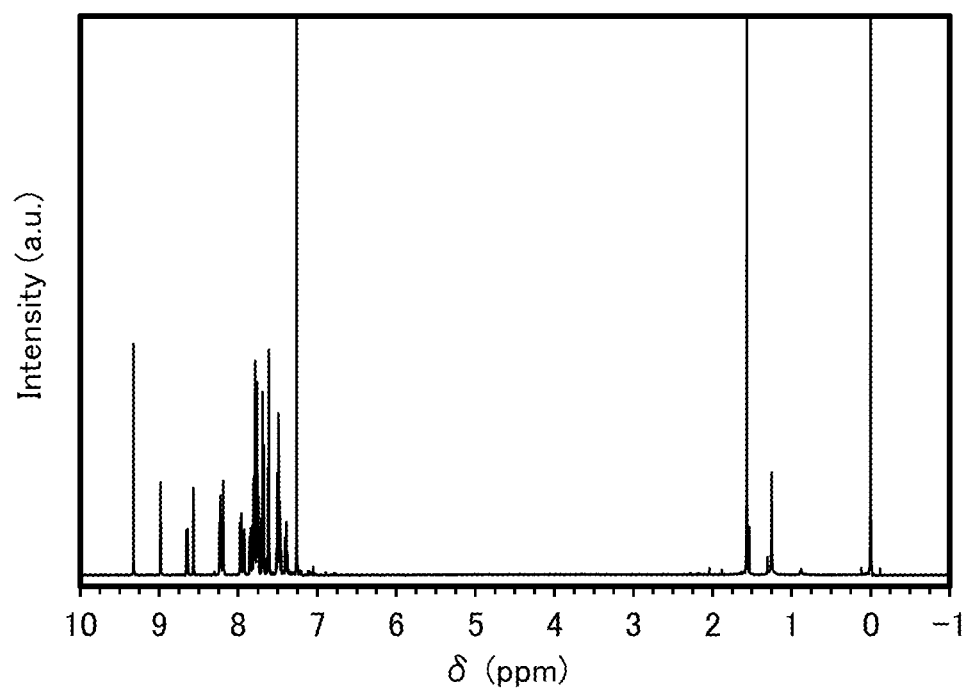
FIG. 33 is a 1H-NMR chart of an organic compound represented by Structural Formula (103).

Note that analysis results by nuclear magnetic resonance ($^1$H-NMR) spectroscopy of the white solid obtained by the above-described reaction are shown below. FIG. 33 shows a $^1$H-NMR chart. The results reveal that 8BP-4mDBtBPBfpm, the organic compound of one embodiment of the present invention represented by Structural Formula (103) above, was obtained in this example.

$^1$H-NMR. δ (CDCl$_3$): 7.37-7.40 (m, 1H), 7.46-7.52 (m, 4H), 7.60-7.85 (m, 14H), 7.92-7.98 (m, 2H), 8.19-8.23 (m, 3H), 8.57 (m, 1H), 8.64-8.66 (m, 1H), 8.98-8.99 (m, 1H), 9.33 (s, 1H).

<<Physical Properties of 8BP-4mDBtBPBfpm>>

Next, the ultraviolet-visible absorption spectra (hereinafter, simply referred to as "absorption spectra") and emission spectra of a toluene solution and a solid thin film of 8BP-4mDBtBPBfpm were measured.

Figure 34:
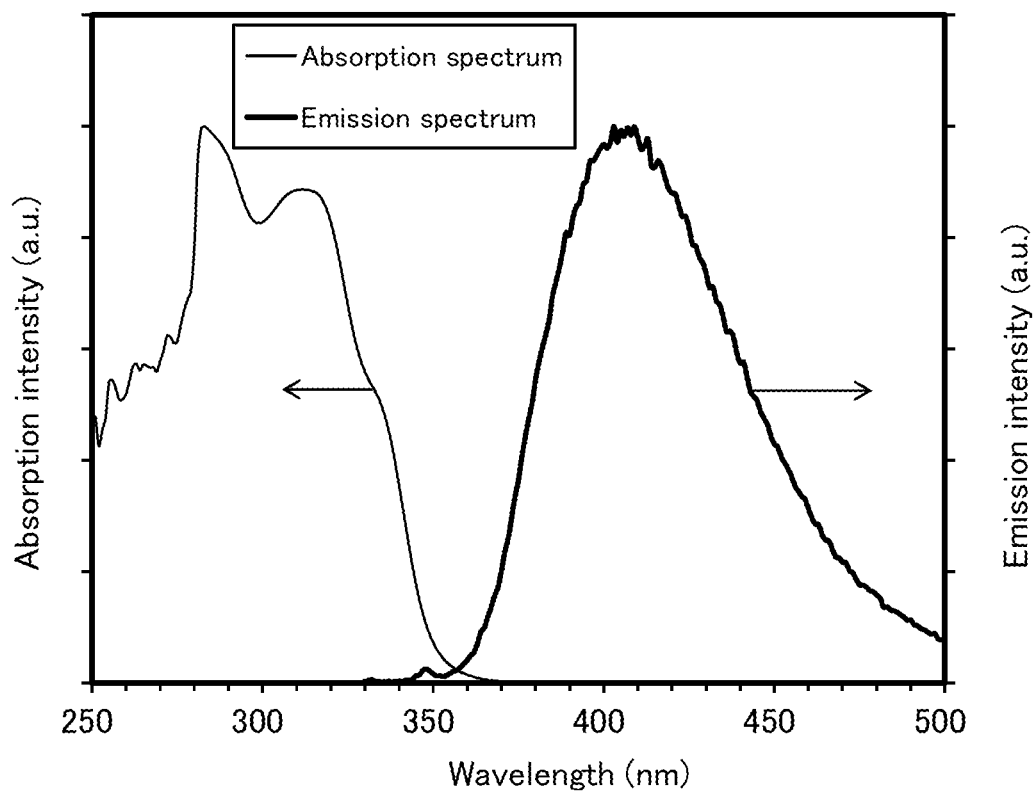
FIG. 34 is an ultraviolet-visible absorption spectrum and an emission spectrum of the organic compound represented by Structural Formula (103) in a toluene solution.

The absorption spectrum in the toluene solution was measured with an ultraviolet-visible spectrophotometer (V550, manufactured by JASCO Corporation). The emission spectrum in the toluene solution was measured with a fluorescence spectrophotometer (FS920, manufactured by Hamamatsu Photonics K.K.). FIG. 34 shows the measurement results on the obtained absorption spectrum and emission spectrum in the toluene solution. The horizontal axis represents the wavelength and the vertical axes represent the absorption intensity and the emission intensity.

As shown in FIG. 34, 8BP-4mDBtBPBfpm in the toluene solution had absorption peaks at approximately 332 nm, 316 nm, and 281 nm, and an emission wavelength peak at 406 nm (at an excitation wavelength of 318 nm).

Figure 35:
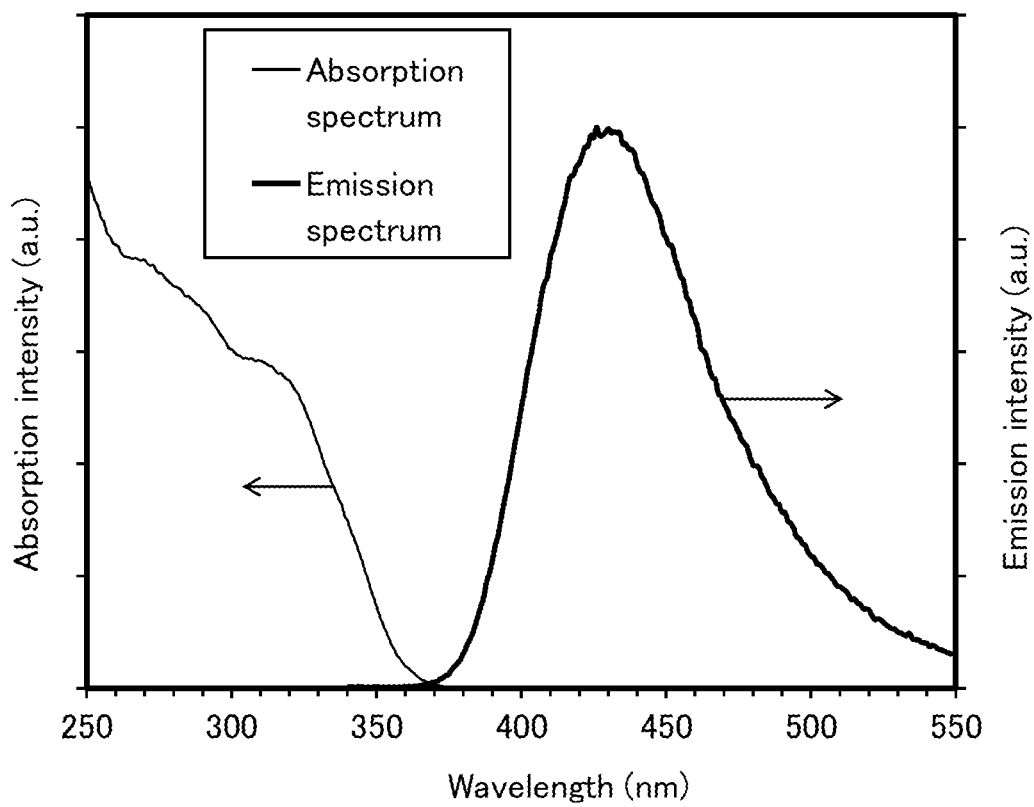
FIG. 35 is an ultraviolet-visible absorption spectrum and an emission spectrum of a solid thin film of the organic compound represented by Structural Formula (103).

For the measurement of the absorption spectrum of the solid thin film, a solid thin film formed on a quartz substrate by a vacuum evaporation method was used, and the measurement was performed with a UV-visible spectrophotometer (U-4100, manufactured by Hitachi High-Technologies Corporation). A solid thin film similar to the above was used for the measurement of the emission spectrum of the solid thin film, and the measurement was performed with a fluorescence spectrophotometer (FS920, manufactured by Hamamatsu Photonics K.K.). FIG. 35 shows the measurement results on the obtained absorption spectrum and emission spectrum of the solid thin film. The horizontal axis represents the wavelength and the vertical axes represent the absorption intensity and the emission intensity.

As shown in FIG. 35, the solid thin film of 8BP-4mDBtBPBfpm had absorption peaks at approximately 340 nm, 310 nm, 290 nm, 270 nm, and 245 nm, and an emission wavelength peak at 426 nm (at an excitation wavelength of 330 nm).

Example 8

Synthesis Example 5

Described in this example is a method for synthesizing 8-[(2,2'-binaphthalen)-6-yl]-4-[3'-(dibenzothiophen-4-yl)biphenyl-3-yl]-[1]benzofuro[3,2-d]pyrimidine (abbreviation: 8(βN2)-4mDBtBPBfpm), which is an organic compound of one embodiment of the present invention represented by Structural Formula (105) in Embodiment 1. Note that the structure of 8(βN2)-4mDBtBPBfpm is shown below.

[Chemical Formula 39]

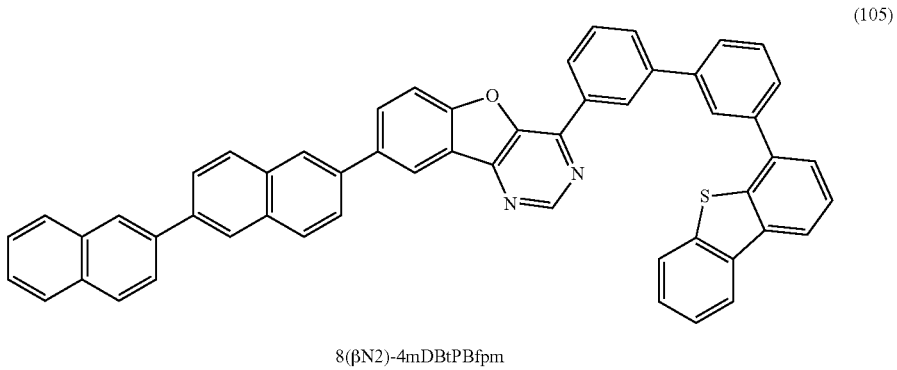

8(βN2)-4mDBtPBfpm

Synthesis of 8(βN2)-4mDBtBPBfpm

Into a three-neck flask, 2.11 g of 8-chloro-4-[3'-(dibenzothiophen-4-yl)biphenyl-3-yl]-[1]benzofuro[3,2-d]pyrimidine, 1.26 g of [2,2'-binaphthalen]-6-ylboronic acid, 2.55 g of tripotassium phosphate, 40 mL of diglyme, and 0.93 g of t-butanol were put, they were degassed by being stirred under reduced pressure, and the air in the flask was replaced with nitrogen. This mixture was heated to 60° C. and 27.0 mg of palladium(II) acetate and 77.8 mg of di(1-adamantyl)-n-butylphosphine were added, followed by stirring at 120° C. for 14 hours. Added were 27.5 mg of palladium(II) acetate and 76.4 mg of di(1-adamantyl)-n-butylphosphine, followed by stirring at 120° C. for 16 hours. Furthermore, 27.6 mg of palladium(II) acetate and 77.9 mg of di(1-adamantyl)-n-butylphosphine were added to this reaction product, followed by stirring at 120° C. for 14.5 hours and at 130° C. for 6.5 hours.

Water was added to this reaction product, suction filtration was performed, and the obtained residue was washed with water and toluene. This residue was dissolved in heated toluene, followed by filtration through a filter aid filled with Celite, alumina, and Celite in this order. The obtained solution was concentrated and dried, and then recrystallized with toluene to give 1.56 g of a target white solid in a yield of 52%.

By a train sublimation method, 1.15 g of the white solid was sublimated and purified. The conditions of the sublimation purification were such that the solid was heated under a pressure of 2.33 Pa at 375° C. while the argon gas flowed at a flow rate of 10 mL/min. After the sublimation purification, 1.06 g of a target pale yellow solid was obtained at a collection rate of 92%. The synthesis scheme is shown in Formula (g-1) below.

Figure 36:
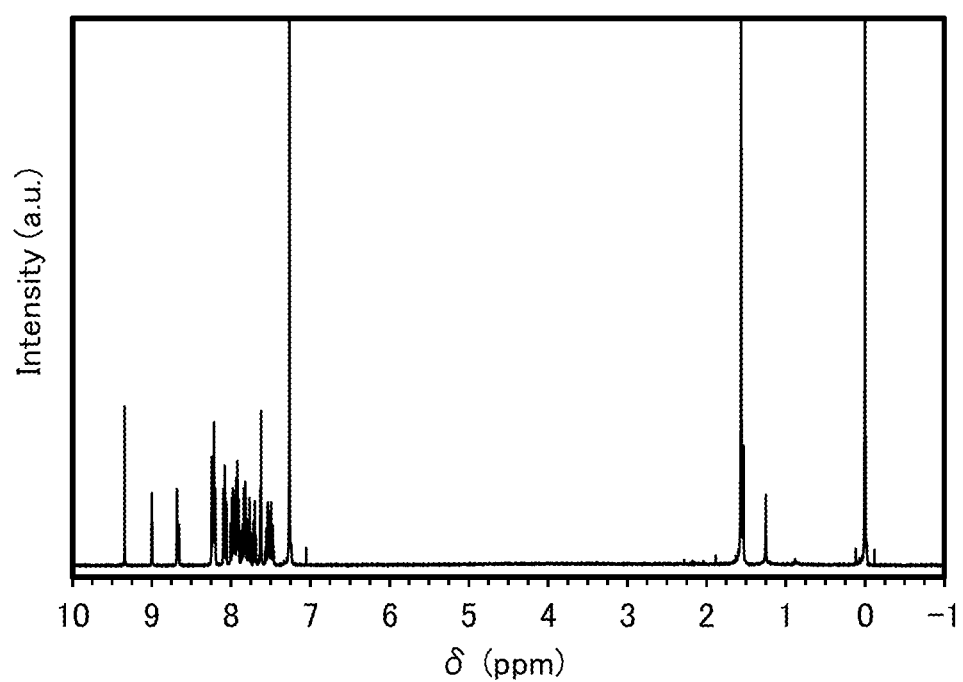
FIG. 36 is a 1H-NMR chart of an organic compound represented by Structural Formula (105).

Note that analysis results by nuclear magnetic resonance ($^1$H-NMR) spectroscopy of the white solid obtained by the above-described reaction are shown below. FIG. 36 shows a $^1$H-NMR chart. The results reveal that 8(βN2)-4mDBtBPBfpm, the organic compound of one embodiment of the present invention represented by Structural Formula (105) above, was obtained in this example.

$^1$H-NMR. δ (CDCl$_3$): 7.46-7.57 (m, 4H), 7.62-7.63 (m, 2H), 7.70 (t, 1H), 7.75-7.87 (m, 5H), 7.90-8.00 (m, 7H), 8.06-8.10 (m, 3H), 8.20-8.24 (m, 6H), 8.66-8.68 (m, 2H), 9.00 (s, 1H), 9.34 (s, 1H).

Physical Properties of 8(βN2)-4mDBtBPBfpm

Next, the ultraviolet-visible absorption spectrum (hereinafter, simply referred to as "absorption spectra") and emission spectrum of a solid thin film of 8(βN2)-4mDBtBPBfpm were measured.

For the measurement of the absorption spectrum of the solid thin film, a solid thin film formed on a quartz substrate by a vacuum evaporation method was used, and the measurement was performed with a UV-visible spectrophotometer (U-4100, manufactured by Hitachi High-Technologies

[Chemical Formulae 40]

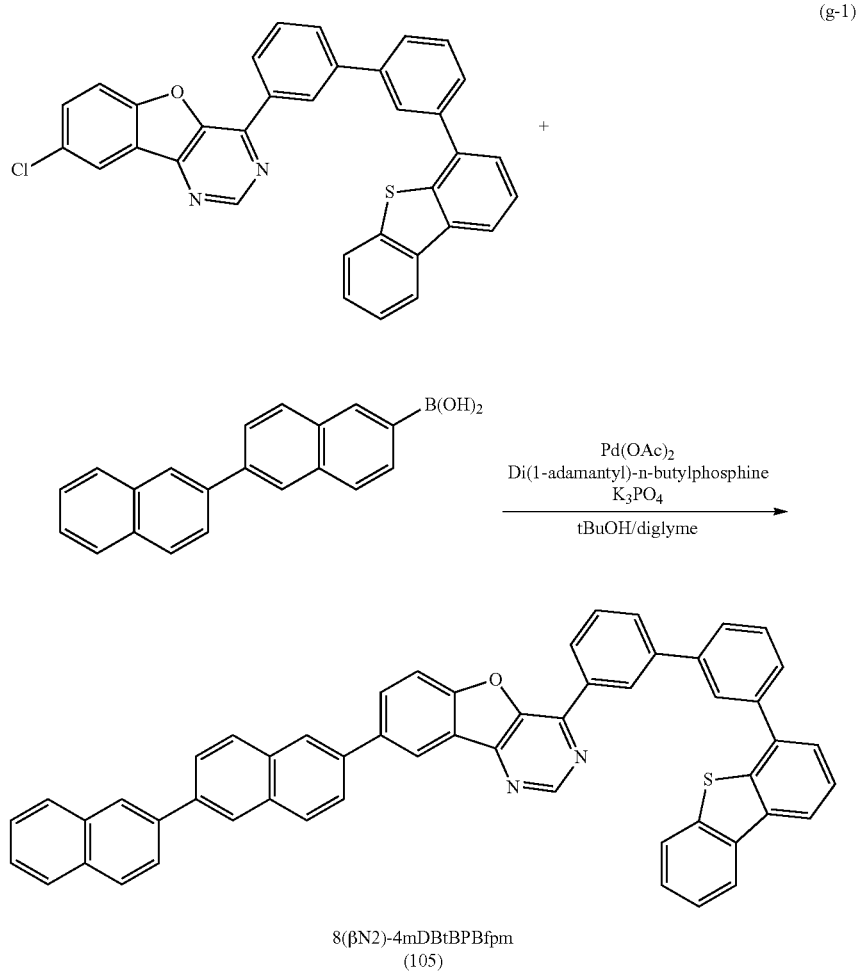

(g-1)

8(βN2)-4mDBtBPBfpm
(105)

Figure 37:
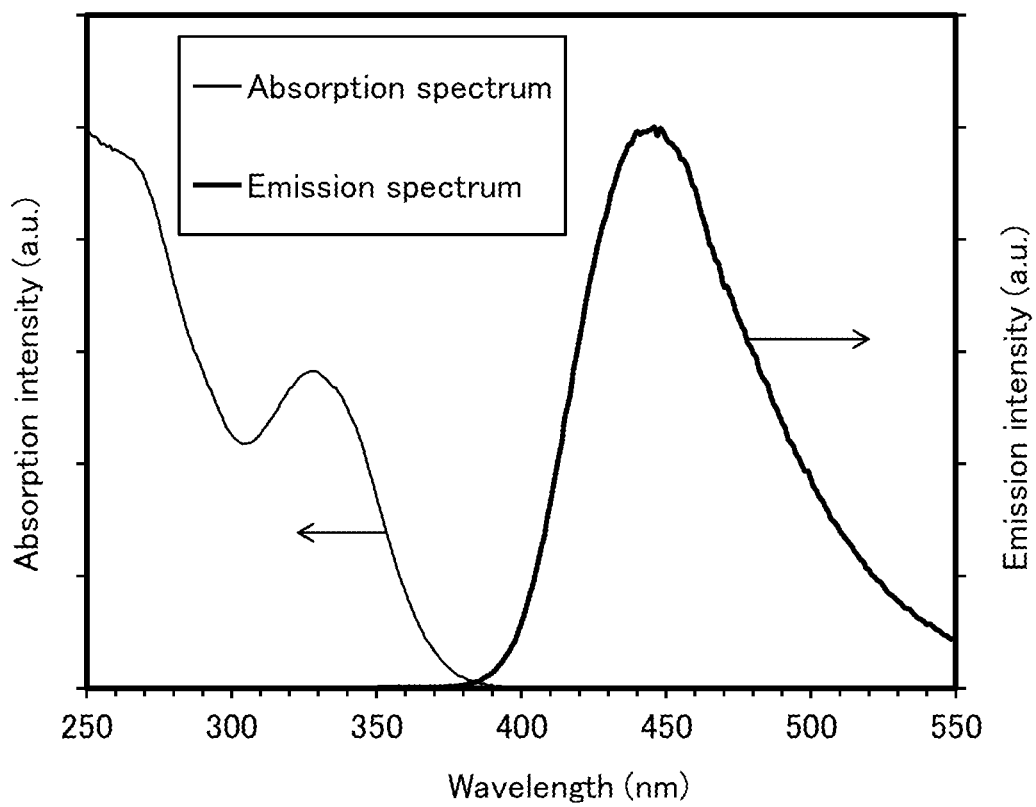
FIG. 37 is an ultraviolet-visible absorption spectrum and an emission spectrum of a solid thin film of the organic compound represented by Structural Formula (105).

Corporation). A solid thin film similar to the above was used for the measurement of the emission spectrum of the solid thin film, and the measurement was performed with a fluorescence spectrophotometer (FS920, manufactured by Hamamatsu Photonics K.K.). FIG. 37 shows the measurement results on the obtained absorption spectrum and emission spectrum of the solid thin film. The horizontal axis represents the wavelength and the vertical axes represent the absorption intensity and the emission intensity.

As shown in FIG. 37, the solid thin film of 8(βN2)-4mDBtBPBfpm had absorption peaks at approximately 328 nm, 290 nm, 267 nm, and 246 nm, and an emission wavelength peak at 446 nm (at an excitation wavelength of 330 nm).

Example 9

Synthesis Example 6

Described in this example is a method for synthesizing 8-(1,1':3',1"-terphenyl-4-yl)-4-[3-(dibenzothiophen-4-yl)phenyl]-[1]benzofuro[3,2-d]pyrimidine (abbreviation: 8pmTP-4mDBtPBfpm), which is an organic compound of one embodiment of the present invention represented by Structural Formula (126) in Embodiment 1. Note that the structure of 8pmTP-4mDBtPBfpm is shown below.

[Chemical Formula 41]

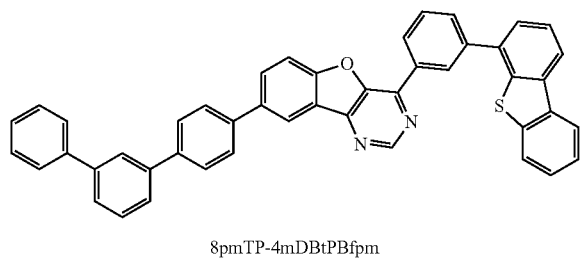

8pmTP-4mDBtPBfpm

Step 1: Synthesis of 4-bromo-8-1,1':3',1"-terphenyl

Into a side-arm flask, 0.50 g of 3-biphenylboronic acid, 1.06 g of 1-bromo-4-iodobenzene, 0.80 g of sodium carbonate, 17 mL of toluene, and 4 mL of ethanol were put, they were degassed by being stirred under reduced pressure, and the air in the flask was replaced with nitrogen. To this mixture, 86.7 mg of tetrakis(triphenylphosphine)palladium (0) was added, followed by stirring at 120° C. for 26 hours. Water was added to this reaction product, suction filtration was performed, and the obtained filtrate was concentrated and to give a brown solid. The solid was dissolved in a mixed solution of toluene and ethyl acetate, silica gel was added to the obtained solution, and concentration was performed. The obtained concentrate was purified by silica gel column chromatography using hexane as a developing solvent to give 0.30 g of a target white solid in a yield of 39%. The synthesis scheme is shown in Formula (h-1) below.

[Chemical Formulae 42]

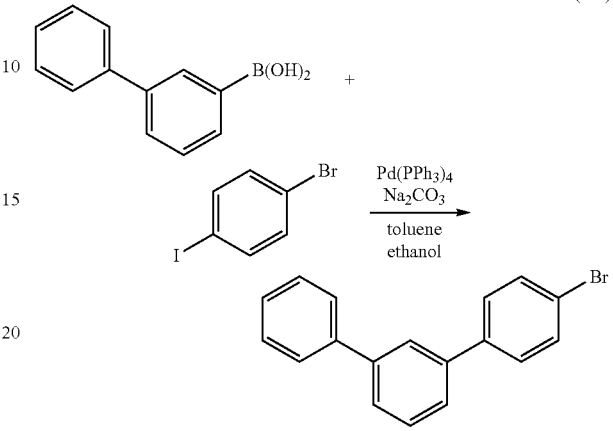

Step 2: Synthesis of 1,1':3',1"-terphenyl-4-boronic acid

Into a three-neck flask, 2.94 g of 4-bromo-1,1':3',1"-terphenyl synthesized in Step 1 was put, the air in the flask was replaced with nitrogen, 53 mL of dehydrated tetrahydrofuran was added, and the mixture was cooled to −78° C. Into this mixture, 8.9 mL of n-butyllithium (a 1.6 M hexane solution) was slowly dripped, followed by stirring at −78° C. for one hour. Into this reaction product, 1.6 mL of trimethyl borate was dripped, followed by stirring at room temperature overnight. Hydrochloric acid was added to the reaction product and extraction with ethyl acetate was performed. The obtained organic layer was washed with water and a saturated saline, and dried with magnesium sulfate. The mixture was gravity filtered, and the filtrate was concentrated to give a solid. The obtained solid was washed with a mixed solution of ethyl acetate and hexane to give 1.57 g of a target white solid in a yield of 60%. The synthesis scheme is shown in Formula (h-2) below.

[Chemical Formulae 43]

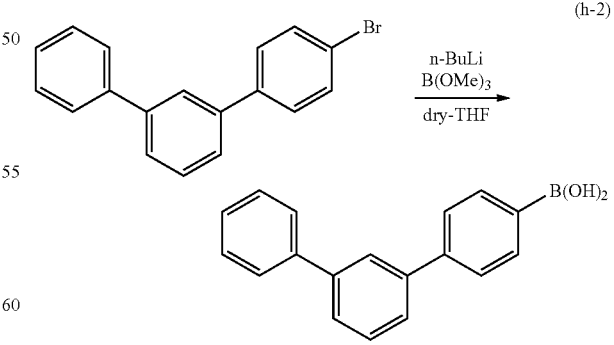

Step 3: Synthesis of 8pmTP-4mDBtPBfpm

Into a three-neck flask, 1.12 g of 1,1':3',1"-terphenyl-4-boronic acid synthesized in Step 2, 1.35 g of 8-chloro-4-[3-

(dibenzothiophen-4-yl)phenyl]-[1]benzofuro[3,2-d]pyrimidine, 1.70 g of cesium fluoride, and 26 mL of mesitylene were put, they were degassed by being stirred under reduced pressure, and the air was replaced with nitrogen.

To this mixture, 343 mg of tris(dibenzylideneacetone)dipalladium(0), 127 mg of di(1-adamantyl)-n-butylphosphine, and 126 mg of 2'-(dicyclohexylphosphino)acetophenone ethylene ketal were added, followed by stirring at 120° C. for 43.5 hours. Water was added to this reaction product, and suction filtration was performed. The obtained residue was washed with water, ethanol, and toluene, dissolved in heated toluene, subjected to filtration through a filter aid filled with Celite, alumina, and Celite in this order, concentrated and dried, and then recrystallized by a diffusion method using toluene/ethanol as a solvent to be separated into two layers to give 702 mg of a target white solid in a yield of 37%.

In addition, hexane was added to the filtrate obtained by the suction filtration of the above-described reaction product, and a precipitated solid was subjected to suction filtration, purified by silica gel column chromatography (toluene:ethyl acetate=50:1), and recrystallized with toluene/ethanol to give 0.18 g of a target white solid in a yield of 9.5%. The target substances were mixed and 633 mg of a white solid was sublimated and purified by a train sublimation method. The conditions of the sublimation purification were such that the solid was heated under a pressure of 2.52 Pa at 330° C. while the argon gas flowed at a flow rate of 10 mL/min. After the sublimation purification, 460 mg of a target pale yellow solid was obtained at a collection rate of 73%. The synthesis scheme is shown in Formula (h-3) below.

[Chemical Formulae 44]

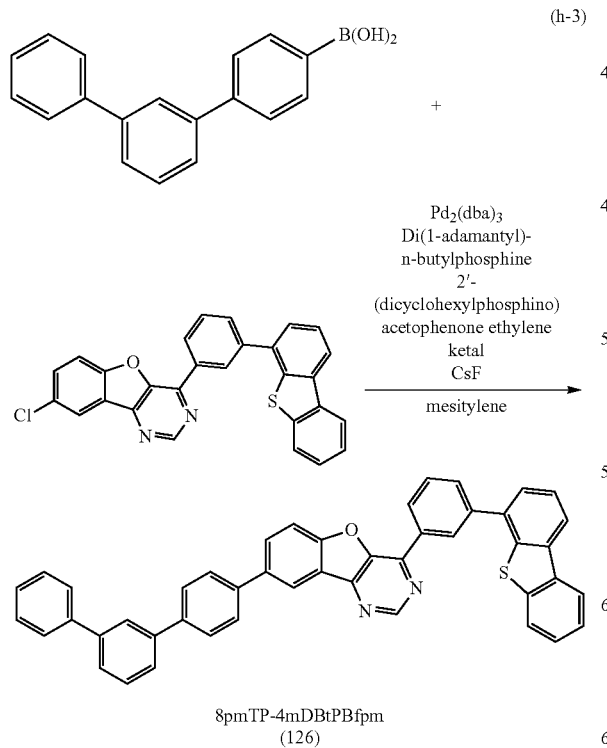

Figure 38:
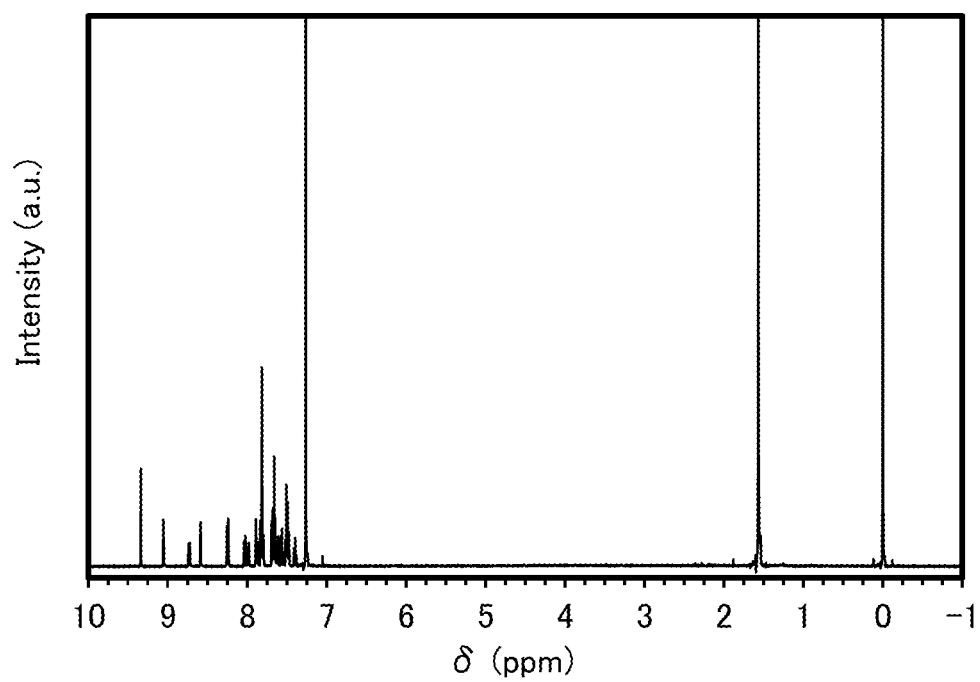
FIG. 38 is a 1H-NMR chart of an organic compound represented by Structural Formula (126).

Note that analysis results by nuclear magnetic resonance ($^1$H-NMR) spectroscopy of the pale yellow solid obtained by the above-described reaction are shown below. FIG. 38 shows a $^1$H-NMR chart. The results reveal that 8pmTP-4mDBtPBfpm, the organic compound of one embodiment of the present invention represented by Structural Formula (126) above, was obtained in this example.

$^1$H-NMR. δ (CDCl$_3$): 7.40 (t, 1H), 7.47-7.70 (m, 11H), 7.79-7.89 (m, 8H), 7.98-8.04 (m, 2H), 8.24-8.26 (m, 2H), 8.59 (d, 1H), 8.73 (d, 1H), 9.05 (t, 1H), 9.34 (s, 1H).

<<Physical Properties of 8pmTP-4mDBtPBfpm>>

Next, the ultraviolet-visible absorption spectra (hereinafter, simply referred to as "absorption spectra") and emission spectra of a toluene solution and a solid thin film of 8pmTP-4mDBtPBfpm were measured.

Figure 39:
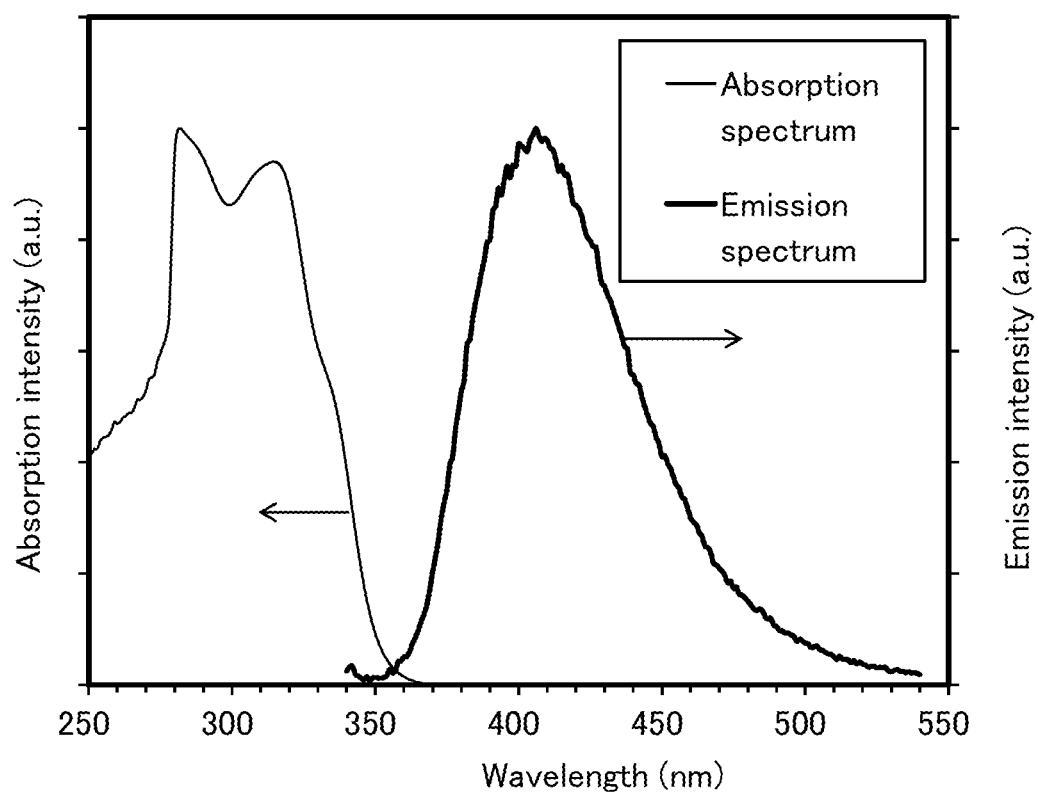
FIG. 39 is an ultraviolet-visible absorption spectrum and an emission spectrum of the organic compound represented by Structural Formula (126) in a toluene solution.

The absorption spectrum in the toluene solution was measured with an ultraviolet-visible spectrophotometer (V550, manufactured by JASCO Corporation). The emission spectrum in the toluene solution was measured with a fluorescence spectrophotometer (FS920, manufactured by Hamamatsu Photonics K.K.). FIG. 39 shows the measurement results on the obtained absorption spectrum and emission spectrum in the toluene solution. The horizontal axis represents the wavelength and the vertical axes represent the absorption intensity and the emission intensity.

As shown in FIG. 39, 8pmTP-4mDBtPBfpm in the toluene solution had absorption peaks at approximately 315 nm and 282 nm, and an emission wavelength peak at 406 nm (at an excitation wavelength of 310 nm).

Figure 40:
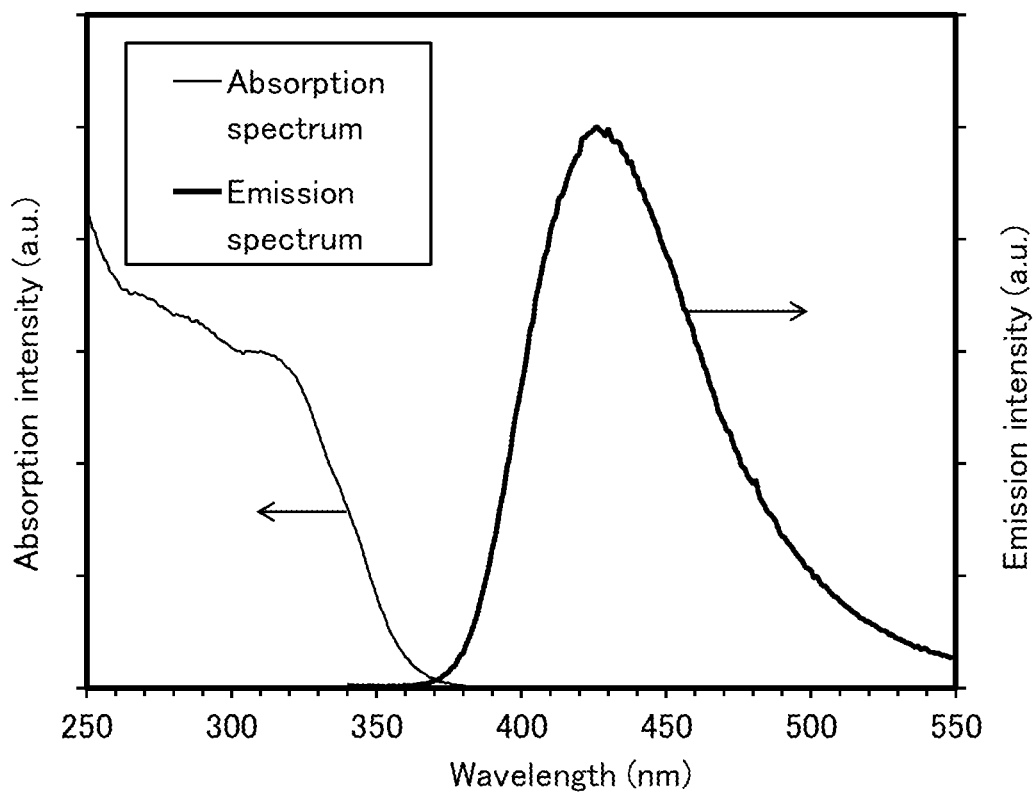
FIG. 40 is an ultraviolet-visible absorption spectrum and an emission spectrum of a solid thin film of the organic compound represented by Structural Formula (126).

For the measurement of the absorption spectrum of the solid thin film, a solid thin film formed on a quartz substrate by a vacuum evaporation method was used, and the measurement was performed with a UV-visible spectrophotometer (U-4100, manufactured by Hitachi High-Technologies Corporation). A solid thin film similar to the above was used for the measurement of the emission spectrum of the solid thin film, and the measurement was performed with a fluorescence spectrophotometer (FS920, manufactured by Hamamatsu Photonics K.K.). FIG. 40 shows the measurement results on the obtained absorption spectrum and emission spectrum of the solid thin film. The horizontal axis represents the wavelength and the vertical axes represent the absorption intensity and the emission intensity.

As shown in FIG. 40, the solid thin film of 8BP-4mDBtBPBfpm had absorption peaks at approximately 340 nm, 310 nm, 288 nm, 270 nm, and 243 nm, and an emission wavelength peak at 426 nm (at an excitation wavelength of 330 nm).

Example 10

Synthesis Example 7

Described in this example is a method for synthesizing 8-(1,1':4',1''-terphenyl-3-yl)-4-[3-(dibenzothiophen-4-yl)phenyl]-[1]benzofuro[3,2-d]pyrimidine (abbreviation: 8mpTP-4mDBtPBfpm), which is an organic compound of one embodiment of the present invention represented by Structural Formula (128) in Embodiment 1. Note that the structure of 8mpTP-4mDBtPBfpm is shown below.

[Chemical Formula 45]

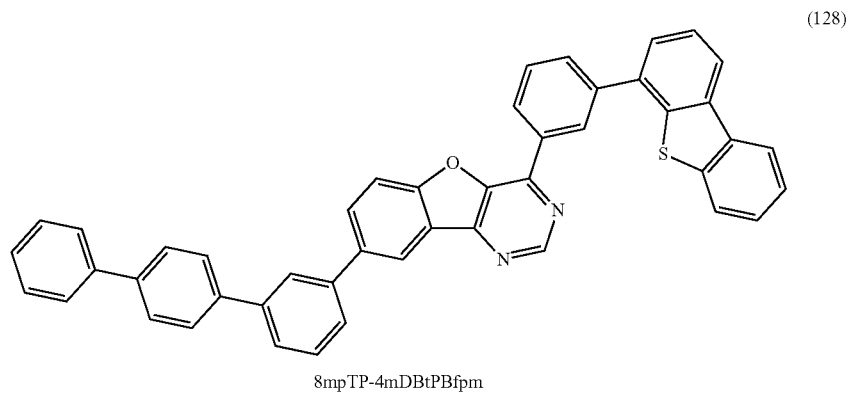

8mpTP-4mDBtPBfpm

Step 1: 2-hydroxy-5-(1,1': 4',1"-terphenyl-3-yl)benzonitrile

Into a three-neck flask, 6.98 g of 5-bromo-2-hydroxybenzonitrile, 10.9 g of β-[1,1': 4',1"-terphenyl]-3-ylboronic acid, 11.0 g of potassium carbonate, 370 mL of toluene, 40 mL of ethanol, and 40 mL of water were put, they were degassed by being stirred under reduced pressure, and the air was replaced with nitrogen. To this mixture, 467 mg of palladium (II) acetate and 1.34 g of tris(2-methylphenyl)phosphine were added, followed by stirring at 80° C. for 4.0 hours. Water was added to this reaction product, suction filtration was performed, and the obtained residue was washed with water, ethanol, toluene, and ethyl acetate to give 12.0 g of a target gray solid in a yield of 98%. The synthesis scheme is shown in Formula (i-1) below.

[Chemical Formulae 46]

(i-1)

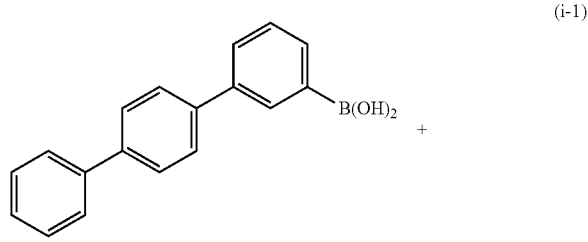

+

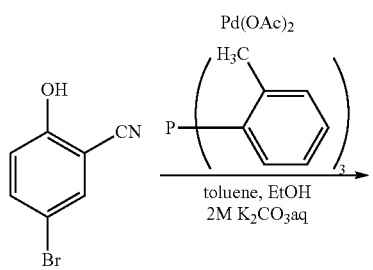

→

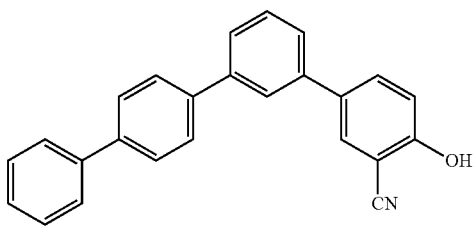

Step 2: Synthesis of 3-amino-5-(1,1':4',1"-terphenyl-3-yl)benzo[b]furan-2-carboxylate Into a three-neck flask, 12.0 g of 2-hydroxy-5-(1,1':4',1"-terphenyl-3-yl)benzonitrile synthesized in Step 1, 7.05 g of ethyl bromoacetate, 9.64 g of potassium carbonate, and 90 mL of dimethylformamide were put. The mixture was stirred at 100° C. for 7.0 hours. Water was added to this reaction liquid, suction filtration was performed, and the obtained residue was washed with water and ethanol. The residue was dissolved in heated ethyl acetate, and suction filtration was performed. The obtained solution was concentrated to give 11.9 g of a target gray solid in a yield of 79%. The synthesis scheme is shown in Formula (i-2) below.

[Chemical Formulae 47]

(i-2)

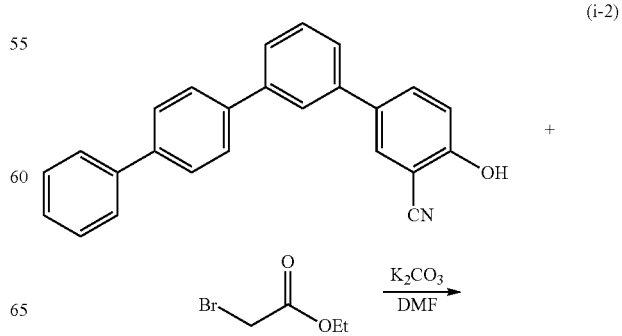

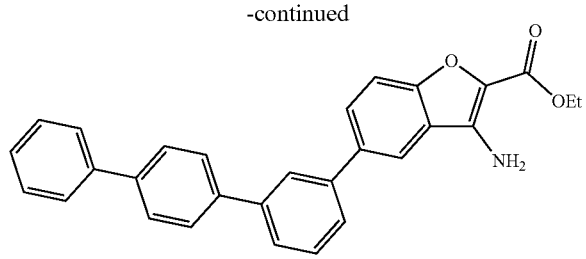

Step 3: Synthesis of 8-(1,1': 4',1''-terphenyl-3-yl)[1]benzofuro[3,2-d]pyrimidin-4(3H)-one Into a three-neck flask, 11.9 g of 3-amino-5-(1,1':4',1''-terphenyl-3-yl)benzo[b]furan-2-carboxylate synthesized in Step 2, 5.81 g of formamidine acetate, and 120 mL of formamide were put. The mixture was stirred at 160° C. for 12.0 hours. Water was added to this reaction liquid, suction filtration was performed, and the obtained residue was washed with water and ethanol to give 10.6 g of a target brown solid in a yield of 93%. The synthesis scheme is shown in Formula (i-3) below.

[Chemical Formulae 48]

(i-3)

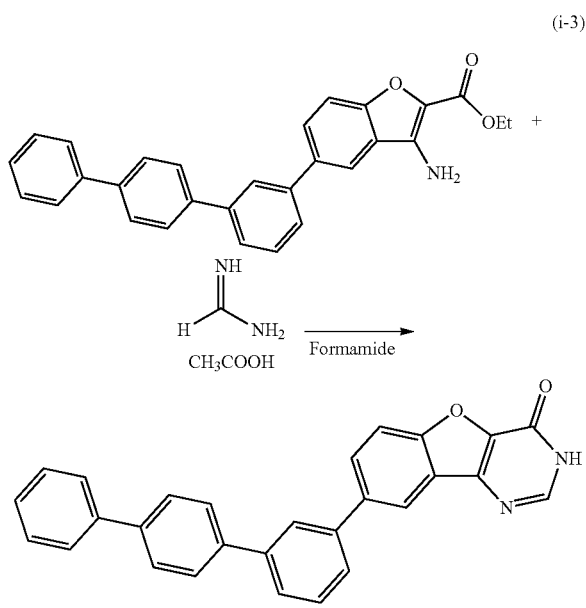

Step 4: 4-chloro-8-(1,1': 4',1''-terphenyl-3-yl)[1]benzofuro[3,2-d]pyrimidine Into a three-neck flask, 10.6 g of 8-(1,1': 4',1''-terphenyl-3-yl)[1]benzofuro[3,2-d]pyrimidin-4(3H)-one synthesized in Step 3, 40 mL of phosphoryl chloride, and 0.02 mL of dimethylformamide were put. The mixture was stirred at 90° C. under a nitrogen stream for 12.0 hours. The obtained reaction product was put into iced water, the solution was neutralized with sodium hydroxide and then a saturated solution of sodium bicarbonate, and stirred for one hour. This mixture was subjected to suction filtration, the residue was dissolved in heated toluene, followed by filtration through a filter aid filled with Celite, alumina, and Celite in this order. The obtained solution was concentrated, and then recrystallized by a diffusion method using toluene/ethanol as a solvent to be separated into two layers to give 8.99 g of a target yellow solid in a yield of 81%. The synthesis scheme is shown in Formula (i-4) below.

[Chemical Formulae 49]

(i-4)

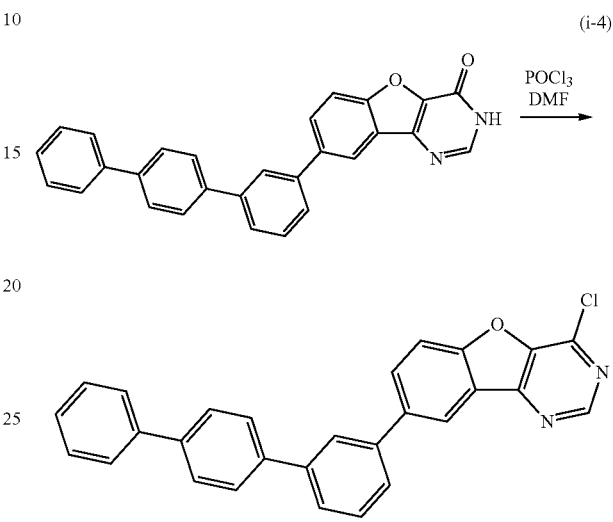

Step 5: Synthesis of 8-(1,1': 4',1''-terphenyl-3-yl)-4-[3-(dibenzothiophen-4-yl)phenyl]-[1]benzofuro[3,2-d]pyrimidine Next, into a three-neck flask, 1.98 g of 4-chloro-8-(1,1': 4',1''-terphenyl-3-yl)[1]benzofuro[3,2-d]pyrimidine obtained in Step 4, 1.69 g of 3-(dibenzothiophen-4-yl)phenylboronic acid, 1.64 g of potassium carbonate, 45 mL of toluene, 5.0 mL of ethanol, and 5.0 mL of water were put, they were degassed by being stirred under reduced pressure, and the air was replaced with nitrogen.

To this mixture, 407 mg of bis(triphenylphosphine)palladium(II) dichloride (abbreviation: $Pd(PPh_3)_2Cl_2$) was added, followed by stirring at 90° C. for 9.0 hours. Water was added to this reaction product, suction filtration was performed. The obtained residue was washed with water, ethanol, and toluene, dissolved in heated toluene, and subjected to filtration through a filter aid filled with Celite, alumina, and Celite in this order. The obtained solution was concentrated and dried, and then recrystallized by a diffusion method using toluene/ethanol as a solvent to be separated into two layers to give 2.57 g of a target white solid in a yield of 85%.

By a train sublimation method, 2.30 g of the white solid was sublimated and purified. The conditions of the sublimation purification were such that the solid was heated under a pressure of 2.5 Pa at 350° C. while the argon gas flowed at a flow rate of 15 mL/min. After the sublimation purification, 1.69 g of 8-(1,1':4',1''-terphenyl-3-yl)-4-[3-(dibenzothiophen-4-yl)phenyl]-[1]benzofuro[3,2-d]pyrimidine, which is a target substance, was obtained (a collection rate was 74%, a white solid). The synthesis scheme is shown in Formula (i-5) below.

[Chemical Formulae 50]

(i-5)

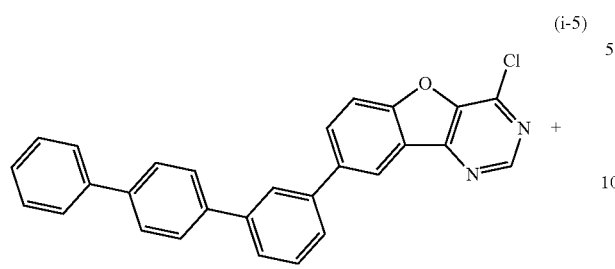

+

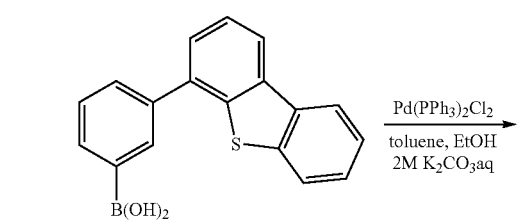

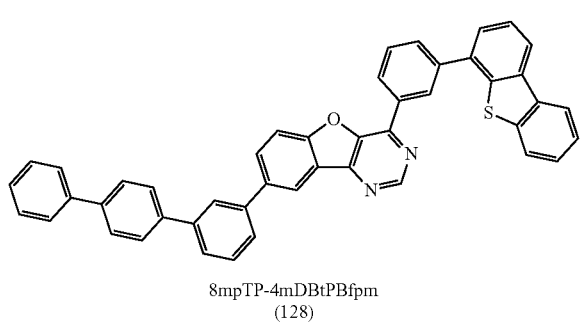

8mpTP-4mDBtPBfpm
(128)

Figure 41:
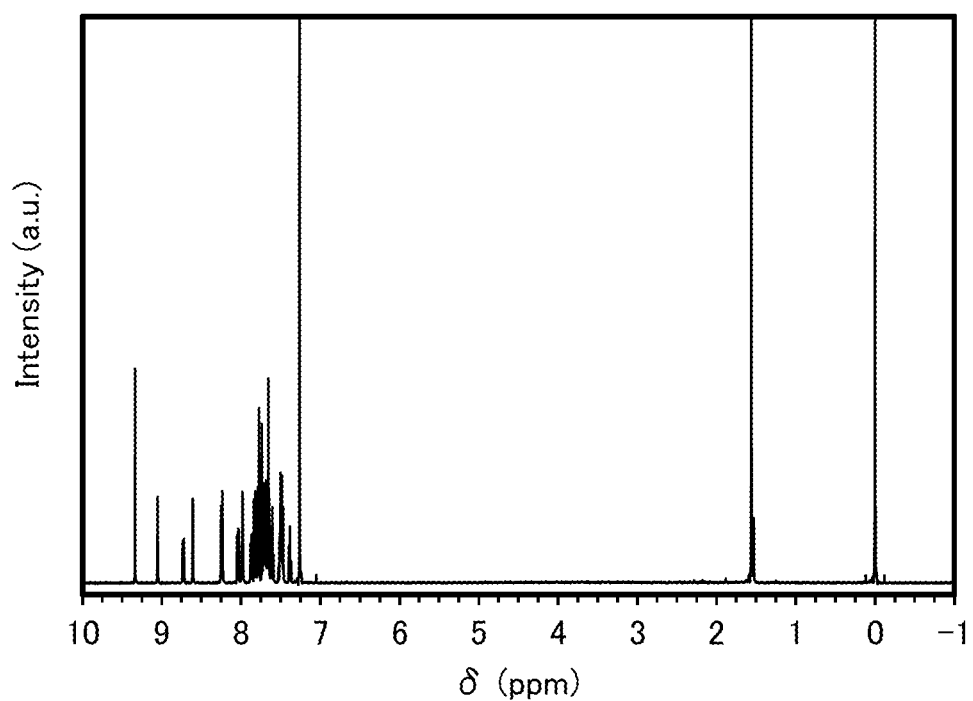
FIG. 41 is a 1H-NMR chart of an organic compound represented by Structural Formula (128).

Note that analysis results by nuclear magnetic resonance (¹H-NMR) spectroscopy of the pale yellow solid obtained by the above-described reaction are shown below. FIG. 41 shows a ¹H-NMR chart. The results reveal that 8mpTP-4mDBtPBfpm, the organic compound of one embodiment of the present invention represented by Structural Formula (128) above, was obtained in this example.

¹H-NMR. δ (CDCl₃): 7.38 (t, 1H), 7.47-7.53 (m, 4H), 7.59-7.74 (m, 9H), 7.77-7.88 (m, 5H), 7.97-7.99 (m, 2H), 8.03-8.05 (m, 1H), 8.23-8.25 (m, 2H), 8.61 (d, 1H), 8.73 (d, 1H), 9.05 (t, 1H), 9.34 (s, 1H).

Example 11

Synthesis Example 8

Described in this example is a method for synthesizing 8-(1,1': 3'1''-terphenyl-5'-yl)-4-[3-(dibenzothiophen-4-yl)phenyl]-[1]benzofuro[3,2-d]pyrimidine (abbreviation: 8mTP-4mDBtPBfpm), which is an organic compound of one embodiment of the present invention represented by Structural Formula (143) in Embodiment 1. Note that the structure of 8mTP-4mDBtPBfpm is shown below.

[Chemical Formula 51]

(143)

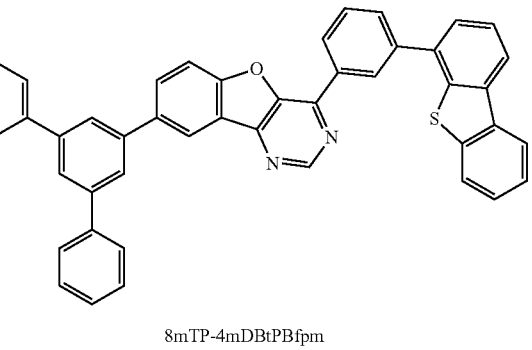

8mTP-4mDBtPBfpm

Step 1: Synthesis of 8mTP-4mDBtPBfpm

Into a three-neck flask, 503 mg of 8-chloro-4-[3-(dibenzothiophen-4-yl)phenyl]-[1]benzofuro[3,2-d]pyrimidine, 923 mg of (3,5-diphenylphenyl)boronic acid, 1.23 g of tripotassium phosphate, 700 mg of tert-butyl alcohol, and 36 mL of diethylene glycol dimethyl ether were put, they were degassed by being stirred under reduced pressure, and the air was replaced with nitrogen. To the mixture, 58.3 mg of palladium(II) acetate and 166 mg of di(1-adamantyl)-n-butylphosphine were added, followed by stirring at 120° C. for 7.5 hours.

Water was added to this reaction product, suction filtration was performed, and the obtained residue was washed with water, ethanol, and toluene. The residue was dissolved in heated toluene, followed by filtration through a filter aid filled with Celite, alumina, and Celite in this order. The obtained solution was concentrated and dried, and then recrystallized by a diffusion method using toluene/ethanol as a solvent to be separated into two layers to give 302 mg of a target white solid in a yield of 25%.

By a train sublimation method, 292 mg of the white solid was sublimated and purified. The conditions of the sublimation purification were such that the solid was heated under a pressure of 2.6 Pa at 340° C. while the argon gas flowed at a flow rate of 10 mL/min. After the sublimation purification, 161 mg of 8mTP-4mDBtPBfpm, which is a target substance, was obtained (a collection rate was 55%, a white solid). The synthesis scheme is shown in Formula (j-1) below.

[Chemical Formulae 52]

(j-1)

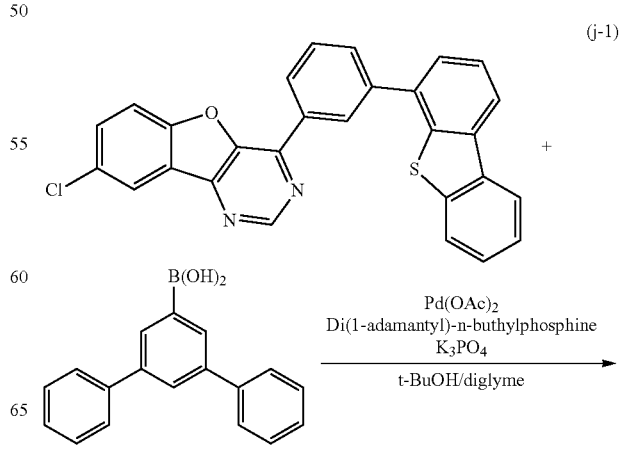

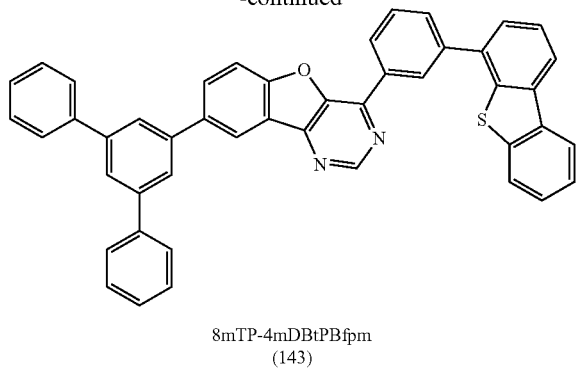

8mTP-4mDBtPBfpm
(143)

Figure 42:
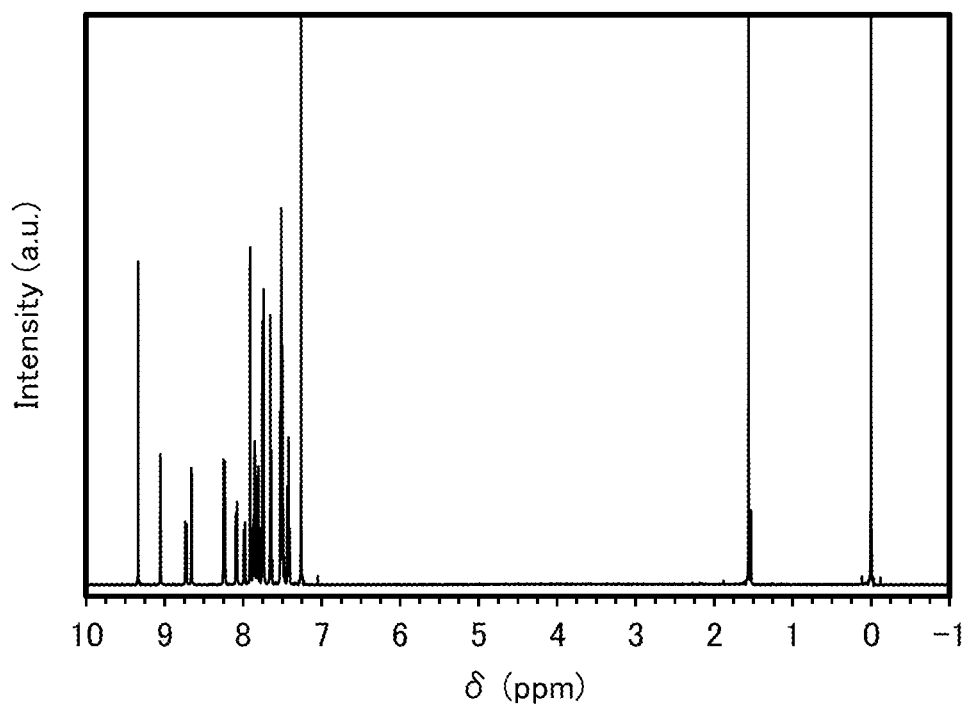
FIG. 42 is a 1H-NMR chart of an organic compound represented by Structural Formula (143).
Figure 43:
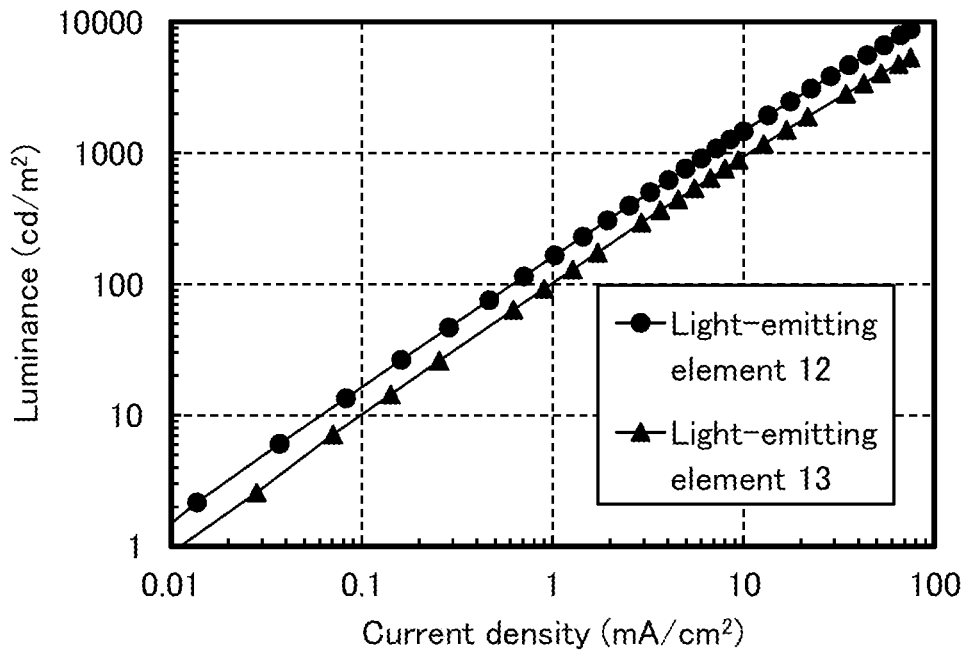
FIG. 43 is a drawing showing current density-luminance characteristics of a light-emitting element 12 and a light-emitting element 13.
Figure 44:
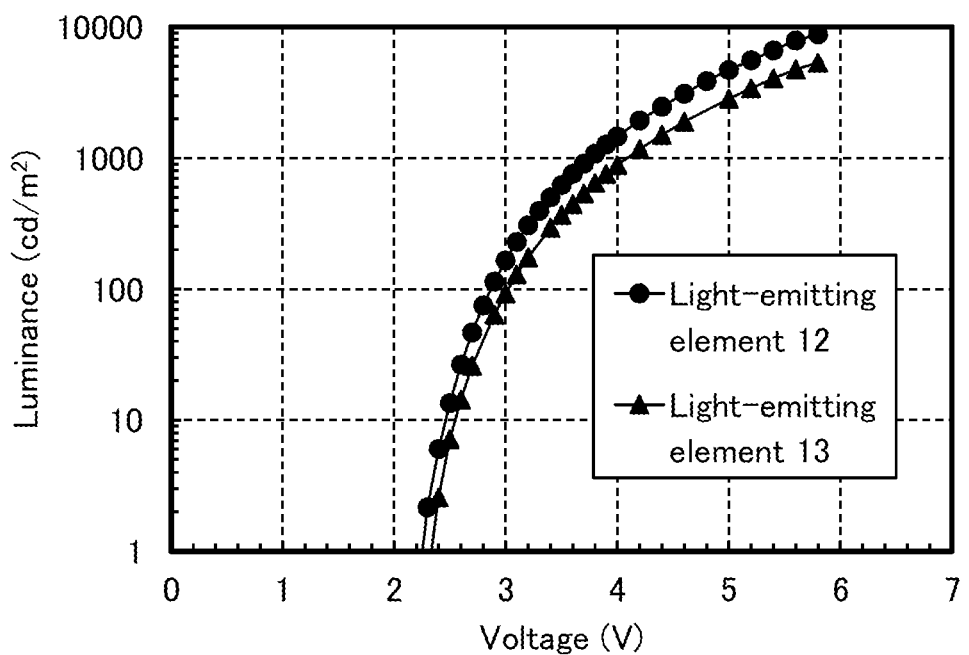
FIG. 44 is a drawing showing voltage-luminance characteristics of the light-emitting element 12 and the light-emitting element 13.
Figure 45:
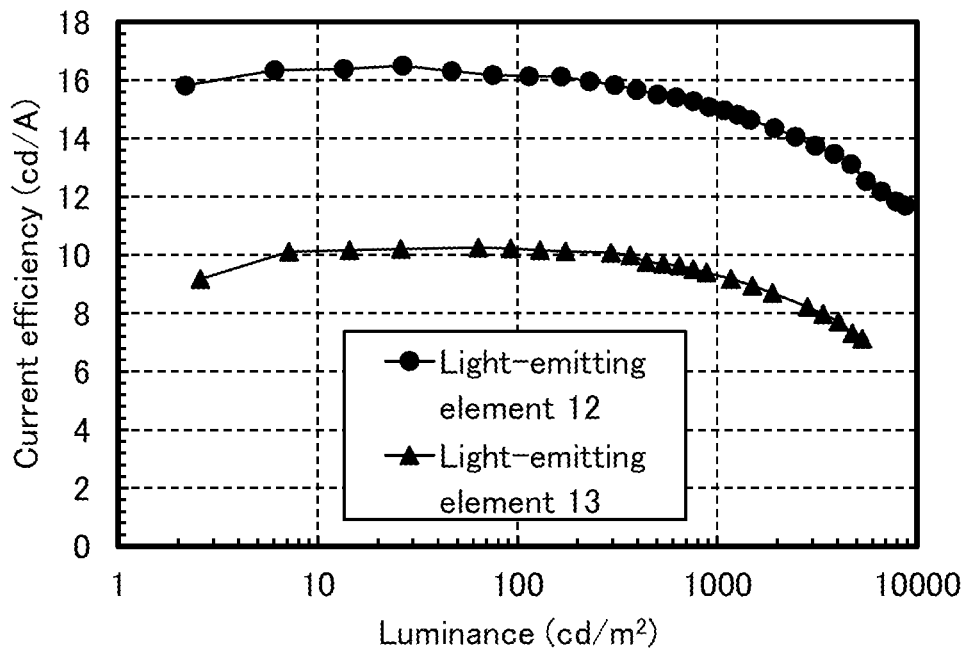
FIG. 45 is a drawing showing luminance-current efficiency characteristics of the light-emitting element 12 and the light-emitting element 13.
Figure 46:
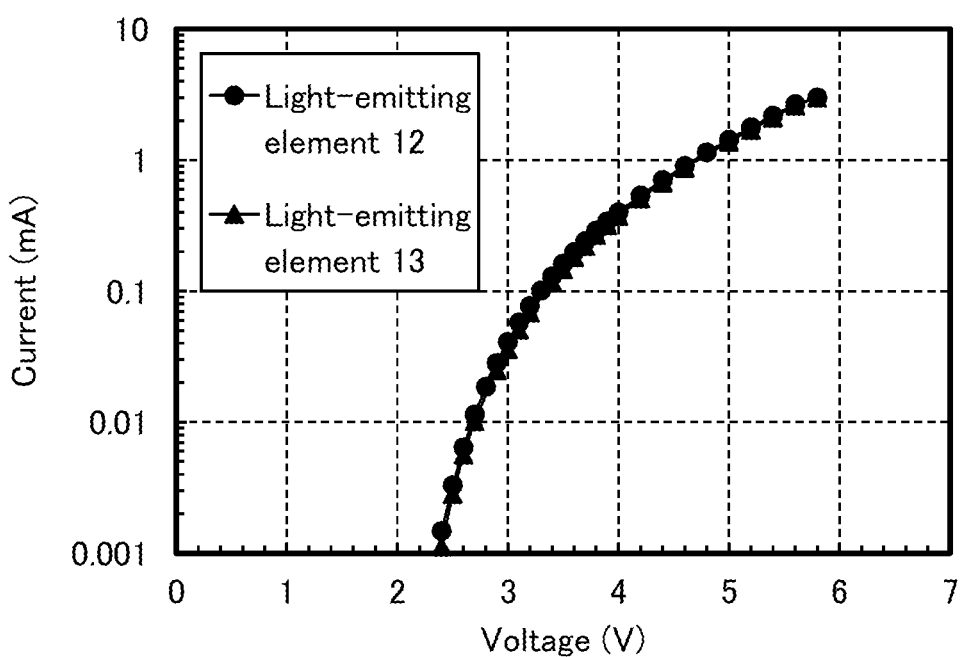
FIG. 46 is a drawing showing voltage-current characteristics of the light-emitting element 12 and the light-emitting element 13.

Note that analysis results by nuclear magnetic resonance (¹H-NMR) spectroscopy of the pale yellow solid obtained by the above-described reaction are shown below. FIG. 42 shows a ¹H-NMR chart. The results reveal that 8mTP-4mDBtPbfpm, the organic compound of one embodiment of the present invention represented by Structural Formula (143) above, was obtained in this example.

¹H-NMR. δ (CDCl$_3$): 7.40-7.43 (m, 2H), 7.47-7.53 (m, 6H), 7.63-7.66 (m, 2H), 7.74-7.76 (m, 4H), 7.79-7.87 (m, 4H), 7.91 (m, 2H), 7.97-7.99 (m, 1H), 8.08-8.09 (m, 1H), 8.22-8.26 (m, 2H), 8.66 (m, 1H), 8.72-8.73 (m, 1H), 9.05-9.06 (m, 1H), 9.34 (s, 1H).

Example 12

Synthesis Example 9

Described in this example is a method for synthesizing 8-(1,1'-biphenyl-4-yl)-4-[3-(9H-carbazol-9-yl)phenyl]-[1]benzofuro[3,2-d]pyrimidine (abbreviation: 8BP-4mCzPBfpm), which is an organic compound of one embodiment of the present invention represented by Structural Formula (144) in Embodiment 1. Note that the structure of 8BP-4mCzPBfpm is shown below.

[Chemical Formula 53]

(144)

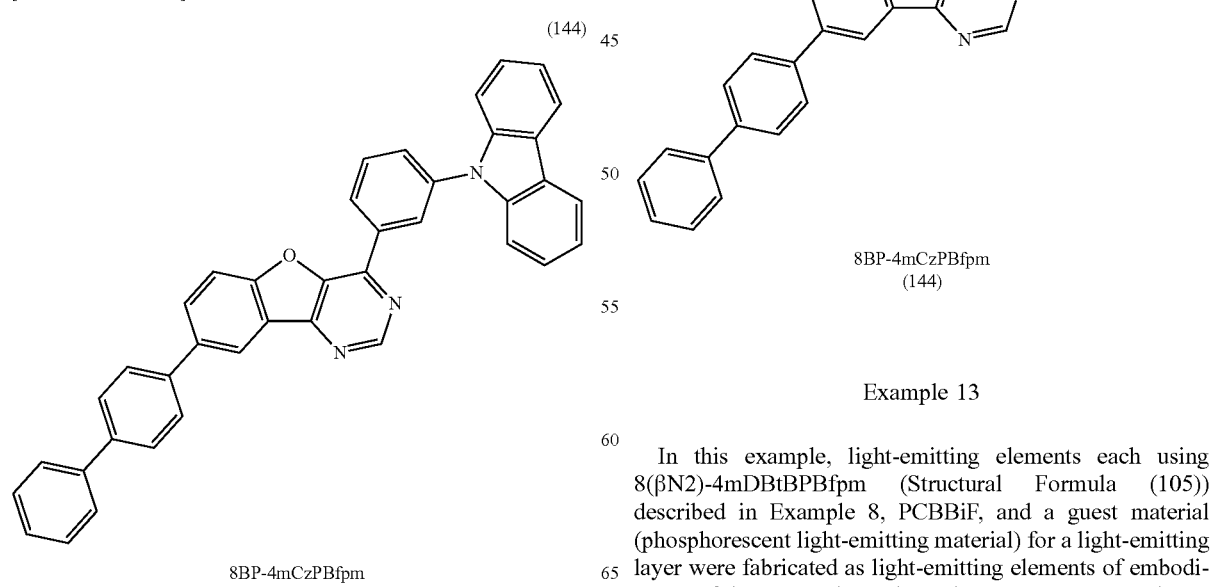

8BP-4mCzPBfpm

Note that 8BP-4mCzPBfpm described above can be synthesized by a synthesis scheme represented by Formula (k-1) below.

[Chemical Formulae 54]

(k-1)

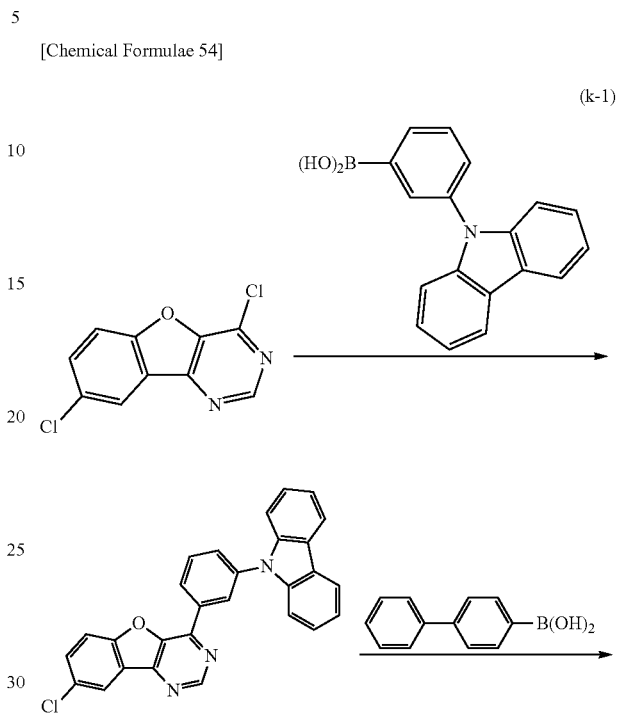

8BP-4mCzPBfpm
(144)

Example 13

In this example, light-emitting elements each using 8(βN2)-4mDBtBPBfpm (Structural Formula (105)) described in Example 8, PCBBiF, and a guest material (phosphorescent light-emitting material) for a light-emitting layer were fabricated as light-emitting elements of embodiments of the present invention. The measurement results on the characteristics will be described. Note that in this example, a light-emitting element using [Ir(dmpqn)$_2$(acac)] as a guest material is a light-emitting element 12, and a light-emitting element using bis{4,6-dimethyl-2-[5-(5-cyano-2-methylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-m5CP)$_2$(dpm)]) as a guest material is a light-emitting element 13.

The element structure of the light-emitting element 12 and the light-emitting element 13 fabricated in this example is similar to that in FIG. 14 mentioned in Example 4, and specific compositions of layers that constitute the element structure are as shown in Table 7. Chemical formulae of materials used in this example are shown below.

TABLE 7

|  | First electrode | Hole-injection layer | Hole-transport layer | Light-emitting layer | Electron-transport layer | Electron-injection layer | Second electrode |
| --- | --- | --- | --- | --- | --- | --- | --- |
| Light-emitting element 12 | ITSO (70 nm) | DBT3P-II:MoO$x$ (2:170nm) | PCBBiF (20 nm) | * | 8(bN2)-4mDBtBPBfpm (30 nm) | NBphen (15 nm) | LiF (1 nm) | Al (200 nm) |
| Light-emitting element 13 | ITSO (70 nm) | DBT3P-II:MoO$x$ (2:170nm) | PCBBiF (20 nm) | ** | 8(bN2)-4mDBtBPBfpm (30 nm) | NBphen (15 nm) | LiF (1 nm) | Al (200 nm) |

* 8(βN2)-4mDBtBPBfpm:PCBBiF:[Ir(dmpqn)$_2$(acac)] (0.85:0.15:0.1 40 nm)

** 8(βN2)-4mDBtBPBfpm:PCBBiF:[Ir(dmdppr-m5CP)$_2$(dpm)] (0.8:0.2:0.1 40 nm)

[Chemical Formulae 55]

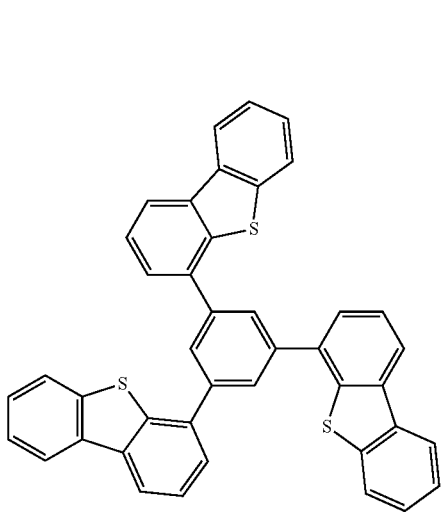

DBT3P-II

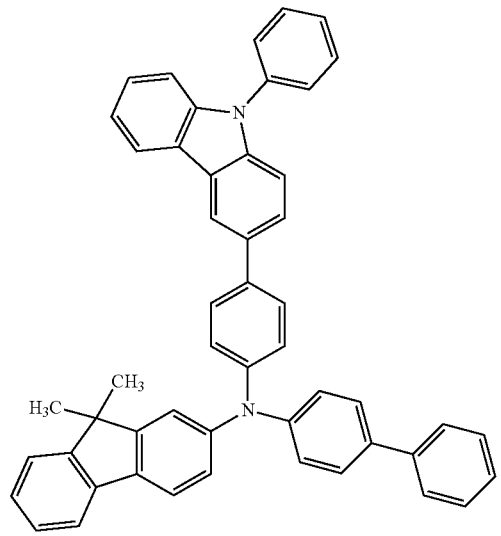

PCBBiF (105)

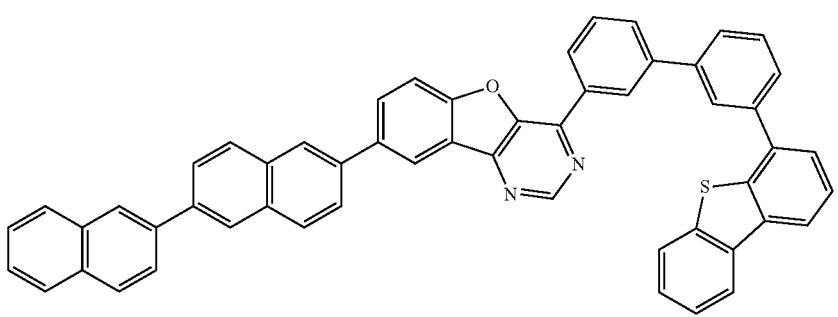

8(β N2)-4mDBtBPBfpm

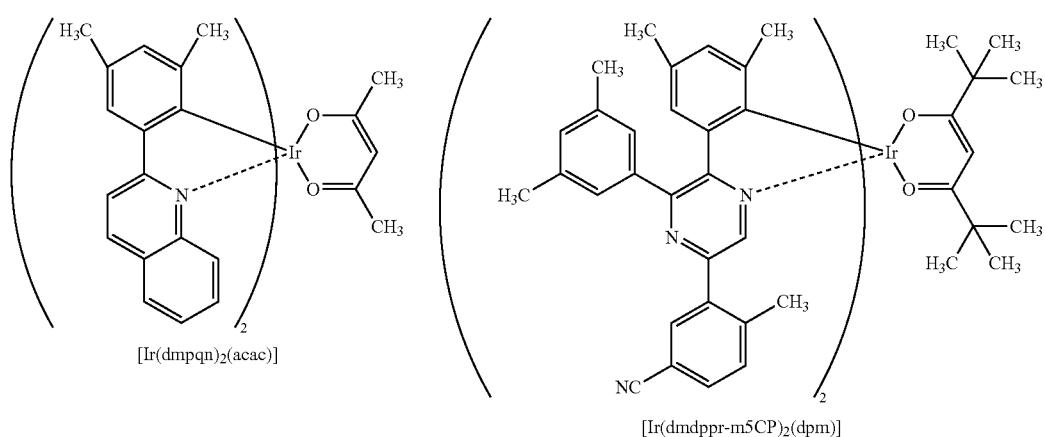

[Ir(dmpqn)₂(acac)]

[Ir(dmdppr-m5CP)₂(dpm)]

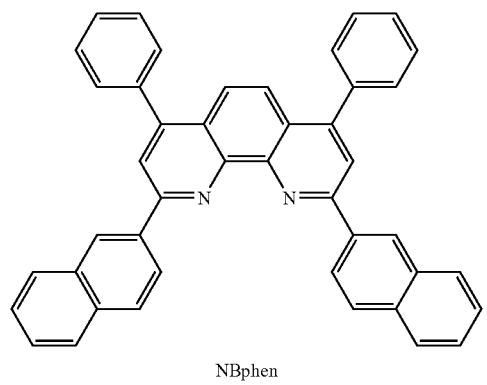

NBphen

<<Operation Characteristics of Light-Emitting Elements>>

Operation characteristics of the fabricated light-emitting element 12 and light-emitting element 13 were measured. Note that the measurement was carried out at room temperature (an atmosphere maintained at 25° C.).

The current density-luminance characteristics, voltage-luminance characteristics, luminance-current efficiency characteristics, and voltage-current characteristics of the light-emitting elements are shown in FIG. 43, FIG. 44, FIG. 45, and FIG. 46, respectively.

Table 8 below shows initial values of main characteristics of each of the light-emitting elements at around 1000 cd/m².

[Ir(dmpqn)₂(acac)] contained in the light-emitting layer 913. The emission spectrum of the light-emitting element 13 has a peak at around 648 nm, which is suggested to be derived from light emission of [Ir(dmdppr-m5CP)₂(dpm)] contained in the light-emitting layer 913.

Figure 48:
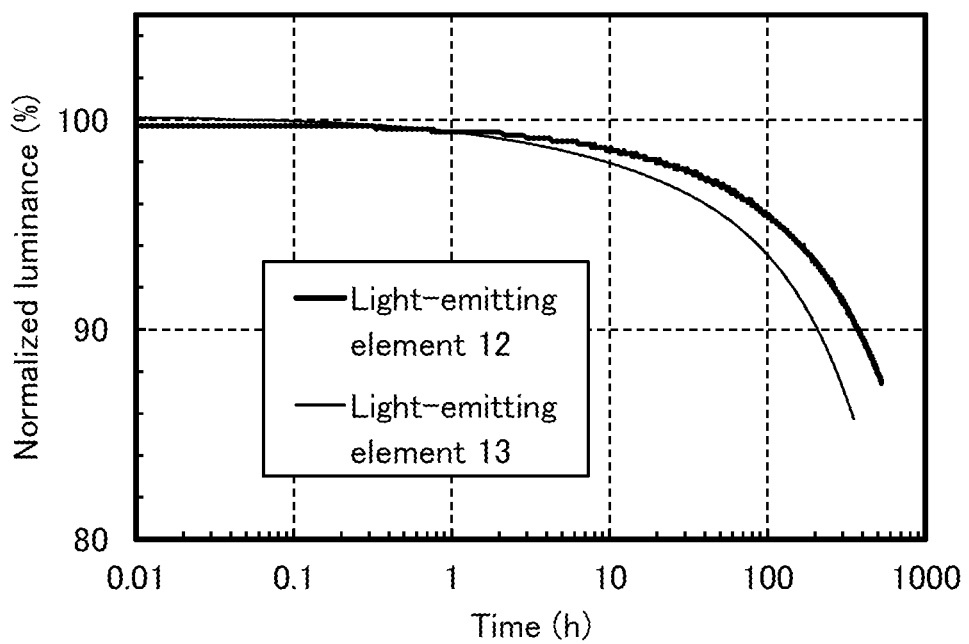
FIG. 48 is a drawing showing reliability of the light-emitting element 12 and the light-emitting element 13.
Figure 49:
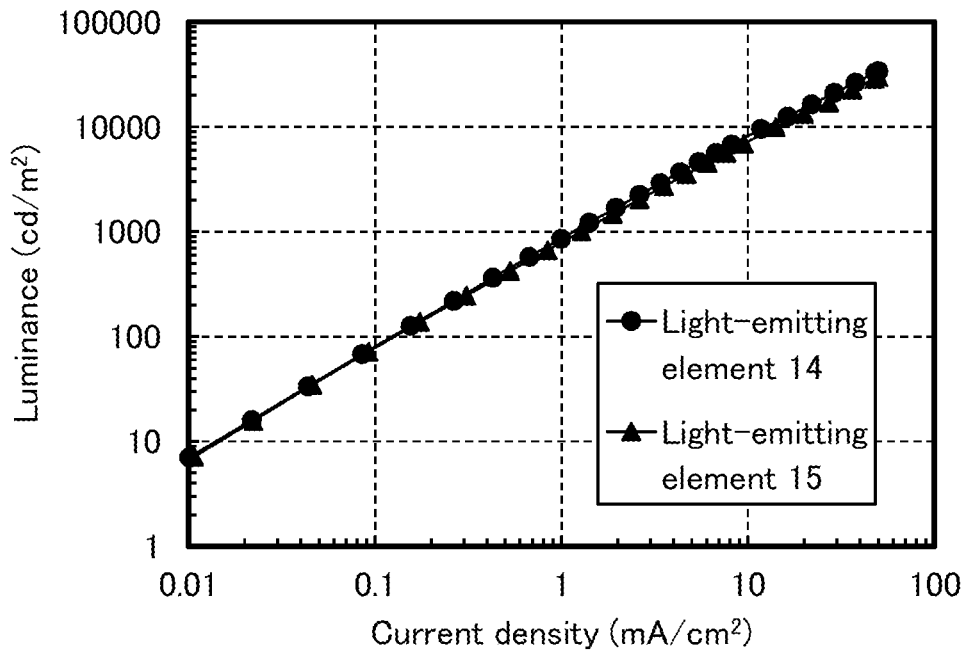
FIG. 49 is a drawing showing current density-luminance characteristics of a light-emitting element 14 and a light-emitting element 15.
Figure 50:
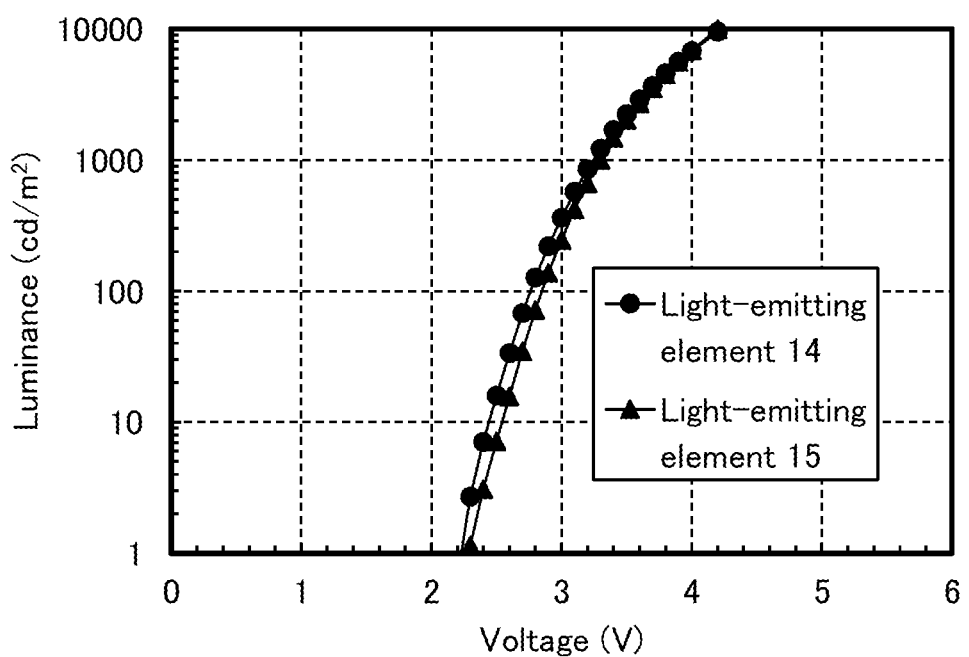
FIG. 50 is a drawing showing voltage-luminance characteristics of the light-emitting element 14 and the light-emitting element 15.
Figure 51:
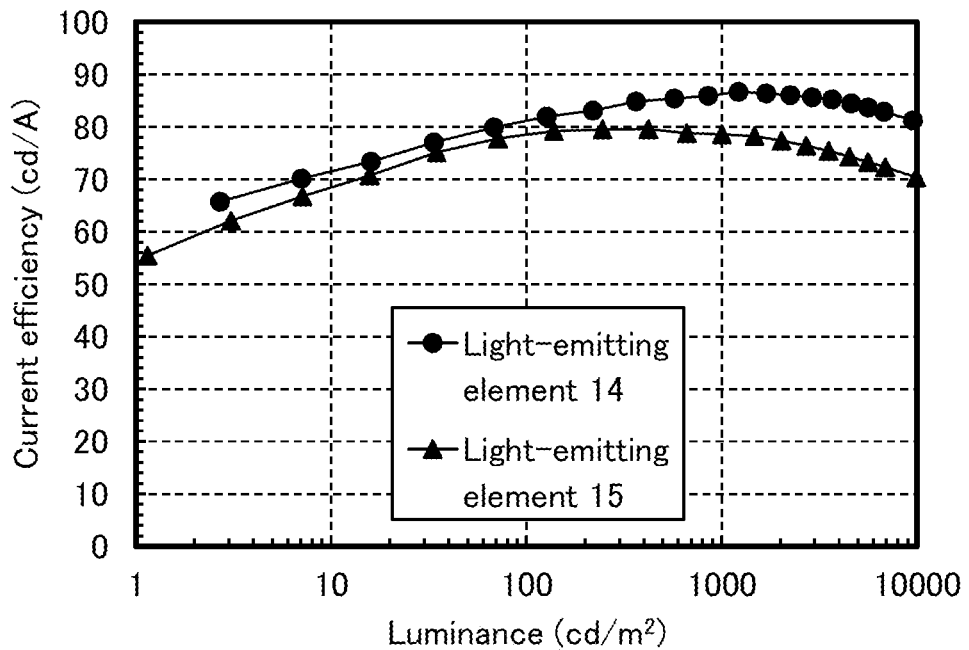
FIG. 51 is a drawing showing luminance-current efficiency characteristics of the light-emitting element 14 and the light-emitting element 15.
Figure 52:
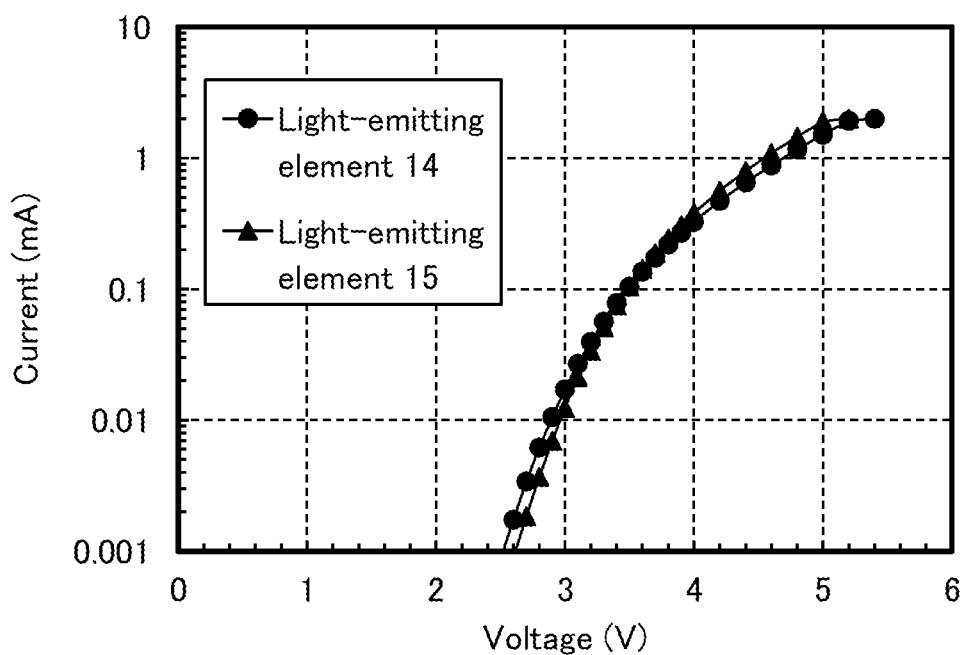
FIG. 52 is a drawing showing voltage-current characteristics of the light-emitting element 14 and the light-emitting element 15.

Next, reliability tests were performed on the light-emitting elements. FIG. 48 shows the results of the reliability tests. In FIG. 48, the vertical axis represents normalized luminance (%) with an initial luminance of 100%, and the horizontal axis represents driving time (h) of the element. As

TABLE 8

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 12 | 3.8 | 0.29 | 7.2 | (0.68, 0.32) | 1100 | 15 | 12 | 18 |
| Light-emitting element 13 | 4.0 | 0.38 | 9.4 | (0.71, 0.29) | 880 | 9.4 | 7.4 | 22 |

Figure 47:
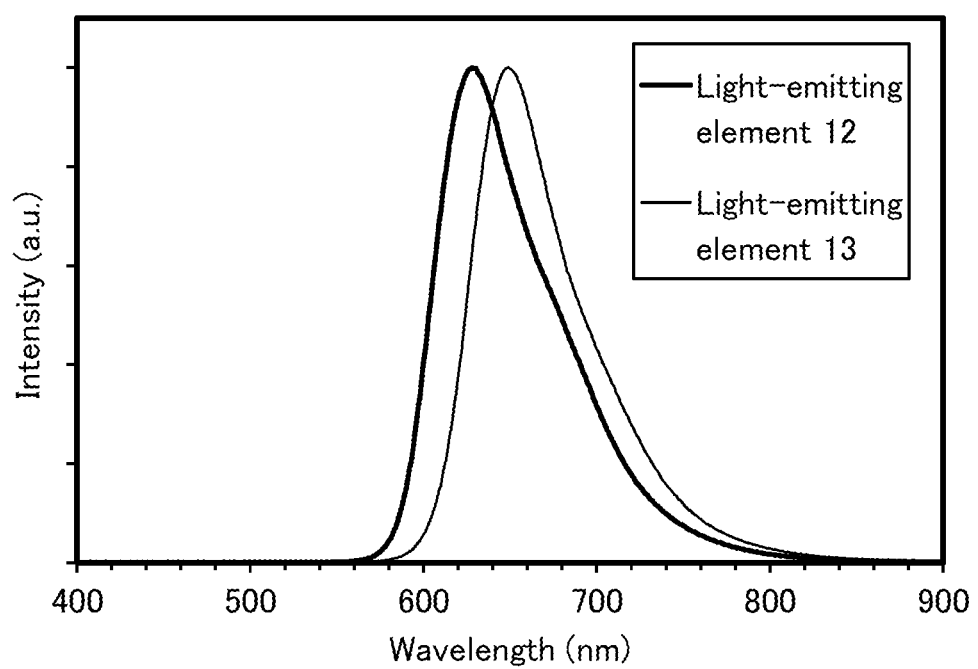
FIG. 47 is a drawing showing emission spectra of the light-emitting element 12 and the light-emitting element 13.

FIG. 47 shows emission spectra when current at a current density of 2.5 mA/cm² was applied to the light-emitting elements. As shown in FIG. 47, the emission spectrum of the light-emitting element 12 has a peak at around 628 nm, which is suggested to be derived from light emission of the reliability tests, constant current driving tests where a constant current was supplied at a current density of 75 mA/cm² were performed.

According to the results of the reliability tests, time taken until the luminance decreases from the initial luminance by 5% (LT95) of the light-emitting element 12 using 8(βN2)-4mDBtBPBfpm (Structural Formula (105)), which is the organic compound of one embodiment of the present invention, for the light-emitting layer was 115 hours, and LT95 of the light-emitting element 13 was 62 hours. This effect is owing to 8(βN2)-4mDBtBPBfpm, which is the organic compound of one embodiment of the present invention, having a structure in which a plurality of naphthyl groups are bonded to the 8-position of a benzofuropyrimidine skeleton. Thus, the use of the organic compound of one embodiment of the present invention is considered effective in improving the reliability of the light-emitting element.

Example 14

In this example, a light-emitting element 14 using 8pmTP-4mDBtPBfpm (Structural Formula (126)) described in Example 9, PCCP, and [Ir(ppy)$_2$(mdppy)] for a light-emitting layer and a light-emitting element 15 using 8BP-4mDBtBPBfpm (Structural Formula (103)) described in Example 7, PCCP, and [Ir(ppy)$_2$(mdppy)] for a light-emitting layer were fabricated as light-emitting elements of embodiments of the present invention. The measurement results on the characteristics will be described.

The element structure of the light-emitting element 14 and the light-emitting element 15 fabricated in this example is similar to that in FIG. 14 mentioned in Example 4, and specific compositions of layers that constitute the element structure are as shown in Table 9. Chemical formulae of materials used in this example are shown below.

TABLE 9

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 14 | ITSO (70 nm) | DBT3P-II:MoOx (2:1 45 nm) | PCBBi1BP (20 nm) | * | 8pmTP-4mDBtPBfpm (20 nm) | NBphen (10 nm) | LiF (1 nm) | Al (200 nm) |
| Light-emitting element 15 | ITSO (70 nm) | DBT3P-II:MoOx (2:1 45 nm) | PCBBi1BP (20 nm) | ** | 8BP-4mDBtBPBfpm (20 nm) | NBphen (10 nm) | LiF (1 nm) | Al (200 nm) |

* 8pmTP-4mDBtPBfpm:PCCP:[Ir(ppy)$_2$(mdppy)] (0.5:0.5:0.1 40 nm)
** 8BP-4mDBtBPBfpm:PCCP:[Ir(ppy)$_2$(mdppy)] (0.5:0.5:0.1 40 nm)

[Chemical Formulae 56]

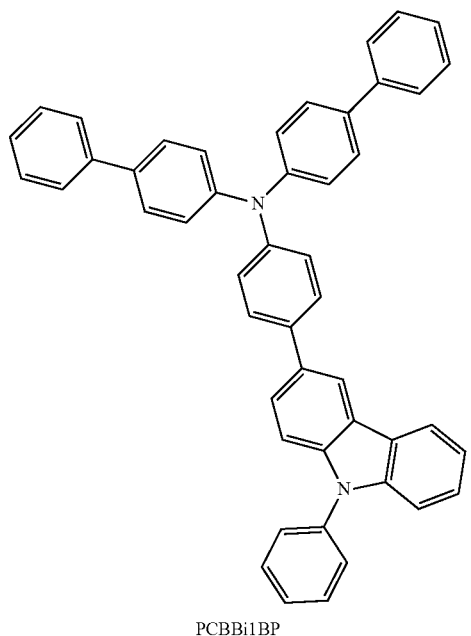

PCBBi1BP

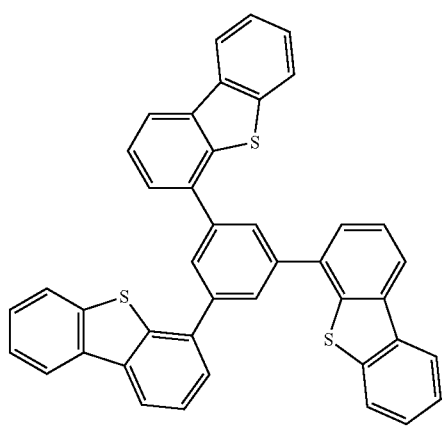

DBT3P-II

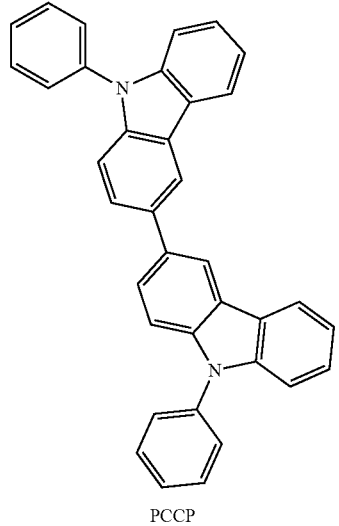

PCCP

-continued

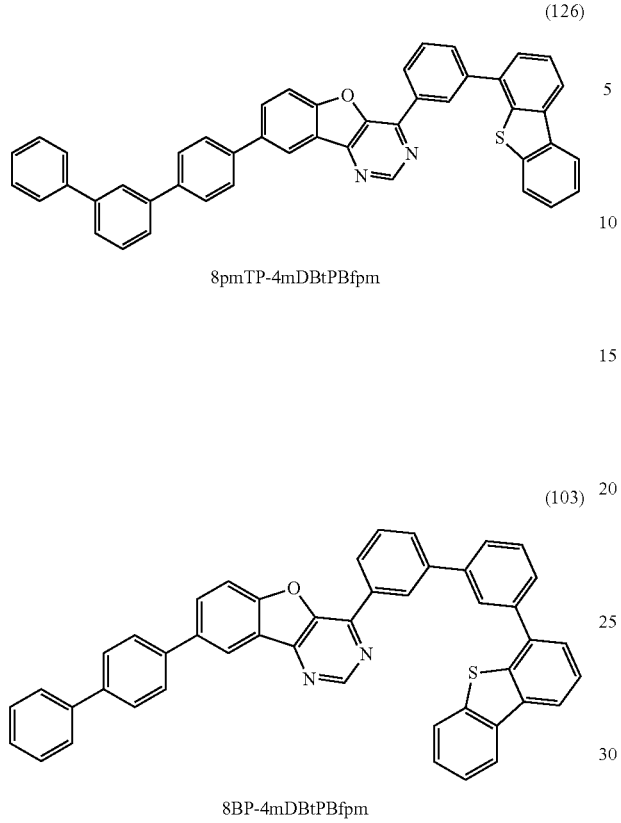

8pmTP-4mDBtPBfpm (126)

8BP-4mDBtPBfpm (103)

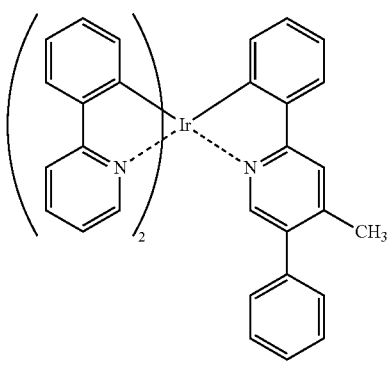

[Ir(ppy)₂(mdppy)]

-continued

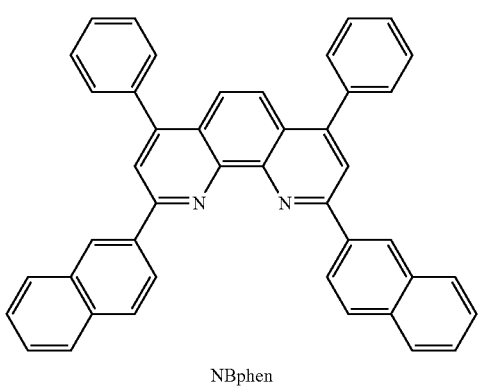

NBphen

<<Operation Characteristics of Light-Emitting Elements>>

Operation characteristics of the fabricated light-emitting element 14 and light-emitting element 15 were measured. Note that the measurement was carried out at room temperature (an atmosphere maintained at 25° C.).

The current density-luminance characteristics, voltage-luminance characteristics, luminance-current efficiency characteristics, and voltage-current characteristics of the light-emitting elements are shown in FIG. 49, FIG. 50, FIG. 51, and FIG. 52, respectively.

Table 10 below shows initial values of main characteristics of each of the light-emitting elements at around 1000 cd/m².

TABLE 10

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting element 14 | 3.2 | 0.040 | 0.99 | (0.34, 0.62) | 850 | 86 | 84 | 23 |
| Light-emitting element 15 | 3.3 | 0.051 | 1.3 | (0.36, 0.61) | 1000 | 79 | 75 | 22 |

Figure 53:
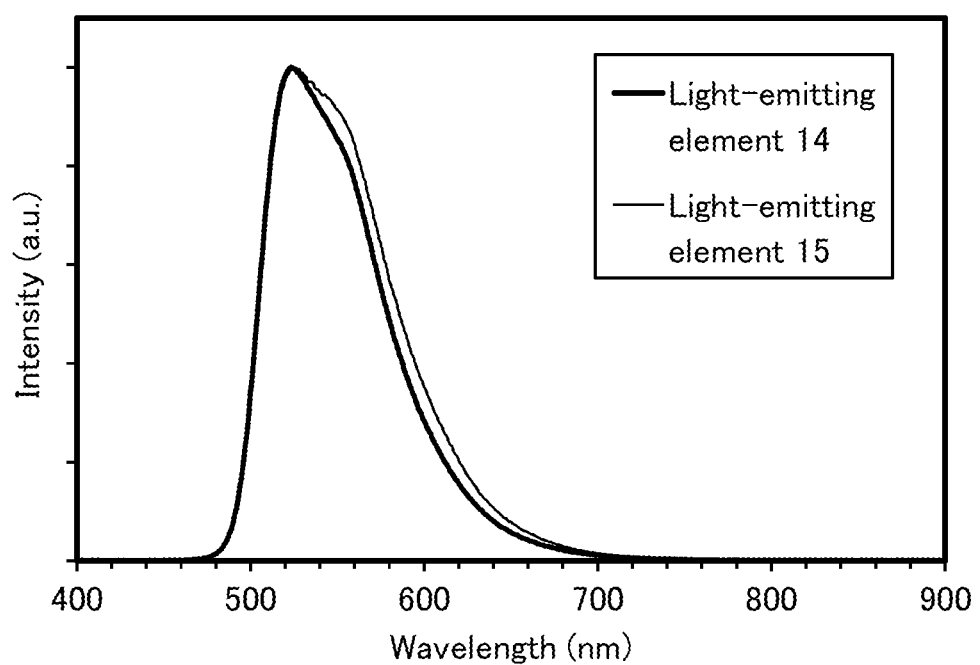
FIG. 53 is a drawing showing emission spectra of the light-emitting element 14 and the light-emitting element 15.

FIG. 53 shows emission spectra when current at a current density of 2.5 mA/cm² was applied to the light-emitting elements. As shown in FIG. 53, the emission spectrum of each light-emitting element has a peak at around 526 nm, which is suggested to be derived from light emission of [Ir(ppy)₂(mdppy)] contained in the light-emitting layer 913.

Figure 54:
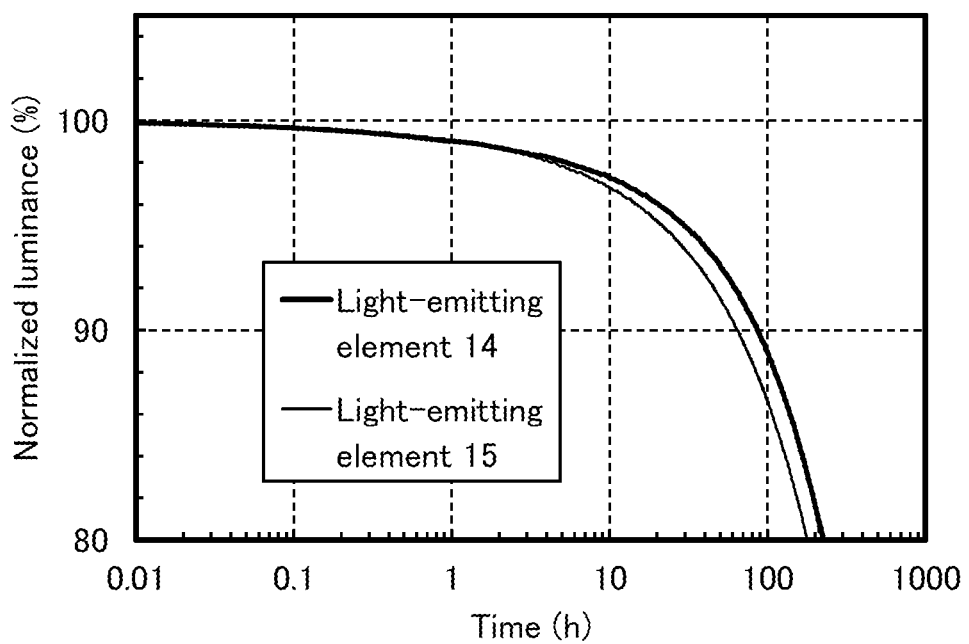
FIG. 54 is a drawing showing reliability of the light-emitting element 14 and the comparative light-emitting element 15.

Next, reliability tests were performed on the light-emitting elements. FIG. 54 shows the results of the reliability tests. In FIG. 54, the vertical axis represents normalized luminance (%) with an initial luminance of 100%, and the horizontal axis represents driving time (h) of the element. As the reliability tests, constant current driving tests where a constant current was supplied at a current density of 50 mA/cm² were performed.

According to the results of the reliability tests, time taken until the luminance decreases from the initial luminance by 5% (LT95) of the light-emitting element 14 using 8pmTP-4mDBtPBfpm (Structural Formula (126)), which is the organic compound of one embodiment of the present invention, for the light-emitting layer was approximately 30 hours, and LT95 of the light-emitting element 15 using 8BP-4mDBtBPBfpm (Structural Formula (103)) for the light-emitting layer was 21 hours. This effect is owing to 8pmTP-4mDBtPBfpm and 8BP-4mDBtBPBfpm, which are the organic compounds of embodiments of the present invention, each having a structure in which a plurality of arylene groups are bonded to the 8-position of a benzofuropyrimidine skeleton, preferably a biphenyl group in which the same two phenyl groups are bonded to each other. Thus, the use of the organic compound of one embodiment of the present invention is considered effective in improving the reliability of the light-emitting element.

REFERENCE NUMERALS

101: first electrode, 102: second electrode, 103: EL layer, 103a, 103b: EL layer, 104, 104a, 104b: charge-generation layer, 111, 111a, 111b: hole-injection layer, 112, 112a, 112b: hole-transport layer, 113, 113a, 113b, 113c: light-emitting layer, 114, 114a, 114b: electron-transport layer, 115, 115a, 115b: electron-injection layer, 200R, 200G, 200B: optical path length, 201: first substrate, 202: transistor (FET), 203R, 203G, 203B, 203W: light-emitting element, 204: EL layer, 205: second substrate, 206R, 206G, 206B: color filter, 206R', 206G', 206B': color filter, 207: first electrode, 208: second electrode, 209: black layer (black matrix), 210R, 210G: conductive layer, 301: first substrate, 302: pixel portion, 303: driver circuit portion (source line driver circuit), 304a, 304b: driver circuit portion (gate line driver circuit), 305: sealant, 306: second substrate, 307: lead wiring, 308: FPC, 309: FET, 310: FET, 311: FET, 312: FET, 313: first electrode, 314: insulator, 315: EL layer, 316: second electrode, 317: light-emitting element, 318: space, 900: substrate, 901: first electrode, 902: EL layer, 903: second electrode, 911: hole-injection layer, 912: hole-transport layer, 913: light-emitting layer, 914: electron-transport layer, 915: electron-injection layer, 4000: lighting device, 4001: substrate, 4002: light-emitting element, 4003: substrate, 4004: first electrode, 4005: EL layer, 4006: second electrode, 4007: electrode, 4008: electrode, 4009: auxiliary wiring, 4010: insulating layer, 4011: sealing substrate, 4012: sealant, 4013: desiccant, 4200: lighting device, 4201: substrate, 4202: light-emitting element, 4204: first electrode, 4205: EL layer, 4206: second electrode, 4207: electrode, 4208: electrode, 4209: auxiliary wiring, 4210: insulating layer, 4211: sealing substrate, 4212: sealant, 4213: barrier film, 4214: planarization film, 5101: light, 5102: wheel, 5103: door, 5104: display portion, 5105: handle, 5106: shifter, 5107: seat, 5108: inner rearview mirror, 7000: housing, 7001: display portion, 7002: second display portion, 7003: speaker, 7004: LED lamp, 7005: operation key, 7006: connection terminal, 7007: sensor, 7008: microphone, 7009: switch, 7010: infrared port, 7011: recording medium reading portion, 7014: antenna, 7015: shutter button, 7016: image receiving portion, 7018: stand, 7021: external connection portion, 7022, 7023: operation button, 7024: connection terminal, 7025: band, 7026: microphone, 7027: icon indicating time, 7028: another icon, 7029: sensor, 7030: speaker, 7052, 7053, 7054: information, 9310: portable information terminal, 9311: display portion, 9312: display region, 9313: hinge, 9315: housing This application is based on Japanese Patent Application Serial No. 2018-105410 filed with Japan Patent Office on May 31, 2018, the entire contents of which are hereby incorporated herein by reference.

The invention claimed is:
1. An organic compound represented by General formula (G1)

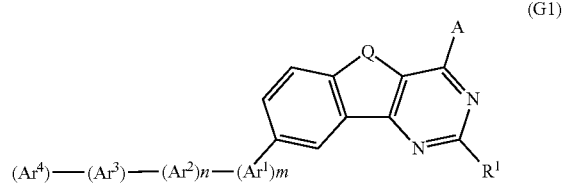

wherein in the formula:
Q represents oxygen or sulfur;
$Ar^1$, $Ar^2$, $Ar^3$, and $Ar^4$ each independently represent a substituted or unsubstituted benzene ring or a substituted or unsubstituted naphthalene ring;
when the substituted or unsubstituted benzene ring or the substituted or unsubstituted naphthalene ring has a substituent, the substituent is any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group;
m and n are each 0 or 1;
A is a group having 12 to 100 carbon atoms in total and comprises one or more of a benzene ring, a naphthalene ring, a fluorene ring, a phenanthrene ring, a triphenylene ring, a heteroaromatic ring comprising a dibenzothiophene ring, a heteroaromatic ring comprising a dibenzofuran ring, a heteroaromatic ring comprising a carbazole ring, a benzimidazole ring, and a triphenylamine structure; and
$R^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

2. An organic compound represented by General formula (G2)

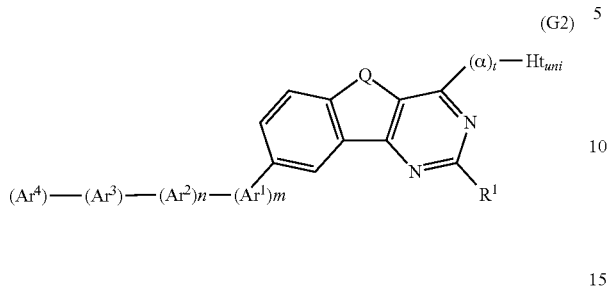

wherein in the formula:

Q represents oxygen or sulfur;

Ar$^1$, Ar$^2$, Ar$^3$, and Ar$^4$ each independently represent a substituted or unsubstituted aromatic hydrocarbon ring;

when the substituted or unsubstituted aromatic hydrocarbon ring has a substituent, the substituent of the aromatic hydrocarbon ring is any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group;

the number of carbon atoms in the aromatic hydrocarbon ring is 6 to 25;

m and n are each 0 or 1;

α represents a substituted or unsubstituted phenylene group;

t represents an integer of 0 to 4;

Ht$_{uni}$ comprises any one of a pyrrole ring structure, a furan ring structure, and a thiophene ring structure; and R$^1$ represents hydrogen, an alkyl group having 1 to 6 carbon atoms, a substituted or unsubstituted monocyclic saturated hydrocarbon group having 5 to 7 carbon atoms, a substituted or unsubstituted polycyclic saturated hydrocarbon group having 7 to 10 carbon atoms, a substituted or unsubstituted aryl group having 6 to 13 carbon atoms, or a substituted or unsubstituted heteroaryl group having 3 to 12 carbon atoms.

3. The organic compound according to claim 2, wherein the organic compound is represented by General formula (G3)

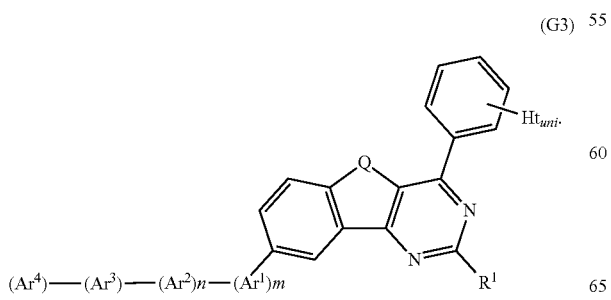

4. The organic compound according to claim 2, wherein the organic compound is represented by General formula (G4)

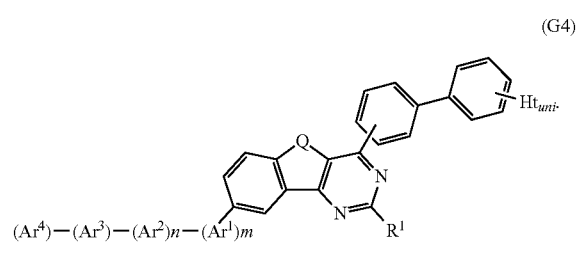

5. The organic compound according to claim 2, wherein the Ht$_{uni}$ is represented by any one of General Formulae (Ht-1) to (Ht-26) below,

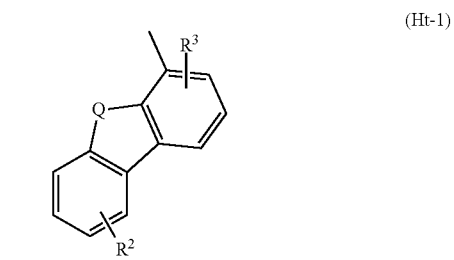

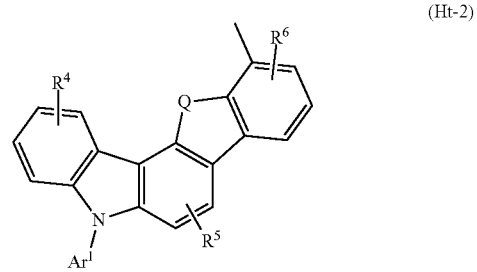

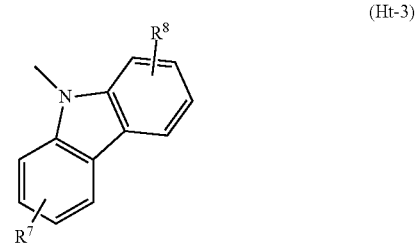

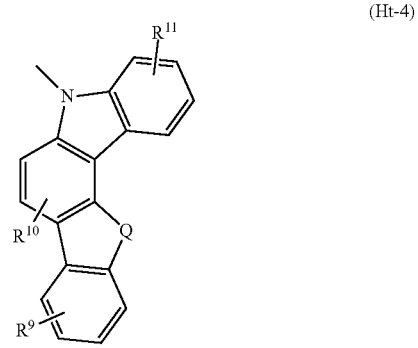

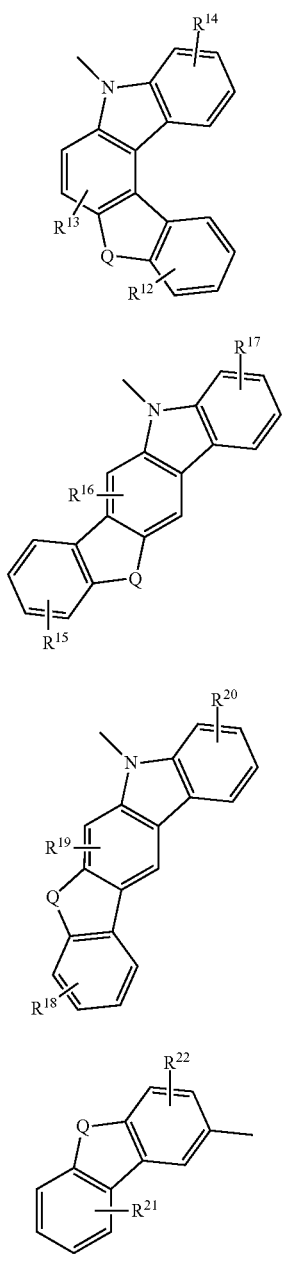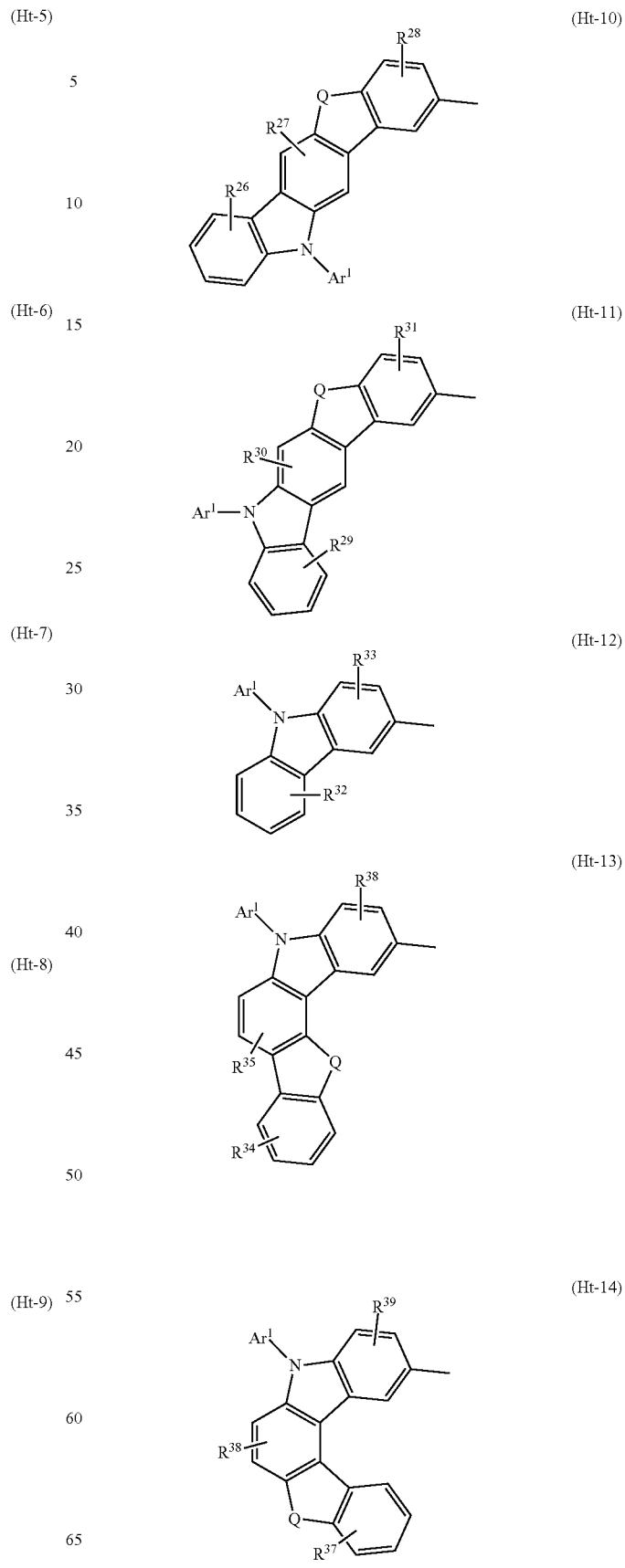

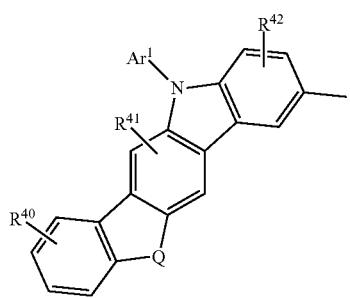 (Ht-15)
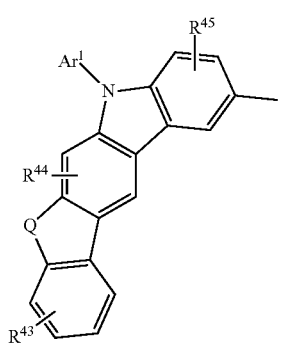 (Ht-16)
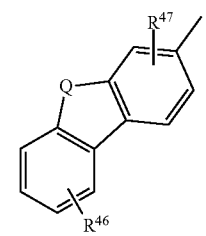 (Ht-17)
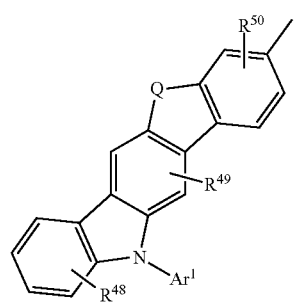 (Ht-18)
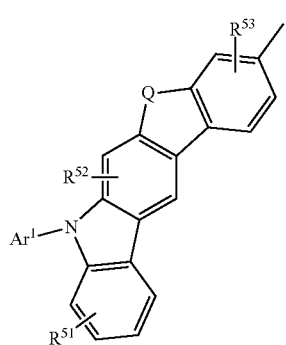 (Ht-19)
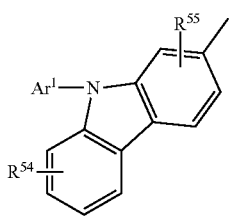 (Ht-20)
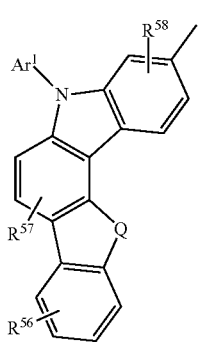 (Ht-21)
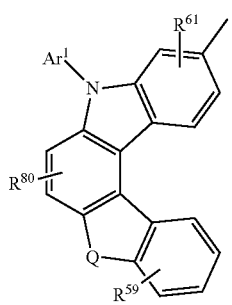 (Ht-22)
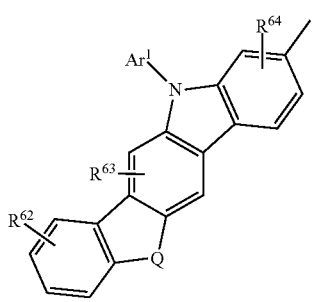 (Ht-23)
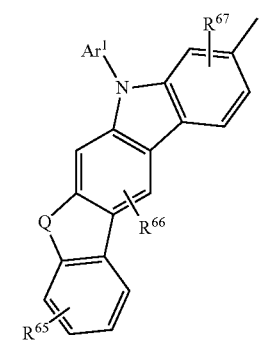 (Ht-24)

(Ht-25)

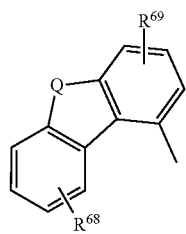

(Ht-26)

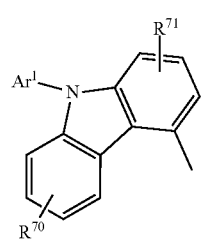

wherein in the formulae:
Q represents oxygen or sulfur;
$R^2$ to $R^{71}$ each represent 1 to 4 substituents and each independently represent any one of hydrogen, an alkyl group having 1 to 6 carbon atoms, and a substituted or unsubstituted phenyl group; and
$Ar^1$ represents a substituted or unsubstituted aryl group having 6 to 13 carbon atoms.

6. The organic compound according to claim 1, wherein $Ar^1$, $Ar^2$, $Ar^3$, and $Ar^4$ are the same.

7. The organic compound according to claim 1, wherein $Ar^1$, $Ar^2$, $Ar^3$, and $Ar^4$ are not substituted.

8. The organic compound according to claim 1, wherein General Formula (G-X), which is a substructure in the General Formulae (G1), is represented by any one of Structural Formulae (G-X-p1) to (G-X-p12) and (G-X-n1) to (G-X-n6)

(G-X)

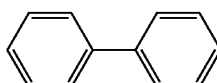

(G-X-p1)

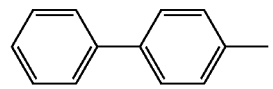

(G-X-p2)

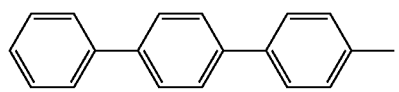

(G-X-p3)

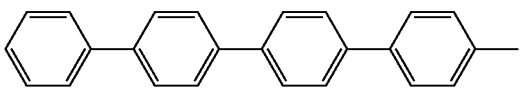

(G-X-p4)

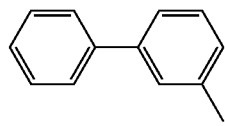

(G-X-p5)

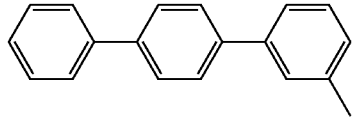

(G-X-p6)

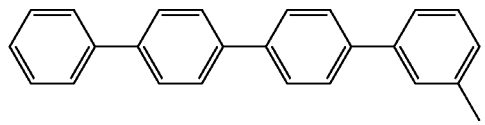

(G-X-p7)

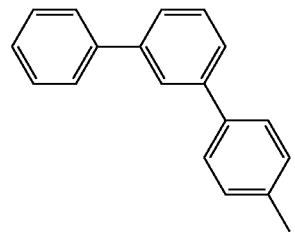

(G-X-p8)

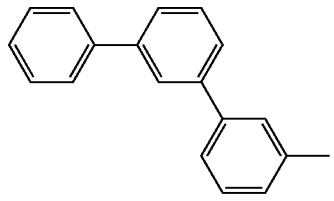

(G-X-p9)

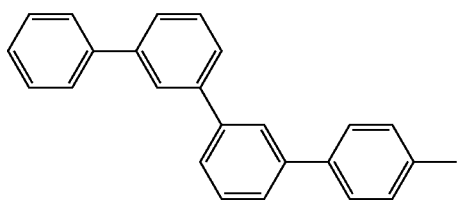

(G-X-p10)

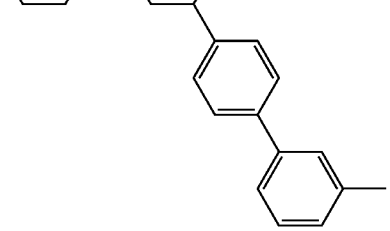

(G-X-p11)

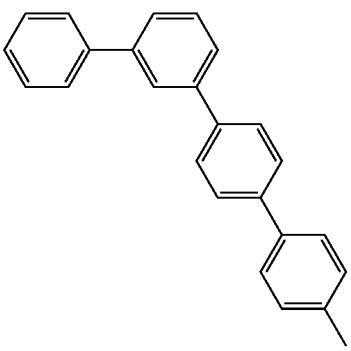

-continued (G-X-p12)
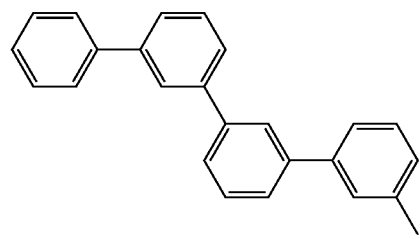

(G-X-n1)
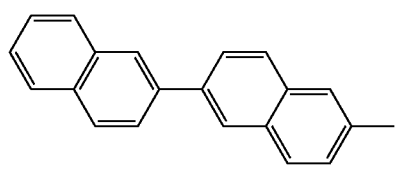

(G-X-n2)

(G-X-n3)

(G-X-n4)
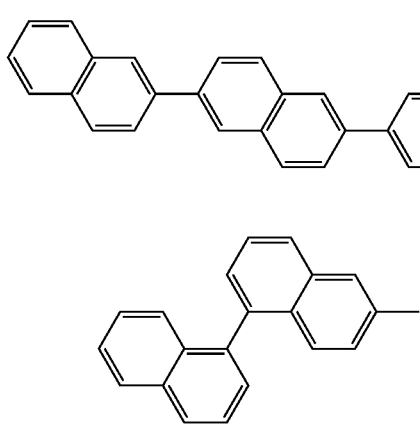

(G-X-n5)
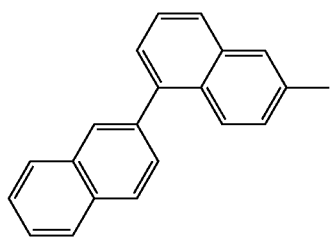

(G-X-n6)
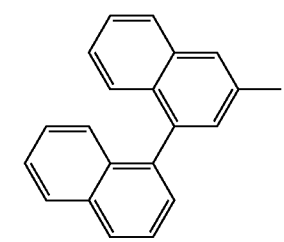

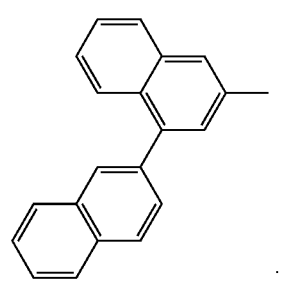

9. An organic compound represented by Structural formula (100), (101), or (102)

(100)
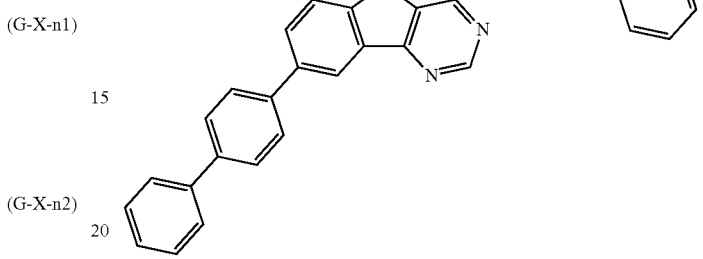

(101)
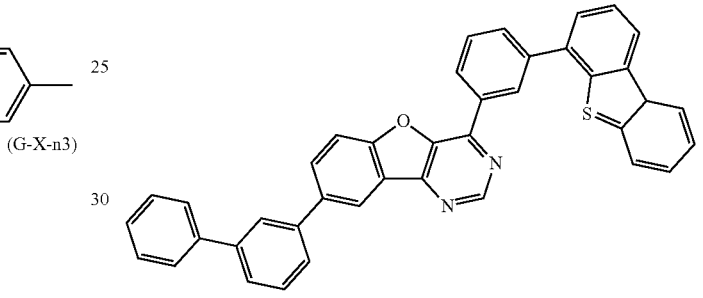

(102)
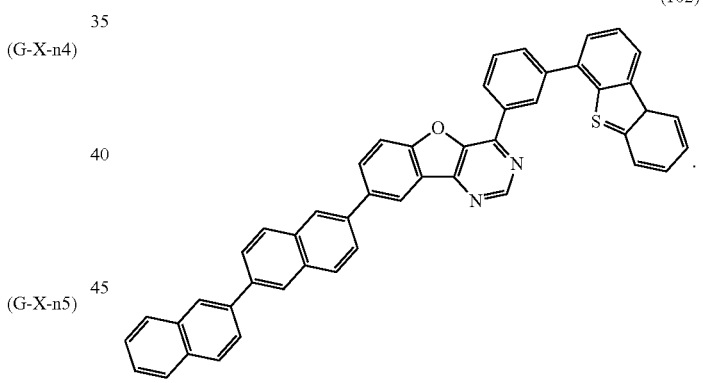

10. A light-emitting element comprising the organic compound according to claim 1.

11. A light-emitting element comprising an EL layer between a pair of electrodes,
    wherein the EL layer comprises a light-emitting layer, and
    wherein the light-emitting layer comprises the organic compound according to claim 1.

12. The light-emitting element according to claim 11,
    wherein the light-emitting layer comprises a phosphorescence material.

13. The light-emitting element according to claim 11,
    wherein the light-emitting layer comprises a phosphorescence material, and a carbazole derivative.

14. The light-emitting element according to claim 13,
    wherein the carbazole derivative is a bicarbazole derivative.

15. A light-emitting device comprising:

the light-emitting element according to claim 10; and at least one of a transistor and a substrate.

16. An electronic device comprising:

the light-emitting device according to claim 15; and at least one of a microphone, a camera, an operation button, an external connection portion, and a speaker.

17. A lighting device comprising:

the light-emitting device according to claim 15; and at least one of a housing, a cover, and a support base.

18. The organic compound according to claim 2, wherein $Ar^1$, $Ar^2$, $Ar^3$, and $Ar^4$ each independently represent a substituted or unsubstituted benzene ring or naphthalene ring.

19. The organic compound according to claim 2, wherein $Ar^1$, $Ar^2$, $Ar^3$, and $Ar^4$ are the same.

20. The organic compound according to claim 2, wherein $Ar^1$, $Ar^2$, $Ar^3$, and $Ar^4$ are not substituted.

21. The organic compound according to claim 2, wherein General Formula (G-X), which is a substructure in the General Formulae (G2), is represented by any one of Structural Formulae (G-X-p1) to (G-X-p12) and (G-X-n1) to (G-X-n6)

$$(Ar^4)\text{---}(Ar^3)\text{---}(Ar^2)_n\text{---}(Ar^1)_m\text{---} \quad (G\text{-}X)$$

(G-X-p1)

(G-X-p2)

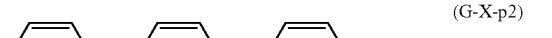
(G-X-p3)

(G-X-p4)

(G-X-p5)

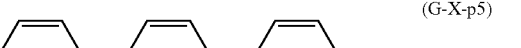
(G-X-p6)

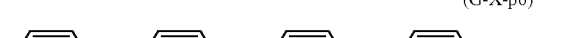

-continued

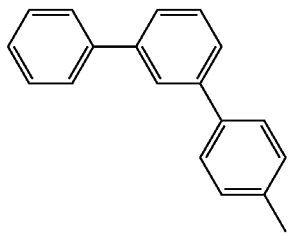
(G-X-p7)

(G-X-p8)

(G-X-p9)

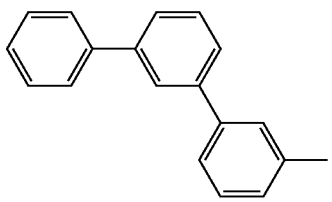

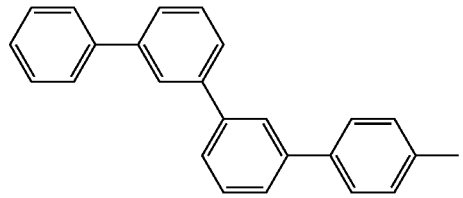
(G-X-p10)

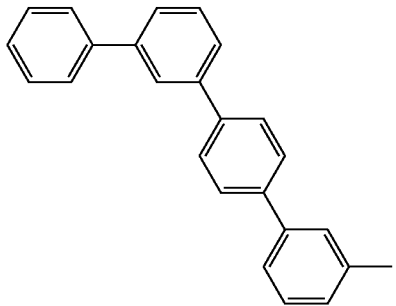
(G-X-p11)

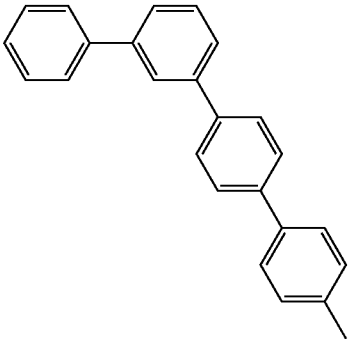
(G-X-p12)

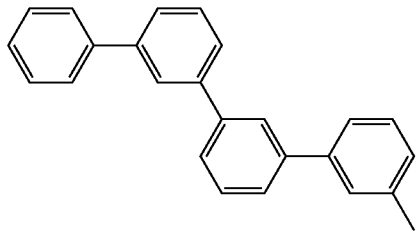

149
-continued
(G-X-n1)
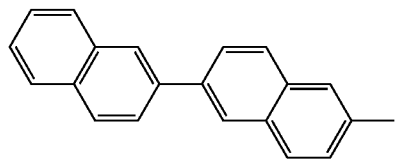
(G-X-n2)
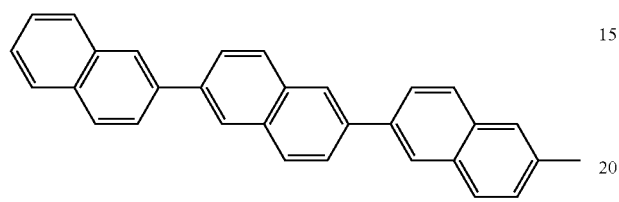
(G-X-n3)
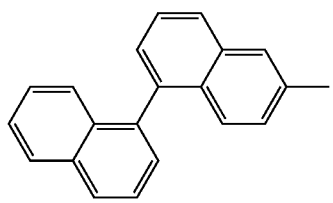
150
-continued
(G-X-n4)
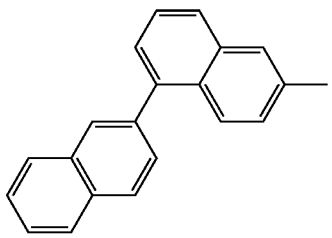
(G-X-n5)
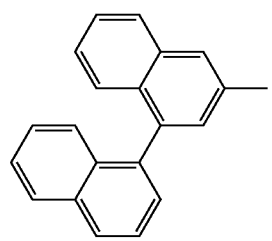
(G-X-n6)
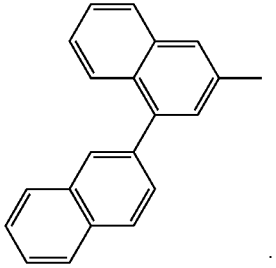
\* \* \* \* \*